US007507729B2

(12) United States Patent
Buettelmann et al.

(10) Patent No.: US 7,507,729 B2
(45) Date of Patent: Mar. 24, 2009

(54) SUBSTITUTED IMIDAZO-[1,5-A][1,2,4]TRIAZOLO[1,5-D][1,4] BENZODIAZEPINE DERIVATIVES

(75) Inventors: Bernd Buettelmann, Schopfheim (DE); Henner Knust, Rheinfelden (DE); Andrew Thomas, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 183 days.

(21) Appl. No.: 11/542,944

(22) Filed: Oct. 4, 2006

(65) Prior Publication Data
US 2007/0082890 A1 Apr. 12, 2007

(30) Foreign Application Priority Data
Oct. 11, 2005 (EP) ................... 05109446

(51) Int. Cl.
A61P 25/28 (2006.01)
A61K 31/55 (2006.01)
C07D 243/00 (2006.01)
(52) U.S. Cl. ..................... 514/219; 540/555
(58) Field of Classification Search ............. 514/219; 540/555
See application file for complete search history.

(56) References Cited

U.S. PATENT DOCUMENTS

| 4,146,721 A | 3/1979 | Rainer |
| 4,328,236 A | 5/1982 | Zeeh et al. |
| 5,387,585 A | 2/1995 | Borer et al. |

FOREIGN PATENT DOCUMENTS

| AU | 715785 | | 8/1997 |
| DE | 2940189 | | 4/1981 |
| DE | 19602505 | A1 | 7/1997 |
| EP | 50407 | | 4/1982 |
| EP | 519 307 | | 12/1992 |
| EP | 1 085 371 | A1 | 3/2001 |
| EP | 1337535 | B1 | 6/2004 |
| GB | 2379218 | A1 | 3/1993 |
| HU | 154810 | | 7/1967 |
| WO | WO 86/04582 | A1 | 8/1986 |
| WO | WO 91/17148 | A1 | 11/1991 |
| WO | WO 96/22350 | A1 | 7/1996 |
| WO | WO 96/28429 | A1 | 9/1996 |
| WO | WO 02/094834 | A1 | 11/2002 |

OTHER PUBLICATIONS

McNamara et al,Psychobiology, 21:101-108, 1993.
Ikekwere, P. O. et al, Synthesis and Reactivity in Inorganic and Metal-Organic Chemistry (1989), 19(6), 599-612.
Oae, Shigeru et al. Journal of the Chemical Society, Perkin Transactions 2: Physical Organic Chemistry (1972-1999) (1974), (15), 1844-1848.
Alanine, A. et al, Bioorganic & Medicinal Chemistry Letters, (2004), 14(3), 817-822.
Gilchrist, T., Synthesis (1983), (2), 153-154.
Angier, R. B. et al. Journal of the American Chemical Society (1950), 72, 74-77.
Nulu, J. R. et al, Journal of Medicinal Chemistry (1969), 12(5), 804-806.
Herke, J. et al, European Journal of Medicinal Chemistry (1979), 14(3), 203-206. English language translation provided.
Lyakhova, E. A. et al, Pharmaceutical Chemistry Journal (Translation of Khimiko-Farmatsevticheskii Zhurnal) (2003), 37(4), 178-183.
Cemischev, B. et al, Pharmazie (1967), 22(8), 432-434. English language translation provided.
Kushner, S et. Al, Journal of the American Chemical Society (1952), 74, 3617-3621.
Iwao, M. et al, Journal of Heterocyclic Chemistry (1978), 15(8), 1425-1430.
Nakamura, N., Chemical & Pharmaceutical Bulletin (1971), 19(1), 46-51.
Newman, M. et al, Journal of the American Chemical Society (1950), 72, 5163-5165.
Izdebski, J., Roczniki Chemii (1965), 39(5), 717-720.
Borg, S. et. Al, Journal of Organic Chemistry (1995), 60(10), 3112-3120.
Barker, J. et al, Journal of Chemical Research, Synopses (1992), (9), 291.
Begley, W. et al, Journal of the Chemical Society, Perkin Transactions 1 (1981), (9), 2620-2624.
Leonardi, A. et al, Bollettino Chimico Farmaceutico (1975), 114(2), 70-72. English language translation provided.
Rosen, G. et al, Journal of Heterocyclic Chemistry (1971), 8(4), 659-662.
Potts, K. et al, Journal of Organic Chemistry (1980), 45(24), 4985-4988.
De Lang, R-J. et al, Synthetic Communications (1998), 28(2), 225-232.
Abstract corresponding to Document B8—HU 154810, Jul. 1967.

*Primary Examiner*—Brenda L Coleman
(74) *Attorney, Agent, or Firm*—George W. Johnston; Patricia S. Rocha-Tramaloni; Kimberly J. Prior

(57) ABSTRACT

The present invention is concerned with substituted imidazo[1,5-a][1,2,4]triazolo[1,5-d][1,4]benzodiazepine derivatives of the following formula

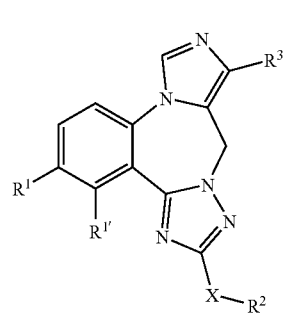

wherein the definition of substituents is described in the claims. This class of compounds shows high affinity and selectivity for GABA A α5 receptor binding sites and might be useful as a cognitive enhancer or for the treatment of cognitive disorders like Alzheimer's disease.

29 Claims, No Drawings

SUBSTITUTED IMIDAZO-[1,5-A][1,2,4]TRIAZOLO[1,5-D][1,4] BENZODIAZEPINE DERIVATIVES

PRIORITY TO RELATED APPLICATIONS

This application claims the benefit of European Application No. 05109446.4, filed Oct. 11, 2005, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in *Psychobiology*, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides substituted imidazo[1,5-a][1,2,4]triazolo[1,5-d][1,4]benzodiazepine derivatives of formula I

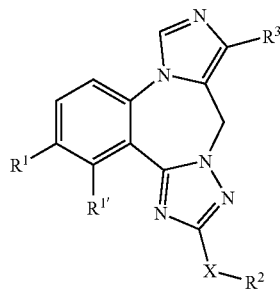

wherein
$R^1$ and $R^{1'}$ are each independently hydrogen, hydroxy, lower alkyl, lower alkynyl, halogen, lower alkoxy, cycloalkyl, or lower alkyl or alkoxy each of which is substituted by halogen;
X is —$CH_2$—, —$CH(CH_3)$—, —$CH_2O$—, —CRR'— or —C(O)—;
$R^2$ is —$(CH_2)_n$—O-lower alkyl,
halogen,
—$NHCH_3$,
—$N(CH_3)C(O)$-cycloalkyl,
—$N(CH_3)C(O)$-lower alkyl,
—$N(CH_3)S(O_2)CH_3$,
—$NHC(O)CH_2OC(O)CH_3$,
—$CF_3$,
cycloalkyl,
hydroxy,
—$CH_2OH$,
cyano,
$S(O)_2CH_3$,
—CH(OH)-lower alkyl,
aryl unsubstituted or substituted by lower alkoxy,
an aromatic or non aromatic heterocyclic ring, containing from 1 to 3 heteroatoms selected from the group consisting of N, O and S, and wherein the ring is unsubstituted or substituted by 1-4 substituents selected from the group consisting of lower alkyl, lower alkoxy, cycloalkyl, =O, $CF_3$, CN, C(O)O-lower alkyl, benzyl, phenyl, —$CH_2O$-lower alkyl, CHO and 3-bromo-10-chloro-9H-imidazo[1,5-a][1,2,4]triazolo[1,5-d][1,4]benzodiazepin-6-ylmethyl,
—C(O)—O-lower alkyl,
—C(O)NH—$(CH_2)_n$-cycloalkyl,
—C(O)NH—$(CH_2)_n$-aromatic or non aromatic heterocyclic ring, wherein the heterocyclic ring contains from 1 to 3 heteroatoms selected from the group consisting of N, O and S,
—C(O)NH—$(CH_2)_n$OH,
—C(O)-aromatic or non aromatic heterocyclic ring, wherein the heterocyclic ring contains from 1 to 3 heteroatoms selected from the group consisting of N, O and S, unsubstituted or substituted by lower alkyl,
—NH—C(O)H,
—N($CH_3$)—C(O)H,
—NH—C(O)-lower alkyl,
—NH—C(O)-cycloalkyl,
—NH—C(O)—O-lower alkyl,
—NH—C(O)—N-di-lower alkyl,
—NH—C(O)—$CH_2$—O-lower alkyl,
—NH—C(O)—$CH_2$—OH,
—NH—$(CH_2)_n$-cycloalkyl,
—NH—$(CH_2)_n S(O)_2 CH_3$,
—NH—$(CH_2)_n$-aromatic or non aromatic heterocyclic ring, wherein the heterocyclic ring contains from 1 to 3 heteroatoms selected from the group consisting of N, O and S, or —NH—$(CH_2)_n$OH; or
X—$R^2$ is lower alkyl with the exception of methyl,
cycloalkyl, unsubstituted or substituted by lower alkyl or hydroxy,
an aromatic or non aromatic heterocyclic ring, which contains from 1 to 3 heteroatoms selected from the group consisting of N, O and S, or
—CHRR';
R is hydroxy;
R' is cycloalkyl, lower alkyl, lower alkyl substituted by halogen, phenyl or pyridinyl;

R³ is hydrogen, halogen, C(O)O-lower alkyl, CH₂OH, CHO, lower alkyl or lower alkyl substituted by halogen; and
n is 0, 1 or 2;

and their pharmaceutically acceptable acid addition salts.

The invention also provides pharmaceutical compositions containing compounds of the invention and processes for the preparation of such compounds and compositions.

This class of compounds shows high affinity and selectivity for GABA A α5 receptor binding sites and might be useful as cognitive enhancer or for the treatment of cognitive disorders. The most preferred indication of the present invention is Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon residue containing from 1-7, preferably from 1-4, carbon atoms, for example, methyl, ethyl, propyl, isopropyl, n-butyl, i-butyl, t-butyl and the like.

As used herein, the term "lower alkoxy" denotes a straight- or branched-chain hydrocarbon residue containing from 1-7, preferably from 1-4, carbon atoms, for example, methyl, ethyl, propyl, isopropyl, n-butyl, i-butyl, t-butyl and the like, as described above, which is attached via an oxygen group.

The term "lower alkynyl" denotes a straight- or branched-chain carbon group containing from 2-7, preferably from 2-4, carbon atoms, having at least one triple bond.

The term "halogen" denotes chlorine, iodine, fluorine and bromine.

The term "cycloalkyl" denotes a saturated cyclic alkyl ring, having from 3 to 7 carbon ring atoms, for example, cyclopropyl, cyclopentyl or cyclohexyl.

The term "an aromatic or non aromatic heterocyclic ring, containing from 1 to 3 heteroatoms selected from the group consisting of N, O and S, and denotes the following groups:

Aromatic in Nature

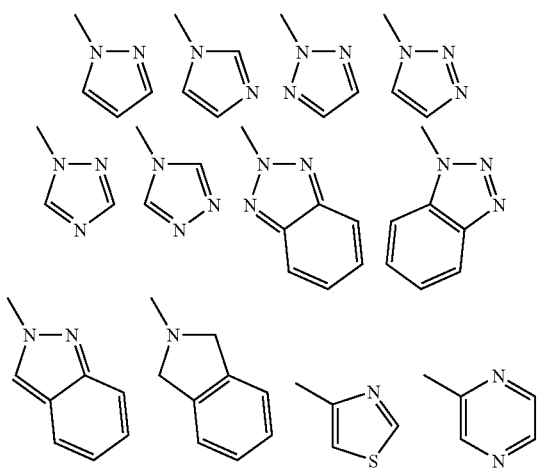

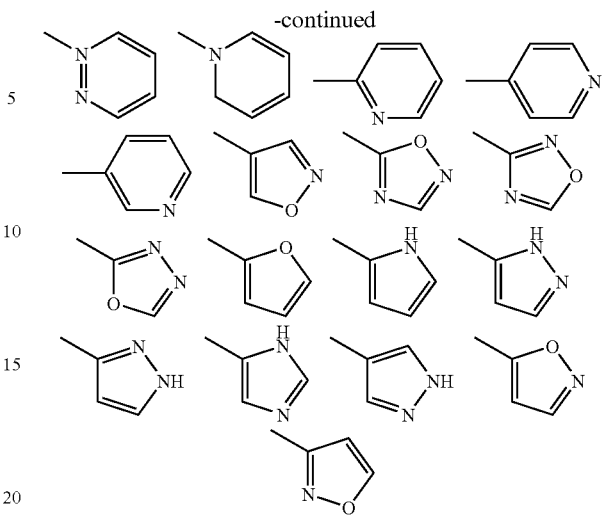

Non Aromatic in Nature

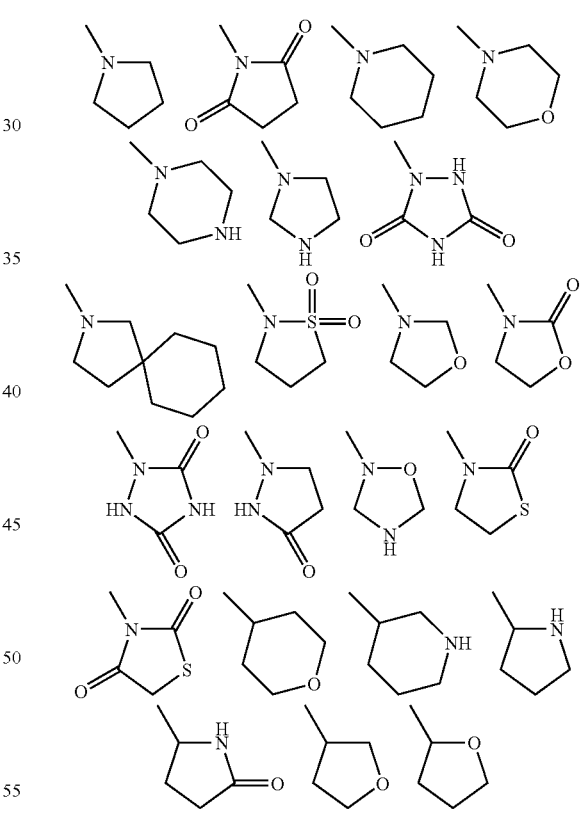

The term "lower alkyl or alkoxy substituted by halogen" denotes a lower alkyl or alkoxy group as defined above, wherein at least one hydrogen atom is replaced by a halogen atom. Examples of preferred groups are CF₃, CHF₂, CH₂F, CH₂CH₂F, CH₂CF₂H, CH₂CF₃, CF₂CH₃, OCF₃, OCHF₂, OCH₂F, OCH₂CH₂F, OCH₂CF₂H, OCH₂CF₃ or OCF₂CH₃.

The term "aryl" denotes a cyclic aromatic hydrocarbon radical consisting of one or more fused rings, in which at least one ring is aromatic in nature, for example a phenyl, benzyl or naphthyl group. Preferred groups are phenyl or benzyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides substituted imidazo[1,5-a][1,2,4]triazolo[1,5-d][1,4]benzodiazepine derivatives of formula I

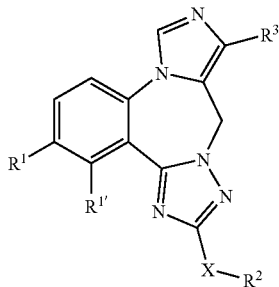

I wherein $R^1$ and $R^{1'}$ are each independently hydrogen, hydroxy, lower alkyl, lower alkynyl, halogen, lower alkoxy, cycloalkyl, or lower alkyl or alkoxy each of which is substituted by halogen;

X is —CH$_2$—, —CH(CH$_3$)—, —CH$_2$O—, —CRR'— or —C(O)—;

$R^2$ is —(CH$_2$)$_n$—O-lower alkyl,
halogen,
—NHCH$_3$,
—N(CH$_3$)C(O)-cycloalkyl,
—N(CH$_3$)C(O)-lower alkyl,
—N(CH$_3$)S(O$_2$)CH$_3$,
—NHC(O)CH$_2$OC(O)CH$_3$,
—CF$_3$,
cycloalkyl,
hydroxy,
—CH$_2$OH,
cyano,
S(O)$_2$CH$_3$,
—CH(OH)-lower alkyl,
aryl unsubstituted or substituted by lower alkoxy,
an aromatic or non aromatic heterocyclic ring, containing from 1 to 3 heteroatoms selected from the group consisting of N, O and S, and wherein the ring is unsubstituted or substituted by 1-4 substituents selected from the group consisting of lower alkyl, lower alkoxy, cycloalkyl, =O, CF$_3$, CN, C(O)O-lower alkyl, benzyl, phenyl, —CH$_2$O-lower alkyl, CHO and 3-bromo-10-chloro-9H-imidazo[1,5-a][1,2,4]triazolo[1,5-d][1,4]benzodiazepin-6-ylmethyl,
—C(O)—O-lower alkyl,
—C(O)NH—(CH$_2$)$_n$-cycloalkyl,
—C(O)NH—(CH$_2$)$_n$-aromatic or non aromatic heterocyclic ring, wherein the heterocyclic ring contains from 1 to 3 heteroatoms selected from the group consisting of N, O and S,
—C(O)NH—(CH$_2$)$_n$OH,
—C(O)-aromatic or non aromatic heterocyclic ring, wherein the heterocyclic ring contains from 1 to 3 heteroatoms selected from the group consisting of N, O and S, unsubstituted or substituted by lower alkyl,
—NH—C(O)H,
—N(CH$_3$)—C(O)H,
—NH—C(O)-lower alkyl,
—NH—C(O)-cycloalkyl,
—NH—C(O)—O-lower alkyl,
—NH—C(O)—N-di-lower alkyl,
—NH—C(O)—CH$_2$—O-lower alkyl,
—NH—C(O)—CH$_2$—OH,
—NH—(CH$_2$)$_n$-cycloalkyl,
—NH—(CH$_2$)$_n$S(O)$_2$CH$_3$,
—NH—(CH$_2$)$_n$-aromatic or non aromatic heterocyclic ring, wherein the heterocyclic ring contains from 1 to 3 heteroatoms selected from the group consisting of N, O and S, or
—NH—(CH$_2$)$_n$OH; or X—$R^2$ is lower alkyl with the exception of methyl,
cycloalkyl, unsubstituted or substituted by lower alkyl or hydroxy,
an aromatic or non aromatic heterocyclic ring, which contains from 1 to 3 heteroatoms selected from the group consisting of N, O and S, or
—CHRR';

R is hydroxy,
R' is cycloalkyl, lower alkyl, lower alkyl substituted by halogen, phenyl or pyridinyl;
$R^3$ is hydrogen, halogen, C(O)O-lower alkyl, CH$_2$OH, CHO, lower alkyl or lower alkyl substituted by halogen; and
n is 0, 1 or 2;

and their pharmaceutically acceptable acid addition salts.

Preferred are compounds that have a binding activity (Ki) of lower than 1 μM, that are selective for GABA A α5 subunits, and that are relatively free of activity at GABA A α1, α2 and α3 receptor binding sites.

Preferred compounds of formula I are those in which X is —CH$_2$— and $R^2$ is —(CH$_2$)$_n$O-lower alkyl, for example the following compounds:
ethyl 3-chloro-6-methoxymethyl-9H-imidazo[1,5-a][1,2,4]triazolo[1,5-d][1,4]benzodiazepine-10-carboxylate and
ethyl 3-bromo-6-methoxymethyl-9H-imidazo[1,5-a][1,2,4]triazolo[1,5-d][1,4]benzodiazepine-10-carboxylate.

Further preferred are compounds, in which X is —CH$_2$— and $R^2$ is an aromatic heterocyclic ring, containing from 1 to 3 heteroatoms selected from the group consisting of N, O and S, and wherein the ring is unsubstituted or substituted by 1-4 substituents selected from the group consisting of lower alkyl, =O, CF$_3$, C(O)O-lower alkyl, benzyl, phenyl, CH$_2$O-lower alkyl and CHO, for example the following compounds
3,10-dichloro-6-[1,2,3]triazol-2-ylmethyl-9H-imidazo[1,5-a][1,2,4]triazolo[1,5-d][1,4]benzodiazepine,
3,10-dichloro-6-[1,2,3]triazol-1-ylmethyl-9H-imidazo[1,5-a][1,2,4]triazolo[1,5-d][1,4]benzodiazepine,
3,10-dichloro-6-[1,2,4]triazol-1-ylmethyl-9H-imidazo[1,5-a][1,2,4]triazolo[1,5-d][1,4]benzodiazepine,
3,10-dichloro-6-pyrazol-1-ylmethyl-9H-imidazo[1,5-a][1,2,4]triazolo[1,5-d][1,4]benzodiazepine,
6-benzotriazol-2-ylmethyl-3,10-dichloro-9H-imidazo[1,5-a][1,2,4]triazolo[1,5-d][1,4]benzodiazepine, 6-benzotriazol-1-ylmethyl-3,10-dichloro-9H-imidazo[1,5-a][1,2,4]triazolo[1,5-d][1,4]benzodiazepine,
3,10-dichloro-6-indazol-2-ylmethyl-9H-imidazo[1,5-a][1,2,4]triazolo[1,5-d][1,4]benzodiazepine,
3-bromo-10-chloro-6-(5-methyl-[1,2,4]oxadiazol-3-ylmethyl)-9H-imidazo[1,5-a][1,2,4]triazolo[1,5-d][1,4]benzodiazepine,
3-bromo-10-methyl-6-(pyridine-4-ylmethyl)-9H-imidazo[1,5-a][1,2,4]triazolo[1,5-d][1,4]benzodiazepine,
3-bromo-10-methyl-6-(3-methyl-isoxazol-5-ylmethyl)-9H-imidazo[1,5-a][1,2,4]triazolo[1,5-d][1,4]benzodiazepine,
3-bromo-10-methyl-6-(6-methyl-pyridin-3-ylmethyl)-9H-imidazo[1,5-a][1,2,4]triazolo[1,5-d][1,4]benzodiazepine,
3-bromo-10-methyl-6-[1,2,3]triazol-1-ylmethyl-9H-imidazo[1,5-a][1,2,4]triazolo[1,5-d][1,4]benzodiazepine,
3-chloro-10-methyl-6-(3-methyl-isoxazol-5-ylmethyl)-9H-imidazo[1,5-a][1,2,4]triazolo[1,5-d][1,4]benzodiazepine,
3-chloro-10-methyl-6-(6-methyl-pyridin-3-ylmethyl)-9H-imidazo[1,5-a][1,2,4]triazolo[1,5-d][1,4]benzodiazepine,
3-chloro-10-methyl-6-(2-methyl-pyridin-4-ylmethyl)-9H-imidazo[1,5-a][1,2,4]triazolo[1,5-d][1,4]benzodiazepine,
3,10-dimethyl-6-(3-methyl-isoxazol-5-ylmethyl)-9H-imidazo[1,5-a][1,2,4]triazolo[1,5-d][1,4]benzodiazepine,
10-methyl-6-(pyridine-2-ylmethyl)-9H-imidazo[1,5-a][1,2,4]triazolo[1,5-d][1,4]benzodiazepine,
10-methyl-6-(pyridine-3-ylmethyl)-9H-imidazo[1,5-a][1,2,4]triazolo[1,5-d][1,4]benzodiazepine,
6-(imidazol-1-ylmethyl)-10-methyl-9H-imidazo[1,5-a][1,2,4]triazolo[1,5-d][1,4]benzodiazepine,
3-bromo-10-methyl-6-(6-oxo-6H-pyridazin-1-ylmethyl)-9H-imidazo[1,5-a][1,2,4]triazolo[1,5-d][1,4]benzodiazepine,
3-bromo-10-methyl-6-(3-methyl-[1,2,4]oxadiazol-5-ylmethyl)-9H-imidazo[1,5-a][1,2,4]triazolo[1,5-d][1,4]benzodiazepine,
3-chloro-10-methyl-6-[1,2,3]triazol-1-ylmethyl-9H-imidazo[1,5-a][1,2,4]triazolo[1,5-d][1,4]benzodiazepine,
10-methyl-6-(2-oxo-2H-pyridin-1-ylmethyl)-9H-imidazo[1,5-a][1,2,4]triazolo[1,5-d][1,4]benzodiazepine and
10-methyl-6-(2H-pyrazol-3-ylmethyl)-9H-imidazo[1,5-a][1,2,4]triazolo[1,5-d][1,4]benzodiazepine.

Preferred compounds of formula I are further those, in which X is —CH$_2$— and R$^2$ is a non aromatic heterocyclic ring, containing from 1 to 3 heteroatoms selected from the group consisting of N, O and S, and wherein the ring is unsubstituted or substituted by 1-4 substituents selected from the group consisting of lower alkyl, =O, CF$_3$, C(O)O-lower alkyl, benzyl, phenyl, CH$_2$O-lower alkyl and CHO, for example the following compounds
3-bromo-10-chloro-6-(2-oxo-pyrrolidin-1-ylmethyl)-9H-imidazo[1,5-a][1,2,4]triazolo[1,5-d][1,4]benzodiazepine,
3-bromo-10-chloro-6-(2-oxo-oxazolidin-3-ylmethyl)-9H-imidazo[1,5-a][1,2,4]triazolo[1,5-d][1,4]benzodiazepine,
3-bromo-10-chloro-6-(5-methoxymethyl-2-oxo-oxazolidin-3-ylmethyl)-9H-imidazo[1,5-a][1,2,4]triazolo[1,5-d][1,4]benzodiazepine,
3-bromo-10-chloro-6-(3-methyl-2-oxo-imidazolidin-1-ylmethyl)-9H-imidazo[1,5-a][1,2,4]triazolo[1,5-d][1,4]benzodiazepine,
3-bromo-10-chloro-6-(2-oxo-imidazolidin-1-ylmethyl)-9H-imidazo[1,5-a][1,2,4]triazolo[1,5-d][1,4]benzodiazepine,
3-bromo-10-chloro-6-(2,4-dioxo-thiazolidin-3-ylmethyl)-9H-imidazo[1,5-a][1,2,4]triazolo[1,5-d][1,4]benzodiazepine,
3-bromo-10-chloro-6-(2,5-dioxo-pyrrolidin-1-ylmethyl)-9H-imidazo[1,5-a][1,2,4]triazolo[1,5-d][1,4]benzodiazepine,
3-bromo-10-chloro-6-(2-oxo-thiazolidin-3-ylmethyl)-9H-imidazo[1,5-a][1,2,4]triazolo[1,5-d][1,4]benzodiazepine,
3-bromo-10-chloro-6-((5S)-5-methyl-2-oxo-oxazolidin-3-ylmethyl)-9H-imidazo[1,5-a][1,2,4]triazolo[1,5-d][1,4]benzodiazepine and
3,10-dichloro-6-(2-oxo-oxazolidin-3-ylmethyl)-9H-imidazo[1,5-a][1,2,4]triazolo[1,5-d][1,4]benzodiazepine.

Further preferred are compounds, wherein X—R$^2$ is —CHRR'R is hydroxyl, and R' is cycloalkyl, lower alkyl, phenyl or pyridinyl, for example the following compounds
3-bromo-10-chloro-6-(hydroxy-phenyl-ethyl)-9H-imidazo[1,5-a][1,2,4]triazolo[1,5-d][1,4]benzodiazepine and
3-bromo-10-chloro-6-(hydroxy-pyridin-3-yl-methyl)-9H-imidazo[1,5-a][1,2,4]triazolo[1,5-d][1,4]benzodiazepine.

Further preferred are compounds, in which X is —CH$_2$— and R$^2$ is —C(O)NH—(CH$_2$)$_n$-cycloalkyl or —C(O)NH—(CH$_2$)$_n$-aromatic or non aromatic heterocyclic ring, wherein the heterocyclic ring contains from 1 to 3 heteroatoms selected from the group consisting of N, O and S, for example the following compounds
3-bromo-10-chloro-6-cyclopentylcarbamoylmethyl-9H-imidazo[1,5-a][1,2,4]triazolo[1,5-d][1,4]benzodiazepine,
3-bromo-10-chloro-6-[(tetrahydro-pyran-4-ylcarbamoyl)-methyl]-9H-imidazo[1,5-a][1,2,4]triazolo[1,5-d][1,4]benzodiazepine,
3-bromo-10-chloro-6-{[(pyridin-3-ylmethyl)-carbamoyl]-methyl}-9H-imidazo[1,5-a][1,2,4]triazolo[1,5-d][1,4]benzodiazepine and
3-bromo-10-chloro-6-[(cyclopropylmethyl-carbamoyl)-methyl]-9H-imidazo[1,5-a][1,2,4]triazolo[1,5-d][1,4]benzodiazepine.

Further preferred are compounds, in which X is —CH$_2$— and R$^2$ is —C(O)NH—(CH$_2$)$_n$OH, for example the following compound
3-bromo-10-chloro-6-[(2-hydroxy-ethylcarbamoyl)-methyl]-9H-imidazo[1,5-a][1,2,4]triazolo[1,5-d][1,4]benzodiazepine.

Further preferred are compounds, wherein X is —CH$_2$— and R$^2$ is aryl unsubstituted or substituted by lower alkoxy, for example the following compound
3-Bromo-6-(2-methoxy-benzyl)-10-methyl-9H-imidazo[1,5-a][1,2,4]triazolo[1,5-d][1,4]benzodiazepine.

The present compounds of formula I and their pharmaceutically acceptable salts can be prepared by methods known in the art, for example, by processes described below, which process comprises
a) reacting a compound of formula

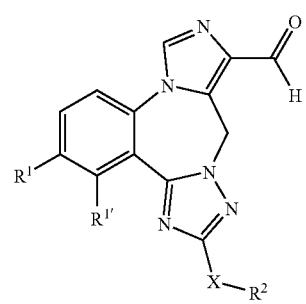

II with [bis(2-methoxyethyl)amino]sulfur trifluoride to obtain a compound of formula c) reacting a compound of formula

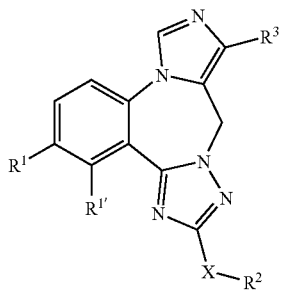
I-1

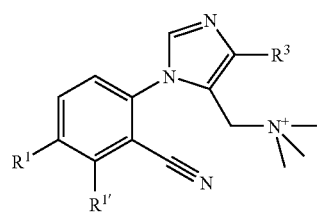
IV wherein $R^1$, $R^{1'}$, $R^2$ and X are as described above, and $R^3$ is C(O)O-lower alkyl, or b) reacting a compound of formula with a compound of formula

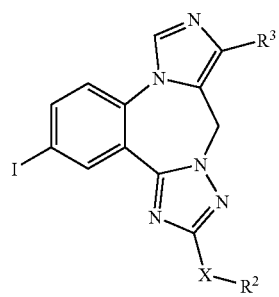
I-2

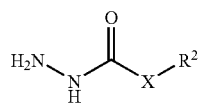
V to obtain a compound of formula with a compound of formula $R^1$—ZnCl III or $R^1$—H IIIA in the presence of Pd(0)

to obtain a compound of formula

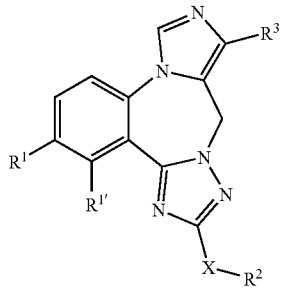
I-4 wherein $R^1$, $R^{1'}$, $R^2$ and $R^3$ are as described above, and X is —CH$_2$—, —CH(CH$_3$)—, CH$_2$O—, or —CRR'— or d) reacting a compound of formula

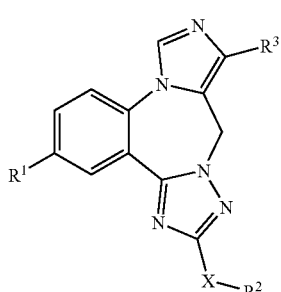
I-3

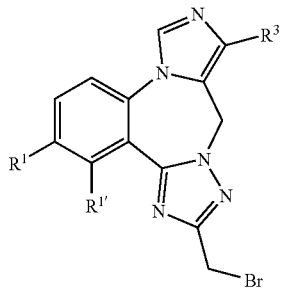
I-5 wherein $R^2$, $R^3$ and X are as described above, and $R^1$ is hydroxy, lower alkyl, lower alkynyl, halogen, lower alkoxy, cycloalkyl, or lower alkyl or alkoxy each of which is substituted by halogen or in the presence of NaCN to obtain a compound of formula

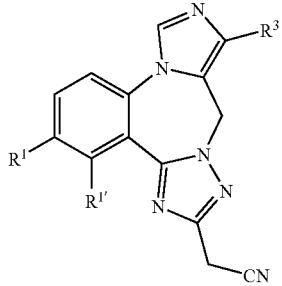

wherein R¹, R¹' and R³ are as described above, or e) reacting a compound of formula

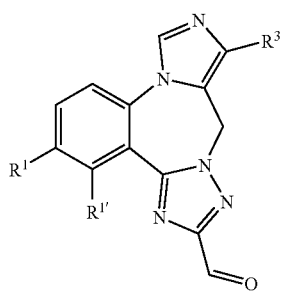

with a compound of formula NaClO₂ to obtain a compound of formula

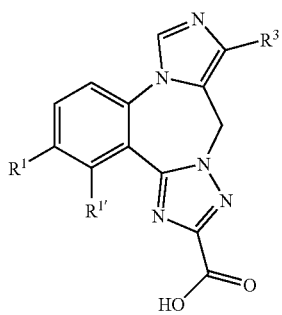

wherein R¹, R¹' and R³ are as described above, or f) reacting a compound of formula

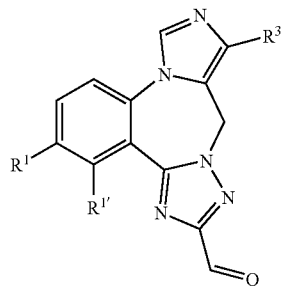

VI

I-6 with a corresponding Grignard-reagent to a compound of formula

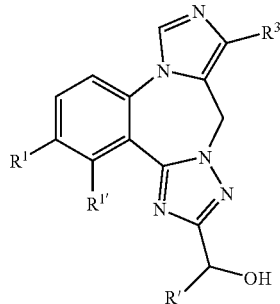

I-8 wherein R¹, R¹' and R³ are as described above and R' is cycloalkyl, lower alkyl, lower alkyl substituted by halogen, phenyl or pyridinyl or g) reacting a compound of formula

I-7

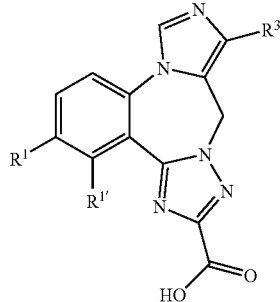

I-7 with a corresponding amine to a compound of formula

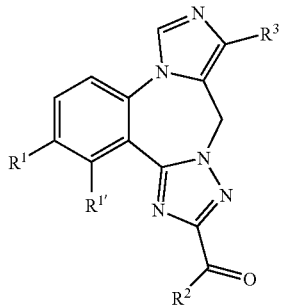

I-9 wherein $R^1$, $R^{1'}$ and $R^3$ are as described above and $R^2$ is —NH—C(O)H, —N(CH$_3$)—C(O)H, —NH—C(O)-lower alkyl, —NH—C(O)-cycloalkyl, —NH—C(O)—O-lower alkyl, —NH—C(O)—N-di-lower alkyl, —NH—C(O)—CH$_2$—O-lower alkyl, —NH—C(O)—CH$_2$—OH, —NH—(CH$_2$)$_n$-cycloalkyl, —NH—(CH$_2$)$_n$S(O)$_2$CH$_3$, —NH—(CH$_2$)$_n$-aromatic or non aromatic heterocyclic ring, wherein the heterocyclic ring contains from 1 to 3 heteroatoms selected from the group consisting of N, O and S, or is —NH—(CH$_2$)$_n$OH; or h) reacting a compound of formula

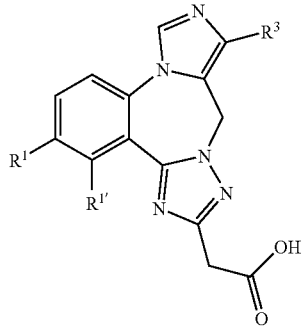

VII with a corresponding amine
to obtain a compound of formula

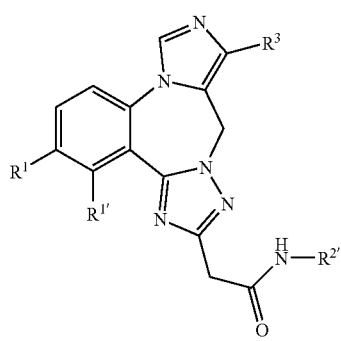

I-10 wherein $R^1$, $R^{1'}$ and $R^3$ are as described above, and $R^{2'}$ is —(CH$_2$)$_n$-cycloalkyl, —(CH$_2$)$_n$-aromatic or non aromatic heterocyclic ring, which contain from 1 to 3 heteroatoms selected from the group consisting of N, O and S, or is —(CH$_2$)$_n$OH, or i) reacting a compound of formula

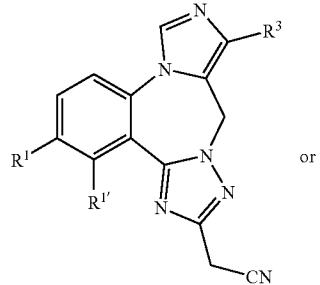

I-6 or

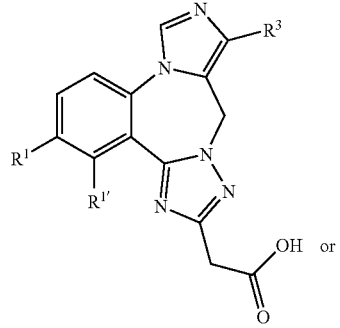

VII

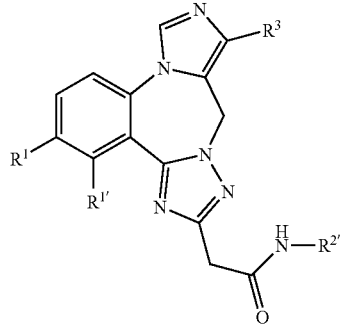

I-10 with hydroxylamine and acetic anhydride
to obtain a compound of formula

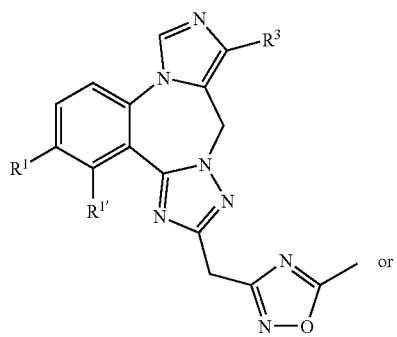

I-11 or

-continued

I-12
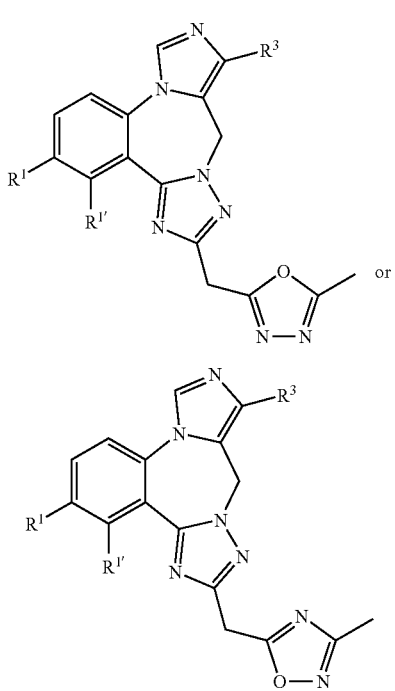
or

I-13 wherein R¹, R¹' and R³ are as described above, or
j) reacting a compound of formula

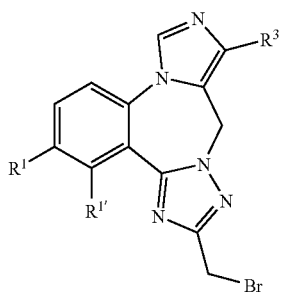

with a corresponding amine
to obtain a compound of formula

I-14
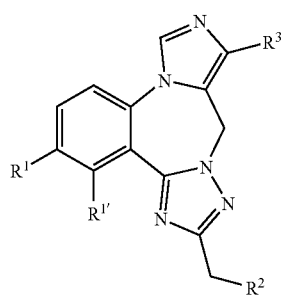

wherein R¹, R¹' and R³ are as described above and R² is
—NH—C(O)H or —N(CH₃)—C(O)H, —NH—C(O)-lower alkyl, —NH—C(O)-cycloalkyl, —NH—C(O)—O-lower alkyl, —NH—C(O)—N-di-lower alkyl, —NH—C(O)—CH₂—O-lower alkyl or —NH—C(O)—CH₂—OH, —NH—(CH₂)$_n$-cycloalkyl, —NH—(CH₂)$_n$S(O)₂CH₃, —NH—(CH₂)$_n$-aromatic or non aromatic heterocyclic ring, wherein the heterocyclic ring contains from 1 to 3 heteroatoms selected from the group consisting of N, O and S, or is —NH—(CH₂)$_n$OH; and, if desired, converting a compound of formula I into a pharmaceutically acceptable salt.

The following schemes (schemes 1-11) describe the processes for preparation of compounds of formula I in more detail. The starting materials are known compounds or can be prepared according to methods known in the art.

Scheme 1

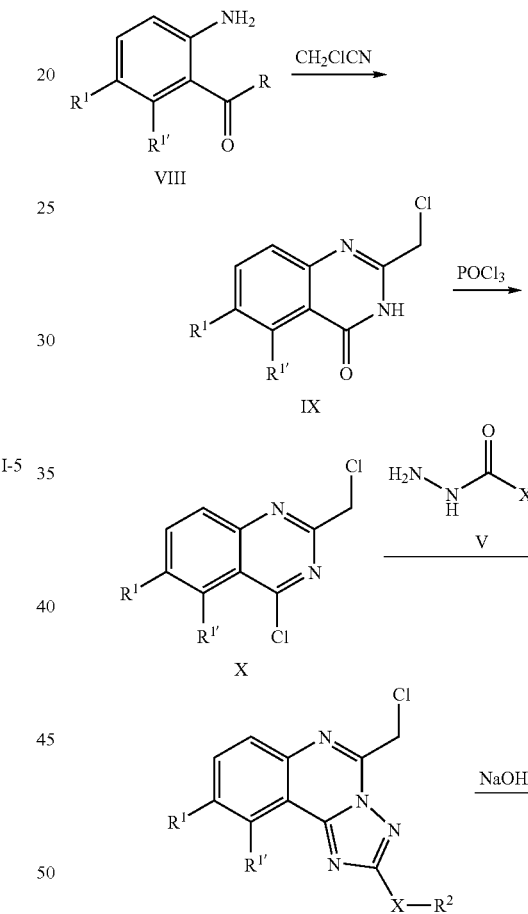

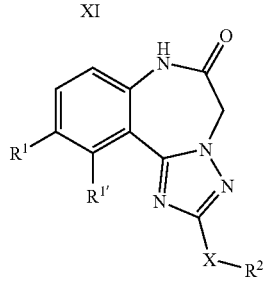

R = OH, alkoxy, amino wherein $R^1$, $R^{1'}$ and $R^2$ and X are as described above.

In accordance with scheme 1, a corresponding intermediate compound of formula XII is known (EP 519 307) and can be prepared by methods, known in the art, for example in the following way.

A corresponding compound of formula VIII, a $R^1$-substituted 2-aminobenzoic acid derivative, and chloroacetonitrile is dissolved in dioxane, and a weak stream of dry HCl is introduced at 5° C. to 15° C. for a period of several hours. After addition of further chloroacetonitrile, the mixture is stirred at ambient temperature for several hours. The obtained compound of formula IX is purified in conventional manner and dissolved in chloroform in the presence of N,N-dimethyl-p-toluidine. Phosphorous oxide chloride is added and the solution heated. The obtained compound of formula X is purified by known methods and heated with a compound of formula V, a acylhydrazide, in toluene for several hours affording a compound of formula XI. Finally, a compound of XII is obtained by dissolving a compound of formula XI in dioxane and treatment with aqueous sodium hydroxide in such manner that the reaction temperature is between 10° C. to 15° C. Conventional workup and purification affords a corresponding intermediate of formula XII.

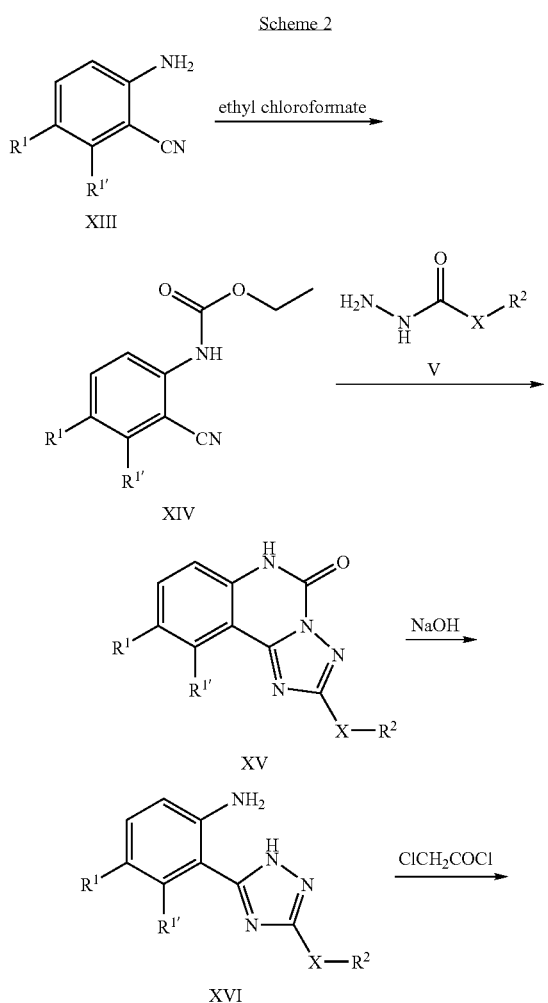

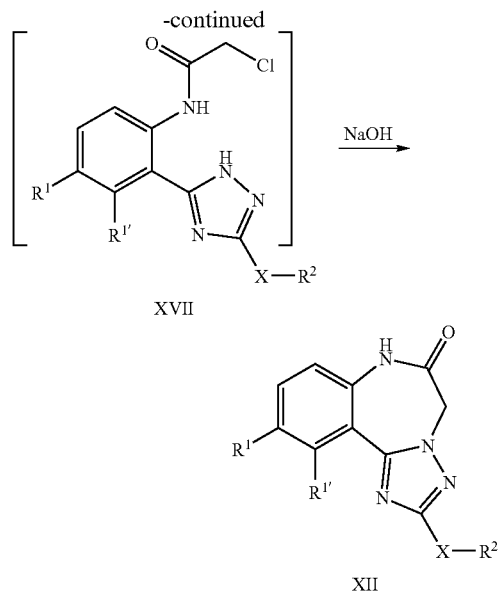

and $R^1$, $R^{1'}$ and $R^2$ and X are as described above.

In accordance with scheme 2, a corresponding intermediate compound of formula XII can be prepared alternatively in the following way:

A corresponding compound of formula XIII, a $R^1$-substituted 2-aminobenzonitrile, is heated with ethyl chloroformate to obtain a carbamic acid ester of formula XIV, which is treated with a compound of formula V, an acylhydrazide, in 1-methyl-2-pyrrolidone at 160° C. under removal of ethanol. Conventional workup provides a urea of formula XV which is heated with aqueous sodium hydroxide in ethylenglycol to obtain a compound of formula XVI. Treatment of a compound of formula XVI with chloroacetyl chloride in acetic acid provides an amide of formula XVII, which is treated with aqueous sodium hydroxide in dioxane at ambient temperature to obtain the intermediate of formula XII. Alternatively, a compound of formula XVI can be directly transformed to a compound of formula XII by dissolving a compound of formula XVII in dioxane and pyridine and adding dropwise chloroacetyl chloride at a temperature between 10° C. to 15° C. After stirring for a short period of time, aqueous sodium hydroxide is added, and the reaction mixture stirred for several hours at ambient temperature to obtain the compound of formula XII.

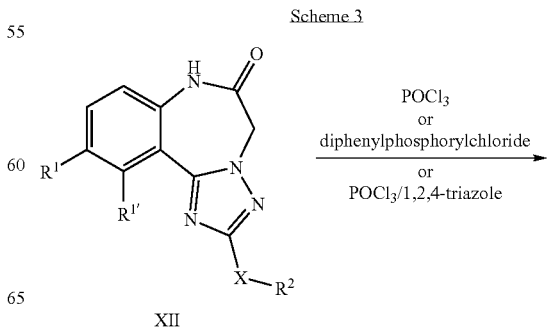

-continued

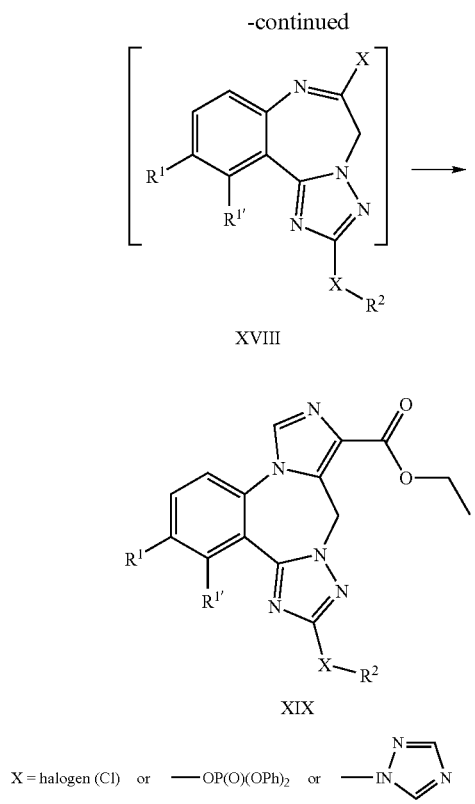

X = halogen (Cl) or —OP(O)(OPh)₂ or —N(triazole)

and R¹, R¹' and R² and X are as described above.

In accordance with scheme 3, a compound of formula XII is treated with an activation agent in the presence of base at elevated temperature, for example phosphorous oxide chloride in toluene or chloroform in the presence of N,N-dimethyl-p-toluidine, to obtain a compound of formula XVIII, which is isolated in conventional manner or directly used in the next reaction step. Finally, a compound of formula XIX is obtained by the reaction of XVIII with a mixture of a cooled solution of lithium diisopropylamide or lithium hexamethyldisilazide in THF and (E)-(dimethylamino-methylenamino)-acetic acid ethyl ester or with a mixture of a cooled solution of ethyl isocyanoacetate in THF and potassium tert-butoxide or sodium hydride.

Scheme 4

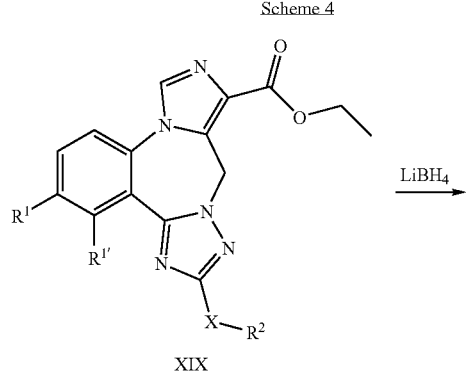

-continued

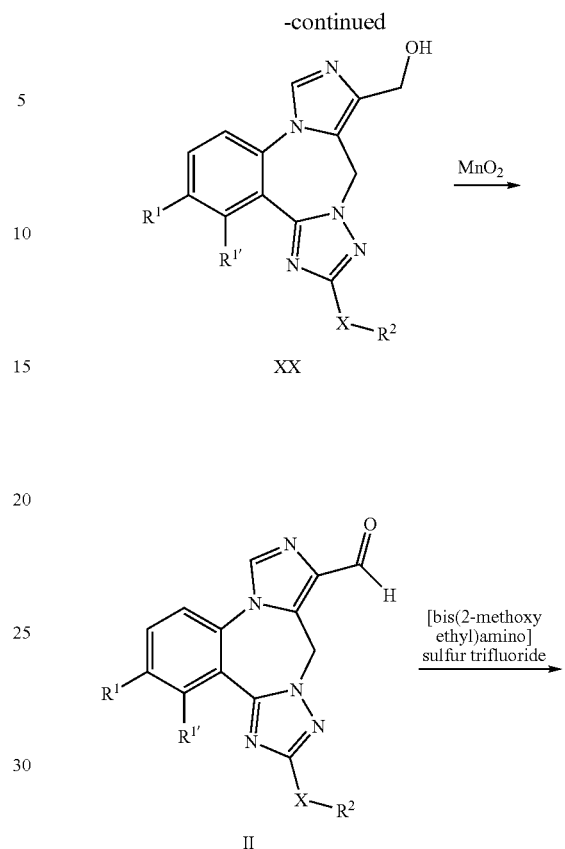

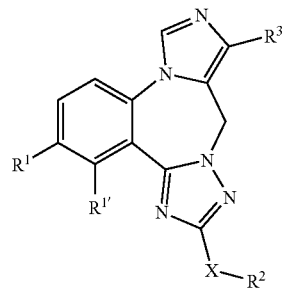

and R¹, R¹' and R² and X are as described above and R³ is C(O)O-lower alkyl.

According to scheme 4, a compound of formula XIX is heated with a reducing agent, for example lithiumborohydride or the like, in a suitable solvent, for example tetrahydrofuran or the like, to obtain an alcohol of formula XX, which is oxidized by treatment with manganese(IV) oxide in dichloromethane at ambient temperature to obtain an aldehyde of general formula II. This aldehyde (II) is treated with [bis(2-methoxyethyl)amino]sulfur trifluoride with or without dichloromethane as solvent at ambient or elevated temperature to obtain a compound of formula I-1.

Scheme 5

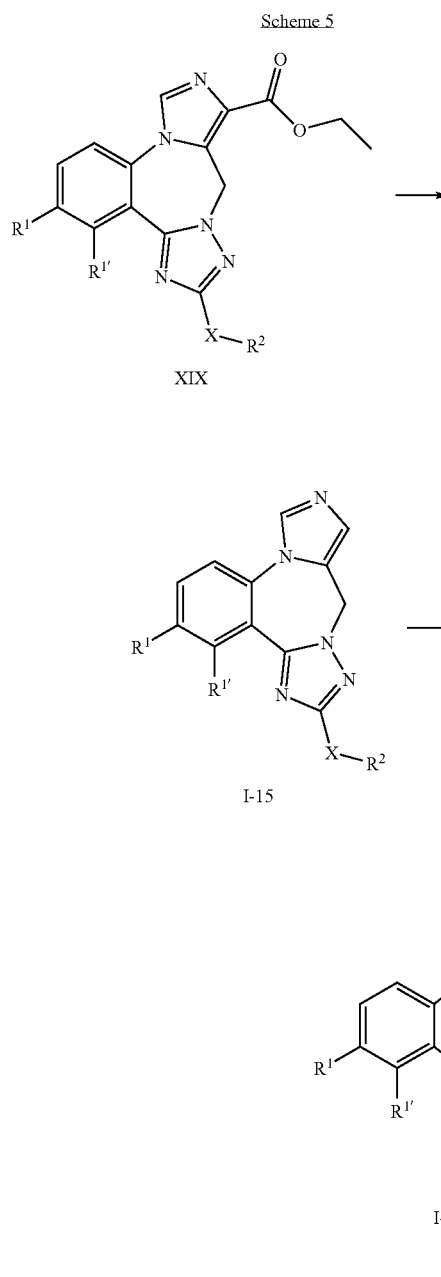

and R$^1$, R$^{1'}$ and R$^2$ and X are as described above.

According to scheme 5, a compound of formula XIX is hydrolyzed to the corresponding carboxylic acid, for example by treatment with sodium hydroxide in ethanol at elevated temperature, which is decarboxylated to a compound of formula I-15 by stirring in an appropriate solvent, for example diethylene glycol dibutyl diethylether, at elevated temperature, for example 200° C. or the like, for some time. Finally, a chloro-substituted compound of formula I-16 can be obtained by reaction with an appropriate chlorination reagent, for example N-chlorosuccinimide or the like, in an appropriate solvent, for example N,N-dimethylformamide or dichloromethane or the like, at ambient or elevated temperature.

Scheme 6

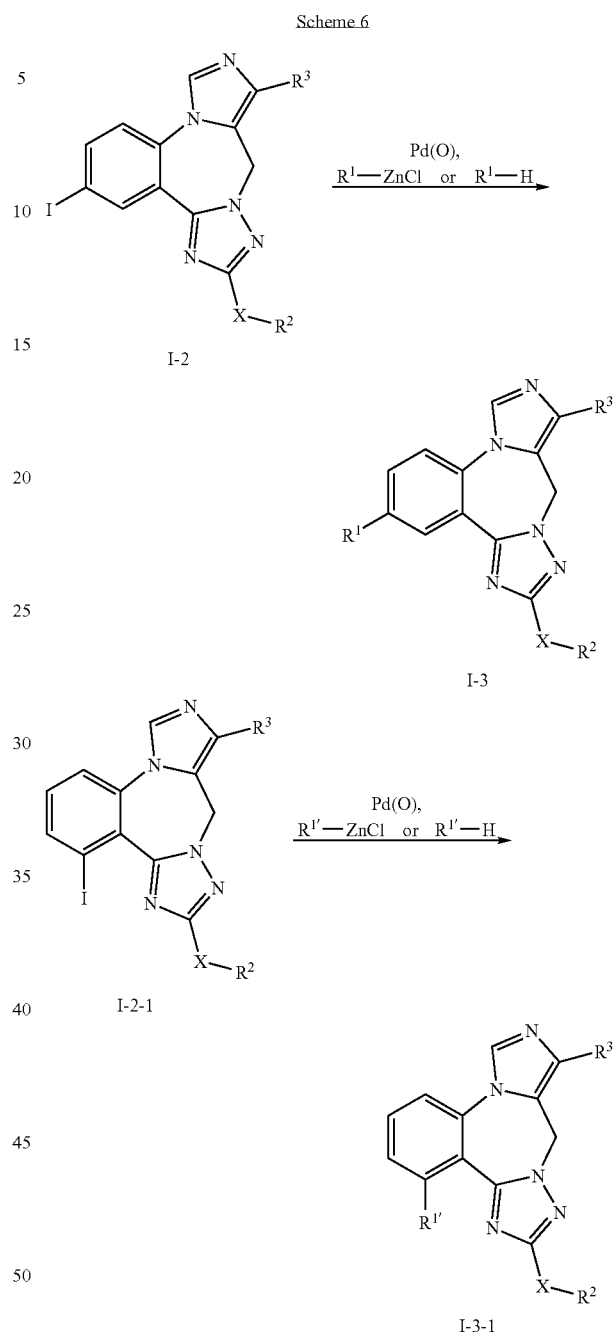

wherein R$^1$/R$^{1'}$ are lower alkyl, lower alkynyl) lower alkoxy, cycloalkyl, or lower alkyl or alkoxy, substituted by halogen and R$^2$ and R$^3$ and X are as described above.

According to scheme 6, a compound of formula I-3 (I-3-1) can be obtained from the corresponding iodo-substituted compound of formula I-2 (I-2-1) by treatment with an alkyl/cycloalkyl-zinc halogenide, for example cyclopropylzinc chloride, or a di-alkyl/cycloalkyl zinc reagent, for example diethylzinc, under palladium(0) catalysis in a suitable solvent, for example THF, at elevated temperature or by treatment with an appropriate alkyne, for example trimethylsilylacetylene, under palladium(0) and copper(I) catalysis in a suitable solvent, for THF, at elevated temperature.

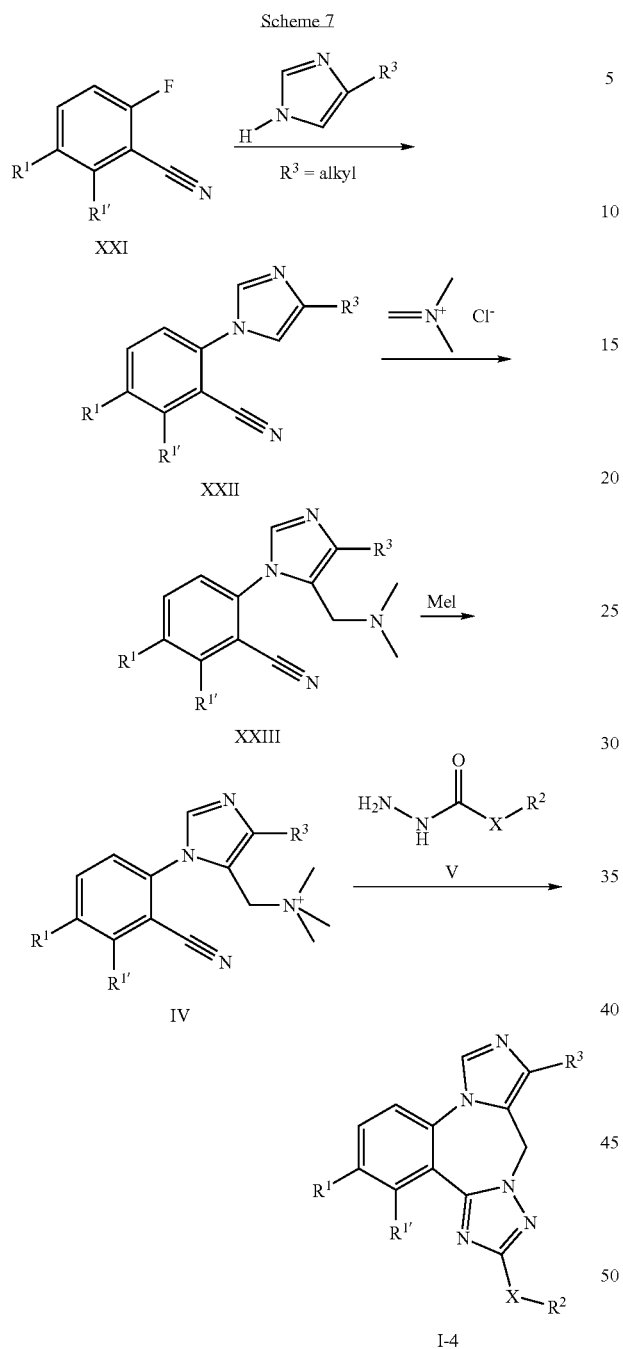

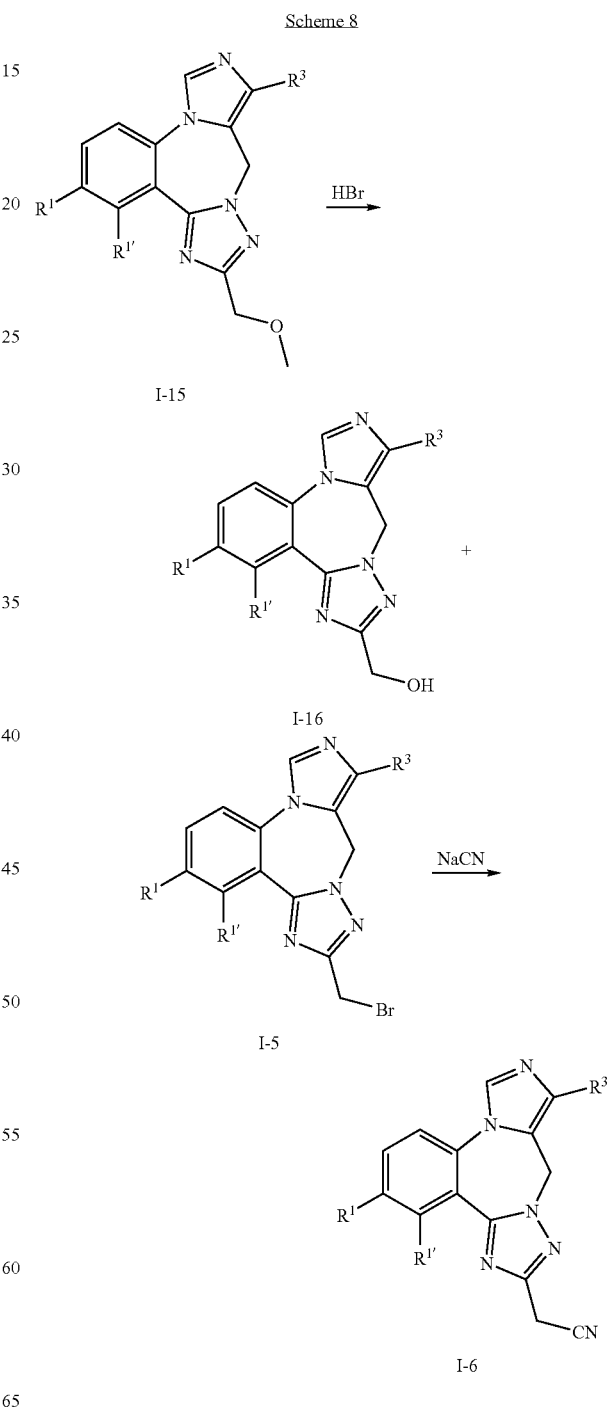

XXIII. Reacting a solution of a compound of formula XXIII in an appropriate solvent like methylene chloride with a methylating agent, such as methyl iodide, leads to a quaternary ammonium salt of formula IV, which may precipitate from the reaction mixture. Finally, treating a compound of formula IV with an optionally substituted hydrazide of formula V in an inert solvent, such as DMF, at elevated temperature leads to a compound of formula I-4, which can be isolated by crystallization from a suitable solvent, for example methanol.

wherein $R^1$, $R^{1'}$, $R^2$ are as described above, $R^3$ is lower alkyl and X is —$CH_2$— or —$CRR'$—.

In accordance with scheme 7, a compound of formula I-4 can also be prepared in the following way:

Treatment of an appropriately substituted 2-fluorobenzonitrile of formula XXI with 4-alkylimidazole leads to the corresponding intermediate XXII. Preferably, the reaction is run in an inert solvent, such as DMSO, at ambient temperature in the presence of a base, such as alkali carbonate. A compound of formula XXII can then be reacted with Eschenmoser's salt in an inert solvent, such as DMF, to afford a dimethylaminomethyl substituted imidazole of formula wherein $R^1$, $R^{1'}$ and $R^3$ are as described above.

According to scheme 8, a compound of formula I-15 can be heated in hydrobromic acid to obtain the demethylated compound of formula I-16 and the corresponding bromo-compound of formula I-5. A cyano-compound of formula I-6 can be obtained by treatment of I-5 with an appropriate cyanide reagent, for example sodium cyanide or potassium cyanide or the like, in a suitable solvent, for example DMSO or the like, at elevated temperature.

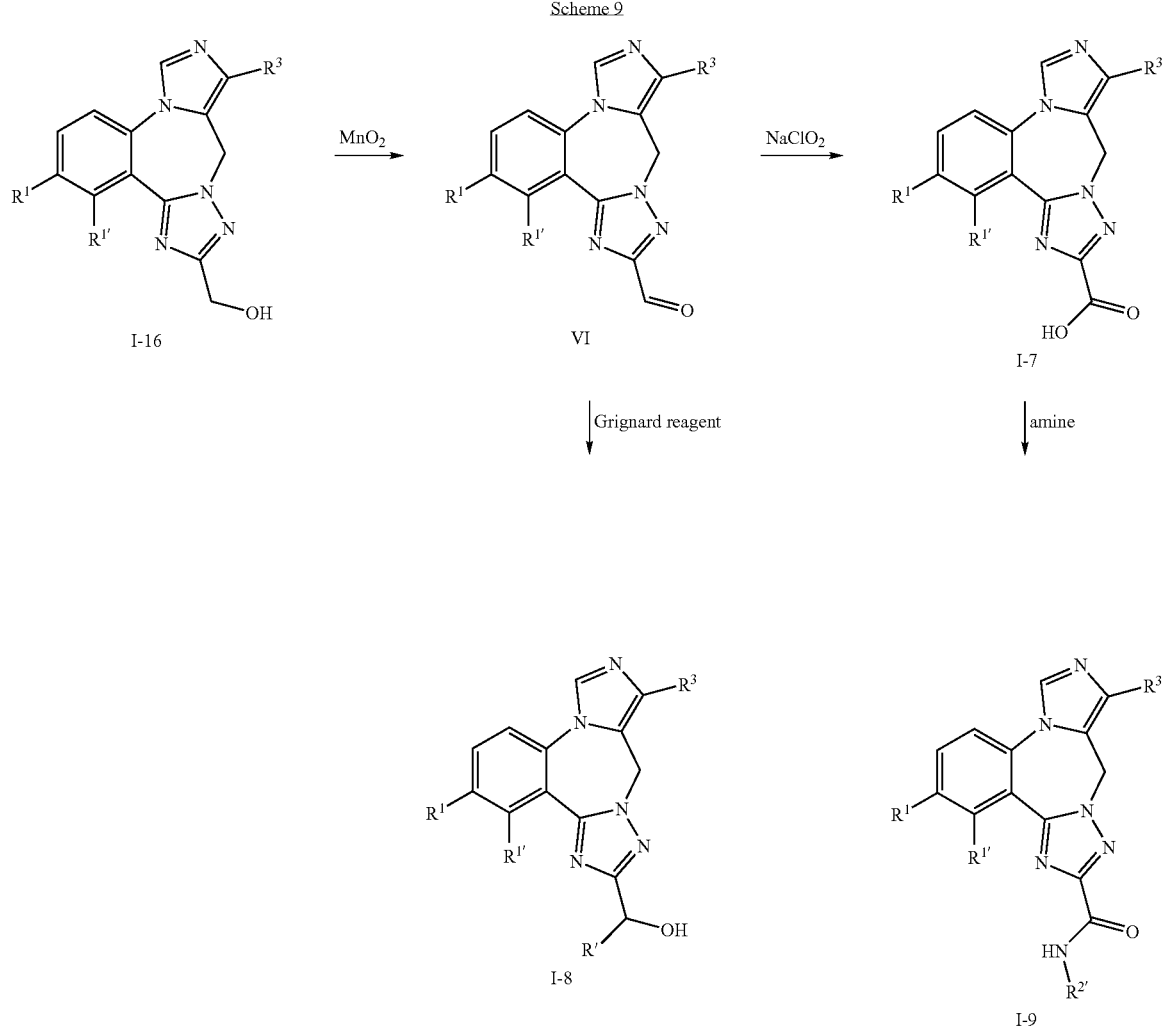

Scheme 9 wherein $R^1$, $R^{1'}$ and $R^3$ are as described above, R' is cycloalkyl, lower alkyl, lower alkyl substituted by halogen, phenyl or pyridinyl and $R^{2'}$ is —C(O)H, —C(O)-lower alkyl, —C(O)-cycloalkyl, —C(O)—O-lower alkyl, —C(O)—$CH_2$—O-lower alkyl, —$(CH_2)_n$-cycloalkyl, —$(CH_2)_n S(O)_2 CH_3$, —$(CH_2)_n$-aromatic or non aromatic heterocyclic ring, which contain from 1 to 3 heteroatoms selected from the group consisting of N, O and S or —$(CH_2)_n$OH;

According to scheme 9, the hydroxy-compound of formula I-16 can be oxidized to an aldehyde of formula VI by an appropriate oxidizing agent, for example manganese(IV) oxide or the like, in a suitable solvent, for example dichloromethane or the like, at ambient or elevated temperature. The aldehyde of formula VI can be treated with Grignard-reagents or other suitable carbon-nucleophile to obtain secondary alcohols of formula I-8 or further oxidized to the corresponding acids of formula I-7, for example by using sodium chlorite as the oxidizing agent, which can then be transformed, after appropriate activation of the acid, into the corresponding amides of formula I-9.

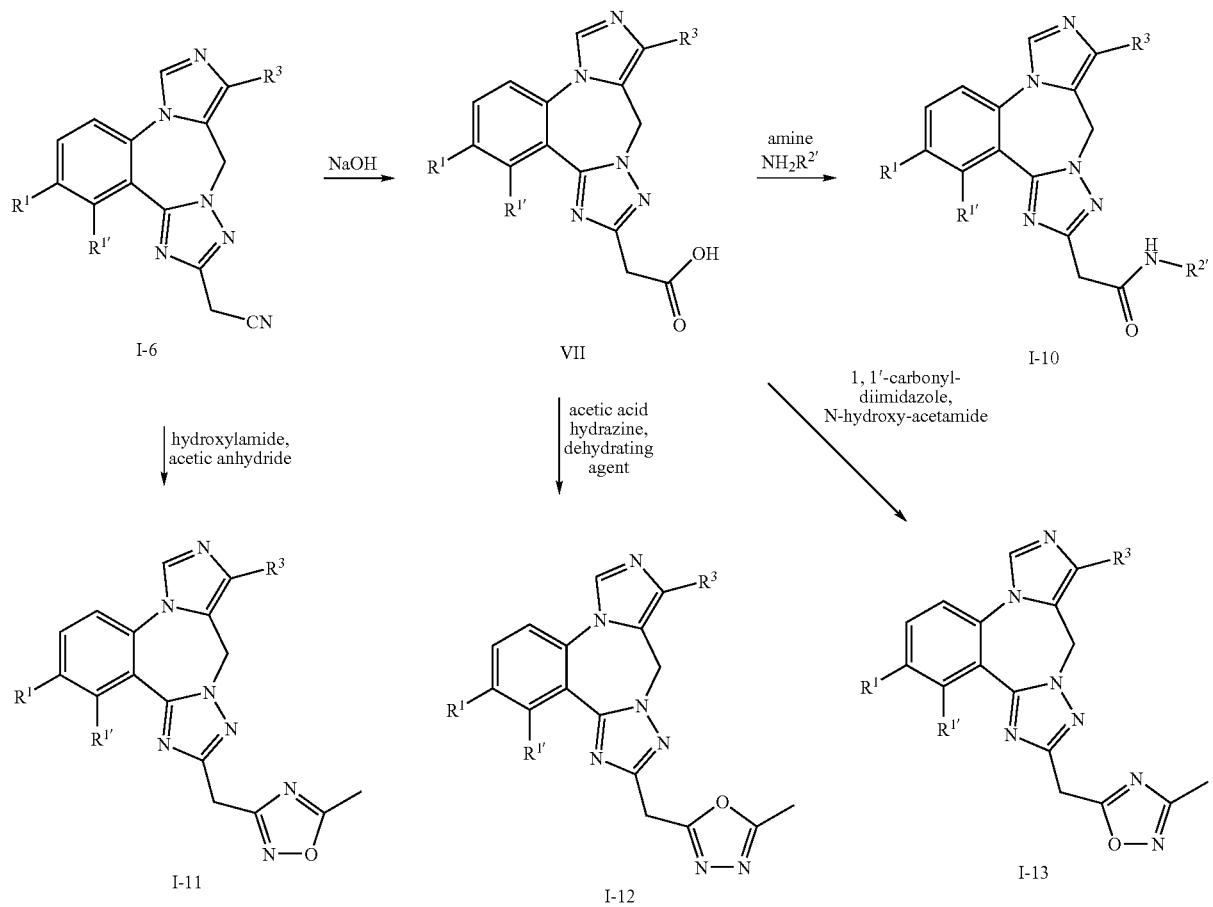

Scheme 10 wherein $R^1$, $R^{1'}$ and $R^3$ are as described above and $R^{2'}$ is —C(O)H, —C(O)-lower alkyl, —C(O)-cycloalkyl, —C(O)—O-lower alkyl, —C(O)—CH$_2$—O-lower alkyl, —(CH$_2$)$_n$-cycloalkyl, —(CH$_2$)$_n$S(O)$_2$CH$_3$, —(CH$_2$)$_n$-aromatic or non aromatic heterocyclic ring, which contain from 1 to 3 heteroatoms selected from the group consisting of N, O and S or —(CH$_2$)$_n$OH.

According to scheme 10, starting from the cyano-compound of formula I-6 the carboxymethyl-compound of formula VII can be obtained by hydrolysis with sodium hydroxide or the like in a suitable solvent, for example dioxane or the like, at elevated temperature, which can then be transformed, after appropriate activation of the acid, into the corresponding amides of formula I-10. The different [1,2,4]- and [1,3,4]-oxadiazoles, I-11, I-12 and I-13, can be obtained by transformation of I-6 with hydroxylamine followed by acetic anhydride in a suitable solvent at elevated temperature, leading to I-11, or by reacting the carboxylic acid VII with either acetic acid hydrazide and a dehydrating agent, for example phosphorous oxy chloride or 2-chloro-1,3-dimethyl-imidazolidiniumhexafluorophosphate or the like, in a suitable solvent, for example dichloromethane or the like, at ambient or elevated temperature (leading to I-12) or by treatment of carboxylic acid VII with an appropriate activation agent, for example 1,1'-carbonyl-diimidazole or oxalyl chloride or the like, followed by N-hydroxy-acetamidine in a suitable solvent at elevated temperature (leading to I-13).

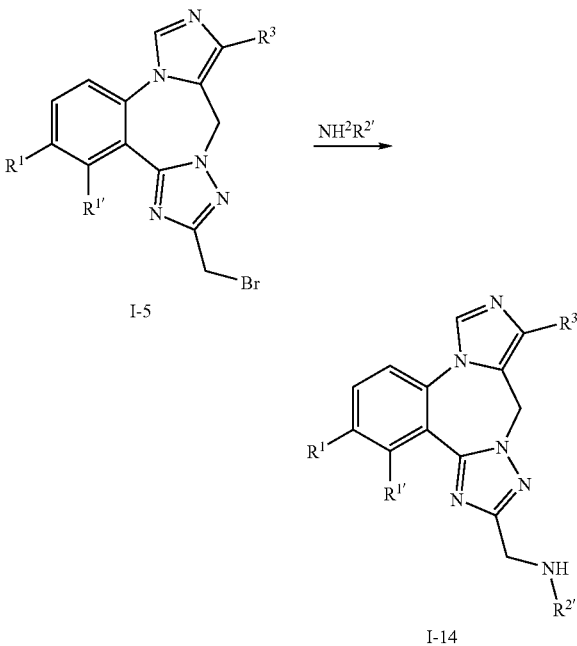

Scheme 11

According to scheme 11, amino-compounds of formula I-14 can be obtained by treatment of the bromo-compound I-5 with an appropriate amine or deprotonated amide in a suitable solvent or without any solvent at ambient or elevated temperature.

As mentioned earlier, the compounds of formula I and their pharmaceutically usable salts possess valuable pharmacological properties. Compounds of the present invention are ligands for GABA A receptors containing the α5 subunit and are therefore useful to enhance cognition.

The compounds were investigated in accordance with the test given hereinafter.

Membrane Preparation and Binding Assay

The affinity of compounds at GABA A receptor subtypes was measured by competition for [$^3$H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl$_2$, 1.2 mM MgCl$_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 μL (96-well plates) which contained 100 μL of cell membranes, [$^3$H]flumazenil at a concentration of 1 nM for α1, α2, α3 subunits and 0.5 nM for α5 subunits and the test compound in the range of $10^{-10}$-$3×10^{-6}$ M.

Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and all were found to possess a Ki value for displacement of [$^3$H]flumazenil from α5 subunits of the rat GABA A receptor of 1 uM or less. In a preferred embodiment the compounds of the invention are binding selective for the α5 subunit relative to the α1, α2 and α3 subunit. In the table below it is shown the activity data of some representative compounds:

| Example No. | Ki[nM] hα5 | Ki[nM] hα1 |
| --- | --- | --- |
| 4 | 0.3 | 8.5 |
| 10 | 0.4 | 63.3 |
| 11 | 0.5 | 48.3 |
| 12 | 0.8 | 51.8 |
| 13 | 0.9 | 30.7 |
| 21 | 1.0 | 133.3 |
| 22 | 0.4 | 53.0 |
| 26 | 1.0 | 111.2 |
| 38 | 0.4 | 6.9 |
| 49 | 0.9 | 113.9 |
| 50 | 1.0 | 85.7 |
| 54 | 0.9 | 34.6 |

| Example No. | Ki[nM] hα5 | Ki[nM] hα1 |
| --- | --- | --- |
| 58 | 0.7 | 69.4 |
| 61 | 0.6 | 91.7 |
| 62 | 0.7 | 88.4 |
| 63 | 0.8 | 64.7 |
| 64 | 0.5 | 68.8 |
| 65 | 1.0 | 149.5 |
| 72 | 0.7 | 98.2 |
| 83 | 1.0 | 113.2 |
| 122 | 0.5 | 150.5 |
| 123 | 0.6 | 188.1 |
| 124 | 1.0 | 219.3 |
| 162 | 1.0 | 151.6 |
| 168 | 1.0 | 63.4 |
| 183 | 0.6 | 279.4 |
| 185 | 0.9 | 247.9 |
| 191 | 1.0 | 265.9 |
| 236 | 0.8 | 496.4 |
| 261 | 0.7 | 26.6 |
| 265 | 0.62 | 39.3 |
| 267 | 0.25 | 20.45 |
| 275 | 0.6 | 33.6 |
| 300 | 0.7 | 62.1 |
| 301 | 0.7 | 50.5 |
| 309 | 0.5 | 55.2 |
| 310 | 0.7 | 69.7 |
| 312 | 0.5 | 60.0 |
| 314 | 0.7 | 32.3 |
| 316 | 0.9 | 116.0 |
| 330 | 0.7 | 134.1 |
| 349 | 0.9 | 469.2 |
| 364 | 1.0 | 133.8 |
| 378 | 0.6 | 42.1 |
| 380 | 1.0 | 56.6 |

The present invention also provides pharmaceutical compositions containing compounds of formula I or a pharmaceutically acceptable acid addition salt thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. The compounds of formula I and their pharmaceutically usable acid addition salts can be processed with pharmaceutically inert, inorganic or organic excipients for the production of tablets, coated tablets, dragées and hard gelatin capsules. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injection solutions.

This class of compounds shows high affinity and selectivity for GABA A α5 receptor binding sites and might be useful as cognitive enhancer or for the treatment of cognitive disorders. The most preferred indication of the present invention is Alzheimer's disease. Thus, the invention provides a method for treating Alzheimer's disease which comprises administering a therapeutically effective amount of a compound of formula I or a pharmaceutically acceptable acid addition salt thereof.

The dosage at which a compound of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples are provided for illustration of the invention. They should not be considered as limiting the scope of the invention, but merely as being representative thereof.

EXAMPLE 1

Ethyl 3-chloro-6-cyclopropyl-9H-imidazo[1,5-a][1,2,4]triazolo[1,5-d][1,4]benzodiazepine-10-carboxylate a) 9-Chloro-2-cyclopropyl-6H-[1,2,4]triazolo[1,5-c]quinazolin-5-one To a solution of (4-chloro-2-cyano-phenyl)-carbamic acid ethyl ester (5.00 g, 22.3 mmol) in N-methylpyrrolidone (25 mL) was added cyclopropylcarboxy acid hydrazide (2.23 g, 22.6 mmol). The reaction mixture was stirred at 160° C. for 6 h under a gentle nitrogen sweep. After cooling below 100° C. and addition of water (50 mL), the resulting slurry was stirred at ambient temperature for 30 min. The solid was collected by filtration and washed with water (30 mL) and 2-propanol (20 mL). Drying in vacuo (75° C.) afforded the title compound (5.22 g, 90%) as a light yellow solid. MS: m/e=259.1 [M−H]⁻.

b) 4-Chloro-2-(5-cyclopropyl-2H-[1,2,4]triazol-3-yl)-phenylamine

To a well stirred slurry of 9-chloro-2-cyclopropyl-6H-[1,2,4]triazolo[1,5-c]quinazolin-5-one (5.20 g, 19.9 mmol) in ethylene glycol (40 mL) which was heated to 100° C. was added aqueous sodium hydroxide (10 N, 4 mL, 39.9 mmol). The slurry was heated at reflux for 18 h. After cooling, water (25 mL) was added to the resulted suspension and the pH was adjusted to 6-7 by adding glacial acetic acid ($CO_2$-evolution). The slurry was stirred for 30 min. The solid was collected by filtration and washed with water (3×15 mL). Drying (HV) afforded the title compound (4.05 g, 86%) as a light brown solid. MS: m/e=235.0 [M+H]⁺.

c) 9-Chloro-2-cyclopropyl-6H-1,3,3a,6-tetraaza-benzo[e]azulen-5-one

A suspension of 4-chloro-2-(5-cyclopropyl-2H-[1,2,4]triazol-3-yl)-phenylamine (3.95 g, 16.8 mmol) in dioxane (120 mL) and pyridine (1.5 mL) was cooled to 10° C. A solution of chloroacetyl chloride (1.54 mL, 19.3 mmol) in diethylether (5 mL) was then added dropwise over 15 min. The reaction mixture was stirred at this temperature for 30 min and was then treated within 10 min with aqueous sodium hydroxide (2 N, 20.2 mL, 40.4 mmol). The mixture was stirred for 22 h at ambient temperature. After the addition of aqueous HCl (1 N, 2.5 mL) the resulting mixture was evaporated. The residue was stirred for 45 min in water (100 mL) and ethyl acetate (5 mL). The resulting crystals were filtered off and washed with water. Drying in vacuo and trituration with ethyl acetate afforded the title compound (3.02 g, 65%) which was obtained as an off-white solid. MS: m/e=275.0 $[M+H]^+$.

d) Ethyl 3-chloro-6-cyclopropyl-9H-imidazo[1,5-a][1,2,4]triazolo[1,5-d][1,4]benzodiazepine-10-carboxylate To a suspension of 9-chloro-2-cyclopropyl-6H-1,3,3a,6-tetraaza-benzo[e]azulen-5-one (2.92 g, 10.6 mmol) in chloroform (70 mL; filtered over basic alox) was added 4-N,N-trimethylaniline (3.82 mL, 26.6 mmol) and phosphorous oxychloride (1.46 mL, 15.9 mmol). The reaction mixture was stirred for 26 h at reflux, cooled to ambient temperature and poured into aqueous sodium hydrogencarbonate (1 N, 200 mL). After 1 h well stirring, the organic layer was separated and the aqueous layer was washed with chloroform (40 mL). The combined organic layers were dried over sodium sulfate and concentrated. To a solution of ethyl isocyanoacetate (1.17 mL, 10.6 mmol) in THF (30 mL) was added potassium tert-butylate (1.19 g, 10.6 mmol) at −50° C. The resulting suspension was allowed to stir for 1 h by warming up to −5° C. It was then cooled to −65° C. and the prepared solution from above was added dropwise over 10 min. The cooling bath was removed and the reaction mixture stirred for 18 h warming up to ambient temperature. After addition of acetic acid (0.45 mL) the mixture was stirred for 15 min, poured into aqueous sodium hydrogencarbonate (5%, 200 mL) and ethyl acetate (10 mL) and stirred for another 30 min. The layers were separated and the aqueous layer extracted with ethyl acetate (100 mL). Evaporation and trituration in aqueous sodium hydrogencarbonate (saturated) and heptane afforded the title compound (3.15 g, 80%) which was obtained as a light brown solid. MS: m/e=370.1 $[M+H]^+$.

EXAMPLE 2

3-Chloro-6-cyclopropyl-9H-imidazo[1,5-a][1,2,4]triazolo[1,5-d][1,4]benzodiazepine a) 3-Chloro-6-cyclopropyl-9H-imidazo[1,5-a][1,2,4]triazolo[1,5-d][1,4]benzodiazepine-10-carboxylic acid To a suspension of ethyl 3-chloro-6-cyclopropyl-9H-imidazo[1,5-a][1,2,4]triazolo[1,5-d][1,4]benzodiazepine-10-carboxylate (2.00 g, 5.41 mmol) in ethanol (30 mL) was added aqueous sodium hydroxide (1 N, 25 mL) and the resulting mixture was heated to 80° C. for 45 min. After cooling, the mixture was evaporated and the residue suspended in water (50 mL) and then acidified with aqueous HCl (1 N, ~26 mL) to pH=1-2 and stirred at 0° C. for 30 min.

Filtration, washing with water (10 mL) and drying afforded the title compound (1.80 g, 98%) as a light brown solid. MS: m/e=342.0 $[M+H]^+$.

b) 3-Chloro-6-cyclopropyl-9H-imidazo[1,5-a][1,2,4]triazolo[1,5-d][1,4]benzodiazepine 3-Chloro-6-cyclopropyl-9H-imidazo[1,5-a][1,2,4]triazolo[1,5-d][1,4]benzodiazepine-10-carboxylic acid (1.00 g, 2.93 mmol) was dissolved in diethylene glycol dibutylether (10 mL) and stirred for 62 h at 200° C. under argon. After cooling, heptane (50 mL) was added and the resulting suspension was stirred at 0° C. for 30 min. Filtration, washing with heptane (10 mL), drying over sodium sulfate and purification by chromatography ($SiO_2$, heptane:ethyl acetate=50:50 to 0:100) afforded the title compound (526 mg, 60%) which was obtained as a light brown solid. MS: m/e=298.1 $[M+H]^+$.

EXAMPLE 3

3,10-Dichloro-6-cyclopropyl-9H-imidazo[1,5-a][1,2,4]triazolo[1,5-d][1,4]benzodiazepine To a suspension of 3-chloro-6-cyclopropyl-9H-imidazo[1,5-a][1,2,4]triazolo[1,5-d][1,4]benzodiazepine (223 mg, 0.75 mmol) in DMF (5 mL) was added 1,3-dichloro-5,5-dimethylhydantoin (81 mg, 0.41 mmol) and the reaction mixture was stirred at ambient temperature for 18 h. Ethyl acetate (50 mL) was added and the mixture washed with aqueous sodium hydrogencarbonate (40 mL) and water (20 mL). After drying over sodium sulfate and purification of the residue by chromatography ($SiO_2$, heptane:ethyl acetate=100:0 to 0:100) afforded the title compound (210 mg, 84%) which was obtained as an off-white solid. MS: m/e=332.1 $[M+H]^+$.

EXAMPLE 4

Ethyl 3-chloro-6-methoxymethyl-9H-imidazo[1,5-a][1,2,4]triazolo[1,5-d][1,4]benzodiazepine-10-carboxylate a) 9-Chloro-2-methoxymethyl-6H-[1,2,4]triazolo[1,5-c]quinazolin-5-one As described for example 1a) (4-chloro-2-cyano-phenyl)-carbamic acid ethyl ester (71.0 g, 316 mmol) using methoxymethyl-carboxylic acid hydrazide instead of cyclopropane-carboxylic acid hydrazide, was converted to the title compound (73.9 g, 88%) which was obtained as a yellow solid. MS: m/e=264.9 $[M+H]^+$.

b) 4-Chloro-2-(5-methoxymethyl-2H-[1,2,4]triazol-3-yl)-phenylamine

As described for example 1b) 9-chloro-2-methoxymethyl-6H-[1,2,4]triazolo[1,5-c]quinazolin-5-one (73.4 g, 277 mmol), instead of 9-chloro-2-cyclopropyl-6H-[1,2,4]triazolo[1,5-c]quinazolin-5-one, was converted to the title compound (61.0 g, 92%) which was obtained as a brown solid. MS: m/e=238.9 $[M+H]^+$.

c) 2-Chloro-N-[4-chloro-2-(5-methoxymethyl-2H-[1,2,4]triazol-3-yl)-phenyl]-acetamide 4-Chloro-2-(5-methoxymethyl-2H-[1,2,4]triazol-3-yl)-phenylamine (60.6 g, 239 mmol) was dissolved in acetic acid (1.2 L) and chloroacetic chloride (40.4 mL, 508 mmol) was added dropwise at 14-16° C. over a period of 30 min. The resulting reaction mixture was stirred for 22 h at ambient temperature. After addition of water (600 mL) and stirring for another 90 min, the solid was filtered off and washed with water (600 mL). Drying in vacuo afforded the title compound (66.2 g, 83%) which was obtained as a yellow solid. MS: m/e=314.9 $[M+H]^+$.

d) 9-Chloro-2-methoxymethyl-6H-1,3,3a,6-tetraaza-benzo[e]azulen-5-one

2-Chloro-N-[4-chloro-2-(5-methoxymethyl-2H-[1,2,4]triazol-3-yl)-phenyl]-acetamide (65.8 g, 209 mmol) was dissolved in dioxane (1.80 L) and vigorously stirred. Aqueous sodium hydroxide (32%, 46.4 mL, 501 mmol) was added dropwise under a nitrogen atmosphere and the resulting mixture was stirred for 3 h at ambient temperature. After addition of aqueous ammonium chloride (1 M, 1.00 L) the mixture was then extracted with dichloromethane, dried over sodium sulfate and concentrated. Trituration of the residue in cyclohexane (200 mL) afforded the title compound (45.7 g, 79%) which was obtained as a light yellow solid. MS: m/e=279.1 [M+H]$^+$.

e) 9-Chloro-2-methoxymethyl-5-[1,2,4]triazol-1-yl-4H-1,3,3a,6-tetraaza-benzoazulene 1,2,4-Triazole (74.3 g, 1.08 mol) was dissolved in acetonitrile (850 mL) and N,N-diisopropylethylamine (195 mL, 1.14 mol) was added. After cooling to 0° C. phosphorous oxychloride (29.8 mL, 326 mmol) was added dropwise and the reaction mixture was stirred at 0-5° C. for 2 h. 9-Chloro-2-methoxymethyl-6H-1,3,3a,6-tetraaza-benzo[e]azulen-5-one (45.4 g, 279 mmol) was added at once and the resulting suspension was heated to reflux for 20 h. After cooling to ambient temperature, water (1.30 L) was added and stirring was continued for another 30 min. The solid was filtered off and washed with water (300 mL) and diethylether (200 mL). Drying in vacuo (65° C.) afforded the title compound (33.8 g, 63%) which was obtained as an off-white solid. MS: m/e=330.1 [M+H]$^+$.

f) Ethyl 3-chloro-6-methoxymethyl-9H-imidazo[1,5-a][1,2,4]triazolo[1,5-d][1,4]benzodiazepine-10-carboxylate Potassium tert-butylate (15.9 g, 142 mmol) was dissolved in DMF (460 mL) and cooled to −50° C. Over a period of 5 min ethyl isocyanoacetate (16.7 mL, 152 mmol) was added dropwise and the resulting mixture was stirred for 1 h at this temperature. 9-Chloro-2-methoxymethyl-5-[1,2,4]triazol-1-yl-4H-1,3,3a,6-tetraaza-benzoazulene (33.4 g, 101 mmol) was added and the mixture was allowed to warm to 10° C. After stirring for another 30 min at 10° C. acetic acid (34.8 mL, 608 mmol) and water (1.40 L) were added. The solid was filtered off and then washed with water (300 mL) and diethylether (100 mL). Drying in vacuo afforded the title compound (29.7 g, 78%) which was obtained as an off-white solid. MS: m/e=374.0 [M+H]$^+$.

EXAMPLE 5

3-Chloro-6-methoxymethyl-9H-imidazo[1,5-a][1,2,4]triazolo[1,5-d][1,4]benzodiazepine a) 3-Chloro-6-methoxymethyl-9H-imidazo[1,5-a][1,2,4]triazolo[1,5-d][1,4]benzodiazepine-10-carboxylic acid As described for example 2a) ethyl 3-chloro-6-methoxymethyl-9H-imidazo[1,5-a][1,2,4]triazolo[1,5-d][1,4]benzodiazepine-10-carboxylate (1.00 g, 2.68 mmol), instead of ethyl 3-chloro-6-cyclopropyl-9H-imidazo[1,5-a][1,2,4]triazolo[1,5-d][1,4]benzodiazepine-10-carboxylate, was converted to the title compound (893 mg, 97%) which was obtained as a white solid. MS: m/e=346.0 [M+H]$^+$.

b) 3-Chloro-6-methoxymethyl-9H-imidazo[1,5-a][1,2,4]triazolo[1,5-d][1,4]benzodiazepine As described for example 2b) 3-chloro-6-methoxymethyl-9H-imidazo[1,5-a][1,2,4]triazolo[1,5-d][1,4]benzodiazepine-10-carboxylic acid (801 mg, 2.32 mmol), instead of 3-chloro-6-cyclopropyl-9H-imidazo[1,5-a][1,2,4]triazolo[1,5-d][1,4]benzodiazepine-10-carboxylic acid, was converted to the title compound (522 mg, 75%) which was obtained as an off-white solid. MS: m/e=302.1 [M+H]$^+$.

EXAMPLE 6

3,10-Dichloro-6-methoxymethyl-9H-imidazo[1,5-a][1,2,4]triazolo[1,5-d][1,4]benzodiazepine As described for example 3, 3-chloro-6-methoxymethyl-9H-imidazo[1,5-a][1,2,4]triazolo[1,5-d][1,4]benzodiazepine (530 mg, 1.76 mmol), instead of 3-chloro-6-cyclopropyl-9H-imidazo[1,5-a][1,2,4]triazolo[1,5-d][1,4]benzodiazepine, was converted to the title compound (287 mg, 49%) which was obtained as an off-white solid. MS: m/e=336.1 [M+H]$^+$.

EXAMPLE 7

6-Bromomethyl-3,10-dichloro-9H-imidazo[1,5-a][1,2,4]triazolo[1,5-d][1,4]benzodiazepine A suspension of 3,10-dichloro-6-methoxymethyl-9H-imidazo[1,5-a][1,2,4]triazolo[1,5-d][1,4]benzodiazepine (7.07 g, 21.0 mmol) in hydrobromic acid (48%, 24 mL, 210 mmol) was stirred for 20 h at 110° C. After the solution was cooled to 0° C. aqueous sodium carbonate (saturated, 140 mL) was added dropwise at this temperature until the pH was slightly basic. The suspension was filtered off and washed with ice cold water (100 mL). The residue was suspended in dichloroethane (50 mL) and phosphorus tribromide (1.5 mL, 16.2 mmol) was added and the reaction mixture was stirred for 2 h at 80° C. After it was cooled to 0° C., water (50 mL) and aqueous sodium carbonate (saturated, 50 mL) were added and stirring was continued for 15 min. The organic layer was washed with water. The aqueous layers were extracted with dichloromethane (50 mL). The concentrated organic layers were suspended in water (50 mL), filtered off and washed with water (20 mL). Drying in vacuo afforded the title compound (5.25 g, 65%) which was obtained as an off-white solid. MS: m/e=385.8/387.8 [M+H]$^+$.

EXAMPLE 8

3,10-Dichloro-6-(2-oxo-pyrrolidin-1-ylmethyl)-9H-imidazo[1,5-a][1,2,4]triazolo[1,5-d][1,4]benzodiazepine To a solution of 2-pyrrolidone (55 mg, 0.57 mmol) in DMF (2 mL) was added at 0° C. under an argon atmosphere potassium bis(trimethylsilyl)amide (0.91 M in THF, 0.63 mL, 0.57 mmol) and the reaction mixture was stirred for 30 min at 0° C. 6-Bromomethyl-3,10-dichloro-9H-imidazo[1,5-a][1,2,4]triazolo[1,5-d][1,4]benzodiazepine (200 mg, 0.52 mmol) was added and stirring was continued for 2 h at 0° C. The resulting suspension was treated with aqueous ammonium chloride (half-saturated, 10 mL) and extracted with dichloromethane. The organic layers were washed with brine and dried over sodium sulfate. Purification by chromatography (SiO$_2$, heptane:ethyl acetate:dichloromethane:methanol=40:50:10:0 to 0:85:10:5) afforded the title compound (56 mg, 28%) as a white solid. MS m/e: 389.0 [M+H]$^+$.

EXAMPLE 9

3,10-Dichloro-6-(3,5-dimethyl-pyrazol-1-ylmethyl)-9H-imidazo[1,5-a][1,2,4]triazolo[1,5-d][1,4]benzodiazepine As described for example 8, 6-bromomethyl-3,10-dichloro-9H-imidazo[1,5-a][1,2,4]triazolo[1,5-d][1,4]benzodiazepine (200 mg, 0.52 mmol), using 3,5-dimethylpyrazole instead of 2-pyrrolidone, was converted to the title compound (61 mg, 29%) which was obtained as a white solid. MS: m/e=399.9 [M+H]+.

EXAMPLE 10

3,10-Dichloro-6-[1,2,3]triazol-2-ylmethyl-9H-imidazo[1,5-a][1,2,4]triazolo[1,5-d][1,4]benzodiazepine To a solution of 6-bromomethyl-3,10-dichloro-9H-imidazo[1,5-a][1,2,4]triazolo[1,5-d][1,4]benzodiazepine (200 mg, 0.52 mmol) in DMSO (2 mL) was added at ambient temperature 1H-1,2,3-triazole (54 mg, 0.78 mmol) and potassium carbonate (86 mg, 0.62 mmol) and the reaction mixture was stirred for 2 h at this temperature. The resulting mixture was then treated with aqueous ammonium chloride (saturated, 0.5 mL), water (4 mL) and ice (2 g). After stirring for 15 min the suspension was filtered off and washed with water (3 mL). Purification by chromatography (SiO$_2$, heptane:ethyl acetate:dichloromethane:methanol=40:50:10:0 to 0:85:10:5) afforded the title compound (50 mg, 26%) as a white solid. MS m/e: 372.9 [M+H]+.

EXAMPLE 11

3,10-Dichloro-6-[1,2,3]triazol-1-ylmethyl-9H-imidazo[1,5-a][1,2,4]triazolo[1,5-d][1,4]benzodiazepine To a solution of 6-bromomethyl-3,10-dichloro-9H-imidazo[1,5-a][1,2,4]triazolo[1,5-d][1,4]benzodiazepine (200 mg, 0.52 mmol) in DMSO (2 mL) was added at ambient temperature 1H-1,2,3-triazole (54 mg, 0.78 mmol) and potassium carbonate (86 mg, 0.62 mmol) and the reaction mixture was stirred for 2 h at this temperature. It was treated with aqueous ammonium chloride (saturated, 0.5 mL), water (4 mL) and ice (2 g). After stirring for 15 min the suspension was filtered off and washed with water (3 mL). Purification by chromatography (SiO$_2$, heptane:ethyl acetate:dichloromethane:methanol=40:50:10:0 to 0:85:10:5) afforded the title compound (102 mg, 53%) as a white solid. MS m/e: 372.9 [M+H]+.

EXAMPLE 12

3,10-Dichloro-6-[1,2,4]triazol-1-ylmethyl-9H-imidazo[1,5-a][1,2,4]triazolo[1,5-d][1,4]benzodiazepine As described for example 10, 6-bromomethyl-3,10-dichloro-9H-imidazo[1,5-a][1,2,4]triazolo[1,5-d][1,4]benzodiazepine (200 mg, 0.52 mmol), using 1,2,4-triazole instead of 1H-1,2,3-triazole, was converted to the title compound (152 mg, 78%) which was obtained as a white solid. MS: m/e=372.9 [M+H]+.

EXAMPLE 13

3,10-Dichloro-6-pyrazol-1-ylmethyl-9H-imidazo[1,5-a][1,2,4]triazolo[1,5-d][1,4]benzodiazepine As described for example 10, 6-bromomethyl-3,10-dichloro-9H-imidazo[1,5-a][1,2,4]triazolo[1,5-d][1,4]benzodiazepine (200 mg, 0.52 mmol), using pyrazole instead of 1H-1,2,3 triazole, was converted to the title compound (SiO$_2$, heptane:ethyl acetate:dichloromethane:methanol=50:30:20:0 to 0:75:20:5, 42 mg, 22%) which was obtained as a white solid. MS: m/e=372.0 [M+H]+.

EXAMPLE 14

3,10-Dichloro-6-(2-methyl-5-oxo-pyrrolidin-1-ylmethyl)-9H-imidazo[1,5-a][1,2,4]triazolo[1,5-d][1,4]benzodiazepine As described for example 8, 6-bromomethyl-3,10-dichloro-9H-imidazo[1,5-a][1,2,4]triazolo[1,5-d][1,4]benzodiazepine (200 mg, 0.52 mmol), using 5-methyl-2-pyrrolidone instead of 2-pyrrolidone, was converted to the title compound (SiO$_2$, heptane:ethyl acetate:dichloromethane:methanol=50:30:20:0 to 0:75:20:5, 93 mg, 44%) which was obtained as a white solid. MS: m/e=403.1 [M+H]+.

EXAMPLE 15

3,10-Dichloro-6-(3-methyl-2-oxo-pyrrolidin-1-ylmethyl)-9H-imidazo[1,5-a][1,2,4]triazolo[1,5-d][1,4]benzodiazepine As described for example 8, 6-bromomethyl-3,10-dichloro-9H-imidazo[1,5-a][1,2,4]triazolo[1,5-d][1,4]benzodiazepine (200 mg, 0.52 mmol), using 3-methyl-2-pyrrolidone instead of 2-pyrrolidone, was converted to the title compound (SiO$_2$, heptane:ethyl acetate:dichloromethane:methanol=50:30:20:0 to 0:75:20:5, 88 mg, 42%) which was obtained as a white solid. MS: m/e=403.1 [M+H]+.

EXAMPLE 16

3,10-Dichloro-6-(3-oxo-morpholin-4-ylmethyl)-9H-imidazo[1,5-a][1,2,4]triazolo[1,5-d][1,4]benzodiazepine As described for example 8, 6-bromomethyl-3,10-dichloro-9H-imidazo[1,5-a][1,2,4]triazolo[1,5-d][1,4]benzodiazepine (200 mg, 0.52 mmol), using morpholin-3-one instead of 2-pyrrolidone, was converted to the title compound (SiO$_2$, heptane:ethyl acetate:dichloromethane:methanol=50:30:20:0 to 0:75:20:5, 84 mg, 40%) which was obtained as a white solid. MS: m/e=405.1 [M+H]+.

EXAMPLE 17

3,10-Dichloro-6-(3-trifluoromethyl-pyrazol-1-ylmethyl)-9H-imidazo[1,5-a][1,2,4]triazolo[1,5-d][1,4]benzodiazepine As described for example 10, 6-bromomethyl-3,10-dichloro-9H-imidazo[1,5-a][1,2,4]triazolo[1,5-d][1,4]benzodiazepine (200 mg, 0.52 mmol), using 3-(trifluoromethyl)pyrazole instead of 1H-1,2,3-triazole, was converted to the title compound (SiO$_2$, heptane:ethyl acetate:dichloromethane:methanol=50:30:20:0 to 0:75:20:5, 160 mg, 70%) which was obtained as a white solid. MS: m/e=440.1/442.0 [M+H]+.

EXAMPLE 18

3,10-Dichloro-6-(4-ethyl-2,3-dioxo-piperazin-1-ylmethyl)-9H-imidazo[1,5-a][1,2,4]triazolo[1,5-d][1,4]benzodiazepine As described for example 8, 6-bromomethyl-3,10-dichloro-9H-imidazo[1,5-a][1,2,4]triazolo[1,5-d][1,4]benzodiazepine (200 mg, 0.52 mmol), using N-ethyl-2,3-diketopiperazine instead of 2-pyrrolidone, was converted to the title compound (SiO$_2$, heptane:ethyl acetate:dichloromethane:methanol=50:30:20:0 to 0:0:90:10, 77 mg, 33%) which was obtained as a white solid. MS: m/e=446.0 [M+H]$^+$.

EXAMPLE 19

3,10-Dichloro-6-(4,4-dimethyl-2,5-dioxo-imidazolidin-1-ylmethyl)-9H-imidazo[1,5-a][1,2,4]triazolo[1,5-d][1,4]benzodiazepine As described for example 8, 6-bromomethyl-3,10-dichloro-9H-imidazo[1,5-a][1,2,4]triazolo[1,5-d][1,4]benzodiazepine (200 mg, 0.52 mmol), using 5,5-dimethylhydantoin instead of 2-pyrrolidone, was converted to the title compound (SiO$_2$, heptane:ethyl acetate:dichloromethane:methanol=50:30:20:0 to 0:75:20:5, 76 mg, 34%) which was obtained as a white solid. MS: m/e=432.1 [M+H]$^+$.

EXAMPLE 20

3,10-Dichloro-6-(5-methyl-pyrazol-1-ylmethyl)-9H-imidazo[1,5-a][1,2,4]triazolo[1,5-d][1,4]benzodiazepine As described for example 10, 6-bromomethyl-3,10-dichloro-9H-imidazo[1,5-a][1,2,4]triazolo[1,5-d][1,4]benzodiazepine (200 mg, 0.52 mmol), using 3-methyl-pyrazole instead of 1H-1,2,3-triazole and 4 h at 80° C. instead of ambient temperature, was converted to the title compound (SiO$_2$, heptane:ethyl acetate:dichloromethane:methanol=50:30:20:0 to 0:75:20:5, 44 mg, 22%) which was obtained as a white solid. MS: m/e=386.1 [M+H]$^+$.

EXAMPLE 21

6-Benzotriazol-2-ylmethyl-3,10-dichloro-9H-imidazo[1,5-a][1,2,4]triazolo[1,5-d][1,4]benzodiazepine As described for example 10, 6-bromomethyl-3,10-dichloro-9H-imidazo[1,5-a][1,2,4]triazolo[1,5-d][1,4]benzodiazepine (200 mg, 0.52 mmol), using benzotriazole instead of 1H-1,2,3-triazole, was converted to the title compound (SiO$_2$, heptane:ethyl acetate:dichloromethane=60:20:20 to 0:80:20, 26 mg, 12%) which was obtained as a white solid. MS: m/e=423.0 [M+H]$^+$.

EXAMPLE 22

6-Benzotriazol-1-ylmethyl-3,10-dichloro-9H-imidazo[1,5-a][1,2,4]triazolo[1,5-d][1,4]benzodiazepine As described for example 10, 6-bromomethyl-3,10-dichloro-9H-imidazo[1,5-a][1,2,4]triazolo[1,5-d][1,4]benzodiazepine (200 mg, 0.52 mmol), using benzotriazole instead of 1H-1,2,3-triazole, was converted to the title compound (SiO$_2$, heptane:ethyl acetate:dichloromethane=60:20:20 to 0:80:20, 133 mg, 61%) which was obtained as a white solid. MS: m/e=423.0 [M+H]$^+$.

EXAMPLE 23

3,10-Dichloro-6-(3-oxo-2-aza-spiro[4.5]dec-2-ylmethyl)-9H-imidazo[1,5-a][1,2,4]triazolo[1,5-d][1,4]benzodiazepine As described for example 8, 6-bromomethyl-3,10-dichloro-9H-imidazo[1,5-a][1,2,4]triazolo[1,5-d][1,4]benzodiazepine (200 mg, 0.52 mmol), using 4,4-pentamethylene-2-pyrrolidinone instead of 2-pyrrolidone, was converted to the title compound (SiO$_2$, heptane:ethyl acetate:dichloromethane=60:20:20 to 0:80:20, 113 mg, 48%) which was obtained as a white solid. MS: m/e=457.1 [M+H]$^+$.

EXAMPLE 24

3,10-Dichloro-6-(4-methyl-pyrazol-1-ylmethyl)-9H-imidazo[1,5-a][1,2,4]triazolo[1,5-d][1,4]benzodiazepine As described for example 10, 6-bromomethyl-3,10-dichloro-9H-imidazo[1,5-a][1,2,4]triazolo[1,5-d][1,4]benzodiazepine (200 mg, 0.52 mmol), using 4-methylpyrazole instead of 1H-1,2,3-triazole, was converted to the title compound (SiO$_2$, heptane:ethyl acetate:dichloromethane=60:20:20 to 0:80:20, 40 mg, 20%) which was obtained as a white solid. MS: m/e=385.9 [M+H]$^+$.

EXAMPLE 25

3,10-Dichloro-6-(1,1-dioxo-1lambda*6*-isothiazolidin-2-ylmethyl)-9H-imidazo[1,5-a][1,2,4]triazolo[1,5-d][1,4]benzodiazepine As described for example 8, 6-bromomethyl-3,10-dichloro-9H-imidazo[1,5-a][1,2,4]triazolo[1,5-d][1,4]benzodiazepine (200 mg, 0.52 mmol), using isothiazolidine 1,1-dioxide instead of 2-pyrrolidone, was converted to the title compound (SiO$_2$, heptane:ethyl acetate:dichloromethane=60:20:20 to 0:80:20, 134 mg, 61%) which was obtained as a white foam. MS: m/e=425.0 [M+H]$^+$.

EXAMPLE 26

3,10-Dichloro-6-indazol-2-ylmethyl-9H-imidazo[1,5-a][1,2,4]triazolo[1,5-d][1,4]benzodiazepine As described for example 10, 6-bromomethyl-3,10-dichloro-9H-imidazo[1,5-a][1,2,4]triazolo[1,5-d][1,4]benzodiazepine (200 mg, 0.52 mmol), using indazole instead of 1H-1,2,3 triazole, was converted to the title compound (SiO$_2$, heptane:ethyl acetate:dichloromethane=60:20:20 to 0:80:20, 26 mg, 12%) which was obtained as a white solid. MS: m/e=421.9 [M+H]$^+$.

EXAMPLE 27

3,10-Dichloro-6-indazol-1-ylmethyl-9H-imidazo[1,5-a][1,2,4]triazolo[1,5-d][1,4]benzodiazepine As described for example 10, 6-bromomethyl-3,10-dichloro-9H-imidazo[1,5-a][1,2,4]triazolo[1,5-d][1,4]benzodiazepine (200 mg, 0.52 mmol), using indazole instead of 1H-1,2,3 triazole, was converted to the title compound (SiO$_2$, heptane:ethyl acetate:dichloromethane=60:20:20 to 0:80:20, 81 mg, 37%) which was obtained as a white solid. MS: m/e=421.9 [M+H]$^+$.

EXAMPLE 28

3,10-Dichloro-6-(3-phenyl-pyrazol-1-ylmethyl)-9H-imidazo[1,5-a][1,2,4]triazolo[1,5-d][1,4]benzodiazepine As described for example 10, 6-bromomethyl-3,10-dichloro-9H-imidazo[1,5-a][1,2,4]triazolo[1,5-d][1,4]benzodiazepine (200 mg, 0.52 mmol), using 3-phenyl-pyrazole instead of 1H-1,2,3 triazole and 4 h at 80° C. instead of ambient temperature, was converted to the title compound (SiO$_2$, heptane:ethyl acetate:dichloromethane=60:20:20:0 to 0:80:20, 99 mg, 43%) which was obtained as a white foam. MS: m/e=448.0[M+H]$^+$.

EXAMPLE 29

10-Chloro-3-cyclopropyl-6-methoxymethyl-9H-imidazo[1,5-a][1,2,4]triazolo[1,5-d][1,4]benzodiazepine 3-Bromo-10-chloro-6-methoxymethyl-9H-imidazo[1,5-a][1,2,4]triazolo[1,5-d][1,4]benzodiazepine (939 mg, 2.47 mmol) was dissolved in hot THF (20 mL) and cooled to ambient temperature. After the flask was evacuated and filled with argon, tetrakis(triphenylphosphine)palladium(0) (143 mg, 0.12 mmol) and cyclopropylzinc chloride solution (0.4 M in THF, 7.7 mL, 3.08 mmol) were added. The resulting solution was stirred for 18 h at ambient temperature and 2 h at 50° C. Further tetrakis(triphenylphosphine)palladium(0) (143 mg; 0.12 mmol) was added and cyclopropylzinc chloride solution (0.4 M in THF, 12 mL; 4.8 mmol) was added at 50° C. dropwise over a period of 45 min. After the end of addition stirring at 50° C. was continued for another 2 h. The reaction mixture was quenched with aqueous ammonium chloride (saturated, 10 mL) and stirred for 15 min at ambient temperature. The aqueous layer was separated, extracted with ethyl acetate (30 mL) and washed with aqueous sodium carbonate (saturated, 25 mL). Drying over sodium sulfate and purification by chromatography (SiO$_2$, heptane:ethyl acetate:dichloromethane=60:20:20 to 0:80:20) afforded the title compound (520 mg, 62%) as a white solid. MS m/e: 342.1 [M+H]$^+$.

EXAMPLE 30

3,10-Dichloro-6-(3,3-dimethyl-2-oxo-pyrrolidin-1-ylmethyl)-9H-imidazo[1,5-a][1,2,4]triazolo[1,5-d][1,4]benzodiazepine As described for example 8, 6-bromomethyl-3,10-dichloro-9H-imidazo[1,5-a][1,2,4]triazolo[1,5-d][1,4]benzodiazepine (200 mg, 0.52 mmol), using 3,3-dimethyl-pyrrolidin-2-one instead of 2-pyrrolidone, was converted to the title compound (SiO$_2$, heptane:ethyl acetate:dichloromethane=40:40:20 to 10:70:20, 22 mg, 10%) which was obtained as a white solid. MS: m/e=417.1 [M+H]$^+$.

EXAMPLE 31

3,10-Dichloro-6-(3-oxo-piperazin-1-ylmethyl)-9H-imidazo[1,5-a][1,2,4]triazolo[1,5-d][1,4]benzodiazepine To a suspension of 6-bromomethyl-3,10-dichloro-9H-imidazo[1,5-a][1,2,4]triazolo[1,5-d][1,4]benzodiazepine (600 mg, 1.56 mmol) in dichloromethane (6 mL) was added piperazine-2-one (234 mg, 2.33 mmol) and N,N-diisopropyl ethyl amine (0.32 mL, 1.87 mmol) and the reaction mixture was stirred for 3 d at ambient temperature. The resulting mixture was then diluted with dichloromethane (20 mL), washed with water (20 mL) and the aqueous layers were reextracted with dichloromethane (20 mL). The combined organic layers were dried over sodium sulfate and concentrated. Purification of the residue by chromatography (SiO$_2$, dichloromethane:methanol=98:2 to 90:10) afforded the title compound (184 mg, 29%) as a white solid. MS m/e: 404.1 [M+H]$^+$.

EXAMPLE 32

3,10-Dichloro-6-(4-ethyl-piperazin-1-ylmethyl)-9H-imidazo[1,5-a][1,2,4]triazolo[1,5-d][1,4]benzodiazepine As described for example 31, 6-bromomethyl-3,10-dichloro-9H-imidazo[1,5-a][1,2,4]triazolo[1,5-d][1,4]benzodiazepine (200 mg, 0.52 mmol), using N-ethylpiperazine instead of piperazine-2-one, was converted to the title compound (SiO$_2$, heptane:ethyl acetate:dichloromethane=40:40:20 to 10:70:20, 162 mg, 75%) which was obtained as a white foam. MS: m/e=418.1 [M+H]$^+$.

EXAMPLE 33

3,10-Dichloro-6-(4-tert-butyloxycarbonyl-2-oxo-piperazin-1-ylmethyl)-9H-imidazo[1,5-a][1,2,4]triazolo[1,5-d][1,4]benzodiazepine As described for example 8, 6-bromomethyl-3,10-dichloro-9H-imidazo[1,5-a][1,2,4]triazolo[1,5-d][1,4]benzodiazepine (1.00 g, 2.60 mmol), using 3-oxo-piperazine-1-carboxylic acid tert-butyl ester instead of 2-pyrrolidone, was converted to the title compound (SiO$_2$, heptane:ethyl acetate:dichloromethane=60:20:20 to 0:80:20, 265 mg, 20%) which was obtained as a white solid. MS: m/e=417.1 [M−BOC+H]$^+$.

EXAMPLE 34

3,10-Dichloro-6-(4-ethyl-3-oxo-piperazin-1-ylmethyl)-9H-imidazo[1,5-a][1,2,4]triazolo[1,5-d][1,4]benzodiazepine To a solution of 3,10-dichloro-6-(3-oxo-piperazin-1-ylmethyl)-9H-imidazo[1,5-a][1,2,4]triazolo[1,5-d][1,4]benzodiazepine (example 31, 159 mg, 0.39 mmol) in DMF (2 mL) was added at 0° C. potassium bis(trimethylsilyl)amide (0.91 M in THF, 0.48 mL, 0.43 mmol). After stirring for 1 h at 0° C. iodoethane (38 µL, 0.47 mmol) was added and stirring was continued for 18 h at ambient temperature. The reaction mixture was diluted with dichloromethane (20 mL) and washed twice with water (20 mL). The aqueous layers were further extracted with dichloromethane (20 mL) and dried over sodium sulfate. Purification of the residue by chromatography (SiO$_2$, ethyl acetate:dichloromethane:methanol=80:20:0 to 70:20:10) afforded the title compound (81 mg, 48%) as a white solid. MS m/e: 432.2 [M+H]$^+$.

EXAMPLE 35

3,10-Dichloro-6-(2-oxo-piperazin-1-ylmethyl)-9H-imidazo[1,5-a][1,2,4]triazolo[1,5-d][1,4]benzodiazepine To a suspension of 3,10-dichloro-6-(4-tert-butyloxycarbonyl-2-oxo-piperazin-1-ylmethyl)-9H-imidazo[1,5-a][1,2,4]triazolo[1,5-d][1,4]benzodiazepine (example 33, 255 mg, 0.51 mmol) in dichloromethane (2 mL) was added at ambient temperature trifluoracetic acid (0.39 mL, 5.06 mmol) and the reaction mixture was stirred for 20 h at this temperature. The solution was then concentrated in vacuo and the residue was extracted with dichloromethane (10 mL) and aqueous sodium carbonate (half-saturated, 20 mL). The aqueous phase was reextracted with dichloromethane (10 mL) and dried over sodium sulfate. The concentrated organic phases were suspended in tert-butylmethylether (3 mL), filtered off and washed with tert-butylmethylether (3 mL) affording the title compound (188 mg, 92%) as a white solid. MS m/e: 404.1 [M+H]$^+$.

EXAMPLE 36

3,10-Dichloro-6-(4-ethyl-2-oxo-piperazin-1-ylmethyl)-9H-imidazo[1,5-a][1,2,4]triazolo[1,5-d][1,4]benzodiazepine To a suspension of 3,10-dichloro-6-(2-oxo-piperazin-1-ylmethyl)-9H-imidazo[1,5-a][1,2,4]triazolo[1,5-d][1,4]benzodiazepine (example 36, 157 mg, 0.39 mmol) in DMF (2 mL) was added N,N-diisopropyl ethyl amine (0.10 mL, 0.58 mmol) and iodoethane (41 µL, 0.51 mmol) and the reaction mixture was stirred for 2 h at ambient temperature and for 18 h at 70° C. The reaction mixture was cooled to 0° C. and potassium bis(trimethylsilyl)amide (0.91 M in THF, 0.56 mL, 0.51 mmol) was added. After stirring for 1 h at 0° C. further iodoethane (41 µL, 0.50 mmol) was added and stirring was continued for 2 d at ambient temperature. It was diluted with dichloromethane (10 mL) and washed with aqueous sodium hydroxide (1 N, 10 mL) and water (10 mL). The aqueous layers were reextracted with dichloromethane (10 mL). Drying over sodium sulfate and purification of the residue by chromatography (SiO$_2$, ethyl acetate:dichloromethane: methanol=80:20:0 to 70:20:10) afforded the title compound (73 mg, 43%) as a white solid. MS m/e: 432.2 [M+H]$^+$.

EXAMPLE 37

3-Bromo-6-hydroxymethyl-10-methyl-9H-imidazo[1,5-a][1,2,4]triazolo[1,5-d][1,4]benzodiazepine 3-Bromo-6-hydroxymethyl-10-methyl-9H-imidazo[1,5-a][1,2,4]triazolo[1,5-d][1,4]benzodiazepine (20 mg, 0.06 mmol) was dissolved in dichloromethane (2.5 mL) and cooled to −10° C. After addition of boron tribromide solution (1 M in dichloromethane, 70 µL, 0.07 mmol) the reaction mixture was stirred for 4 h at ambient temperature. Aqueous sodium carbonate (saturated, 30 mL) was added and stirring was continued for another 30 min. The mixture was then extracted with dichloromethane, dried over sodium sulfate and concentrated. Purification by chromatography (SiO$_2$, dichloromethane:methanol=100:1 to 30:1) afforded the title compound (7 mg, 36%) as a white solid. MS m/e: 345.0/347.0 [M+H]$^+$.

EXAMPLE 38

Ethyl 3-bromo-6-methoxymethyl-9H-imidazo[1,5-a][1,2,4]triazolo[1,5-d][1,4]benzodiazepine-10-carboxylate a) 9-Bromo-2-methoxymethyl-6H-[1,2,4]triazolo[1,5-c]quinazolin-5-one As described for example 1a) (4-bromo-2-cyano-phenyl)-carbamic acid ethyl ester (19.9 g, 74.2 mmol) instead of (4-chloro-2-cyano-phenyl)-carbamic acid ethyl ester using methoxymethyl-carboxylic acid hydrazide instead of cyclopropane-carboxylic acid hydrazide, was converted to the title compound (21.1 g, 92%) which was obtained as a light yellow solid. MS: m/e=308.9/310.9 [M+H]$^+$.

b) 4-Bromo-2-(5-methoxymethyl-2H-[1,2,4]triazol-3-yl)-phenylamine

As described for example 1b) 9-bromo-2-methoxymethyl-6H-[1,2,4]triazolo[1,5-c]quinazolin-5-one (20.9 g, 67.6 mmol), instead of 9-chloro-2-cyclopropyl-6H-[1,2,4]triazolo[1,5-c]quinazolin-5-one, was converted to the title compound (19.1 g, 99%) which was obtained as an off-white solid. MS: m/e=282.7/284.7 [M+H]$^+$.

c) 2-Chloro-N-[4-bromo-2-(5-methoxymethyl-2H-[1,2,4]triazol-3-yl)-phenyl]-acetamide As described for example 4c) 4-bromo-2-(5-methoxymethyl-2H-[1,2,4]triazol-3-yl)-phenylamine (19.1 g, 67.5 mmol), instead of 4-chloro-2-(5-methoxymethyl-2H-[1,2,4]triazol-3-yl)-phenylamine, was converted to the title compound (20.0 g, 82%) which was obtained as a white solid. MS: m/e=358.8/360.9 [M+H]$^+$.

d) 9-Bromo-2-methoxymethyl-6H-1,3,3a,6-tetraaza-benzo[e]azulen-5-one

As described for example 4d) 2-chloro-N-[4-bromo-2-(5-methoxymethyl-2H-[1,2,4]triazol-3-yl)-phenyl]-acetamide (20.6 g, 57.3 mmol), instead of 2-chloro-N-[4-chloro-2-(5-methoxymethyl-2H-[1,2,4]triazol-3-yl)-phenyl]-acetamide, was converted to the title compound (12.6 g, 68%) which was obtained as an off-white solid. MS: m/e=322.0/324.0 [M+H]$^+$.

e) 9-Bromo-2-methoxymethyl-5-[1,2,4]triazol-1-yl-4H-1,3,3a,6-tetraaza-benzoazulene As described for example 4e) 9-bromo-2-methoxymethyl-6H-1,3,3a,6-tetraaza-benzo[e]azulen-5-one (12.5 g, 38.7 mmol), instead of 9-chloro-2-methoxymethyl-6H-1,3,3a,6-tetraaza-benzo[e]azulen-5-one, was converted to the title compound (11.4 g, 79%) which was obtained as a light yellow solid. MS: m/e=373.0/375.1 [M+H]$^+$.

f) Ethyl 3-bromo-6-methoxymethyl-9H-imidazo[1,5-a][1,2,4]triazolo[1,5-d][1,4]benzodiazepine-10-carboxylate As described for example 4f) 9-bromo-2-methoxymethyl-5-[1,2,4]triazol-1-yl-4H-1,3,3a,6-tetraaza-benzoazulene (11.4 g, 30.3 mmol), instead of 9-chloro-2-methoxymethyl-5-[1,2,4]triazol-1-yl-4H-1,3,3a,6-tetraaza-benzoazulene, was converted to the title compound (9.00 g, 71%) which was obtained as a white solid. MS: m/e=417.0/419.0 [M+H]$^+$.

EXAMPLE 39

3-Bromo-6-methoxymethyl-9H-imidazo[1,5-a][1,2,4]triazolo[1,5-d][1,4]benzodiazepine a) 3-Bromo-6-methoxymethyl-9H-imidazo[1,5-a][1,2,4]triazolo[1,5-d][1,4]benzodiazepine-10-carboxylic acid As described for example 2a) ethyl 3-bromo-6-methoxymethyl-9H-imidazo[1,5-a][1,2,4]triazolo[1,5-d][1,4]benzodiazepine-10-carboxylate (26.9 g, 64.3 mmol), instead of ethyl 3-chloro-6-cyclopropyl-9H-imidazo[1,5-a][1,2,4]triazolo[1,5-d][1,4]benzodiazepine-10-carboxylate, was converted to the title compound (24.8 g, 99%) which was obtained as a white solid. MS: m/e=389.0/391.2 [M+H]$^+$.

b) 3-Bromo-6-methoxeththyl-9H-imidazo[1,5-a][1,2,4]triazolo[1,5-d][1,4]benzodiazepine As described for example 2b) 3-bromo-6-methoxymethyl-9H-imidazo[1,5-a][1,2,4]triazolo[1,5-d][1,4]benzodiazepine-10-carboxylic acid (12.5 g, 32.0 mmol), instead of 3-chloro-6-cyclopropyl-9H-imidazo[1,5-a][1,2,4]triazolo[1,5-d][1,4]benzodiazepine-10-carboxylic acid, was converted to the title compound (11.0 g, 99%) which was obtained a white solid. MS: m/e=345.0 [M+H]$^+$.

EXAMPLE 40

3-Bromo-10-chloro-6-methoxymethyl-9H-imidazo[1,5-a][1,2,4]triazolo[1,5-d][1,4]benzodiazepine As described for example 3, 3-bromo-6-methoxymethyl-9H-imidazo[1,5-a][1,2,4]triazolo[1,5-d][1,4]benzodiazepine (22.0 g, 63.6 mmol), instead of 3-chloro-6-cyclopropyl-9H-imidazo[1,5-a][1,2,4]triazolo[1,5-d][1,4]benzodiazepine, was converted to the title compound (17.2 g, 71%) which was obtained as a light yellow foam. MS: m/e=379.0/381.0 [M+H]$^+$.

EXAMPLE 41

3-Bromo-10-hydroxymethyl-6-methoxymethyl-9H-imidazo[1,5-a][1,2,4]triazolo[1,5-d][1,4]benzodiazepine To a suspension of ethyl 3-bromo-6-methoxymethyl-9H-imidazo[1,5-a][1,2,4]triazolo[1,5-d][1,4]benzodiazepine-10-carboxylate (8.7 g, 20.8 mmol) in THF (250 mL) was added at ambient temperature lithium borohydride (544 mg, 25.0 mmol) and the reaction mixture was heated at reflux for 4 h. After cooling to 0° C. aqueous HCl (1 M, 52 mL) was added dropwise and the mixture heated under reflux for 30 min. the resulting mixture was then concentrated, and then diluted with water (240 mL) and aqueous ammonium hydroxide (25%) added (pH=10). The resulting solid was filtered off and washed with water. Drying in vacuo (70° C.) afforded the title compound (5.95 g, 76%) which was obtained as a white solid. MS: m/e=376.2/378.2 [M+H]$^+$.

EXAMPLE 42

3-Bromo-6-methoxymethyl-9H-imidazo[1,5-a][1,2,4]triazolo[1,5-d][1,4]benzodiazepine-10-carbaldehyde To a suspension of 3-bromo-10-hydroxymethyl-6-methoxymethyl-9H-imidazo[1,5-a][1,2,4]triazolo[1,5-d][1,4]benzodiazepine (5.95 g, 15.8 mmol) in dichloromethane (1.07 L) was added manganese(IV) oxide (27.5 g, 316 mmol) and the resulting mixture was stirred at ambient temperature for 3 h and then filtered through Dicalit® and washed with dichloromethane. Concentration afforded the title compound (4.39 g, 74%) which was obtained as a white solid. MS: m/e=374.1/376.2 [M+H]$^+$.

EXAMPLE 43

3-Bromo-10-difluoromethyl-6-methoxymethyl-9H-imidazo[1,5-a][1,2,4]triazolo[1,5-d][1,4]benzodiazepine To a solution of 3-bromo-6-methoxymethyl-9H-imidazo[1,5-a][1,2,4]triazolo[1,5-d][1,4]benzodiazepine-10-carbaldehyde (4.39 g, 11.7 mmol) in dichloromethane (250 mL) was added bis(2-methoxyethyl)aminosulfur trifluoride (11.4 mL, 58.7 mmol) und ethanol (0.14 mL, 0.02 mmol). The resulting mixture was heated under reflux for 4 h. It was poured onto aqueous sodium carbonate (saturated, 200 mL) and stirred for 30 min. The mixture was then extracted with dichloromethane, dried over sodium sulfate and concentrated. Purification by chromatography (SiO$_2$, ethyl acetate: cyclohexane=80:20) afforded the title compound (4.10 mg, 88%) as a white solid. MS m/e: 396.0/398.1 [M+H]$^+$.

EXAMPLE 44

3-Bromo-10-chloro-6-morpholin-4-ylmethyl-9H-imidazo[1,5-a][1,2,4]triazolo[1,5-d][1,4]benzodiazepine b) 3-Bromo-6-bromomethyl-10-chloro-9H-imidazo[1,5-a][1,2,4]triazolo[1,5-d][1,4]benzodiazepine To 3-bromo-6-hydroxymethyl-10-chloro-9H-imidazo[1,5-a][1,2,4]triazolo[1,5-d][1,4]benzodiazepine (3.10 g, 8.47 mmol) in 1,2-ethylenchloride (70 mL) was added dropwise at ambient temperature phosphorus tribromide (2.29 g, 8.48 mmol) and the resulting mixture was heated at reflux for 2 h. After cooling to ambient temperature it was poured onto water and aqueous sodium carbonate (saturated). Extraction with dichloromethane and drying over sodium sulfate afforded the title compound (3.30 mg, 91%) as a white solid. MS m/e: 429.0 [M+H]$^+$.

b) 3-Bromo-10-chloro-6-morpholin-4-ylmethyl-9H-imidazo[1,5-a][1,2,4]triazolo[1,5-d][1,4]benzodiazepine A mixture of 3-bromo-6-bromomethyl-10-chloro-9H-imidazo[1,5-a][1,2,4]triazolo[1,5-d][1,4]benzodiazepine (70 mg, 0.23 mmol) and morpholine (2 mL) was stirred at 50° C. for 1 h. After cooling to ambient temperature the mixture was poured onto dichloromethane and aqueous sodium carbonate (saturated). Extraction with dichloromethane, drying over sodium sulfate and recrystallisation with dichloromethane/cyclohexane afforded the title compound (32 mg, 65%) as an off-white solid. MS m/e: 435.2/437.1 [M+H]$^+$.

EXAMPLE 45

3-Bromo-10-chloro-6-pyrrolidin-1-ylmethyl-9H-imidazo[1,5-a][1,2,4]triazolo[1,5-d][1,4]benzodiazepine As described for example 44b, 3-bromo-6-bromomethyl-10-chloro-9H-imidazo[1,5-a][1,2,4]triazolo[1,5-d][1,4]benzodiazepine (70 mg, 0.23 mmol), using pyrrolidine instead of morpholine, was converted to the title compound (37 mg, 78%) which was obtained as an off-white solid. MS: m/e=418.9/421.0 [M+H]+.

EXAMPLE 46

3-Bromo-10-difluoromethyl-6-morpholin-4-ylm-ethyl-9H-imidazo[1,5-a][1,2,4]triazolo[1,5-d][1,4]benzodiazepine a) 3-Bromo-6-bromomethyl-10-difluoromethyl-9H-imidazo[1,5-a][1,2,4]triazolo[1,5-d][1,4]benzodiazepine As described for example 44a, 3-bromo-10-difluoromethyl-6-hydroxymethyl-9H-imidazo[1,5-a][1,2,4]triazolo[1,5-d][1,4]benzodiazepine (400 mg, 1.05 mmol) instead of 3-bromo-10-chloro-6-hydroxymethyl-9H-imidazo[1,5-a][1,2,4]triazolo[1,5-d][1,4]benzodiazepine was converted to the title compound (370 mg, 79%) which was obtained as a white solid. MS: m/e=444.1/446.1 [M+H]+.

b) 3-Bromo-10-difluoromethyl-6-morpholin-4-ylmethyl-9H-imidazo[1,5-a][1,2,4]triazolo[1,5-d][1,4]benzodiazepine As described for example 44b, 3-bromo-6-bromomethyl-10-difluoromethyl-9H-imidazo[1,5-a][1,2,4]triazolo[1,5-d][1,4]benzodiazepine (81 mg, 0.18 mmol) instead of 3-bromo-6-bromomethyl-10-chloro-9H-imidazo[1,5-a][1,2,4]triazolo[1,5-d][1,4]benzodiazepine was converted to the title compound (50 mg, 61%) which was obtained as a white solid. MS: m/e=451.0/453.0 [M+H]+.

EXAMPLE 47

3-Bromo-10-chloro-6-pyrrolidin-1-ylmethyl-9H-imidazo[1,5-a][1,2,4]triazolo[1,5-d][1,4]benzodiazepine As described for example 44b, 3-bromo-6-bromomethyl-10-difluoromethyl-9H-imidazo[1,5-a][1,2,4]triazolo[1,5-d][1,4]benzodiazepine (81 mg, 0.18 mmol) instead of 3-bromo-6-bromomethyl-10-chloro-9H-imidazo[1,5-a][1,2,4]triazolo[1,5-d][1,4]benzodiazepine, using pyrrolidine instead of morpholine, was converted to the title compound (23 mg, 29%) which was obtained as a white solid. MS: m/e=435.2/437.1 [M+H]+.

EXAMPLE 48

3-Bromo-10-difluoromethyl-6-hydroxymethyl-9H-imidazo[1,5-a][1,2,4]triazolo[1,5-d][1,4]benzodiazepine 3-Bromo-10-difluoromethyl-6-methoxymethyl-9H-imidazo[1,5-a][1,2,4]triazolo[1,5-d][1,4]benzodiazepine (0.50 g, 1.26 mmol) in hydrobromic acid (48%, 3.55 mL) was stirred at 100° C. for 5 h. After cooling to ambient temperature water (100 mL) was added and aqueous sodium carbonate (2 N) until pH=8. After stirring for 15 min the solid was filtered off and washed with water. Drying in vacuo (70° C.) afforded the title compound (0.40 g, 83%) as a white solid. MS m/e: 382.0/384.1 [M+H]+.

EXAMPLE 49

3-Bromo-10-chloro-6-(2-oxo-pyrrolidin-1-ylm-ethyl)-9H-imidazo[1,5-a][1,2,4]triazolo[1,5-d][1,4]benzodiazepine To a solution of 2-pyrrolidone (14 mg, 0.16 mmol) in DMF (4 mL) was added at 0° C. sodium hydride (60% in mineral oil, 7 mg, 0.18 mmol) and the resulting mixture was stirred for 30 min at this temperature. 3-Bromo-6-bromomethyl-10-chloro-9H-imidazo[1,5-a][1,2,4]triazolo[1,5-d][1,4]benzodiazepine (69 mg, 0.16 mmol) was added and stirred at ambient temperature for 1 h. The reaction mixture was poured onto water and extracted with dichloromethane. The organic layers were dried over sodium sulfate and concentrated. Purification by chromatography (SiO$_2$, dichloromethane:methanol=200:1) afforded the title compound (34 mg, 49%) as an off-white solid. MS m/e: 433.0/434.9 [M+H]+.

EXAMPLE 50

3-Bromo-10-chloro-6-(2-oxo-oxazolidin-3-ylm-ethyl)-9H-imidazo[1,5-a) ][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (69 mg, 0.16 mmol) using 2-oxazolidone instead of 2-pyrrolidone was converted to the title compound (58 mg, 82%) which was obtained as an off-white foam. MS: m/e=435.0/436.9 [M+H]+.

EXAMPLE 51

3-Bromo-10-chloro-6-hydroxymethyl-9H-imidazo[1,5-a][1,2,4]triazolo[1,5-d][1,4]benzodiazepine As described for example 48, 3-bromo-6-bromomethyl-10-chloro-9H-imidazo[1,5-a][1,2,4]triazolo[1,5-d][1,4]benzodiazepine (1.00 g, 2.63 mmol) instead of 3-bromo-6-bromomethyl-10-difluoromethyl-9H-imidazo[1,5-a][1,2,4]triazolo[1,5-d][1,4]benzodiazepine was converted to the title compound (920 mg, 96%) which was obtained as a white solid. MS: m/e=365.0/366.9 [M+H]+.

EXAMPLE 52

3-Bromo-10-difluoromethyl-6-(2-oxo-pyrrolidin-1-ylmethyl)-9H-imidazo[1,5-a][1,2,4]triazolo[1,5-d][1,4]benzodiazepine As described for example 49, 3-bromo-6-bromomethyl-10-difluoro-9H-imidazo[1,5-a][1,2,4]triazolo[1,5-d][1,4]benzodiazepine (100 mg, 0.22 mmol) instead of 3-bromo-6-bromomethyl-10-chloro-9H-imidazo[1,5-a][1,2,4]triazolo[1,5-d][1,4]benzodiazepine was converted to the title compound (40 mg, 39%) which was obtained as an off-white foam. MS: m/e=449.2/451.2 [M+H]+.

EXAMPLE 53

3-Bromo-10-chloro-6-(1-hydroxy-ethyl)-9H-imidazo[1,5-a][1,2,4]triazolo[1,5-d][1,4]benzodiazepine a) 3-Bromo-10-chloro-6-formyl-9H-imidazo[1,5-a][1,2,4]triazolo[1,5-d][1,4]benzodiazepine To a suspension of 3-bromo-10-chloro-6-hydroxymethyl-9H-imidazo[1,5-a][1,2,4]triazolo[1,5-d][1,4]benzodiazepine (2.20 g, 6.00 mmol) in dichloromethane (500 mL) was added manganese(IV) oxide (56.7 g, 132 mmol) and the reaction mixture was stirred at ambient temperature for 16 h. After filtration over Dicalit® it was concentrated purification by chromatography ($SiO_2$, dichloromethane:ethyl acetate=5:1 to 3:1) afforded the title compound (600 mg, 27%) as an white solid. MS m/e: 364.0/365.9 $[M+H]^+$.

b) 3-Bromo-10-chloro-6-(1-hydroxy-ethyl)-9H-imidazo[1,5-a][1,2,4]triazolo[1,5-d][1,4]benzodiazepine 3-Bromo-10-chloro-6-formyl-9H-imidazo[1,5-a][1,2,4]triazolo[1,5-d][1,4]benzodiazepine (150 mg, 0.41 mmol) was suspended in THF (5 mL) and cooled to 0° C. After dropwise addition of methylmagnesium bromide (3 M in diethylether, 0.15 mL, 0.45 mmol) the resulting solution was stirred for 3 h at ambient temperature. Aqueous ammonium chloride (3 mL) and aqueous HCl (2M, 8 mL) were added and the resulting solid was filtered off. Purification by chromatography ($SiO_2$, ethyl acetate) afforded the title compound (60 mg, 38%) as a white solid. MS m/e: 379.0/381.0 $[M+H]^+$.

EXAMPLE 54

3-Bromo-10-chloro-6-(hydroxy-phenyl-ethyl)-9H-imidazo[1,5-a][1,2,4]triazolo[1,5-d][1,4]benzodiazepine As described for example 53b, 3-bromo-10-chloro-6-formyl-9H-imidazo[1,5-a][1,2,4]triazolo[1,5-d][1,4]benzodiazepine (150 mg, 0.41 mmol) using phenylmagnesium bromide (3 M in diethylether) instead of methylmagnesium bromide (3 M in diethylether) was converted to the title compound (140 mg, 77%) which was obtained as a white solid. MS: m/e=441.1/443.1 $[M+H]^+$.

EXAMPLE 55

3-Bromo-10-chloro-6-(cyclopropyl-hydroxy-methyl)-9H-imidazo[1,5-a][1,2,4]triazolo[1,5-d][1,4]benzodiazepine As described for example 53b, 3-bromo-10-chloro-6-formyl-9H-imidazo[1,5-a][1,2,4]triazolo[1,5-d][1,4]benzodiazepine (150 mg, 0.41 mmol) using cyclopropylmagnesium bromide (freshly prepared) instead of methylmagnesium bromide (3 M in diethylether) was converted to the title compound (85 mg, 51%) which was obtained as a white foam. MS: m/e=405.0/407.0 $[M+H]^+$.

EXAMPLE 56

3-Bromo-10-chloro-6-(1-hydroxy-propyl)-9H-imidazo[1,5-a][1,2,4]triazolo[1,5-d][1,4]benzodiazepine As described for example 53b, 3-bromo-10-chloro-6-formyl-9H-imidazo[1,5-a][1,2,4]triazolo[1,5-d][1,4]benzodiazepine (150 mg, 0.41 mmol) using ethylmagnesium bromide (3 M in diethylether) instead of methylmagnesium bromide (3 M in diethylether) was converted to the title compound (28 mg, 17%) which was obtained as a white foam. MS: m/e=393.0/395.0 $[M+H]^+$.

EXAMPLE 57

3-Bromo-10-chloro-6-(3-oxo-morpholin-4-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (150 mg, 0.35 mmol) using morpholin-3-one instead of 2-pyrrolidone was converted to the title compound (108 mg, 69%) which was obtained as a white solid. MS: m/e=449.1/451.1 $[M+H]^+$.

EXAMPLE 58

3-Bromo-10-chloro-6-(hydroxy-pyridin-3-yl-methyl)-9H-imidazo[1,5-a][1,2,4]triazolo[1,5-d][1,4]benzodiazepine As described for example 53b, 3-bromo-10-chloro-6-formyl-9H-imidazo[1,5-a][1,2,4]triazolo[1,5-d][1,4]benzodiazepine (150 mg, 0.41 mmol) using 3-pyridinylmagnesium chloride (freshly prepared) instead of methylmagnesium bromide (3 M in diethylether) was converted to the title compound (50 mg, 27%) which was obtained as an off-white foam. MS: m/e=442.1/444.0 $[M+H]^+$.

EXAMPLE 59

3-Bromo-10-chloro-6-cyanomethyl-9H-imidazo[1,5-a][1,2,4]triazolo[1,5-d][1,4]benzodiazepine To a mixture of sodiumcyanide (274 mg, 5.59 mmol) in DMSO (5 mL) was added dropwise at 120° C. a solution of 3-bromo-6-bromomethyl-10-chloro-9H-imidazo[1,5-a][1,2,4]triazolo[1,5-d][1,4]benzodiazepine (1.60 g, 3.73 mmol) in DMSO (12 mL) and the resulting mixture was stirred for 12 min at this temperature. The reaction mixture was poured onto water (350 mL) and the resulting solid was filtered off and dried. Purification by chromatography ($SiO_2$, dichloromethane:methanol=60:1) afforded the title compound (1.35 mg, 96%) as an off-white solid. MS m/e: 374.0/376.0 $[M+H]^+$.

EXAMPLE 60

3-Bromo-10-chloro-6-(3,5-dioxo-[1,2,4]oxadiazolidin-2-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (150 mg, 0.35 mmol) using [1,2,4]oxadiazolidine-3,5-dione instead of 2-pyrrolidone was converted to the title compound ($SiO_2$, dichloromethane:methanol=10:1 to 7:1, 70 mg, 44%) which was obtained as a white foam. MS: m/e=450.0/452.2 $[M+H]^+$.

EXAMPLE 61

3-Bromo-10-chloro-6-cyclopentylcarbamoylmethyl-9H-imidazo[1,5-a][1,2,4]triazolo[1,5-d][1,4]benzodiazepine a) 3-Bromo-6-carboxymethyl-10-chloro-9H-imidazo[1,5-a][1,2,4]triazolo[1,5-d][1,4]benzodiazepine To a suspension of 3-bromo-10-chloro-6-cyanomethyl-9H-imidazo[1,5-a][1,2,4]triazolo[1,5-d][1,4]benzodiazepine (1.00 g, 2.67 mmol) in dioxane was added aqueous sodium hydroxide (2 M, 10 mL) and the resulting mixture was heated at reflux for 2 h. After cooling to ambient temperature it was acidified by addition of aqueous HCl (25%). The solid was filtered off and washed with water and diethylether afforded the title compound (975 mg, 93%) as an off-white solid. MS m/e: 393.0/395.0 [M−H]$^-$.

b) 3-Bromo-10-chloro-6-cyclopentylcarbamoylmethyl-9H-imidazo[1,5-a][1,2,4]triazolo[1,5-d][1,4]benzodiazepine To a solution of 3-bromo-6-carboxymethyl-10-chloro-9H-imidazo[1,5-a][1,2,4]triazolo[1,5-d][1,4]benzodiazepine (100 mg, 0.25 mmol) in DMF (2 mL) added 2-(1H-benzotriazol-1-yl)-1,1,3,3-tetramethyluronium tetrafluoroborate (90 mg, 0.28 mmol), N-ethyldiisopropylamine (164 mg, 1.27 mmol) and cyclopentylamine (24 mg, 0.28 mmol) and the reaction mixture was stirred for 60 h at ambient temperature. It was poured onto aqueous sodium hydrogencarbonate (0.5 M, 15 mL), extracted with dichloromethane and dried over sodium sulfate. Purification by chromatography (SiO$_2$, ethyl acetate:methanol=1:0 to 20:1) afforded the title compound (44 mg, 38%) as a white solid. MS m/e: 461.0/463.0 [M+H]$^+$.

EXAMPLE 62

3-Bromo-10-chloro-6-[(tetrahydro-pyran-4-ylcarbamoyl)-methyl]-9H-imidazo[1,5-a][1,2,4]triazolo[1,5-d][1,4]benzodiazepine As described for example 61b, 3-bromo-6-carboxymethyl-10-chloro-9H-imidazo[1,5-a][1,2,4]triazolo[1,5-d][1,4]benzodiazepine (100 mg, 0.25 mmol) using 4-aminotetrahydropyrane instead of cyclopentylamine was converted to the title compound (62 mg, 51%) which was obtained as a white solid. MS: m/e=476.9/479.0 [M+H]$^+$.

EXAMPLE 63

3-Bromo-10-chloro-6-{[(Pyridin-3-ylmethyl)-carbamoyl]-methyl}-9H-imidazo[1,5-a][1,2,4]triazolo[1,5-d][1,4]benzodiazepine As described for example 61b, 3-bromo-6-carboxymethyl-10-chloro-9H-imidazo[1,5-a][1,2,4]triazolo[1,5-d][1,4]benzodiazepine (100 mg, 0.25 mmol) using 3-picolylamine instead of cyclopentylamine was converted to the title compound (50 mg, 41%) which was obtained as an off-white solid. MS: m/e=484.0/486.1 [M+H]$^+$.

EXAMPLE 64

3-Bromo-10-chloro-6-[(cyclopropylmethyl-carbamoyl)-methyl]-9H-imidazo[1,5-a][1,2,4]triazolo[1,5-d][1,4]benzodiazepine As described for example 61b, 3-bromo-6-carboxymethyl-10-chloro-9H-imidazo[1,5-a][1,2,4]triazolo[1,5-d][1,4]benzodiazepine (100 mg, 0.25 mmol) using cyclopropylmethylamine instead of cyclopentylamine was converted to the title compound (62 mg, 55%) which was obtained as an off-white solid. MS: m/e=446.9/448.9 [M+H]$^+$.

EXAMPLE 65

3-Bromo-10-chloro-6-[(2-hydroxy-ethylcarbamoyl)-methyl]-9H-imidazo[1,5-a][1,2,4]triazolo[1,5-d][1,4]benzodiazepine As described for example 61b, 3-bromo-6-carboxymethyl-10-chloro-9H-imidazo[1,5-a][1,2,4]triazolo[1,5-d][1,4]benzodiazepine (100 mg, 0.25 mmol) using 2-hydroxy-ethylamine instead of cyclopentylamine was converted to the title compound (59 mg, 53%) which was obtained as an off-white solid. MS: m/e=437.0/439.1 [M+H]$^+$.

EXAMPLE 66

3-Bromo-10-chloro-6-[(tetrahydro-pyran-4-ylamino)-methyl]-9H-imidazo[1,5-a][1,2,4]triazolo[1,5-d][1,4]benzodiazepine 4-Aminotetrahydropyrane (88 mg, 0.87 mmol) and N,N-diisopropyl ethyl amine (45 mg, 0.35 mmol) were dissolved in dichloromethane (12 mL) and 3-bromo-6-bromomethyl-10-chloro-9H-imidazo[1,5-a][1,2,4]triazolo[1,5-d][1,4]benzodiazepine (75 mg, 0.18 mmol) was added and the resulting mixture was stirred for 26 h at ambient temperature. It was then poured onto aqueous sodium carbonate (0.5 M, 15 mL), extracted with dichloromethane and dried over sodium sulfate. Purification by chromatography (SiO$_2$, ethyl acetate:methanol=15:1 to 10:1) afforded the title compound (58 mg, 74%) as a white foam. MS m/e: 449.0/451.0 [M+H]$^+$.

EXAMPLE 67

3-Bromo-10-chloro-6-cyclopentylaminomethyl-9H-imidazo[1,5-a][1,2,4]triazolo[1,5-d][1,4]benzodiazepine As described for example 66, 3-bromo-6-bromomethyl-10-chloro-9H-imidazo[1,5-a][1,2,4]triazolo[1,5-d][1,4]benzodiazepine (75 mg, 0.18 mmol) using cyclopentylamine instead of 4-aminotetrahydropyrane was converted to the title compound (61 mg, 81%) which was obtained as an off-white solid. MS: m/e=433.0/435.0 [M+H]$^+$.

EXAMPLE 68

3-Bromo-10-chloro-6-[(cyclopropylmethyl-amino)-methyl]-9H-imidazo[1,5-a][1,2,4]triazolo[1,5-d][1,4]benzodiazepine As described for example 66, 3-bromo-6-bromomethyl-10-chloro-9H-imidazo[1,5-a][1,2,4]triazolo[1,5-d][1,4]benzodiazepine (75 mg, 0.18 mmol) using cyclopropylmethylamine instead of 4-aminotetrahydropyrane was converted to the title compound (57 mg, 78%) which was obtained as an off-white solid. MS: m/e=419.0/421.0 [M+H]$^+$.

EXAMPLE 69

3-Bromo-10-chloro-6-[(2-hydroxy-ethylamino)-methyl]-9H-imidazo[1,5-a][1,2,4]triazolo[1,5-d][1,4]benzodiazepine As described for example 66, 3-bromo-6-bromomethyl-10-chloro-9H-imidazo[1,5-a][1,2,4]triazolo[1,5-d][1,4]benzodiazepine (75 mg, 0.18 mmol) using 2-hydroxy-ethylamine instead of 4-aminotetrahydropyrane was converted to the title compound (27 mg, 38%) which was obtained as a light yellow solid. MS: m/e=409.0/411.0 [M+H]$^+$.

EXAMPLE 70

3-Bromo-10-chloro-6-methoxycarbonylmethyl-9H-imidazo[1,5-a][1,2,4]triazolo[1,5-d][1,4]benzodiazepine To a solution of 3-bromo-6-carboxymethyl-10-chloro-9H-imidazo[1,5-a][1,2,4]triazolo[1,5-d][1,4]benzodiazepine (150 mg, 0.38 mmol) in DMF (5 mL) was added at ambient temperature 1,1'-carbonyl-diimidazole (68 mg, 0.42 mmol) and the reaction mixture was stirred for 15 min at this temperature and 30 min at 50° C. After addition of methanol (1 mL) it was stirred for 4 h at ambient temperature. The reaction mixture was poured onto aqueous sodium carbonate (0.5 M) and was extracted with dichloromethane. Drying over sodium sulfate and purification by chromatography (SiO$_2$, ethyl acetate:cyclohexane=4:1) afforded the title compound (86 mg, 55%) as a white solid. MS m/e: 407.0/408.9 [M+H]$^+$.

EXAMPLE 71

3-Bromo-10-chloro-6-{[(pyridin-3-ylmethyl)-amino]-methyl}-9H-imidazo[1,5-a][1,2,4]triazolo[1,5-d][1,4]benzodiazepine As described for example 66, 3-bromo-6-bromomethyl-10-chloro-9H-imidazo[1,5-a][1,2,4]triazolo[1,5-d][1,4]benzodiazepine (75 mg, 0.18 mmol) using ethyl-pyridin-3ylmethyl-amine instead of 4-aminotetrahydropyrane was converted to the title compound (27 mg, 34%) which was obtained as a light yellow foam. MS: m/e=456.1/458.0 [M+H]$^+$.

EXAMPLE 72

3-Bromo-10-chloro-6-(3-methyl-[1,2,4]oxadiazol-5-ylmethyl)-9H-imidazo[1,5-a][1,2,4]triazolo[1,5-d][1,4]benzodiazepine To a solution of 3-bromo-6-carboxymethyl-10-chloro-9H-imidazo[1,5-a][1,2,4]triazolo[1,5-d][1,4]benzodiazepine (150 mg, 0.38 mmol) in DMF (5 mL) was added at ambient temperature 1,1'-carbonyl-diimidazole (68 mg, 0.42 mmol) and the reaction mixture was stirred for 15 min at this temperature and 30 min at 50° C. After addition of N-hydroxyacetamidine (31 mg, 0.42 mmol) it was stirred for 4 h at 110° C. Acetic acid (1 drop) was added and stirring continued at 130° C. for 3 h. After cooling to ambient temperature the reaction mixture was poured onto aqueous sodium carbonate (0.5 M) and was extracted with dichloromethane. Drying over sodium sulfate and purification by chromatography (SiO$_2$, ethyl acetate:cyclohexane=4:1) afforded the title compound (93 mg, 57%) as a white solid. MS m/e: 432.0/434.0 [M+H]$^+$.

EXAMPLE 73

3-Bromo-10-chloro-6-(5-methyl-[1,2,4]oxadiazol-3-ylmethyl)-9H-imidazo[1,5-a][1,2,4]triazolo[1,5-d][1,4]benzodiazepine To a mixture of hydroxylamine hydrochloride (50 mg, 0.73 mmol) and triethylamine (73 mg, 0.72 mmol) in DMF (4 mL) was added 3-bromo-10-chloro-6-cyanomethyl-9H-imidazo[1,5-a][1,2,4]triazolo[1,5-d][1,4]benzodiazepine (150 mg, 0.40 mmol) and the resulting mixture was stirred for 16 h at ambient temperature. It was concentrated, acetic anhydride (82 mg, 1.24 mmol) was added and the mixture heated to 110° C. for 1 h and 130° C. for 4 h. After cooling to ambient temperature the reaction mixture was poured onto aqueous sodium carbonate (half saturated) and then extracted with dichloromethane. Drying over sodium sulfate and purification by chromatography (SiO$_2$, ethyl acetate:cyclohexane=2:1) afforded the title compound (34 mg, 20%) as a white solid. MS m/e: 433.0/435.0 [M+H]$^+$.

EXAMPLE 74

3-Bromo-10-chloro-6-(tetrahydro-pyran-4-ylcarbamoyl)-9H-imidazo[1,5-a][1,2,4]triazolo[1,5-d][1,4]benzodiazepine a) 3-Bromo-10-chloro-9H-imidazo[1,5-a][1,2,4]triazolo[1,5-d][1,4]benzodiazepine-6-carboxylic acid 3-Bromo-10-chloro-6-formyl-9H-imidazo[1,5-a][1,2,4]triazolo[1,5-d][1,4]benzodiazepine (450 mg, 1.23 mmol) was dissolved in THF (28 mL) and tert-butanol (62 mL) and 2-methyl-2-butene (100 mg, 1.42 mmol) added. After addition of sodium chlorite (419 mg, 3.70 mmol) and a solution of sodium dihydrogenphosphate (667 mg, 5.55 mmol) in water (5 mL) the reaction mixture was stirred for 1 h at ambient temperature. The solid was filtered off, washed with water and diethylether. Drying in vacuo afforded the tide compound (450 mg, 96%) as a white solid. MS m/e: 378.3/380.2 [M−H]$^-$.

b) 3-Bromo-10-chloro-6-(tetrahydro-pyran-4-ylcarbamoyl)-9H-imidazo[1,5-a][1,2,4]triazolo[1,5-d][1,4]benzodiazepine As described for example 61b, 3-bromo-10-chloro-9H-imidazo[1,5-a][1,2,4]triazolo[1,5-d][1,4]benzodiazepine-6-carboxylic acid (70 mg, 0.18 mmol) instead of 3-bromo-6-carboxymethyl-10-chloro-9H-imidazo[1,5-a][1,2,4]triazolo[1,5-d][1,4]benzodiazepine using 4-aminotetrahydropyrane instead of cyclopentylamine was converted to the title compound (21 mg, 23%) which was obtained as a white solid. MS: m/e=462.0/464.1 [M+H]$^+$.

EXAMPLE 75

3-Bromo-10-chloro-6-(cyclopropylmethyl-carbamoyl)-9H-imidazo[1,5-a][1,2,4]triazolo[1,5-d][1,4]benzodiazepine As described for example 61b, 3-bromo-10-chloro-9H-imidazo[1,5-a][1,2,4]triazolo[1,5-d][1,4]benzodiazepine-6-carboxylic acid (70 mg, 0.18 mmol) instead of 3-bromo-6-carboxymethyl-10-chloro-9H-imidazo[1,5-a][1,2,4]triazolo[1,5-d][1,4]benzodiazepine using cyclopropylmethylamine instead of cyclopentylamine was converted to the title compound (19 mg, 21%) which was obtained as a white solid. MS: m/e=432.1/434.1 [M+H]$^+$.

EXAMPLE 76

3-Bromo-10-chloro-6-(cyclopentyl-carbamoyl)-9H-imidazo[1,5-a][1,2,4]triazolo[1,5-d][1,4]benzodiazepine As described for example 61b, 3-bromo-10-chloro-9H-imidazo[1,5-a][1,2,4]triazolo[1,5-d][1,4]benzodiazepine-6-carboxylic acid (70 mg, 0.18 mmol) instead of 3-bromo-6-carboxymethyl-10-chloro-9H-imidazo[1,5-a][1,2,4]triazolo[1,5-d][1,4]benzodiazepine was converted to the title compound (27 mg, 33%) which was obtained as a white solid. MS: m/e=447.0/449.0 [M+H]$^+$.

EXAMPLE 77

3-Bromo-10-chloro-6-(5-methyl-[1,3,4]oxadiazol-2-ylmethyl)-9H-imidazo[1,5-a][1,2,4]triazolo[1,5-d][1,4]benzodiazepine To a suspension of 3-bromo-6-carboxymethyl-10-chloro-9H-imidazo[1,5-a][1,2,4]triazolo[1,5-d][1,4]benzodiazepine (100 mg, 0.25 mmol) in dichloromethane (10 mL) were then added acetic acid hydrazide (19 mg, 0.25 mmol) and 2-chloro-1,3-dimethyl-imidazolidiniumhexafluorophosphate (148 mg, 0.53 mmol) at ambient temperature. After dropwise addition of triethylamine (103 mg, 1.02 mmol) the resulting mixture was stirred for 18 h at this temperature. Water (30 mL) and aqueous sodium hydroxide (1 M, 5 mL) were added and extracted with dichloromethane. Drying over sodium sulfate and purification by chromatography ($SiO_2$, ethyl acetate:dichloromethane=20:80 to 100:0) afforded the title compound (12 mg, 11%) as a yellow solid. MS m/e: 432.0/434.0 [M+H]$^+$.

EXAMPLE 78

3-Bromo-10-chloro-6-((S)-4-Isopropyl-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (S)-4-isopropyl-2-oxazolidinone instead of 2-pyrrolidone was converted to the title compound (65 mg, 58%) which was obtained as a white foam. MS: m/e=476.9/479.0 [M+H]$^+$.

EXAMPLE 79

3-Bromo-10-chloro-6-((R)-4-Isopropyl-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (R)-4-isopropyl-2-oxazolidinone instead of 2-pyrrolidone was converted to the title compound (57 mg, 51%) which was obtained as a white foam. MS: m/e=477.0/479.1 [M+H]$^+$.

EXAMPLE 80

6-((S)-4-Benzyl-2-oxo-oxazolidin-3-ylmethyl)-3-bromo-10-chloro-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (S)-4-benzyl-2-oxazolidinone instead of 2-pyrrolidone was converted to the title compound (70 mg, 57%) which was obtained as a white foam. MS: m/e=525.0/527.0 [M+H]$^+$.

EXAMPLE 81

6-((R)-4-Benzyl-2-oxo-oxazolidin-3-ylmethyl)-3-bromo-10-chloro-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (R)-4-benzyl-2-oxazolidinone instead of 2-pyrrolidone was converted to the title compound (48 mg, 39%) which was obtained as a white foam. MS: m/e=525.0/526.9 [M+H]$^+$.

EXAMPLE 82

3-Bromo-10-chloro-6-((S)-4-phenyl-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (S)-4-phenyl-2-oxazolidinone instead of 2-pyrrolidone was converted to the title compound (86 mg, 72%) which was obtained as a white foam. MS: m/e=511.1/513.0 [M+H]$^+$.

EXAMPLE 83

3-Bromo-10-chloro-6-(5-methoxymethyl-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using 5-methoxymethyl-oxazolidin-2-one instead of 2-pyrrolidone was converted to the title compound (77 mg, 69%) which was obtained as a white foam. MS: m/e=479.1/481.1 [M+H]$^+$.

EXAMPLE 84

3-Bromo-6-(2-furyl)-10-methyl-9H-imidazo[1,5-a][1,2,4]triazolo[1,5-d][1,4]benzodiazepine hydrochloride (1:1)

a) 5-Bromo-2-(4-methyl-imidazol-1-yl)-benzonitrile

A mixture of 5-bromo-2-fluorobenzonitrile (25.0 g, 125 mmol), 4-methylimidazole (12.5 g, 152 mmol), potassium carbonate (34.55 g, 250 mmol) in DMSO (500 mL) was stirred at 90° C. for 16 h. Water (1.5 L) was added and the resulting suspension was stirred with ice-bath cooling for 1 h. The precipitate was then filtered off, washed with water (0.5 L) and dried at 50° C. over KOH. The resulting raw material (25.6 g) was dissolved in boiling ethyl acetate (300 mL). After addition of diisopropylether (300 mL) the solution was allowed to cool to room temperature. Filtration and drying afforded the title compound (19.35 g, 59%) as a white solid. Mp 166° C.

b) 5-Bromo-2-(5-dimethylaminomethyl-4-methyl-imidazol-1-yl)-benzonitrile

A solution of 5-bromo-2-(4-methyl-imidazol-1-yl)-benzonitrile (11.0 g, 42.0 mmol) and N,N-dimethylmethyleneiminium chloride (5.0 g, 53.4 mmol) in DMF (75 mL) was stirred at 90° C. for 16 h. The solvent was evaporated and the oily residue was partitioned between saturated aqueous sodium bicarbonate solution and ethyl acetate. The organic phase was dried over sodium sulfate, concentrated and chromatographed (SiO$_2$, dichloromethane:methanol=1000:0 to 965:35) to afford the title compound as an oil that solidifies on standing (10.62 g, 79%). MS: m/e=321.3/319.2 [M+H]$^+$.

c) [3-(4-Bromo-2-cyano-phenyl)-5-methyl-3H-imidazol-4-ylmethyl]-trimethyl-ammonium; iodide A solution of 5-bromo-2-(5-dimethylaminomethyl-4-methyl-imidazol-1-yl)-benzonitrile (5.57 g, 17.4 mmol) in dichloromethane (130 mL) was treated with methyl iodide (1.3 mL, 20.9 mmol) and kept at 4° C. for 72 h. The white crystalline material formed was filtered off and dried. Yield 6.4 g (80%) MS: m/e=276.0/274.0 [M−NMe$_3$]$^+$.

d) 3-Bromo-6-(2-furyl)-10-methyl-9H-imidazo[1,5-a][1,2,4]triazolo[1,5-d][1,4]benzodiazepine hydrochloride (1:1)

A mixture of [3-(4-bromo-2-cyano-phenyl)-5-methyl-3H-imidazol-4-ylmethyl]trimethyl-ammonium; iodide (462 mg, 1 mmol) and 2-furoic acid hydrazide (151 mg, 1.2 mmol) in DMF (5 mL) was stirred at 120° C. for 6 h, then the mixture was heated to 150° C. for another 12 h. After cooling to rt water (20 mL) was added, the precipitate filtered off and dried. Treatment with HCl in methanol and crystallization from methanol/diethylether afforded the title compound as a light brown solid (100 mg, 24%). MS: m/e=383.9/382.1 [M+H]$^+$.

EXAMPLE 85

3-Bromo-10-methyl-6-(2-pyridinyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with 2-picolinyl hydrazide. After aqueous workup the free base of the title compound was filtered off. Treatment with HCl in methanol and crystallization from methanol/diethylether afforded the title compound as a light brown solid (yield: 40%). MS: m/e=394.9/393.0 [M+H]$^+$.

EXAMPLE 86

3-Bromo-10-methyl-6-propyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with butyric acid hydrazide. After aqueous workup and crystallization from ethyl acetate the title compound was obtained as an off-white solid (yield: 5%). MS: m/e=360.0/358.0 [M+H]$^+$.

EXAMPLE 87

3-Bromo-6-methoxymethyl-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with methoxyacetic acid hydrazide. After evaporation of the solvent and crystallization from methanol the title compound was obtained as a white solid (yield: 42%). MS: m/e=362.1/360.1 [M+H]$^+$.

EXAMPLE 88

3-Bromo-10-methyl-6-(5-methyl-pyrazol-3-yl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with 3-methylpyrazole-5-carboxylic acid hydrazide. After evaporation of the solvent the residue was stirred with ethyl acetate and water. The insoluble material was then filtered off, dried and chromatographed (SiO$_2$, dichloromethane:methanol=1000:0 to 965:35). Crystallization from methanol afforded the title compound as a white solid (yield: 8%). MS: m/e=398.0/395.8 [M+H]$^+$.

EXAMPLE 89

3-Bromo-6-tert.-butyl-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with pivalic acid hydrazide. After evaporation of the solvent the residue was stirred with methanol. The mixture was filtered and the filtrate was concentrated and chromatographed (SiO$_2$, dichloromethane:methanol=1000:0 to 965:35). Triturationwith hexane afforded the title compound as a light yellow solid (yield: 3%). MS: m/e=373.9/372.0 [M+H]$^+$.

EXAMPLE 90

3-Bromo-6-cyclopropyl-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with cyclopropane carboxylic acid hydrazide. After evaporation of the solvent the residue was triturated with methanol to afford the title compound as an off-white solid (yield: 15%). MS: m/e=357.9/356.1 [M+H]$^+$.

EXAMPLE 91

3-Bromo-6-cyclobutyl-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with cyclobutane carboxylic acid hydrazide (Ikekwere, P. O.; Patel, K. S.; Nwabueze, J. N.; Synthesis and Reactivity in Inorganic and Metal- Organic Chemistry (1989), 19(6), 599-612). After evaporation of the solvent the residue was triturated with methanol to afford the title compound as an off-white solid (yield: 32%). MS: m/e=372.0/369.9 [M+H]$^+$.

EXAMPLE 92

3-Bromo-6-cyclopropylmethyl-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with cyclopropylacetic acid hydrazide (Oae, Shigeru et al. Journal of the Chemical Society, Perkin Transactions 2: Physical Organic Chemistry (1972-1999) (1974), (15), 1844-8). After evaporation of the solvent the residue was chromatographed (SiO$_2$, dichloromethane:methanol=1000:0 to 965:35). Trituration with hexane afforded the title compound as a light yellow solid (yield: 5%). MS: m/e=372.0/369.9 [M+H]$^+$.

EXAMPLE 93

(rac.)-3-Bromo-6-(1-formyl-piperidine-3yl)-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (rac.)-piperidine-3-carboxylic acid hydrazide (Alanine, Alexander et al. Bioorganic & Medicinal Chemistry Letters (2004), 14(3), 817-822). After evaporation of the solvent the residue was chromatographed (SiO$_2$, dichloromethane:methanol=100:0 to 97:3). Trituration with diethylether afforded the title compound as a light brown solid (yield: 22%). MS: m/e=429.1/427.1 [M+H]$^+$.

EXAMPLE 94

3-Bromo-6-ethyl-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with propionic acid hydrazide. After evaporation of the solvent the residue was triturated with methanol to afford the title compound as a light grey solid (yield: 26%). MS: m/e=345.9 343.9 [M+H]$^+$.

EXAMPLE 95

3-Bromo-6-(but-3-enyl)-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with pent-4-enoic acid hydrazide (Gilchrist, Thomas L.; Richards, Pamela; Synthesis (1983), (2), 153-4). After evaporation of the solvent the residue was chromatographed (SiO$_2$, dichloromethane:methanol=100:0 to 97:3). Trituration with diethylether afforded the title compound as a light yellow solid (yield: 32%). MS: m/e=372.1/370.0 [M+H]$^+$.

EXAMPLE 96

(S)-3-Bromo-10-methyl-6-(5-oxo-pyrrolidin-2-yl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (S)-5-oxo-pyrrolidine-2-carboxylic acid hydrazide (Angier, R. B. et al. Journal of the American Chemical Society (1950), 72, 74-7). After evaporation of the solvent the residue was triturated with methanol to afford the title compound as a light grey solid (yield: 53%). MS: m/e=401.2/399.1 [M+H]$^+$.

EXAMPLE 97

3-Bromo-10-methyl-6-(3-methyl-butyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with 4-methyl-pentanoic acid hydrazide (Reitz, David B. Preparation of (triazolylmethyl)biphenyl as cardiovascular agents. PCT Int. Appl. (1991), WO 9117148 A1). After evaporation of the solvent the residue was triturated with methanol to afford the title compound as a light yellow solid (yield: 21%). MS: m/e=388.0/386.0 [M+H]$^+$.

EXAMPLE 98

3-Bromo-10-methyl-6-(2-methyl-propyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with 3-methyl-butyric acid hydrazide. After evaporation of the solvent the residue was chromatographed (SiO$_2$, dichloromethane:methanol=100:0 to 97:3). Trituration with diisopropylether afforded the title compound as a light yellow solid (yield: 36%). MS: m/e=373.9/372.0 [M+H]$^+$.

EXAMPLE 99

3-Bromo-6-ethoxy-methyl-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with ethoxy-acetic acid hydrazide (Brands, Michael et. al. Preparation of azinyl- and azolylsulfones as chemokine IL-8 receptor binding inhibitors. Brit. UK Pat. Appl. (2003), GB 2379218 A1). Upon cooling to rt the title compound crystallized from the reaction mixture as a white solid (yield: 23%). MS: m/e=376.0/373.9 [M+H]$^+$.

EXAMPLE 100

(rac.)-3-Bromo-10-methyl-6-(tetrahydro-furan-3-yl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (rac.)-tetrahydro-furan-3-carboxylic acid hydrazide. After evaporation of the solvent the residue was chromatographed (SiO$_2$, dichloromethane:methanol=100:0 to 97:3). Trituration with diisopropylether afforded the title compound as a light yellow solid (yield: 43%). MS: m/e=388.0/385.9 [M+H]$^+$.

EXAMPLE 101

3-Bromo-10-methyl-6-(2-oxo-pyrrolidin-1-ylmethyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (2-oxo-pyrrolidin-1-yl)-acetic acid hydrazide. After evaporation of the solvent the residue was chromatographed (SiO$_2$, dichloromethane:methanol=100:0 to 97:3). Trituration with diisopropylether afforded the title compound as a light brown solid (yield: 32%). MS: m/e=415.0/413.0 [M+H]$^+$.

EXAMPLE 102

(rac.)-3-Bromo-6-(1-hydroxy-ethyl)-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (rac.)-lacthydrazide. Upon cooling to rt the title compound crystallized from the reaction mixture as a white solid (yield: 33%). MS: m/e=362.0/359.9 [M+H]$^+$.

EXAMPLE 103

3-Bromo-10-methyl-6-(2-methyl-cyclopropyl)-9H-imidazo[1,5-a][1,2,4]triazolo[1,5-d][1,4]benzodiazepine (mixture of isomers)

As described for example 84d, [3-(4-bromo-2-cyano-phenyl)-5-methyl-3H-imidazol-4-ylmethyl]-trimethyl-ammonium; iodide (example 84c) was reacted with 2-methyl-cyclopropanecarboxylic acid hydrazide (mixture of isomers) (Rector, Douglas L.; Conder, George A.; Folz, Sylvester D. Anthelmintic pyridinyl acylhydrazones. PCT Int. Appl. (1986), WO 8604582 A1). After evaporation of the solvent the residue was chromatographed (SiO$_2$, dichloromethane:methanol=100:0 to 97:3). Trituration with diisopropylether afforded the title compound as a light brown solid (yield: 32%). MS: m/e=372.1/370.0 [M+H]$^+$.

EXAMPLE 104

3-Bromo-6-(2,2,-dimethyl-propyl)-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with 3,3-dimethyl-butyric acid hydrazide. After evaporation of the solvent the residue was chromatographed (SiO$_2$, dichloromethane:methanol=100:0 to 97:3). Trituration with diisopropyl ether afforded the title compound as a light grey solid (yield: 11%). MS: m/e=388.2/386.1 [M+H]$^+$.

EXAMPLE 105

3-Bromo-6-(2-methoxy-ethyl)-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with 3-methoxy-propionic acid hydrazide. Upon cooling to rt the title compound crystallized from the reaction mixture as a white solid (yield: 45%). MS: m/e=376.2/374.1 [M+H]$^+$.

EXAMPLE 106

3-Bromo-6-(1H-imidazol-4-yl)-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with 3H-imidazole-4-carboxylic acid hydrazide (Nulu, J. R.; Nematollahi, Jay. Journal of Medicinal Chemistry (1969), 12(5), 804-6). After evaporation of the solvent the residue was chromatographed (SiO$_2$, dichloromethane:methanol=100:0 to 97:3). A second chromatographic purification (SiO$_2$, dichloromethane:methanol:aq.ammonia (25%)=100:0:0 to 180:10:1) and trituration with methanol afforded the title compound as a light yellow solid (yield: 5%). MS: m/e=384.1/382.0 [M+H]$^+$.

EXAMPLE 107

3-Bromo-10-methyl-6-(5-methyl-1H-imidazol-4-yl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with 5-methyl-3H-imidazole-4-carboxylic acid hydrazide (Herke, Juergen; Schunack, Walter. European Journal of Medicinal Chemistry (1979), 14(3), 203-6). After evaporation of the solvent the residue was chromatographed (SiO$_2$, dichloromethane:methanol:aq.ammonia (25%)=100:0:0 to 180:10:1) and trituration with methanol afforded the title compound as a white solid (yield: 4%). MS: m/e=398.1/396.1 [M+H]$^+$.

EXAMPLE 108

3-Bromo-10-methyl-6-(2,2,2-trifluoro-ethyl)-9H-imidazo[1,5-a][1,2,4]triazolo[1,5-d][1,4]benzodiazepine a) 3,3,3-Trifluoro-propionic acid hydrazide A solution of 3,3,3-trifluoro-propionic acid methyl ester (24.6 g, 173 mmol) in methanol (173 mL) was treated with hydrazine hydrate (8.4 mL, 173 mmol). The resulting mixture was then heated under reflux for 16 h and filtered. The filtrate was adsorbed on silica, evaporated and chromatographed (SiO$_2$, dichloromethane:methanol=95:5 to 90:10). The title compound (14.2 g, 58%) was obtained as a white solid. MS: m/e=142.1 [M]$^+$.

b) 3-Bromo-10-methyl-6-(2,2,2-trifluoro-ethyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with 3,3,3-trifluoropropionic acid hydrazide. After evaporation of the solvent the residue was chromatographed (SiO$_2$, dichloromethane:methanol=100:0 to 97:3). Trituration with diisopropylether afforded the title compound as a white solid (yield: 43%). MS: m/e=400.0/398.1 [M+H]$^+$.

EXAMPLE 109

3-Bromo-6-(1,5,-dimethyl-1H-pyrazol-3-yl)-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with 1,5-dimethyl-1H-pyrazole-3-carboxylic acid hydrazide. After evaporation of the solvent the residue was chromatographed (SiO$_2$, dichloromethane:methanol=100:0 to 97:3). Crystallization from methanol afforded the title compound as a white solid (yield: 11%). MS: m/e=412.1/410.1 [M+H]$^+$.

EXAMPLE 110

3-Bromo-10-methyl-6-(1-methyl-1H-pyrazol-3-yl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with 1-methyl-1H-pyrazole-3-carboxylic acid hydrazide. After evaporation of the solvent the residue was chromatographed (SiO$_2$, dichloromethane:methanol=100:0 to 97:3). Trituration with diisopropylether afforded the title compound as a light brown solid (yield: 15%). MS: m/e=398.0/395.8 [M+H]$^+$.

EXAMPLE 111

3-Bromo-10-methyl-6-(1-methyl-1H-pyrazol-4-yl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with 1-methyl-1H-pyrazole-4-carboxylic acid hydrazide. Upon cooling to rt the title compound crystallized from the reaction mixture as a white solid (yield: 57%). MS: m/e=398.1/396.1 [M+H]$^+$.

EXAMPLE 112

(rac.)-3-Bromo-10-methyl-6-(tetrahydro-furan-2-ylmethyl)-9H-imidazo[1,5-a][1,2,4]triazolo[1,5-d][1,4]benzodiazepine hydrochloride (1:1)

a) (rac.)-(Tetrahydro-furan-2-yl)-acetic acid hydrazide

A solution of (rac.)-(tetrahydro-furan-2-yl)-acetic acid ethyl ester (3.84 g, 24 mmol) in n-butanol (24 mL) was treated with hydrazine hydrate (1.4 mL, 29 mmol) and the resulting mixture was then heated under reflux for 3 h. The solvent was evaporated and residual volatile components were azeotropically removed by coevaporation with toluene. Chromatographic purification (SiO$_2$, dichloromethane:methanol:aq.ammonia (25%)=100:0:0 to 90:10:1) afforded the title compound as a viscous, colorless oil (1.1 g, 32%). $^1$H-NMR (300 MHz, DMSO): δ=1.45 (mc, 1H), 1.70-1.95 (m, 3H), 2.13 (dd, J=6 Hz, J=14 Hz, 1H), 2.24 (dd, J=7 Hz, J=14 Hz, 1H), 3.56 (dd, J=8 Hz, J=14 Hz, 1H), 3.72 (dd, J=7 Hz, J=14 Hz, 1H), 4.05 (mc, 1H), 4.16 (s, 2H), 8.94 (s, 1H).

b) (rac.)-3-Bromo-10-methyl-6-(tetrahydro-furan-2-ylmethyl)-9H-imidazo[1,5-a][1,2,4]triazolo][1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (rac.)-(tetrahydro-furan-2-yl)-acetic acid hydrazide. After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as an off-white solid (yield: 35%). MS: m/e=402.0/399.9 [M+H]$^+$.

EXAMPLE 113

3-Bromo-10-methyl-6-(pyrrolidin-1-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with pyrrolidin-1-yl-acetic acid hydrazide (Lyakhova, E. A. et al. Pharmaceutical Chemistry Journal (Translation of Khimiko-Farmatsevticheskii Zhurnal) (2003), 37(4), 178-183). After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as an off-white solid (yield: 40%). MS: m/e=401.0/398.9 [M+H]$^+$.

EXAMPLE 114

3-Bromo-10-methyl-6-(pyridine-2-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with pyridine-2-yl-acetic acid hydrazide (Cemischev, B.; Popov, D.; Pharmazie (1967), 22(8), 432-4). After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as an off-white solid (yield: 4%). MS: m/e=409.2/407.1 [M+H]$^+$.

EXAMPLE 115

3-Bromo-6-methanesulfonylmethyl-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with methanesulfonyl-acetic acid hydrazide (Bays) David Edmund; Carey, Linda; Hayes, Roger. 3,5-Disubstituted-1,2,4-triazole compounds and pharmaceutical compositions containing them.

Eur. Pat. Appl. (1982), EP 50407). After evaporation of the solvent the residue was triturated with methanol and the title compound was obtained as the free base. Treatment with HCl in methanol and crystallization from methanol/diethylether afforded the title compound as a light grey solid (yield: 72%). MS: m/e=410.0/408.1 [M+H]$^+$.

EXAMPLE 116

3-Bromo-10-methyl-6-(1-methyl-1H-pyrrol-2-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (1-methyl-1H-pyrrol-2-yl)-acetic acid hydrazide. After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as an orange solid (yield: 6%). MS: m/e=411.1/409.2 [M+H]$^+$.

EXAMPLE 117

3-Bromo-10-methyl-6-(pyridine-3-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with pyridine-3-yl-acetic acid hydrazide (Cemischev, B.; Popov, D.; Pharmazie (1967), 22(8), 432-4). After evaporation of the solvent the residue was triturated with methanol and the title compound was obtained as the free base. Treatment with HCl in methanol and crystallization from methanol/diethylether afforded the title compound as a light grey solid (yield: 10%). MS: m/e=409.2/407.1 [M+H]$^+$.

EXAMPLE 118

3-Bromo-6-(cyclohexylmethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with cyclohexyl-acetic acid hydrazide. After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a white solid (yield: 25%). MS: m/e=414.1/412.0 [M+H]$^+$.

EXAMPLE 119

3-Bromo-10-methyl-6-(3-oxo-morpholin-4-ylmethyl)-9H-imidazo[1,5-a][1,2,4]triazolo[1,5-d][1,4]benzodiazepine hydrochloride (1:1)

a) (3-Oxo-morpholin-4-yl)-acetic acid ethyl ester
A solution of 3-oxo-morpholine (6.5 g, 4 mmol) (Willey, Alan David; Kott, Kevin Lee; Miracle, Gregory Scot; Gosselink, Eugene Paul; Burckett-St. Laurent, James Charles Theophile Roger. Bleaching compositions containing bleach activators having alpha-modified lactam leaving-groups. PCT Int. Appl. (1996), WO 9622350 A1) in DMF (45 mL) was treated at rt in 3 portions with sodium hydride (3.34 g, 60% dispersion in mineral oil, 84 mmol). After 30 min a solution of ethyl bromoacetate (11.8 g, 71 mmol) in DMF (20 mL) was added dropwise. After 3 h the solvent was evaporated, the residue was taken up with ethyl acetate and washed with water. The organic phase was dried over sodium sulfate, concentrated and chromatographed (SiO$_2$, dichloromethane:methanol=1000:0 to 995:5). The title compound was obtained as a light yellow oil (3.34 g, 28%). $^1$H-NMR (300 MHz, DMSO): δ=1.19 (t, J=7 Hz, 3H), 3.40 (mc, 2H), 3.85 (mc, 2H), 4.05-4.28 (m, 6H)

b) (3-Oxo-morpholin-4-yl)-acetic acid hydrazide
As described for example 112a, (3-oxo-morpholin-4-yl)-acetic acid ethyl ester in butanol was reacted with hydrazine hydrate at 100° C. for 6 h. Evaporation of all volatiles and chromatography (SiO$_2$, dichloromethane:methanol:aq.ammonia (25%)=100:0:0 to 90:10:1) afforded the title compound as a white solid (yield: 56%). MS: m/e=174.4 [M+H]$^+$.

c) 3-Bromo-10-methyl-6-(3-oxo-morpholin-4-ylmethyl)-9H-imidazo[1,5-a][1,2,4]triazolo[1,5-d][1,4]benzodiazepine hydrochloride (1:1)
As described for example 84d, [3-(4-bromo-2-cyano-phenyl)-5-methyl-3H-imidazol-4-ylmethyl]-trimethyl-ammonium; iodide (example 84c) was reacted with (3-oxo-morpholin-4-yl)-acetic acid hydrazide. After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as an off-white solid (yield: 54%). MS: m/e=430.9/429.0 [M+H]$^+$.

EXAMPLE 120

3-Bromo-10-methyl-6-(pyrazin-2-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with pyrazin-2-yl-acetic acid hydrazide (Kushner, S et. al. Journal of the American Chemical Society (1952), 74 3617-21). After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a light brown solid (yield: 30%). MS: m/e=410.1/408.2 [M+H]$^+$.

EXAMPLE 121

3-Bromo-10-methyl-6-(pyridine-4-carbonyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with pyridin-4-yl-acetic acid hydrazide (Iwao, Masatomo; Kuraishi, Tsukasa. Journal of Heterocyclic Chemistry (1978), 15(8), 1425-30). After evaporation of the solvent the residue was chromatographed (SiO$_2$, dichloromethane:methanol:aq.ammonia (25%)=100:0:0 to 300:10:1). Trituration with diisopropylether afforded the title compound as a light yellow solid (yield: 4%). MS: m/e=422.0/420.0 [M]$^+$.

EXAMPLE 122

3-Bromo-10-methyl-6-(pyridine-4-ylmethyl)-9H-imidazo[1,5-a][1,2,4]triazolo[1,5-d][1,4]benzodiazepine In the chromatographic purification step of 3-bromo-10-methyl-6-(pyridine-4-carbonyl)-9H-imidazo[1,5-a][1,2,4]triazolo[1,5-d][1,4]benzodiazepine (example 121) the title compound eluted from the column as a second (more polar) compound. Trituration with diisopropylether provided a white solid (yield: 6%). MS: m/e=409.2/407.2 [M+H]$^+$.

EXAMPLE 123

3-Bromo-10-methyl-6-(3-methyl-isoxazol-5-ylmethyl)-9H-imidazo[1,5-a][1,2,4]triazolo[1,5-d][1,4]benzodiazepine a) (3-Methyl-isoxazol-5-yl)-acetic acid hydrazide A solution of 3-methyl-5-isoxazole acetic acid (10.2 g, 72.6 mmol) in methanol (100 mL) was treated with p-toluene-4-sulfonic acid monohydrate (1.0 g, cat.) and the resulting mixture was then heated under reflux for 4 h. After cooling, the mixture was then evaporated and the brownish residue stirred with saturated sodium bicarbonate solution and diethylether. The organic phase was dried over sodium sulfate and concentrated to afford (3-methyl-isoxazol-5-yl)-acetic acid methyl ester (9.62 g) as a light yellow oil. This was then dissolved in butanol and reacted with hydrazine hydrate As described for example 112a. The resulting mixture was then heated under reflux for 16 h and after cooling and evaporation, the residue was crystallized from n-butanol/toluene to afford the title compound as a white solid (5.30 g). Concentration of the mother liquor provided another crop of solid material (2.95 g, overall yield: 73%). $^1$H-NMR (300 MHz, DMSO): δ=2.19 (s, 3H), 3.25 (s, 2H), 4.29 (s, 2H), 6.17 (s, 1H), 9.29 (s, 1H).

b) 3-Bromo-10-methyl-6-(3-methyl-isoxazol-5-ylmethyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (3-methyl-isoxazol-5-yl)-acetic acid hydrazide. After evaporation of the solvent the residue was triturated with methanol and the title compound was obtained as a white solid (yield: 46%). MS: m/e=412.9/410.9 [M+H]$^+$.

EXAMPLE 124

3-Bromo-10-methyl-6-(6-methyl-pyridin-3-ylmethyl)-9H-imidazo[1,5-a][1,2,4]triazolo[1,5-d][1,4]benzodiazepine a) (6-Methyl-pyridin-3-yl)-acetic acid hydrazide As described for example 112a, (6-methyl-pyridin-3-yl)-acetic acid ethyl ester in butanol was reacted with hydrazine hydrate (2 equivalents) and the resulting mixture was then heated under reflux for 20 h. Evaporation of all volatiles and crystallization from n-butanol and toluene afforded the title compound as a white solid (yield: 72%). $^1$H-NMR (300 MHz, DMSO): δ=2.42 (s, 3H), 3.32 (s, 2H), 4.21 (s, 2H), 7.17 (d, J=8 Hz, 1H), 7.53 (dd, J=2 Hz, J=8 Hz, 1H), 8.30 (d, J=2 Hz, 1H), 9.23 (s, 1H).

b) 3-Bromo-10-methyl-6-(6-methyl-pyridin-3-ylmethyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (6-methyl-pyridin-3-yl)-acetic acid hydrazide. After evaporation of the solvent the residue was triturated with methanol and the title compound was obtained as an off-white solid (yield: 39%). MS: m/e=422.9/420.9 [M+H]$^+$.

EXAMPLE 125

3-Bromo-6-(2,5-dimethyl-thiazol-4-ylmethyl)-10-methyl-9H-imidazo[1,5-a][1,2,4]triazolo[1,5-d][1,4]benzodiazepine a) (2,5-Dimethyl-thiazol-4-yl)-acetic acid hydrazide As described for example 112a, (2,5-dimethyl-thiazol-4-yl)-acetic acid methyl ester in butanol was reacted with hydrazine hydrate (2 equivalents) and the resulting mixture was then heated under reflux for 20 h. Evaporation of all volatiles and crystallization from n-butanol and toluene afforded the title compound as a white solid (yield: 68%). $^1$H-NMR (300 MHz, DMSO): δ=2.31 (s, 3H), 2.51 (s, 3H), 3.37 (s, 2H), 4.20 (s, 2H), 9.10 (s, 1H).

b) 3-Bromo-6-(2,5-dimethyl-thiazol-4-ylmethyl)-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (2,5-dimethyl-thiazol-4-yl)-acetic acid hydrazide. After evaporation of the solvent the residue was triturated with methanol and the title compound was obtained as a white solid (yield: 66%). MS: m/e=443.0/441.0 [M+H]$^+$.

EXAMPLE 126

3-Bromo-6-(imidazol-1-ylmethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with imidazol-1-yl-acetic acid hydrazide (Loccufier, Johan; Lingier, Stefaan; Meeus, Pascal. Photographic material containing a novel hydrazide type. Eur. Pat. Appl. (2001), EP 1085371 A1). After evaporation of the solvent the residue was chromatographed (SiO$_2$, dichloromethane:methanol=100:0 to 96:4) and the title compound was obtained as the free base. Treatment with HCl in methanol and crystallization from methanol/diethylether afforded the title compound as a white solid (yield: 33%). MS: m/e=398.0/395.8 [M+H]$^+$.

EXAMPLE 127

3-Bromo-10-methyl-6-(pyrazol-1-ylmethyl)-9H-imidazo[1,5-a][1,2,4]triazolo[1,5-d][1,4]benzodiazepine hydrochloride (1:1)

a) 3-Bromo-6-chloromethyl-10-methyl-9H-imidazo[1,5-a][1,2,4]triazolo[1,5-d][1,4]benzodiazepine hydrochloride (1:1)

Thionyl chloride ((860 mg, 7.2 mmol) was cooled to 0° C. and 3-bromo-6-hydroxymethyl-10-methyl-9H-imidazo[1,5-a][1,2,4]triazolo[1,5-d][1,4]benzodiazepine (example 37) (0.50 g, 1.4 mmol) was added in 3 portions. The mixture was then stirred for 2 h at rt. After addition of diethylether (20 mL) the precipitate was filtered off and dried to afford the title compound as a light brown solid (0.50 g, 86%). MS: m/e=365.9/364.0 [M+H]$^+$.

b) 3-Bromo-10-methyl-6-(pyrazol-1-ylmethyl)-9H-imidazo[1,5-a][1,2,4]triazolo[1,5-d][1,4]benzodiazepine hydrochloride (1:1)

A solution of pyrazole (47 mg, 0.7 mmol) in DMF (7 mL) was treated in 3 portions with sodium hydride (3×65 mg, 60% dispersion in mineral oil, 4.9 mmol). The mixture was then stirred at rt for 1 h, then cooled in an ice bath and 3-bromo-6-chloromethyl-10-methyl-9H-imidazo[1,5-a][1,2,4]triazolo[1,5-d][1,4]benzodiazepine hydrochloride (1:1) (250 mg, 0.6 mmol) was added in 2 portions. After addition of water (1 mL) and evaporation of all volatiles the residue was extracted with water and dichloromethane. The organic phase was then dried over sodium sulfate and concentrated. Trituration with ethyl acetate and methanol provided the title compound as the free base. Treatment with HCl in methanol and crystallization from methanol/diethylether afforded the title compound as an off-white solid (yield: 13%). MS: m/e=398.1/396.1 [M+H]$^+$.

EXAMPLE 128

3-Bromo-6-(3-hydroxy-isoxazol-5-ylmethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (3-hydroxy-isoxazol-5-yl)-acetic acid hydrazide (Nakamura, Norio. Chemical & Pharmaceutical Bulletin (1971), 19(1), 46-51). After evaporation of the solvent the residue was chromatographed (SiO$_2$, dichloromethane:methanol:aq.ammonia (25%)=100:0:0 to 180:10:1) and the title compound was obtained as the free base. Treatment with HCl in methanol and crystallization from methanol/diethylether afforded the title compound as a light brown solid (yield: 12%). MS: m/e=415.1/413.0 [M+H]$^+$.

EXAMPLE 129

3-Bromo-6-(2-ethyl-imidazol-1-ylmethyl)-10-methyl-9H-imidazo[1,5-a][1,2,4]triazolo[1,5-d][1,4]benzodiazepine hydrochloride (1:1)

a) (2-Ethyl-imidazol-1-yl)-acetic acid ethyl ester

2-Ethyl-imidazole (10.0 g, 104 mmol) was dissolved in acetone (80 mL) and then ethyl bromoacetate (17.4 g, 104 mmol) and potassium carbonate (2.6 g, 18.7 mmol) was added and the resulting mixture was heated under reflux for 12 h. After filtration and evaporation the residue was extracted with water and dichloromethane. The organic phase was dried over sodium sulfate and evaporated to afford the title compound as a light yellow solid (5.76 g, 30%). MS: m/e=183.1 [M+H]$^+$.

b) (2-Ethyl-imidazol-1-yl)-acetic acid hydrazide

As described for example 112a, (2-ethyl-imidazol-1-yl)-acetic acid ethyl ester in butanol was reacted with hydrazine hydrate (1.2 equivalents) at 100° C. for 6 h. Evaporation of all volatiles and crystallization from methanol/diisopropylether afforded the title compound as a white solid (yield: 94%). MS: m/e=169.3 [M+H]$^+$.

c) 3-Bromo-6-(2-ethyl-imidazol-1-ylmethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (2-ethyl-imidazol-1-yl)-acetic acid hydrazide. After evaporation of the solvent the residue was chromatographed (SiO$_2$, dichloromethane:methanol:aq.ammonia (25%)=100:0:0 to 180:10:1) and the title compound was obtained as the free base. Treatment with HCl in methanol and crystallization from methanol/diethylether afforded the title compound as a white solid (yield: 42%). MS: m/e=425.8/424.0 [M+H]$^+$.

EXAMPLE 130

3-Bromo-10-methyl-6-(morpholin-4-ylmethyl)-9H-imidazo[1,5-a][1,2,4]triazolo[1,5-d][1,4]benzodiazepine hydrochloride (1:1)

a) Morpholin-4-yl-acetic acid hydrazide

As described for example 112a, morpholin-4-yl-acetic acid methyl ester in butanol was reacted with hydrazine hydrate (1.2 equivalents) at 100° C. for 1 h. Evaporation of all volatiles and crystallization from n-butanol/toluene afforded the title compound as a white solid (yield: 68%). $^1$H-NMR (300 MHz, DMSO): δ=2.40 (m, 4H), 2.90 (s, 2H), 3.57 (m, 4H), 4.24 (s, 2H), 8.91 (s, 1H).

b) 3-Bromo-10-methyl-6-(morpholin-4-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with morpholin-4-yl-acetic acid hydrazide. After evaporation of the solvent the residue was chromatographed (SiO$_2$, dichloromethane:methanol=100:0 to 95:5) and the title compound was obtained as the free base. Treatment with HCl in methanol and crystallization from methanol/diethylether afforded the title compound as a white solid (yield: 45%). MS: m/e=415.0/417.0 [M+H]$^+$.

EXAMPLE 131

3-Bromo-10-methyl-6-(2-methyl-imidazol-1-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (2-methyl-imidazol-1-yl)-acetic acid hydrazide (Toth, Jozsef et al.

Substituted imidazole derivatives. Hung. (1968), HU 154810). After evaporation of the solvent the residue was chromatographed (SiO$_2$, dichloromethane:methanol:aq.ammonia (25%)=100:0:0 to 180:10:1) and the title compound was obtained as the free base. Treatment with HCl in methanol and crystallization from methanol/diethylether afforded the title compound as a light yellow solid (yield: 18%). MS: m/e=411.9/410.0 [M+H]$^+$.

EXAMPLE 132

3-Bromo-6-(3,5-dimethyl-pyrazol-1-ylmethyl)-10-methyl-9H-imidazo[1,5-a][1,2,4]triazolo[1,5-d][1,4]benzodiazepine hydrochloride (1:1)

As described for example 127b, 3,5-dimethyl-1H-pyrazole was reacted first with sodium hydride, then with 3-bromo-6-chloromethyl-10-methyl-9H-imidazo[1,5-a][1,2,4]triazolo[1,5-d][1,4]benzodiazepine hydrochloride (1:1) (example 127a). Evaporation, extraction and trituration provided the title compound as the free base. Treatment with HCl in methanol and crystallization from methanol/diethylether afforded the title compound as an off-white solid (yield: 13%). MS: m/e=426.1/424.1 [M+H]$^+$.

EXAMPLE 133

3-Bromo-10-methyl-6-(4-methyl-pyrazol-1-ylmethyl)-9H-imidazo[1,5-a][1,2,4]triazolo[1,5-d][1,4]benzodiazepine hydrochloride (1:1)

As described for example 127b, 4-methyl-1H-pyrazole was reacted first with sodium hydride, then with 3-bromo-6-chloromethyl-10-methyl-9H-imidazo[1,5-a][1,2,4]triazolo[1,5-d][1,4]benzodiazepine hydrochloride (1:1) (example 127a). Evaporation, extraction and trituration provided the title compound as the free base. Treatment with HCl in methanol and crystallization from methanol/diethylether afforded the title compound as an off-white solid (yield: 45%). MS: m/e=412.1/410.1 [M+H]$^+$.

EXAMPLE 134

3-Bromo-10-methyl-6-(2-oxo-piperidin-1-ylmethyl)-9H-imidazo[1,5-a][1,2,4]triazolo[1,5-d][1,4]benzodiazepine hydrochloride (1:1)

As described for example 127b, piperidin-2-one was reacted first with sodium hydride, then with 3-bromo-6-chloromethyl-10-methyl-9H-imidazo[1,5-a][1,2,4]triazolo[1,5-d][1,4]benzodiazepine hydrochloride (1:1) (example 127a). Evaporation, extraction and trituration provided the title compound as the free base. Treatment with HCl in methanol and crystallization from methanol/diethylether afforded the title compound as an off-white solid (yield: 14%). MS: m/e=429.3/427.2 [M+H]$^+$.

EXAMPLE 135

3-Bromo-10-methyl-6-(2-oxo-oxazolidin-3-ylmethyl)-9H-imidazo[1,5-a][1,2,4]triazolo[1,5-d][1,4]benzodiazepine hydrochloride (1:1)

As described for example 127b, oxazolidin-2-one was reacted first with sodium hydride, then with 3-bromo-6-chloromethyl-10-methyl-9H-imidazo[1,5-a][1,2,4]triazolo[1,5-d][1,4]benzodiazepine hydrochloride (1:1) (example 127a). Evaporation, extraction and chromatography (SiO$_2$, dichloromethane:methanol=100:0 to 97:3) provided the title compound as the free base. Treatment with HCl in methanol and crystallization from methanol/diethylether afforded the title compound as an off-white solid (yield: 8%). MS: m/e=417.2/415.2 [M+H]$^+$.

EXAMPLE 136

3-Bromo-6-cyanomethyl-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with cyano-acetic acid hydrazide. After evaporation of the solvent the residue was chromatographed (SiO$_2$, dichloromethane:methanol=100:0 to 95:5) and the title compound was obtained as the free base. Treatment with HCl in methanol and crystallization from methanol/diethylether afforded the title compound as an off-white solid (yield: 27%). MS: m/e=357.0/354.9 [M+H]$^+$.

EXAMPLE 137

3-Bromo-6-(1,3-dioxo-1,3-dihydro-isoindol-2-ylmethyl)-10-methyl-9H-imidazo[1,5-a][1,2,4]triazolo[1,5-d][1,4]benzodiazepine A suspension of 3-bromo-6-chloromethyl-10-methyl-9H-imidazo[1,5-a][1,2,4]triazolo[1,5-d][1,4]benzodiazepine hydrochloride (1:1) (example 127a) (0.67 g, 1.8 mmol) in DMF (15 mL) was treated with phtalimide potassium salt. The mixture was stirred at 60° C. for 12 h, poured onto water (50 mL) and the precipitate was filtered off and dried to afford the title compound as an off-white solid (0.64 g, 73%). MS: m/e=476.9/474.9 [M+H]$^+$.

EXAMPLE 138

3-Bromo-6-(isoxazol-5-ylmethyl)-10-methyl-9H-imidazo[1,5-a][1,2,4]triazolo[1,5-d][1,4]benzodiazepine hydrochloride (1:1)

a) Isoxazol-5-yl-acetic acid methyl ester

A suspension of isoxazole-5-carboxylic acid in THF (45 mL) was treated with DMF (0.1 mL, catalytic) and oxalyl chloride (4.6 mL, 54 mmol). After 30 min at rt evolution of gas had ceased and the clear solution was concentrated to provide the acid chloride as a light yellow oil. It was then dissolved in diethylether (45 mL) and ethereal diazomethane solution (180 mL, ~1 M solution) was added at such a rate that the reaction temperature did not exceed 5° C. The reaction mixture was stirred for 30 min at rt, then cooled to −30° C. The precipitated diazoketone was filtered off, dissolved in methanol (45 mL) and treated with a solution of silver nitrate (0.50 g, 2.9 mmol) in triethylamine (6.3 mL) (this method has been described by Newman, M. S.; Beal, P. F. Journal of the American Chemical Society (1950), 72, 5163-5). The reaction mixture was refluxed for 1 h, cooled to rt and filtered. After evaporation of the solvent the residue was chromatographed (SiO$_2$, heptanes:ethyl acetate=100:0 to 70:30) to afford the title compound as a colorless oil (1.33 g, 21%). $^1$H-NMR (300 MHz, DMSO): δ=3.67 (s, 3H), 4.05 (s, 2H), 6.43 (s, 1H), 8.51 (s, 1H).

b) Isoxazol-5-yl-acetic acid hydrazide

As described for example 112a, isoxazol-5-yl-acetic acid methyl ester in butanol was reacted with hydrazine hydrate (2 equivalents) and the resulting mixture was heated under reflux for 4 h. Evaporation of all volatiles and chromatography (SiO$_2$, dichloromethane:methanol:aq.ammonia (25%)=100:0:0 to 90:10:1) afforded the title compound as a white solid (yield: 41%). $^1$H-NMR (300 MHz, DMSO): δ=3.65 (s, 2H), 4.31 (s, 2H), 6.32 (s, 1H), 8.46 (s, 1H), 9.32 (s, 1H).

c) 3-Bromo-6-(isoxazol-5-ylmethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with isoxazol-5-yl-acetic acid hydrazide. After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a yellow solid (yield: 12%). MS: m/e=399.1/397.1 [M+H]$^+$.

EXAMPLE 139

3-Bromo-10-methyl-6-(6-methyl-pyridin-2-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (6-methyl-pyridin-2-yl)-acetic acid hydrazide (Izdebski, Jan. Roczniki Chemii (1965), 39(5), 717-20). After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a yellow solid (yield: 40%). MS: m/e=423.2/421.0 [M+H]$^+$.

EXAMPLE 140

3-Bromo-10-methyl-6-(5-methyl-isoxazol-3-ylmethyl)-9H-imidazo[1,5-a][1,2,4]triazolo[1,5-d][1,4]benzodiazepine a) (5-Methyl-isoxazol-3-yl)-acetic acid methyl ester As described for example 138a, 5-methylisoxazole-3-carboxylate was reacted with oxalyl chloride followed by treatment with diazomethane to provide the respective diazoketone. This was reacted with methanol under silver catalysis. Aqueous workup and chromatographic purification (SiO$_2$, heptanes:ethyl acetate=100:0 to 70:30) afforded the title compound as a colorless oil (yield: 36%). $^1$H-NMR (300 MHz, DMSO): δ=2.38 (s, 3H), 3.64 (s, 3H), 3.75 (s, 2H), 6.20 (s, 1H).

b) (5-Methyl-isoxazol-3-yl)-acetic acid hydrazide

As described for example 112a, (5-methyl-isoxazol-3-yl)-acetic acid methyl ester in butanol was reacted with hydrazine hydrate (2 equivalents) and the resulting mixture was heated under reflux for 90 min. Evaporation of all volatiles afforded the title compound as a white solid (yield: 90%). $^1$H-NMR (300 MHz, DMSO): δ=2.36 (d, J=0.7 Hz, 3H), 3.39 (s, 2H), 4.25 (s, 2H), 6.13 (d, J=0.7 Hz, 1H), 9.27 (s, 1H).

c) 3-Bromo-10-methyl-6-(5-methyl-isoxazol-3-ylmethyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (5-methyl-isoxazol-3-yl)-acetic acid hydrazide. After evaporation of the solvent the residue was chromatographed (SiO$_2$, dichloromethane:methanol=100:0 to 96:4) and triturated with diisopropylether to afford the title compound as a white solid (yield: 43%). MS: m/e=413.2/411.1 [M+H]$^+$.

EXAMPLE 141

3-Bromo-6-(3,5-dimethyl-isoxazol-4-ylmethyl)-10-methyl-9H-imidazo[1,5-a][1,2,4]triazolo[1,5-d][1,4]benzodiazepine a) (3,5-Dimethyl-isoxazol-4-yl)-acetic acid hydrazide As described for example 112a, (3,5-dimethyl-isoxazol-4-yl)-acetic acid ethyl ester (Bacon, Edward R.; Daum, Sol J.; Singh, Baldev. 6-Substituted pyrazolo[3,4-d]pyrimidin-4-ones and compositions and methods of use as c-GMP phosphodiesterase inhibitors. PCT Int. Appl. (1996), WO 9628429 A1) in butanol was reacted with hydrazine hydrate (3.2 equivalents) and the resulting mixture was heated under reflux for 24 h. Evaporation of all volatiles and crystallization from n-butanol/toluene afforded the title compound as a white solid (yield: 87%). MS: m/e=170.2 [M+H]$^+$.

b) 3-Bromo-6-(3,5-dimethyl-isoxazol-4-ylmethyl)-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (3,5-dimethyl-isoxazol-4-yl)-acetic acid hydrazide. After evaporation of the solvent the residue was extracted with ethyl acetate and water. The organic phase was dried over sodium sulfate, concentrated and crystallized from ethyl acetate to afford the title compound as a white solid (yield: 26%). MS: m/e=427.1/425.1 [M+H]$^+$.

EXAMPLE 142

3-Bromo-10-methyl-6-(propionylamino-methyl)-9H-imidazo[1,5-a][1,2,4]triazolo[1,5-d][1,4]benzodiazepine a) 6-Aminomethyl-3-bromo-10-methyl-9H-imidazo[1,5-a][1,2,4]triazolo[1,5-d][1,4]benzodiazepine A suspension of 3-bromo-6-(1,3-dioxo-1,3-dihydro-isoindol-2-ylmethyl)-10-methyl-9H-imidazo[1,5-a][1,2,4]triazolo[1,5-d][1,4]benzodiazepine (example 137) (1.60 g, 3.4 mmol) in ethanol (50 mL) was treated with hydrazine hydrate (0.25 mL, 5.1 mmol) and the resulting mixture was heated under reflux for 2 h. The mixture was cooled to rt, filtered and evaporated. Crystallization from ethanol afforded the title compound as an off-white solid (1.05 g, 90%). MS: m/e=347.1/345.0 [M+H]$^+$.

b) 3-Bromo-10-methyl-6-(propionylamino-methyl)-9H-imidazo[1,5-a][1,2,4]triazolo[1,5-d][1,4]benzodiazepine A suspension of 6-aminomethyl-3-bromo-10-methyl-9H-imidazo[1,5-a][1,2,4]triazolo[1,5-d][1,4]benzodiazepine (0.35 g, 1.0 mmol) in THF (5.0 mL) was treated with triethylamine (0.17 mL, 1.2 mmol) and cooled in an ice bath. After addition of propionyl chloride (0.10 mL, 1.2 mmol) the mixture was stirred for 90 min at rt. The precipitate was filtered off and the filtrate adsorbed on silica. Evaporation and chromatography ($SiO_2$, dichloromethane:methanol:aq.ammonia (25%)=100:0:0 to 130:10:1) followed by crystallization from methanol/diisopropylether afforded the title compound as a white solid (0.16 g, 39%). MS: m/e=403.3/401.1 $[M+H]^+$.

EXAMPLE 143

6-(Acetylamino-methyl)-3-bromo-10-methyl-9H-imidazo[1,5-a][1,2,4]triazolo[1,5-d][1,4]benzodiazepine As described for example 142b, 6-aminomethyl-3-bromo-10-methyl-9H-imidazo[1,5-a][1,2,4]triazolo[1,5-d][1,4]benzodiazepine (example 142a) was reacted with acetyl chloride and triethylamine. After workup and chromatography followed by crystallization from methanol/diisopropylether the title compound was obtained as a white solid (yield: 25%). MS: m/e=389.2/387.1 $[M+H]^+$.

EXAMPLE 144

3-Bromo-6-[(2-methoxy-acetylamino)-methyl]-10-methyl-9H-imidazo[1,5-a][1,2,4]triazolo[1,5-d][1,4]benzodiazepine As described for example 142b, 6-aminomethyl-3-bromo-10-methyl-9H-imidazo[1,5-a][1,2,4]triazolo[1,5-d][1,4]benzodiazepine (example 142a) was reacted with methoxy acetyl chloride and triethylamine. Aqueous workup and chromatography followed by crystallization from methanol/diisopropylether afforded the title compound as a white solid (yield: 59%). MS: m/e=419.1/417.2 $[M+H]^+$.

EXAMPLE 145

3-Bromo-10-methyl-6-(2-methyl-pyridine-4-carbonyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with 2-methyl-pyridin-4-yl-acetic acid hydrazide (Iwao, Masatomo; Kuraishi, Tsukasa. Journal of Heterocyclic Chemistry (1978), 15(8), 1425-30). After evaporation of the solvent the residue was chromatographed ($SiO_2$, dichloromethane:methanol=100:0: to 92:8). Trituration with diethylether afforded the title compound as a light yellow solid (yield: 6%). MS: m/e=437.1/435.2 $[M]^+$.

EXAMPLE 146

3-Bromo-6-formylaminomethyl-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (tert.-butyloxycarbonyl)-amino acetic acid hydrazide (Borg, Susanna et. al. Journal of Organic Chemistry (1995), 60(10), 3112-20). After evaporation of the solvent the residue was chromatographed ($SiO_2$, dichloromethane:methanol=100:0: to 95:5; the title compound eluted after the BOC protected analogue of example 147). Crystallization from methanol/diisopropylether afforded the title compound as an off-white solid (yield: 12%). MS: m/e=375.1/373.1 $[M]^+$.

EXAMPLE 147

3-Bromo-6-(tert.butyloxycarbonylamino-methyl)-10-methyl-9H-imidazo[1,5-a][1,2,4]triazolo[1,5-d][1,4]benzodiazepine

[3-(4-Bromo-2-cyano-phenyl)-5-methyl-3H-imidazol-4-ylmethyl]-trimethyl-ammonium; iodide (example 84c) was reacted with (tert.-butyloxycarbonyl)-amino acetic acid hydrazide (Borg, Susanna et. al. Journal of Organic Chemistry (1995), 60(10), 3112-20) as described in example 146.

After evaporation of the solvent the residue was chromatographed ($SiO_2$, dichloromethane:methanol=100:0: to 95:5). Crystallization from methanol/diisopropylether afforded the title compound (less polar than the formyl-analogue of example 146) as an off-white solid (yield: 12%). MS: m/e=446.9/445.1$[M]^+$.

EXAMPLE 148

3-Bromo-10-methyl-6-(2H-pyrazol-3-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (2H-pyrazol-3-yl)-acetic acid hydrazide (Barker, John M.; Huddleston, Patrick R.; Wood, Michael L. Journal of Chemical Research, Synopses (1992), (9), 291). After evaporation of the solvent the residue was triturated with methanol to afford the free base of the title compound. Treatment with HCl in methanol and crystallization from methanol/diethylether afforded the title compound as a light yellow solid (yield: 38%). MS: m/e=398.0/395.8 $[M+H]^+$.

EXAMPLE 149

3-Bromo-6-(3,5-dimethyl-1H-pyrazol-4-ylmethyl)-10-methyl-9H-imidazo[1,5-a][1,2,4]triazolo[1,5-d][1,4]benzodiazepine hydrochloride (1:1)

a) (3,5-Dimethyl-1H-pyrazol-4-yl)-acetic acid hydrazide

As described for example 112a, (3,5-dimethyl-1H-pyrazol-4-yl)-acetic acid ethyl ester (Rainer, Georg. 4-Pyrazoleacetic acid derivatives. U.S. (1979), U.S. Pat. No. 4,146,721) in butanol was reacted with hydrazine hydrate (3 equivalents) and the resulting mixture was heated under reflux for 6 h. Evaporation of all volatiles afforded the title compound as a colourless oil (yield: 68%). MS: m/e=183.3 $[M+H]^+$.

b) 3-Bromo-6-(3,5-dimethyl-1H-pyrazol-4-ylmethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (3,5-dimethyl- 1H-pyrazol-4-yl)-acetic acid hydrazide. After evaporation of the solvent the residue was triturated with methanol to afford the free base of the title compound. Treatment with HCl in methanol and crystallization from methanol/diethylether afforded the title compound as a light yellow solid (yield: 13%). MS: m/e=426.1/424.2 [M+H]$^+$.

EXAMPLE 150

3-Bromo-10-methyl-6-(5-methyl-2H-pyrazol-3-ylmethyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (5-methyl-2H-pyrazol-3-yl)-acetic acid hydrazide (Boettcher, Henning; et. al. Pyrazolylethylpieridinylindoles with central nervous system effects. Ger. Offen. (1997), DE 19602505A1). After evaporation of the solvent the residue was chromatographed (SiO$_2$, dichloromethane:methanol:aq.ammonia (25%)=100:0:0:0 to 220:10:1). Trituration with diisopropylether afforded the title compound as a white solid (yield: 16%). MS: m/e=412.0/410.0 [M+H]$^+$.

EXAMPLE 151

3-Bromo-10-methyl-6-(2-oxo-2H-pyridin-1-ylmethyl)-9H-imidazo[1,5-a][1,2,4]triazolo[1,5-d][1,4]benzodiazepine hydrochloride (1:1)

a) (2-Oxo-2H-pyridin-1-yl)-acetic acid hydrazide

As described for example 112a, (2-oxo-2H-pyridin-1-yl)-acetic acid ethyl ester (Begley, William J. et. al. Journal of the Chemical Society, Perkin Transactions 1 (1981), (9), 2620-4) in ethanol was reacted with hydrazine hydrate (1.1 equivalents) at 60° C. for 36 h. The mixture was cooled to rt and the precipitated product was filtered off and dried to afford the title compound as a white solid (yield: 78%). MS: m/e=168.2 [M+H]$^+$.

b) 3-Bromo-10-methyl-6-(2-oxo-2H-pyridin-1-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (2-oxo-2H-pyridin-1-yl)-acetic acid hydrazide. After evaporation of the solvent the residue was triturated with methanol and diisopropylether to afford the free base of the title compound. Treatment with HCl in methanol and crystallization from methanol/diethylether afforded the title compound as an off-white solid (yield: 52%). MS: m/e=425.1/423.2 [M+H]$^+$.

EXAMPLE 152

3-Bromo-10-methyl-6-(3-methyl-pyrazol-1-ylmethyl)-9H-imidazo[1,5-a][1,2,4]triazolo[1,5-d][1,4]benzodiazepine hydrochloride (1:1)

a) (3-Methyl-pyrazol-1-yl)-acetic acid ethyl ester

A solution of 4-methoxy-3-buten-2-one (4.68 g, 46.7 mmol) in ethanol (90 mL) was treated with ethyl hydrazinoacetate HCl (7.23 g, 46.7 mmol) and sodium acetate (3.84 g, 46.7 mmol). The mixture was stirred at rt for 4 days. After evaporation of the solvent the residue was extracted with ethyl acetate and water. The organic phase was dried over sodium sulfate, concentrated and chromatographed (SiO$_2$, heptanes:ethyl acetate=100:0 to 70:30) to afford a light yellow oil (7.08 g, 90%) that contains 72% (based on NMR) of the title compound and 28% of regioisomeric (5-methyl-pyrazol-1-yl)-acetic acid ethyl ester. Title compound: $^1$H-NMR (300 MHz, DMSO): δ=1.20 (t, J=7 Hz, 3H), 2.14 (s, 3H), 4.14 (m, 2H), 4.93 (s, 2H), 6.04 (d, J=2 Hz, 1H), 7.58 (d, J=2 Hz, 1H).

b) (3-Methyl-pyrazol-1-yl)-acetic acid hydrazide

As described for example 112a, (3-methyl-pyrazol-1-yl)-acetic acid ethyl ester in ethanol was reacted with hydrazine hydrate (2 equivalents) and the resulting mixture was heated under reflux for 4 h. The mixture was then cooled to rt and the precipitated product was filtered off and crystallized from ethanol. The title compound (>95% purity) was obtained as a white solid (yield: 68%). $^1$H-NMR (300 MHz, DMSO): δ=2.12 (s, 3H), 4.29 (s, 2H), 4.60 (s, 2H), 6.00 (d, J=2 Hz, 1H), 7.55 (d, J=2 Hz, 1H), 9.26 (s, 1H).

c) 3-Bromo-10-methyl-6-(3-methyl-pyrazol-1-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (3-methyl-pyrazol-1-yl)-acetic acid hydrazide. After evaporation of the solvent the residue was triturated with methanol and diisopropylether to afford the free base of the title compound. Treatment with HCl in methanol and crystallization from methanol/diethylether afforded the title compound as an off-white solid (yield: 56%). MS: m/e=412.1/410.1 [M+H]$^+$.

EXAMPLE 153

3-Bromo-6-(2,5-dimethyl-2H-pyrazol-3-ylmethyl)-10-methyl-9H-imidazo[1,5-a][1,2,4]triazolo[1,5-d][1,4]benzodiazepine hydrochloride (1:1)

a) (2,5-Dimethyl-2H-pyrazol-3-yl)-acetic acid N-methyl-hydrazide

To a cooled solution of 4-hydroxy-6-methyl-2-pyrone (6.31 g, 50 mmol) in methanol (90 mL) was added methylhydrazine (6.6 mL, 125 mmol) at such a rate that temperature did not exceed 10° C. The mixture was stirred in the ice bath for 1 h, then for 16 h at rt. After refluxing for 1 h all volatiles were evaporated and the residue was chromatographed (SiO$_2$, dichloromethane:methanol:aq.ammonia (25%)=100:0:0:0 to 130:10:1) to afford a red oil (9.05 g, 100%) that contained 82% (based on NMR) of the title compound and 12% of regioisomers. Title compound: $^1$H-NMR (400 MHz, CDCl$_3$): δ=2.22 (s, 3H), 3.17 (s, 3H), 3.78 (s, 3H), 3.84 (s, 2H), 3.91 (s, 2H), 5.91 (s, 2H).

b) (2,5-Dimethyl-2H-pyrazol-3-yl)-acetic acid ethyl ester

To a solution of (2,5-dimethyl-2H-pyrazol-3-yl)-acetic acid N-methyl-hydrazide (9.1 g, 41 mmol) in dioxane (50 mL) aqueous sodium hydroxide solution was added (5 N, 50 mL) and the and the resulting mixture was heated under reflux for 4 h. After addition of hydrochloric acid (5 N, 50 mL), all volatiles were evaporated. The residue was extracted with refluxing ethanol (150 mL) and the solvent was evaporated. Residual volatiles were azeotropically removed by coevaporation with toluene to afford (2,5-dimethyl-2H-pyrazol-3-yl)-acetic acid as a viscous oil. It was dissolved in ethanol (100 ml), p-toluene sulfonic acid (2.0 g, catalytic) was added and the resulting mixture was heated under reflux for 16 h. After evaporation of the solvent, the residue was extracted with ethyl acetate and water. The organic phase was dried over sodium sulfate, concentrated and chromatographed (SiO$_2$, heptanes:ethyl acetate=100:0 to 40:60) to afford the title compound as a colorless oil (7.6 g, 100%). $^1$H-NMR (400 MHz, CDCl$_3$): δ=1.22 (t, J=7 Hz, 3H), 2.22 (s, 3H), 3.61 (s, 2H), 3.75 (s, 2H), 4.18 (q, J=7 Hz, 2H), 5.95 (s, 1H).

c) (2,5-Dimethyl-2H-pyrazol-3-yl)-acetic acid hydrazide

As described for example 112a, (2,5-dimethyl-2H-pyrazol-3-yl)-acetic acid ethyl ester in ethanol was reacted with hydrazine hydrate (2 equivalents) at reflux for 16 h. Evaporation of all volatiles and chromatography (SiO$_2$, dichloromethane:methanol:aq.ammonia (25%)=100:0:0 to 90:10:1) afforded the title compound as a white solid (yield: 78%). MS: m/e=169.3 [M+H]$^+$.

d) 3-Bromo-6-(2,5-dimethyl-2H-pyrazol-3-ylmethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (2,5-dimethyl-2H-pyrazol-3-yl)-acetic acid hydrazide. After evaporation of the solvent the residue was triturated with methanol to afford the free base of the title compound. Treatment with HCl in methanol and crystallization from methanol/diethylether afforded the title compound as a light yellow solid (yield: 46%). MS: m/e=426.1/424.1 [M+H]$^+$.

EXAMPLE 154

(rac.)-3-Bromo-6-(hydroxyl-phenyl-methyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (rac.)-mandelic acid hydrazide. After evaporation of the solvent the residue was triturated with methanol to afford the free base of the title compound. Treatment with HCl in methanol and crystallization from methanol/diethylether afforded the title compound as a white solid (yield: 54%). MS: m/e=424.1/422.1 [M+H]$^+$.

EXAMPLE 155

3-Bromo-10-methyl-6-(5-methyl-pyrazol-1-ylmethyl)-9H-imidazo[1,5-a][1,2,4]triazolo[1,5-d][1,4]benzodiazepine a) (5-Methyl-pyrazol-1-yl)-acetic acid ethyl ester A solution of 1-dimethylamino-buten-3-one (3.31 g, 29.3 mmol) in ethanol (60 mL) was treated with ethyl hydrazinoacetate HCl (4.53 g, 29.3 mmol) and sodium acetate (2.40 g, 29.3 mmol) and the resulting mixture was heated under reflux for 2 h. After evaporation of the solvent the residue was extracted with ethyl acetate and water. The organic phase was dried over sodium sulfate, concentrated and chromatographed (SiO$_2$, heptanes:ethyl acetate=100:0 to 70:30) to afford a light yellow oil (4.95 g, 100%) that contained 92% (based on NMR) of the title compound and 8% of regioisomeric (3-methyl-pyrazol-1-yl)-acetic acid ethyl ester. Title compound: $^1$H-NMR (300 MHz, DMSO): δ=1.20 (t, J=7 Hz, 3H), 2.20 (s, 3H), 4.14 (q with fine splitting, J=7 Hz, 2H), 4.98 (s, 2H), 6.05 (mc, 1H), 7.31 (d, J=2 Hz, 1H).

b) (5-Methyl-pyrazol-1-yl)-acetic acid hydrazide

As described for example 112a, (5-methyl-pyrazol-1-yl)-acetic acid ethyl ester in ethanol was reacted with hydrazine hydrate (2 equivalents) and the resulting mixture was heated under reflux for 8 h. The mixture was cooled to rt and the precipitated product was filtered off, dried and crystallized from toluene. The title compound (95% purity, based on NMR) was obtained as a white solid (yield: 45%). $^1$H-NMR (300 MHz, DMSO): δ=2.24 (s, 3H), 4.29 (s, 2H), 4.65 (s, 2H), 6.00 (d, J=1 Hz, 1H), 7.55 (d, J=1 Hz, 1H), 9.27 (s, 1H).

c) 3-Bromo-10-methyl-6-(5-methyl-pyrazol-1-ylmethyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (5-methyl-pyrazol-1-yl)-acetic acid hydrazide. After evaporation of the solvent the residue was triturated with methanol to afford the title compound as a white solid (yield: 56%). MS: m/e=412.0/410.0 [M+H]$^+$.

EXAMPLE 156

3-Bromo-6-[(cyclopropanecarbonyl-amino)-methyl]-10-methyl-9H-imidazo[1,5-a][1,2,4]triazolo[1,5-d][1,4]benzodiazepine As described for example 142b, 6-aminomethyl-3-bromo-10-methyl-9H-imidazo[1,5-a][1,2,4]triazolo[1,5-d][1,4]benzodiazepine was reacted with cyclopropanecarbonyl chloride and triethylamine. Aqueous workup and chromatography followed by crystallization from methanol/diisopropylether afforded the title compound as a white solid (yield: 50%). MS: m/e=415.2/413.2[M+H]$^+$.

EXAMPLE 157

3-Bromo-6-(isobutyrylamino-methyl)-10-methyl-9H-imidazo[1,5-a][1,2,4]triazolo[1,5-d][1,4]benzodiazepine As described for example 142b, 6-aminomethyl-3-bromo-10-methyl-9H-imidazo[1,5-a][1,2,4]triazolo[1,5-d][1,4]benzodiazepine (example 142a) was reacted with isobutyryl chloride and triethylamine. Aqueous workup and chromatography followed by crystallization from methanol/diisopropylether afforded the title compound as a white solid (yield: 37%). MS: m/e=417.2/415.3[M+H]$^+$.

EXAMPLE 158

3-Bromo-6-[(2,2-dimethyl-propionylamino)-methyl]-10-methyl-9H-imidazo[1,5-a][1,2,4]triazolo[1,5-d][1,4]benzodiazepine As described for example 142b, 6-aminomethyl-3-bromo-10-methyl-9H-imidazo[1,5-a][1,2,4]triazolo[1,5-d][1,4]benzodiazepine (example 142a) was reacted with pivaloyl chloride and triethylamine. Aqueous workup and chromatography followed by crystallization from methanol/diisopropylether afforded the title compound as a white solid (yield: 35%). MS: m/e=431.3/429.3[M+H]$^+$.

EXAMPLE 159

3-Bromo-6-(butyrylamino-methyl)-10-methyl-9H-imidazo[1,5-a][1,2,4]triazolo[1,5-d][1,4]benzodiazepine As described for example 142b, 6-aminomethyl-3-bromo-10-methyl-9H-imidazo[1,5-a][1,2,4]triazolo[1,5-d][1,4]benzodiazepine (example 142a) was reacted with butyryl chloride and triethylamine. Aqueous workup and chromatography followed by crystallization from methanol/diisopropylether afforded the title compound as a white solid (yield: 22%). MS: m/e=417.2/415.3[M+H]$^+$.

EXAMPLE 160

3-Bromo-6-[(cyclobutanecarbonyl-amino)-methyl]-10-methyl-9H-imidazo[1,5-a][1,2,4]triazolo[1,5-d][1,4]benzodiazepine As described for example 142b, 6-aminomethyl-3-bromo-10-methyl-9H-imidazo[1,5-a][1,2,4]triazolo[1,5-d][1,4]benzodiazepine (example 142a) was reacted with cyclobutanecarbonyl chloride and triethylamine. Aqueous workup and chromatography followed by crystallization from methanol/diisopropylether afforded the title compound as a white solid (yield: 47%). MS: m/e=429.3/427.2[M+H]$^+$.

EXAMPLE 161

3-Bromo-6-(methanesulfonylamino-methyl)-10-methyl-9H-imidazo[1,5-a][1,2,4]triazolo[1,5-d][1,4]benzodiazepine A suspension of 6-aminomethyl-3-bromo-10-methyl-9H-imidazo[1,5-a][1,2,4]triazolo[1,5-d][1,4]benzodiazepine (example 142a) (0.38 g, 1 mmol) in pyridine (5 mL) was treated with 4-dimethylaminopyridine (0.012 g, 0.1 mmol) and methanesulfonyl chloride (0.14 g, 1.2 mmol). After 16 h at rt another portion of 4-dimethylaminopyridine (0.14 g, 1.2 mmol) and methanesulfonyl chloride (0.14 g, 1.2 mmol) was added. Stirring was continued for 24 h, then all volatiles were evaporated and the residue was stirred with water. The precipitate was filtered off, dried and chromatographed (SiO$_2$, dichloromethane:methanol:aq.ammonia (25%)=100:0:0 to 150:10:1). Trituration with methanol/diisopropylether afforded the title compound as an off-white solid (yield: 18%). MS: m/e=425.1/423.1[M+H]$^+$.

EXAMPLE 162

3-Bromo-10-methyl-6-[1,2,3]triazol-1-ylmethyl-9H-imidazo[1,5-a][1,2,4]triazolo[1,5-d][1,4]benzodiazepine hydrochloride (1:1)

a) [1,2,3]Triazol-1-yl-acetic acid hydrazide

As described for example 112a, [1,2,3]triazol-1-yl-acetic acid ethyl ester in ethanol was reacted with hydrazine hydrate (2 equivalents) and the resulting mixture heated under reflux for 3 h. The mixture was cooled to 4° C. and the precipitated product was filtered off and dried to afford the title compound as a white solid (yield: 73%). MS: m/e=141.2[M]$^+$.

b) 3-Bromo-10-methyl-6-[1,2,3]triazol-1-ylmethyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with [1,2,3]triazol-1-yl-acetic acid hydrazide. After evaporation of the solvent the residue was triturated with methanol to afford the free base of the title compound. Treatment with HCl in methanol and crystallization from methanol/diethylether afforded the title compound as a white solid (yield: 41%). MS: m/e=399.1/397.1 [M+H]$^+$.

EXAMPLE 163

3-Bromo-6-(4-ethyl-2,3-dioxo-piperazin-1-ylmethyl)-10-methyl-9H-imidazo[1,5-a][1,2,4]triazolo[1,5-d][1,4]benzodiazepine hydrochloride (1:1)

a) (4-Ethyl-2,3-dioxo-piperazin-1-yl)-acetic acid ethyl ester

As described for example 119a, 1-ethyl-piperazine-2,3-dione was reacted with sodium hydride followed by reaction with ethyl bromoacetate. Aqueous workup followed by chromatography (SiO$_2$, dichloromethane:methanol=100:0 to 94:4) afforded the title compound as a light yellow oil (yield: 72%). MS: m/e=229.4 [M+H]$^+$.

b) (4-Ethyl-2,3-dioxo-piperazin-1-yl)-acetic acid hydrazide

As described for example 112a, (4-ethyl-2,3-dioxo-piperazin-1-yl)-acetic acid ethyl ester in ethanol was reacted with hydrazine hydrate (1.2 equivalents) and the resulting mixture heated under reflux for 16 h. The precipitated product was filtered off and dried to afford the title compound as a white solid (yield: 77%). MS: m/e=215.4 [M+H]$^+$.

c) 3-Bromo-6-(4-ethyl-2,3-dioxo-piperazin-1-ylmethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (4-ethyl-2,3-dioxo-piperazin-1-yl)-acetic acid hydrazide. After evaporation of the solvent the residue was chromatographed (SiO$_2$, dichloromethane:methanol=100:0 to 95:5) and the title compound was obtained as the free base. Treatment with HCl in methanol and crystallization from methanol/diethylether afforded the title compound as a light brown solid (yield: 57%). MS: m/e=472.2/470.3 [M+H]$^+$.

EXAMPLE 164

3-Bromo-6-isoxazol-3-ylmethyl-10-methyl-9H-imidazo[1,5-a][1,2,4]triazolo[1,5-d][1,4]benzodiazepine hydrochloride (1:1)

a) Isoxazol-3-yl-acetic acid methyl ester

As described for example 138a, isoxazole-3-carboxylate (Zeeh, Bernd; et. al. Fungicidal isoxazolecarboxylic acid anilides. Ger. Offen. (1981), DE 2940189) was reacted with oxalyl chloride followed by treatment with diazomethane to provide the respective diazoketone. This was reacted with methanol under silver catalysis. After workup and chromatographic purification (SiO$_2$, heptanes:ethyl acetate=100:0 to 70:30) the title compound was isolated as a colorless oil (yield: 25%). $^1$H-NMR (300 MHz, DMSO): δ=3.66 (s, 3H), 3.85 (s, 2H), 6.57 (d, J=2 Hz, 1H), 8.87 (d, J=2 Hz, 1H).

b) Isoxazol-3-yl-acetic acid hydrazide

As described for example 112a, isoxazol-3-yl-acetic acid methyl ester in ethanol was reacted with hydrazine hydrate (2 equivalents) at rt for 16 h. After evaporation of the solvent the residue was chromatographed (SiO$_2$, dichloromethane:methanol:aq.ammonia (25%)=100:0:0 to 90:10:1) to afford the title compound as a white solid (yield: 78%). MS: m/e=142.1 [M+H]$^+$.

c) 3-Bromo-6-isoxazol-3-ylmethyl-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with isoxazol-3-yl-acetic acid hydrazide. After evaporation of the solvent the residue was triturated with methanol to afford the free base of the title compound. Treatment with HCl in methanol and crystallization from methanol/diethylether afforded the title compound as a white solid (yield: 20%). MS: m/e=399.1.1/397.1 [M+H]$^+$.

EXAMPLE 165

3-Bromo-10-methyl-6-[1,2,4]triazol-1-ylmethyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with [1,2,4]triazol-1-yl-acetic acid hydrazide (Leonardi, A.; Nardi, D.; Veronese, M. Bollettino Chimico Farmaceutico (1975), 114(2), 70-2). After evaporation of the solvent the residue was triturated with methanol and crystallized from ethyl acetate/diisopropylether to afford the title compound as a white solid (yield: 28%). MS: m/e=399.1/397.1 [M+H]$^+$.

EXAMPLE 166

3-Bromo-10-methyl-6-[1,2,3]triazol-2-ylmethyl-9H-imidazo[1,5-a][1,2,4]triazolo[1,5-d][1,4]benzodiazepine hydrochloride (1:1)

a) [1,2,3]triazol-2-yl-acetic acid hydrazide

As described for example 112a, [1,2,3]triazol-2-yl-acetic acid ethyl ester in ethanol was reacted with hydrazine hydrate (2 equivalents) and the resulting mixture heated under reflux for 3 h. The mixture was cooled to rt and the precipitated product was filtered off and dried to afford the title compound as a white solid (yield: 68%). MS: m/e=141.1 [M]$^+$.

b) 3-Bromo-10-methyl-6-[1,2,3]triazol-2-ylmethyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with [1,2,3]triazol-2-yl-acetic acid hydrazide. Upon cooling to rt the title compound crystallized from the reaction mixture as the free base. Treatment with HCl in methanol and crystallization from methanol/diethylether afforded the title compound as a white solid (yield: 61%). MS: m/e=399.1.1/397.1 [M+H]$^+$.

EXAMPLE 167

3-Bromo-6-(4-methoxy-benzyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (4-methoxy-phenyl)-acetic acid hydrazide. After evaporation of the solvent the residue was triturated with methanol to afford the free base of the title compound. Treatment with HCl in methanol and crystallization from methanol/diethylether afforded the title compound as an off-white solid (yield: 22%). MS: m/e=438.3/436.1 [M+H]$^+$.

EXAMPLE 168

3-Bromo-6-(2-methoxy-benzyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (2-methoxy-phenyl)-acetic acid hydrazide (Rosen, Gerald M. et al. Journal of Heterocyclic Chemistry (1971), 8(4), 659-62). After evaporation of the solvent the residue was triturated with methanol to afford the free base of the title compound. Treatment with HCl in methanol and crystallization from methanol/diethylether afforded the title compound as an off-white solid (yield: 40%). MS: m/e=438.2/436.1 [M+H]$^+$.

EXAMPLE 169

6-Benzyl-3-bromo-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with phenyl-acetic acid hydrazide. After evaporation of the solvent the residue was triturated with methanol to afford the free base of the title compound. Treatment with HCl in methanol and crystallization from methanol/diethylether afforded the title compound as a white solid (yield: 32%). MS: m/e=408.2/406.1 [M+H]$^+$.

EXAMPLE 170

3-Chloro-6-cyclopropylmethyl-10-methyl-9H-imidazo[1,5-a][1,2,4]triazolo[1,5-d][1,4]benzodiazepine hydrochloride (1:1)

a) 5-Chloro-2-(4-methyl-imidazol-1-yl)-benzonitrile

As described for example 84a, 5-chloro-2-fluoro-benzonitrile was reacted with 4-methylimidazole and potassium carbonate for 20 h at 90° C. After aqueous workup and crystallization from ethyl acetate the title compound was obtained as a white solid (yield: 63%). MS: m/e=218.2 [M+H]$^+$.

b) 5-Chloro-2-(5-dimethylaminomethyl-4-methyl-imidazol-1-yl)-benzonitrile

As described for example 84b, 5-chloro-2-(4-methyl-imidazol-1-yl)-benzonitrile was reacted with Eschenmoser's salt in DMF for 16 h at 90° C. Evaporation of the solvent, aqueous workup and crystallization from ethyl acetate afforded the title compound as a white solid (yield: 17%). MS: m/e=275.1 [M+H]$^+$.

c) [3-(4-Chloro-2-cyano-phenyl)-5-methyl-3H-imidazol-4-ylmethyl]-trimethyl-ammonium; iodide As described for example 84c, 5-chloro-2-(5-dimethylaminomethyl-4-methyl-imidazol-1-yl)-benzonitrile was reacted with methyl iodide for 4 days at 4° C. The title compound was obtained as a white crystalline material (yield: 94%). MS: m/e=230.2 [M−NMe$_3$]$^+$.

d) 3-Chloro-6-cyclopropylmethyl-10-methyl-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide was reacted with cyclopropylacetic acid hydrazide (Oae, Shigeru et al. Journal of the Chemical Society, Perkin Transactions 2: Physical Organic Chemistry (1972-1999) (1974), (15), 1844-8). After evaporation of the solvent the residue was chromatographed (SiO$_2$, dichloromethane:methanol=100:0 to 97:3) to afford the free base of the title compound. Treatment with HCl in methanol and crystallization from methanol/diethylether afforded the title compound as an off-white solid (yield: 9%). MS: m/e=326.2 [M+H]$^+$.

EXAMPLE 171

3-Chloro-10-methyl-6-(morpholin-4-ylmethyl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with morpholin-4-yl-acetic acid hydrazide (example 130a). After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a light yellow solid (yield: 40%). MS: m/e=371.1 [M+H]$^+$.

EXAMPLE 172

3-Chloro-6-(2-methoxy-ethyl)-10-methyl-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with 3-methoxy-propionic acid hydrazide. Upon cooling to rt the title compound crystallized from the reaction mixture as a white solid (yield: 11%). MS: m/e=330.1 [M+H]$^+$.

EXAMPLE 173

3-Chloro-10-methyl-6-(2-oxo-pyrrolidin-1-ylmethyl)-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with (2-oxo-pyrrolidin-1-yl)-acetic acid hydrazide. After evaporation of the solvent the residue was chromatographed (SiO$_2$, dichloromethane:methanol=100:0 to 97:3). Trituration with diisopropylether afforded the title compound as a light yellow solid (yield: 42%). MS: m/e=369.1 [M+H]$^+$.

EXAMPLE 174

(rac.)-3-Chloro-6-(1-hydroxy-ethyl)-10-methyl-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with (rac.)-lacthydrazide. After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a light yellow solid (yield: 11%). MS: m/e=316.0 [M+H]$^+$.

EXAMPLE 175

3-Chloro-10-methyl-6-(2,2,2-trifluoro-ethyl)-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with 3,3,3-trifluoro-propionic acid hydrazide (example 108a). After evaporation of the solvent the residue was chromatographed (SiO$_2$, dichloromethane:methanol=100:0 to 97:3). Trituration with diisopropylether afforded the title compound as a white solid (yield: 31%). MS: m/e=354.1 [M+H]$^+$.

EXAMPLE 176

3-Chloro-6-methanesulfonylmethyl-10-methyl-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with methanesulfonyl-acetic acid hydrazide (Bays, David Edmund; Carey, Linda; Hayes, Roger. 3,5-Disubstituted-1,2,4-triazole compounds and pharmaceutical compositions containing them. Eur. Pat. Appl. (1982), EP 50407). After evaporation of the solvent the residue was chromatographed (SiO$_2$, dichloromethane:methanol=100:0 to 97:3). Treatment with HCl in methanol and crystallization from methanol/diethylether afforded the title compound as a white solid (yield: 34%). MS: m/e=364.1 [M+H]$^+$.

EXAMPLE 177

3-Chloro-10-methyl-6-(pyridine-3-ylmethyl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with pyridine-3-yl-acetic acid hydrazide (Cemischev, B.; Popov, D.; Pharmazie (1967), 22(8), 432-4). After evaporation of the solvent the residue was triturated with methanol and the title compound was obtained as the free base. Treatment with HCl in metha-

EXAMPLE 178

3-Chloro-6-ethoxy-methyl-10-methyl-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with ethoxy-acetic acid hydrazide (Brands, Michael et. al. Preparation of azinyl- and azolylsulfones as chemokine IL-8 receptor binding inhibitors. Brit. UK Pat. Appl. (2003), GB 2379218 A1). After evaporation of the solvent the residue was triturated with methanol to afford the title compound as a white solid (yield: 35%). MS: m/e=330.1 [M+H]$^+$.

EXAMPLE 179

(rac.)-3-Chloro-10-methyl-6-(tetrahydro-furan-2-ylmethyl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with (rac.)-(tetrahydro-furan-2-yl)-acetic acid hydrazide (example 112a). After evaporation of the solvent the residue was chromatographed (SiO$_2$, dichloromethane:methanol:aq.ammonia (25%)=100:0:0 to 300:10:1) and the title compound was obtained as the free base. Treatment with HCl in methanol and crystallization from methanol/diethylether afforded the title compound as a white solid (yield: 23%). MS: m/e=356.1 [M+H]$^+$.

EXAMPLE 180

3-Chloro-6-(cyclohexylmethyl)-10-methyl-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with cyclohexyl-acetic acid hydrazide. After evaporation of the solvent the residue was chromatographed (SiO$_2$, dichloromethane:methanol:aq.ammonia (25%)=100:0:0 to 300:10:1) and the title compound was obtained as the free base. Treatment with HCl in methanol and crystallization from methanol/diethylether afforded the title compound as a white solid (yield: 12%). MS: m/e=368.0 [M+H]$^+$.

EXAMPLE 181

3-Chloro-10-methyl-6-(pyridine-2-ylmethyl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with pyridine-2-yl-acetic acid hydrazide (Cemischev, B.; Popov, D.; Pharmazie (1967), 22(8), 432-4). After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a light yellow solid (yield: 15%). MS: m/e=363.2 [M+H]$^+$.

EXAMPLE 182

3-Chloro-10-methyl-6-(3-oxo-morpholin-4-ylmethyl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with (3-oxo-morpholin-4-yl)-acetic acid hydrazide (example 119b). After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a light yellow solid (yield: 42%). MS: m/e=385.1 [M+H]$^+$.

EXAMPLE 183

3-Chloro-10-methyl-6-(3-methyl-isoxazol-5-ylmethyl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with (3-methyl-isoxazol-5-yl)-acetic acid hydrazide (example 123a). After evaporation of the solvent the residue was chromatographed (SiO$_2$, dichloromethane:methanol=100:0 to 96:4) and the title compound was obtained as the free base. Treatment with HCl in methanol and crystallization from methanol/diethylether afforded the title compound as a white solid (yield: 5%). MS: m/e=367.0 [M+H]$^+$.

EXAMPLE 184

3-Chloro-6-(2,5-dimethyl-thiazol-4-ylmethyl)-10-methyl-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with (2,5-dimethyl-thiazol-4-yl)-acetic acid hydrazide (example 125a). Upon cooling to rt the title compound crystallized from the reaction mixture as a white solid (yield: 59%). MS: m/e=397.0 [M+H]$^+$.

EXAMPLE 185

3-Chloro-10-methyl-6-(6-methyl-pyridin-3-ylmethyl)-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with (6-methyl-pyridin-3-yl)-acetic acid hydrazide (example 124a). Upon cooling to rt the title compound crystallized from the reaction mixture as a white solid (yield: 35%). MS: m/e=377.1 [M+H]$^+$.

EXAMPLE 186

3-Chloro-6-(imidazol-1-ylmethyl)-10-methyl-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with imidazol-1-yl-acetic acid hydrazide (Loccufier, Johan; Lingier, Stefaan; Meeus, Pascal. Photographic material containing a novel hydrazide type. Eur. Pat. Appl. (2001), EP 1085371 A1). After evaporation of the solvent the residue was chromatographed (SiO$_2$, dichloromethane:methanol=100:0 to 96:4) and the title compound was obtained as the free base. Treatment with HCl in methanol and crystallization from methanol/diethylether afforded the title compound as a white solid (yield: 33%). MS: m/e=352.1 [M+H]$^+$.

EXAMPLE 187

3-Chloro-10-methyl-6-(1-methyl-1H-pyrazol-3-yl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with l-methyl-1H-pyrazole-3-carboxylic acid hydrazide. After evaporation of the solvent the residue was chromatographed (SiO$_2$, dichloromethane:methanol:aq.ammonia (25%)=100:0:0 to 180:10:1) and the title compound was obtained as the free base. Treatment with HCl in methanol and crystallization from methanol/diethylether afforded the title compound as an off-white solid (yield: 22%). MS: m/e=351.9 [M+H]$^+$.

EXAMPLE 188

3-Chloro-6-(2-ethyl-imidazol-1-ylmethyl)-10-methyl-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with (2-ethyl-imidazol-1-yl)-acetic acid hydrazide (example 129b). After evaporation of the solvent the residue was chromatographed (SiO$_2$, dichloromethane:methanol:aq.ammonia (25%)=100:0:0 to 180:10:1) and the title compound was obtained as the free base. Treatment with HCl in methanol and crystallization from methanol/diethylether afforded the title compound as a white solid (yield: 38%). MS: m/e=379.9 [M+H]$^+$.

EXAMPLE 189

3-Chloro-10-methyl-6-(2-methyl-imidazol-1-ylmethyl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with (2-methyl-imidazol-1-yl)-acetic acid hydrazide (Toth, Jozsef et al. Substituted imidazole derivatives. Hung. (1968), HU 154810). After evaporation of the solvent the residue was chromatographed (SiO$_2$, dichloromethane:methanol:aq.ammonia (25%)=100:0:0 to 180:10:1) and the title compound was obtained as the free base. Treatment with HCl in methanol and crystallization from methanol/diethylether afforded the title compound as a light yellow solid (yield: 27%). MS: m/e=366.1 [M+H]$^+$.

EXAMPLE 190

3-Chloro-6-(isoxazol-5-ylmethyl)-10-methyl-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with isoxazol-5-yl-acetic acid hydrazide (example 138b). After evaporation of the solvent the residue was chromatographed (SiO$_2$, dichloromethane:methanol=100:0 to 92:8) and triturated with diethylether to afford the title compound as a light yellow solid (yield: 5%). MS: m/e=353.0[M+H]$^+$.

EXAMPLE 191

3-Chloro-10-methyl-6-(2-methyl-pyridin-4-ylmethyl)-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with 2-methyl-pyridin-4-yl-acetic acid hydrazide (Iwao, Masatomo; Kuraishi, Tsukasa. Journal of Heterocyclic Chemistry (1978), 15(8), 1425-30). After evaporation of the solvent the residue was chromatographed (SiO$_2$, dichloromethane:methanol=100:0: to 92:8). Trituration with diethylether afforded the title compound as an off-white solid (yield: 11%). MS: m/e=377.3[M]$^+$.

EXAMPLE 192

3-Chloro-10-methyl-6-(6-methyl-pyridin-2-ylmethyl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with (6-methyl-pyridin-2-yl)-acetic acid hydrazide (Izdebski, Jan. Roczniki Chemii (1965), 39(5), 717-20). After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a yellow solid (yield: 41%). MS: m/e=377.3 [M+H]$^+$.

EXAMPLE 193

3-Chloro-10-methyl-6-(5-methyl-isoxazol-3-ylmethyl)-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with (5-methyl-isoxazol-3-yl)-acetic acid hydrazide (example 140b). After evaporation of the solvent the residue was chromatographed (SiO$_2$, dichloromethane:methanol=100:0 to 96:4) and triturated with diethylether to afford the title compound as a white solid (yield: 14%). MS: m/e=367.1 [M+H]$^+$.

EXAMPLE 194

3-Chloro-6-(3,5-dimethyl-isoxazol-4-ylmethyl)-10-methyl-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with (3,5-dimethyl-isoxazol-4-yl)-acetic acid hydrazide (example 141a). After evaporation of the solvent the residue was chromatographed (SiO$_2$, dichloromethane:methanol=100:0 to 96:4) and triturated with diethylether to afford the title compound as a light yellow solid (yield: 40%). MS: m/e=381.1 [M+H]$^+$.

EXAMPLE 195

3-Chloro-10-methyl-6-(5-methyl-isoxazol-3-yl)-9H-imidazo[1,5-a][1,2,4]triazolo[1,5-d][1,4]benzodiazepine a) 5-Methyl-isoxazole-3-carboxylic acid hydrazide As described for example 112a, 5-methyl-isoxazole-3-carboxylic acid methyl ester in butanol was reacted with hydrazine hydrate (2 equivalents) at 100° C. for 2 h. Evaporation of all volatiles and chromatography (SiO$_2$, dichloromethane:methanol:aq.ammonia (25%)=100:0:0 to 90:10:1) afforded the title compound as a white solid (yield: 64%). $^1$H-NMR (300 MHz, DMSO): δ=2.44 (d, J=1 Hz, 3H), 4.57 (s, 2H), 6.52 (d, J=1 Hz, 1H), 9.94 (s, 1H).

b) 3-Chloro-10-methyl-6-(5-methyl-isoxazol-3-yl)-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with 5-methyl-isoxazole-3-carboxylic acid hydrazide. After evaporation of the solvent the residue was chromatographed (SiO$_2$, dichloromethane:methanol=100:0 to 96:4) and triturated with diethylether to afford the title compound as a light yellow solid (yield: 11%). MS: m/e=353.2 [M+H]$^+$.

EXAMPLE 196

3-Iodo-6-(2-methoxy-ethyl)-10-methyl-9H-imidazo[1,5-a][1,2,4]triazolo[1,5-d][1,4]benzodiazepine a) 5-Iodo-2-(4-methyl-imidazol-1-yl)-benzonitrile As described for example 84a, 2-fluoro-5-iodo-benzonitrile was reacted with 4-methylimidazole and potassium carbonate for 20 h at 90° C. Aqueous workup afforded a 1.9:1 mixture of the title compound and its regioisomer [5-iodo-2-(5-methyl-imidazol-1-yl)-benzonitrile] as a white solid (yield: 92%). MS: m/e=310.1 [M+H]$^+$.

b) 2-(5-Dimethylaminomethyl-4-methyl-imidazol-1-yl)-5-iodo-benzonitrile

As described for example 84b, 5-iodo-2-(4-methyl-imidazol-1-yl)-benzonitrile (+regioisomer) was reacted with Eschenmoser's salt in DMF for 72 h at 90° C. Evaporation of the solvent, aqueous workup and chromatography (SiO$_2$, dichloromethane:methanol=100:0 to 97:3) afforded the title compound as a white solid (yield: 38%). MS: m/e=367.0 [M+H]$^+$.

c) [3-(2-Cyano-4-iodo-phenyl)-5-methyl-3H-imidazol-4-ylmethyl]-trimethyl-ammonium; iodide As described for example 84c, 2-(5-dimethylaminomethyl-4-methyl-imidazol-1-yl)-5-iodo-benzonitrile was reacted with methyl iodide for 3 days at 4° C. The title compound was obtained as a white crystalline material (yield: 94%). MS: m/e=322.1 [M−NMe$_3$]$^+$.

d) 3-Iodo-6-(2-methoxy-ethyl)-10-methyl-9H-imidazo[1,5-a][1,2,4]triazolo[1,5-d][1,4]benzodiazepine As described for example 84d, [3-(2-cyano-4-iodo-phenyl)-5-methyl-3H-imidazol-4-ylmethyl]-trimethyl-ammonium; iodide was reacted with 3-methoxy-propionic acid hydrazide. Upon cooling in an ice bath the title compound crystallized as a white solid (yield: 22%). MS: m/e=421.8 [M+H]$^+$.

EXAMPLE 197

6-Cyclopropylmethyl-3-iodo-10-methyl-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with cyclopropylacetic acid hydrazide (Oae, Shigeru et al. Journal of the Chemical Society, Perkin Transactions 2: Physical Organic Chemistry (1972-1999) (1974), (15), 1844-8). After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a white solid (yield: 11%). MS: m/e=418.1 [M+H]$^+$.

EXAMPLE 198

3-Iodo-10-methyl-6-(morpholin-4-ylmethyl)-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with morpholin-4-yl-acetic acid hydrazide (example 130a). After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a white solid (yield: 34%). MS: m/e=463.3 [M+H]$^+$.

EXAMPLE 199

3-Iodo-10-methyl-6-(2-oxo-pyrrolidin-1-ylmethyl)-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with (2-oxo-pyrrolidin-1-yl)-acetic acid hydrazide. After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a light yellow solid (yield: 22%). MS: m/e=461.2 [M+H]$^+$.

EXAMPLE 200

3-Iodo-10-methyl-6-(2,2,2-trifluoro-ethyl)-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with 3,3,3-trifluoro-propionic acid hydrazide (example 108a). After evaporation of the solvent the residue was triturated with methanol and the title compound was obtained as the free base. Treatment with HCl in methanol and crystallization from methanol/diethylether afforded the title compound as a white solid (yield: 26%). MS: m/e=446.1 [M+H]$^+$.

EXAMPLE 201

(rac.)-6-(1-Hydroxy-ethyl)-3-iodo-10-methyl-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with (rac.)-lacthydrazide. After evaporation of the solvent the residue was triturated with methanol and the title compound was obtained as the free base. Treatment with HCl in methanol and crystallization from methanol/diethylether afforded the title compound as an off-white solid (yield: 23%). MS: m/e=408.1 [M+H]$^+$.

EXAMPLE 202

3-Iodo-6-methanesulfonylmethyl-10-methyl-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with methanesulfonyl-acetic acid hydrazide (Bays, David Edmund; Carey, Linda; Hayes, Roger. 3,5-Disubstituted-1,2,4-triazole compounds and pharmaceutical compositions containing them. Eur. Pat. Appl. (1982), EP 50407). After evaporation of the solvent the residue was chromatographed (SiO$_2$, dichloromethane:methanol:aq.ammonia (25%)=100:0:0 to 300:10:1) and the title compound was obtained as the free base. Treatment with HCl in methanol and crystallization from methanol/diethylether afforded the title compound as a white solid (yield: 55%). MS: m/e=456.2 [M+H]$^+$.

EXAMPLE 203

3-Iodo-10-methyl-6-(pyridine-2-ylmethyl)-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with pyridine-2-yl-acetic acid hydrazide (Cemischev, B.; Popov, D.; Pharmazie (1967), 22(8), 432-4). After evaporation of the solvent the residue was chromatographed (SiO$_2$, dichloromethane:methanol:aq.ammonia (25%)=100:0:0 to 300:10:1) and the title compound was obtained as the free base. Treatment with HCl in methanol and crystallization from methanol/diethylether afforded the title compound as a yellow solid (yield: 17%). MS: m/e=455.2 [M+H]$^+$.

EXAMPLE 204

3-Iodo-10-methyl-6-(1-methyl-1H-pyrrol-2-ylmethyl)-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with (1-methyl-1H-pyrrol-2-yl)-acetic acid hydrazide. After evaporation of the solvent the residue was chromatographed (SiO$_2$, dichloromethane:methanol:aq.ammonia (25%)=100:0:0 to 300:10:1) and the title compound was obtained as the free base. Treatment with HCl in methanol and crystallization from methanol/diethylether afforded the title compound as a light brown solid (yield: 19%). MS: m/e=457.3 [M+H]$^+$.

EXAMPLE 205

3-Iodo-10-methyl-6-(pyridine-3-ylmethyl)-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with pyridine-3-yl-acetic acid hydrazide (Cemischev, B.; Popov, D.; Pharmazie (1967), 22(8), 432-4). After evaporation of the solvent the residue was chromatographed (SiO$_2$, dichloromethane:methanol:aq.ammonia (25%)=100:0:0 to 300:10:1) and the title compound was obtained as the free base. Treatment with HCl in methanol and crystallization from methanol/diethylether afforded the title compound as a white solid (yield: 37%). MS: m/e=455.2 [M+H]$^+$.

EXAMPLE 206

3-Iodo-10-methyl-6-(pyridine-4-ylmethyl)-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with pyridin-4-yl-acetic acid (Iwao, Masatomo; Kuraishi, Tsukasa. Journal of Heterocyclic Chemistry (1978), 15(8), 1425-30). After evaporation of the solvent the residue was chromatographed (SiO$_2$, dichloromethane:methanol:aq.ammonia (25%)=100:0:0 to 300:10:1) and the title compound was obtained as the free base. Treatment with HCl in methanol and crystallization from methanol/diethylether afforded the title compound as an off-white solid (yield: 17%). MS: m/e=455.2 [M+H]$^+$.

EXAMPLE 207

6-Ethoxy-methyl-3-iodo-10-methyl-9H-imidazo[1,5-a][1,2,4]triazolo[1,5-d][1,4]benzodiazepine As described for example 84d, [3-(2-cyano-4-iodo-phenyl)-5-methyl-3H-imidazol-4-ylmethyl]-trimethyl-ammonium; iodide (example 196c) was reacted with ethoxy-acetic acid hydrazide (Brands, Michael et. al. Preparation of azinyl- and azolylsulfones as chemokine IL-8 receptor binding inhibitors. Brit. UK Pat. Appl. (2003), GB 2379218 A1). Upon cooling to rt the title compound crystallized from the reaction mixture as a white solid (yield: 24%). MS: m/e=421.8 $[M+H]^+$.

EXAMPLE 208

3-Iodo-10-methyl-6-(pyrrolidin-1-ylmethyl)-9H-imidazo[1,5-a][1,2,4]triazolo[1,5-d][1,4]benzodiazepine As described for example 84d, [3-(2-cyano-4-iodo-phenyl)-5-methyl-3H-imidazol-4-ylmethyl]-trimethyl-ammonium; iodide (example 196c) was reacted with pyrrolidin-1-yl-acetic acid hydrazide (Lyakhova, E. A. et al. Pharmaceutical Chemistry Journal (Translation of Khimiko-Farmatsevticheskii Zhurnal) (2003), 37(4), 178-183). After evaporation of the solvent the residue was chromatographed ($SiO_2$, dichloromethane:methanol:aq.ammonia (25%)=100:0:0 to 300:10:1) and crystallized from ethyl acetate to afford the title compound as a white solid (yield: 20%). MS: m/e=447.1 $[M+H]^+$.

EXAMPLE 209

(rac.)-3-Iodo-10-methyl-6-(tetrahydro-furan-2-ylmethyl)-9H-imidazo[1,5-a][1,2,4]triazolo[1,5-d][1,4]benzodiazepine As described for example 84d, [3-(2-cyano-4-iodo-phenyl)-5-methyl-3H-imidazol-4-ylmethyl]-trimethyl-ammonium; iodide (example 196c) was reacted with (rac.)-(tetrahydro-furan-2-yl)-acetic acid hydrazide (example 112a). After evaporation of the solvent the residue was triturated with methanol and the title compound was obtained as the free base. Treatment with HCl in methanol and crystallization from methanol/diethylether afforded the title compound as a light brown solid (yield: 54%). MS: m/e=447.9 $[M+H]^+$.

EXAMPLE 210

3-Iodo-10-methyl-6-(3-oxo-morpholin-4-ylmethyl)-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with (3-oxo-morpholin-4-yl)-acetic acid hydrazide (example 119b). After evaporation of the solvent the residue was chromatographed ($SiO_2$, dichloromethane:methanol=100:0 to 97:3) and the title compound was obtained as the free base. Treatment with HCl in methanol and crystallization from methanol/diethylether afforded the title compound as an off-white solid (yield: 41%). MS: m/e=476.9 $[M+H]^+$.

EXAMPLE 211

6-(Cyclohexylmethyl)-3-iodo-10-methyl-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with cyclohexyl-acetic acid hydrazide. After evaporation of the solvent the residue was stirred with dichloromethane, filtered off and evaporated to afford the title compound as the free base. Treatment with HCl in methanol and crystallization from methanol/diethylether afforded the title compound as a light brown solid (yield: 39%). MS: m/e=460.2 $[M+H]^+$.

EXAMPLE 212

3-Iodo-10-methyl-6-(2-oxo-oxazolidin-3-ylmethyl)-9H-imidazo[1,5-a][1,2,4]triazolo[1,5-d][1,4]benzodiazepine hydrochloride (1:1)

a) (2-Oxo-oxazolidin-3-yl)-acetic acid hydrazide

As described for example 112a, (2-oxo-oxazolidin-3-yl)-acetic acid ethyl ester (Potts, Kevin T.; Bhattacharjee, Debkumar; Kanemasa, Shuji. Journal of Organic Chemistry (1980), 45(24), 4985-8.) in ethanol was reacted with hydrazine hydrate (1 equivalent) at rt for 72 h. Evaporation of all volatiles and chromatography ($SiO_2$, dichloromethane:methanol:aq.ammonia (25%)=100:0:0 to 90:10:1) afforded the title compound as a white solid (yield: 77%). MS: m/e=160.2 $[M+H]^+$.

b) 3-Iodo-10-methyl-6-(2-oxo-oxazolidin-3-ylmethyl)-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with (2-oxo-oxazolidin-3-yl)-acetic acid hydrazide. After evaporation of the solvent the residue was triturated with methanol and the title compound was obtained as the free base. Treatment with HCl in methanol and crystallization from methanol/diethylether afforded the title compound as a light yellow solid (yield: 30%). MS: m/e=463.1 $[M+H]^+$.

EXAMPLE 213

3-Iodo-10-methyl-6-(2-oxo-2H-pyridin-1-ylmethyl)-9H-imidazo[1,5-a][1,2,4]triazolo[1,5-d][1,4]benzodiazepine hydrochloride (1:1)

As described for example 84d, [3-(2-cyano-4-iodo-phenyl)-5-methyl-3H-imidazol-4-ylmethyl]-trimethyl-ammonium; iodide (example 196c) was reacted with (2-oxo-2H-pyridin-1-yl)-acetic acid hydrazide (example 151a). After evaporation of the solvent the residue was triturated with methanol to afford the free base of the title compound. Treatment with HCl in methanol and crystallization from methanol/diethylether afforded the title compound as an off-white solid (yield: 63%). MS: m/e=471.2 $[M+H]^+$.

EXAMPLE 214

3-Fluoro-10-methyl-6-(morpholin-4-ylmethyl)-9H-imidazo[1,5-a][1,2,4]triazolo[1,5-d][1,4]benzodiazepine hydrochloride (1:1)

a) 5-Fluoro-2-(4-methyl-imidazol-1-yl)-benzonitrile

As described for example 84a, 2,5-difluoro-benzonitrile was reacted with 4-methylimidazole and potassium carbonate for 20 h at 90° C. After aqueous workup and crystallization from ethyl acetate the title compound was obtained as a white solid (yield: 41%). MS: m/e=202.3 [M+H]$^+$.

b) 2-(5-Dimethylaminomethyl-4-methyl-imidazol-1-yl)-5-fluoro-benzonitrile

As described for example 84b, 5-fluoro-2-(4-methyl-imidazol-1-yl)-benzonitrile was reacted with Eschenmoser's salt in DMF for 24 h at 90° C. Evaporation of the solvent, aqueous workup and crystallization from ethyl acetate/diisopropylether afforded the title compound as a white solid (yield: 34%). MS: m/e=259.2 [M+H]$^+$.

c) [3-(2-Cyano-4-fluoro-phenyl)-5-methyl-3H-imidazol-4-ylmethyl]-trimethyl-ammonium; iodide As described for example 84c, 2-(5-dimethylaminomethyl-4-methyl-imidazol-1-yl)-5-fluoro-benzonitrile was reacted with methyl iodide for 4 days at 4° C. The title compound was obtained as a white crystalline material (yield: 98%). MS: m/e=214.1 [M–NMe$_3$]$^+$.

d) 3-Fluoro-10-methyl-6-(morpholin-4-ylmethyl)-9H-imidazo[1,5-a][1,2,4]triazolo[1,5-d][1,4]benzodiazepine hydrochloride (1:1)

As described for example 84d, [3-(2-cyano-4-fluoro-phenyl)-5-methyl-3H-imidazol-4-ylmethyl]-trimethyl-ammonium; iodide was reacted with morpholin-4-yl-acetic acid hydrazide (example 130a) in DMF for 24 h at 150° C. After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a light yellow solid (yield: 32%). MS: m/e=355.2 [M+H]$^+$.

EXAMPLE 215

3-Fluoro-10-methyl-6-(2-oxo-pyrrolidin-1-ylmethyl)-9H-imidazo[1,5-a][1,2,4]triazolo[1,5-d][1,4]benzodiazepine hydrochloride (1:1)

As described for example 84d, [3-(2-cyano-4-fluoro-phenyl)-5-methyl-3H-imidazol-4-ylmethyl]-trimethyl-ammonium; iodide (example 214c) was reacted with (2-oxo-pyrrolidin-1-yl)-acetic acid hydrazide in DMF for 24 h at 150° C. After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a light yellow solid (yield: 33%). MS: m/e=353.2 [M+H]$^+$.

EXAMPLE 216

3-Fluoro-10-methyl-6-(2,2,2-trifluoro-ethyl)-9H-imidazo[1,5-a][1,2,4]triazolo[1,5-d][1,4]benzodiazepine As described for example 84d, [3-(2-cyano-4-fluoro-phenyl)-5-methyl-3H-imidazol-4-ylmethyl]-trimethyl-ammonium; iodide (example 214c) was reacted with 3,3,3-trifluoro-propionic acid hydrazide (example 108a). After evaporation of the solvent the residue was chromatographed (SiO$_2$, dichloromethane:methanol=100:0 to 97:3) and triturated with diisopropylether to afford the title compound as a white solid (yield: 47%). MS: m/e=338.1 [M+H]$^+$.

EXAMPLE 217

3-Fluoro-6-(2-methoxy-ethyl)-10-methyl-9H-imidazo[1,5-a][1,2,4]triazolo[1,5-d][1,4]benzodiazepine As described for example 84d, [3-(2-cyano-4-fluoro-phenyl)-5-methyl-3H-imidazol-4-ylmethyl]-trimethyl-ammonium; iodide (example 214c) was reacted with 3-methoxy-propionic acid hydrazide. After evaporation of the solvent the residue was chromatographed (SiO$_2$, dichloromethane:methanol=100:0 to 97:3) and triturated with diisopropylether to afford the title compound as an off-white solid (yield: 39%). MS: m/e=314.0 [M+H]$^+$.

EXAMPLE 218

6-Cyclopropylmethyl-3-fluoro-10-methyl-9H-imidazo[1,5-a][1,2,4]triazolo[1,5-d][1,4]benzodiazepine hydrochloride (1:1)

As described for example 84d, [3-(2-cyano-4-fluoro-phenyl)-5-methyl-3H-imidazol-4-ylmethyl]-trimethyl-ammonium; iodide (example 214c) was reacted with cyclopropylacetic acid hydrazide (Oae, Shigeru et al. Journal of the Chemical Society, Perkin Transactions 2: Physical Organic Chemistry (1972-1999) (1974), (15), 1844-8). After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as an off-white solid (yield: 7%). MS: m/e=310.3 [M+H]$^+$.

EXAMPLE 219

(rac.)-3-Fluoro-6-(1-hydroxy-ethyl)-10-methyl-9H-imidazo[1,5-a][1,2,4]triazolo[1,5-d][1,4]benzodiazepine hydrochloride (1:1)

As described for example 84d, [3-(2-cyano-4-fluoro-phenyl)-5-methyl-3H-imidazol-4-ylmethyl]-trimethyl-ammonium; iodide (example 214c) was reacted with (rac.)-lacthydrazide After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as a light yellow solid (yield: 27%). MS: m/e=300.4 [M+H]$^+$.

EXAMPLE 220

6-(Cyclohexylmethyl)-3-fluoro-10-methyl-9H-imidazo[1,5-a][1,2,4]triazolo[1,5-d][1,4]benzodiazepine hydrochloride (1:1)

As described for example 84d, [3-(2-cyano-4-fluoro-phenyl)-5-methyl-3H-imidazol-4-ylmethyl]-trimethyl-ammonium; iodide (example 214c) was reacted with cyclohexyl-acetic acid hydrazide. After evaporation of the solvent the residue was chromatographed (SiO$_2$, dichloromethane:methanol:aq.ammonia (25%)=100:0:0 to 300:10:1) and the title compound was obtained as the free base. Treatment with HCl in methanol and crystallization from methanol/diethylether afforded the title compound as a white solid (yield: 26%). MS: m/e=352.3 [M+H]$^+$.

EXAMPLE 221

6-Ethoxy-methyl-3-fluoro-10-methyl-9H-imidazo[1,5-a][1,2,4]triazolo[1,5-d][1,4]benzodiazepine As described for example 84d, [3-(2-cyano-4-fluoro-phenyl)-5-methyl-3H-imidazol-4-ylmethyl]-trimethyl-ammonium; iodide (example 214c) was reacted with ethoxy-acetic acid hydrazide (Brands, Michael et. al. Preparation of azinyl- and azolylsulfones as chemokine IL-8 receptor binding inhibitors. Brit. UK Pat. Appl. (2003), GB 2379218 A1). After evaporation of the solvent the residue was triturated with methanol and crystallized from ethyl acetate to afford the title compound as a white solid (yield: 35%). MS: m/e=314.0 [M+H]$^+$.

EXAMPLE 222

3-Fluoro-10-methyl-6-(1-methyl-1H-pyrrol-2-ylmethyl)-9H-imidazo[1,5-a][1,2,4]triazolo[1,5-d][1,4]benzodiazepine hydrochloride (1:1)

As described for example 84d, [3-(2-cyano-4-fluoro-phenyl)-5-methyl-3H-imidazol-4-ylmethyl]-trimethyl-ammonium; iodide (example 214c) was reacted with (1-methyl-1H-pyrrol-2-yl)-acetic acid hydrazide. After evaporation of the solvent the residue was chromatographed (SiO$_2$, dichloromethane:methanol:aq.ammonia (25%)=100:0:0 to 300:10:1) and the title compound was obtained as the free base. Treatment with HCl in methanol and crystallization from methanol/diethylether afforded the title compound as a light brown solid (yield: 25%). MS: m/e=349.3 [M+H]$^+$.

EXAMPLE 223

3-Fluoro-10-methyl-6-(3-oxo-morpholin-4-ylmethyl)-9H-imidazo[1,5-a][1,2,4]triazolo[1,5-d][1,4]benzodiazepine hydrochloride (1:1)

As described for example 84d, [3-(2-cyano-4-fluoro-phenyl)-5-methyl-3H-imidazol-4-ylmethyl]-trimethyl-ammonium; iodide (example 214c) was reacted with (3-oxo-morpholin-4-yl)-acetic acid hydrazide (example 119b). After evaporation of the solvent the residue was chromatographed (SiO$_2$, dichloromethane:methanol=100:0 to 97:3) and the title compound was obtained as the free base. Treatment with HCl in methanol and crystallization from methanol/diethylether afforded the title compound as an off-white solid (yield: 59%). MS: m/e=368.9 [M+H]$^+$.

EXAMPLE 224

(rac.)-3-Fluoro-10-methyl-6-(tetrahydro-furan-2-ylmethyl)-9H-imidazo[1,5-a][1,2,4]triazolo[1,5-d][1,4]benzodiazepine As described for example 84d, [3-(2-cyano-4-fluoro-phenyl)-5-methyl-3H-imidazol-4-ylmethyl]-trimethyl-ammonium; iodide (example 214c) was reacted with (rac.)-(tetrahydro-furan-2-yl)-acetic acid hydrazide (example 112a). After evaporation of the solvent the residue was chromatographed (SiO$_2$, dichloromethane:methanol=100:0 to 97:3) and crystallized from ethyl acetate/diisopropylether to afford the title compound as a light brown solid (yield: 18%). MS: m/e=340.1 [M+H]$^+$.

EXAMPLE 225

3-Fluoro-10-methyl-6-(pyridine-3-ylmethyl)-9H-imidazo[1,5-a][1,2,4]triazolo[1,5-d][1,4]benzodiazepine As described for example 84d, [3-(2-cyano-4-fluoro-phenyl)-5-methyl-3H-imidazol-4-ylmethyl]-trimethyl-ammonium; iodide (example 214c) was reacted with pyridine-3-yl-acetic acid hydrazide (Cemischev, B.; Popov, D.; Pharmazie (1967), 22(8), 432-4). After evaporation of the solvent the residue was crystallized from ethyl acetate to afford the title compound as a light brown solid (yield: 20%). MS: m/e=347.0 [M+H]$^+$.

EXAMPLE 226

3-Fluoro-6-methanesulfonylmethyl-10-methyl-9H-imidazo[1,5-a][1,2,4]triazolo[1,5-d][1,4]benzodiazepine hydrochloride (1:1)

As described for example 84d, [3-(2-cyano-4-fluoro-phenyl)-5-methyl-3H-imidazol-4-ylmethyl]-trimethyl-ammonium; iodide (example 214c) was reacted with methanesulfonyl-acetic acid hydrazide (Bays, David Edmund; Carey, Linda; Hayes, Roger. 3,5-Disubstituted-1,2,4-triazole compounds and pharmaceutical compositions containing them. Eur. Pat. Appl. (1982), EP 50407). After evaporation of the solvent the residue was triturated with methanol and the title compound was obtained as the free base. Treatment with HCl in methanol and crystallization from methanol/diethylether afforded the title compound as an off-white solid (yield: 39%). MS: m/e=348.0 [M+H]$^+$.

EXAMPLE 227

3-Fluoro-10-methyl-6-(pyridine-2-ylmethyl)-9H-imidazo[1,5-a][1,2,4]triazolo[1,5-d][1,4]benzodiazepine As described for example 84d, [3-(2-cyano-4-fluoro-phenyl)-5-methyl-3H-imidazol-4-ylmethyl]-trimethyl-ammonium; iodide (example 214c) was reacted with pyridine-2-yl-acetic acid hydrazide (Cemischev, B.; Popov, D.; Pharmazie (1967), 22(8), 432-4). After evaporation of the solvent the residue was crystallized from ethyl acetate to afford the title compound as a light brown solid (yield: 21%). MS: m/e=347.0 [M+H]$^+$.

EXAMPLE 228

3-Fluoro-10-methyl-6-(pyrrolidin-1-ylmethyl)-9H-imidazo[1,5-a][1,2,4]triazolo[1,5-d][1,4]benzodiazepine As described for example 84d, [3-(2-cyano-4-fluoro-phenyl)-5-methyl-3H-imidazol-4-ylmethyl]-trimethyl-ammonium; iodide (example 214c) was reacted with pyrrolidin-1-yl-acetic acid hydrazide (Lyakhova, E. A. et al. Pharmaceutical Chemistry Journal (Translation of Khimiko-Farmatsevticheskii Zhurnal) (2003)) 37(4), 178-183). After evaporation of the solvent the residue was chromatographed (SiO$_2$, dichloromethane:methanol=100:0 to 95:5) and triturated with diisopropylether to afford the title compound as a white solid (yield: 34%). MS: m/e=339.1 [M+H]$^+$.

EXAMPLE 229

10-Methyl-6-(2-oxo-pyrrolidin-1-ylmethyl)-3-trifluoromethyl-9H-imidazo[1,5-a][1,2,4]triazolo[1,5-d][1,4]benzodiazepine hydrochloride (1:1)

a) 2-(4-Methyl-imidazol-1-yl)-5-trifluoromethyl-benzonitrile

As described for example 84a, 2-fluoro-5-(trifluoromethyl)-benzonitrile was reacted with 4-methylimidazole and potassium carbonate for 16 h at 90° C. After aqueous workup and extraction with ethyl acetate the organic phase was dried over sodium sulfate and concentrated to afford a 3.4:1 mixture of the title compound and its regioisomer [2-(5-methyl-imidazol-1-yl)-5-trifluoromethyl-benzonitrile] as a light brown oil (yield: 85%). MS: m/e=252.3 [M+H]$^+$.

b) 2-(5-Dimethylaminomethyl-4-methyl-imidazol-1-yl)-5-trifluoromethyl-benzonitril As described for example 84b, 2-(4-methyl-imidazol-1-yl)-5-trifluoromethyl-benzonitrile (+regioisomer) was reacted with Eschenmoser's salt in DMF for 16 h at 90° C. Evaporation of the solvent, aqueous workup and chromatography afforded the title compound as a yellow oil that was sufficiently pure to be used in the next step (yield: 53%). MS: m/e=309.3 [M+H]$^+$.

c) [3-(2-Cyano-4-trifluoromethyl-phenyl)-5-methyl-3H-imidazol-4-ylmethyl]-trimethyl-ammonium; iodide As described for example 84c, 2-(5-dimethylaminomethyl-4-methyl-imidazol-1-yl)-5-trifluoromethyl-benzonitrile was reacted with methyl iodide for 3 days at 4° C. The title compound was obtained as a white crystalline material (yield: 61%). MS: m/e=323.3 [M]$^+$.

d) 10-Methyl-6-(2-oxo-pyrrolidin-1-ylmethyl)-3-trifluoromethyl-9H-imidazo[1,5-a][1,2,4]triazolo[1,5-d][1,4]benzodiazepine hydrochloride (1:1)

As described for example 84d, [3-(2-cyano-4-trifluoromethyl-phenyl)-5-methyl-3H-imidazol-4-ylmethyl]-trimethyl-ammonium; iodide was reacted with (2-oxo-pyrrolidin-1-yl)-acetic acid hydrazide in DMF for 16 h at 150° C. Evaporation of the solvent and chromatography (SiO$_2$, dichloromethane:methanol=100:0 to 97:3) afforded the title compound as the free base. Treatment with HCl in methanol and crystallization from methanol/diethylether afforded the title compound as an off-white solid (yield: 30%). MS: m/e=403.4 [M+H]$^+$.

EXAMPLE 230

3,10-Dimethyl-6-(2,2-dimethyl-propyl)-9H-imidazo[1,5-a][1,2,4]triazolo[1,5-d][1,4]benzodiazepine hydrochloride (1:1)

a) 5-Methyl-2-(4-methyl-imidazol-1-yl)-benzonitrile

As described for example 84a, 2-fluoro-5-methyl-benzonitrile was reacted with 4-methylimidazole and potassium carbonate for 16 h at 90° C. After aqueous workup the title compound was obtained as a white solid (yield: 48%). MS: m/e=198.4 [M+H]$^+$.

b) 2-(5-Dimethylaminomethyl-4-methyl-imidazol-1-yl)-5-methyl-benzonitrile

As described for example 84b, 5-methyl-2-(4-methyl-imidazol-1-yl)-benzonitrile was reacted with Eschenmoser's salt in DMF for 4 h at 90° C. Evaporation of the solvent, aqueous workup and chromatography afforded the title compound as an oil that solidified upon standing (yield: 64%). MS: m/e=255.2 [M+H]$^+$.

c) [3-(2-Cyano-4-methyl-phenyl)-5-methyl-3H-imidazol-4-ylmethyl]-trimethyl-ammonium; iodide As described for example 84c, 2-(5-dimethylaminomethyl-4-methyl-imidazol-1-yl)-5-methyl-benzonitrile was reacted with methyl iodide for 7 days at 4° C. The title compound was obtained as a white crystalline material (yield: 83%). MS: m/e=269.5 [M]$^+$.

d) 3,10-Dimethyl-6-(2,2-dimethyl-propyl)-9H-imidazo[1,5-a][1,2,4]triazolo[1,5-d][1,4]benzodiazepine hydrochloride (1:1)

As described for example 84d, [3-(2-cyano-4-methyl-phenyl)-5-methyl-3H-imidazol-4-ylmethyl]-trimethyl-ammonium; iodide was reacted with 3,3-dimethyl-butyric acid hydrazide. After evaporation of the solvent the residue was chromatographed (SiO$_2$, dichloromethane:methanol=100:0 to 96:4) to afford the free base of the title compound. Treatment with HCl in methanol, evaporation and trituration with diisopropylether afforded the title compound as an off-white solid (yield: 19%). MS: m/e=322.3 [M+H]$^+$.

EXAMPLE 231

3,10-Dimethyl-6-(2-methyl-imidazol-1-ylmethyl)-9H-imidazo[1,5-a][1,2,4]triazolo[1,5-d][1,4]benzodiazepine hydrochloride (1:1)

As described for example 84d, [3-(2-cyano-4-methyl-phenyl)-5-methyl-3H-imidazol-4-ylmethyl]-trimethyl-ammonium; iodide (example 230c) was reacted with (2-methyl-imidazol-1-yl)-acetic acid hydrazide (Toth, Jozsef et al. Substituted imidazole derivatives. Hung. (1968), HU 154810). After evaporation of the solvent the residue was chromatographed (SiO$_2$, dichloromethane:methanol:aq.ammonia (25%)=100:0:0 to 225:10:1) and the title compound was obtained as the free base. Treatment with HCl in methanol and crystallization from methanol/diethylether afforded the title compound as a light yellow solid (yield: 12%). MS: m/e=346.3[M+H]$^+$.

EXAMPLE 232

3,10-Dimethyl-6-(2-oxo-pyrrolidin-1-ylmethyl)-9H-imidazo[1,5-a][1,2,4]triazolo[1,5-d][1,4]benzodiazepine As described for example 84d, [3-(2-cyano-4-methyl-phenyl)-5-methyl-3H-imidazol-4-ylmethyl]-trimethyl-ammonium; iodide (example 230c) was reacted with (2-oxo-pyrrolidin-1-yl)-acetic acid hydrazide. After evaporation of the solvent the residue was chromatographed (SiO$_2$, dichloromethane:methanol=100:0 to 96:4). Trituration with diisopropylether afforded the title compound as a light brown solid (yield: 34%). MS: m/e=349.4 [M+H]$^+$.

EXAMPLE 233

3,10-Dimethyl-6-(3-oxo-morpholin-4-ylmethyl)-9H-imidazo[1,5-a][1,2,4]triazolo[1,5-d][1,4]benzodiazepine As described for example 84d, [3-(2-cyano-4-methyl-phenyl)-5-methyl-3H-imidazol-4-ylmethyl]-trimethyl-ammonium; iodide (example 230c) was reacted with (3-oxo-morpholin-4-yl)-acetic acid hydrazide (example 119b). After evaporation of the solvent the residue was chromatographed (SiO$_2$, dichloromethane:methanol=100:0 to 96:4) and triturated with diisopropylether to afford the title compound as a light yellow solid (yield: 24%). MS: m/e=365.1 [M+H]$^+$.

EXAMPLE 234

6-Ethoxy-methyl-3,10-dimethyl-9H-imidazo[1,5-a][1,2,4]triazolo[1,5-d][1,4]benzodiazepine hydrochloride (1:1)

As described for example 84d, [3-(2-cyano-4-methyl-phenyl)-5-methyl-3H-imidazol-4-ylmethyl]-trimethyl-ammonium; iodide (example 230c) was reacted with ethoxy-acetic acid hydrazide (Brands, Michael et. al. Preparation of azinyl- and azolylsulfones as chemokine IL-8 receptor binding inhibitors. Brit. UK Pat. Appl. (2003), GB 2379218 A1). After evaporation of the solvent the residue was chromatographed (SiO$_2$, dichloromethane:methanol=100:0 to 96:4) and the title compound was obtained as the free base. Treatment with HCl in methanol, evaporation and trituration with diisopropylether afforded the title compound as an off-white solid (yield: 12%). MS: m/e=310.3 [M+H]$^+$.

EXAMPLE 235

6-(2-Methoxy-ethyl)-3,10-dimethyl-9H-imidazo[1,5-a][1,2,4]triazolo[1,5-d][1,4]benzodiazepine hydrochloride (1:1)

As described for example 84d, [3-(2-cyano-4-methyl-phenyl)-5-methyl-3H-imidazol-4-ylmethyl]-trimethyl-ammonium; iodide (example 230c) was reacted with 3-methoxy-propionic acid hydrazide. After evaporation of the solvent the residue was chromatographed (SiO$_2$, dichloromethane:methanol=100:0 to 96:4) and the title compound was obtained as the free base. Treatment with HCl in methanol, evaporation and trituration with diethylether afforded the title compound as an off-white solid (yield: 49%). MS: m/e=310.3 [M+H]$^+$.

EXAMPLE 236

3,10-Dimethyl-6-(3-methyl-isoxazol-5-ylmethyl)-9H-imidazo[1,5-a][1,2,4]triazolo[1,5-d][1,4]benzodiazepine As described for example 84d, [3-(2-cyano-4-methyl-phenyl)-5-methyl-3H-imidazol-4-ylmethyl]-trimethyl-ammonium; iodide (example 230c) was reacted with (3-methyl-isoxazol-5-yl)-acetic acid hydrazide (example 123a). After evaporation of the solvent the residue was chromatographed (SiO$_2$, dichloromethane:methanol=100:0 to 96:4) and triturated with diisopropylether to afford the title compound as a light brown solid (yield: 15%). MS: m/e=347.2 [M+H]$^+$.

EXAMPLE 237

3-Methoxy-10-methyl-6-(2-oxo-pyrrolidin-1-ylmethyl)-9H-imidazo[1,5-a][1,2,4]triazolo[1,5-d][1,4]benzodiazepine a) 5-Methoxy-2-(4-methyl-imidazol-1-yl)-benzonitrile As described for example 84a, 2-fluoro-5-methoxy-benzonitrile was reacted with 4-methylimidazole and potassium carbonate for 48 h at 100° C. After aqueous workup and crystallization from ethyl acetate/diisopropylether the title compound was obtained as a white solid (yield: 72%). MS: m/e=214.1 [M+H]$^+$.

b) 2-(5-Dimethylaminomethyl-4-methyl-imidazol-1-yl)-5-methoxy-benzonitrile

As described for example 84b, 5-methoxy-2-(4-methyl-imidazol-1-yl)-benzonitrile was reacted with Eschenmoser's salt in DMF for 16 h at 70° C. Evaporation of the solvent, aqueous workup and chromatography afforded the title compound as an oil (yield: 83%). MS: m/e=271.4 [M+H]$^+$.

c) [3-(2-Cyano-4-methoxy-phenyl)-5-methyl-3H-imidazol-4-ylmethyl]-trimethyl-ammonium; iodide As described for example 84c, 2-(5-dimethylaminomethyl-4-methyl-imidazol-1-yl)-5-methoxy-benzonitrile was reacted with methyl iodide for 6 days at 4° C. The title compound was obtained as a white crystalline material (yield: 89%). MS: m/e=285.1 [M]$^+$.

d) 3-Methoxy-10-methyl-6-(2-oxo-pyrrolidin-1-ylmethyl)-9H-imidazo[1,5-a][1,2,4]triazolo[1,5-d][1,4]benzodiazepine As described for example 84d, [3-(2-cyano-4-methoxy-phenyl)-5-methyl-3H-imidazol-4-ylmethyl]-trimethyl-ammonium; iodide was reacted with (2-oxo-pyrrolidin-1-yl)-acetic acid hydrazide. After evaporation of the solvent the residue was chromatographed (SiO$_2$, dichloromethane:methanol=100:0 to 96:4) and triturated with diisopropylether to afford the title compound as a light brown solid (yield: 21%). MS: m/e=365.1 [M+H]$^+$.

EXAMPLE 238

3-Methoxy-10-methyl-6-(3-oxo-morpholin-4-ylmethyl)-9H-imidazo[1,5-a][1,2,4]triazolo[1,5-d][1,4]benzodiazepine hydrochloride (1:1)

As described for example 84d, [3-(2-cyano-4-methoxyphenyl)-5-methyl-3H-imidazol-4-ylmethyl]-trimethyl-ammonium; iodide (example 237c) was reacted with (3-oxo-morpholin-4-yl)-acetic acid hydrazide (example 119b). After evaporation of the solvent the residue was chromatographed (SiO$_2$, dichloromethane:methanol=100:0 to 96:4) and the title compound was obtained as the free base. Treatment with HCl in methanol and crystallization from methanol/diethylether afforded the title compound as a light yellow solid (yield: 48%). MS: m/e=381.2 [M+H]$^+$.

EXAMPLE 239

3-Methoxy-6-(2-methoxy-ethyl)-10-methyl-9H-imidazo[1,5-a][1,2,4]triazolo[1,5-d][1,4]benzodiazepine As described for example 84d, [3-(2-cyano-4-methoxyphenyl)-5-methyl-3H-imidazol-4-ylmethyl]-trimethyl-ammonium; iodide (example 237c) was reacted with 3-methoxy-propionic acid hydrazide. After evaporation of the solvent the residue was chromatographed (SiO$_2$, dichloromethane:methanol=100:0 to 96:4) and triturated with diisopropylether to afford the title compound as a white solid (yield: 43%). MS: m/e=326.3 [M+H]$^+$.

EXAMPLE 240

6-Ethoxy-methyl-3-methoxy-10-methyl-9H-imidazo[1,5-a][1,2,4]triazolo[1,5-d][1,4]benzodiazepine As described for example 84d, [3-(2-cyano-4-methoxyphenyl)-5-methyl-3H-imidazol-4-ylmethyl]-trimethyl-ammonium; iodide (example 237c) was reacted with ethoxy-acetic acid hydrazide (Brands, Michael et. al. Preparation of azinyl- and azolylsulfones as chemokine IL-8 receptor binding inhibitors. Brit. UK Pat. Appl. (2003), GB 2379218 A1). After evaporation of the solvent the residue was chromatographed (SiO$_2$, dichloromethane:methanol=100:0 to 96:4) and triturated with diisopropylether to afford the title compound as a white solid (yield: 40%). MS: m/e=326.4 [M+H]$^+$.

EXAMPLE 241

3-Methoxy-10-methyl-6-(3-methyl-isoxazol-5-ylmethyl)-9H-imidazo[1,5-a][1,2,4]triazolo[1,5-d][1,4]benzodiazepine As described for example 84d, [3-(2-cyano-4-methoxyphenyl)-5-methyl-3H-imidazol-4-ylmethyl]-trimethyl-ammonium; iodide (example 237c) was reacted with (3-methyl-isoxazol-5-yl)-acetic acid hydrazide (example 123a). After evaporation of the solvent the residue was chromatographed (SiO$_2$, dichloromethane:methanol=100:0 to 96:4) and triturated with diisopropylether to afford the title compound as a dark grey solid (yield: 49%). MS: m/e=363.3 [M+H]$^+$.

EXAMPLE 242

3-Methoxy-10-methyl-6-(2-methyl-imidazol-1-ylmethyl)-9H-imidazo[1,5-a][1,2,4]triazolo[1,5-d][1,4]benzodiazepine As described for example 84d, [3-(2-cyano-4-methoxyphenyl)-5-methyl-3H-imidazol-4-ylmethyl]-trimethyl-ammonium; iodide (example 237c) was reacted with (2-methyl-imidazol-1-yl)-acetic acid hydrazide (Toth, Jozsef et al. Substituted imidazole derivatives. Hung. (1968), HU 154810). After evaporation of the solvent the residue was extracted (ethyl acetate/saturated aqueous sodium bicarbonate solution), chromatographed (SiO$_2$, dichloromethane:methanol=100:0 to 94:6) and triturated with diisopropylether to afford the title compound as a light yellow solid (yield: 9%). MS: m/e=362.2 [M+H]$^+$.

EXAMPLE 243

10-Methyl-6-(2-oxo-pyrrolidin-1-ylmethyl)-3-trifluoromethoxy-9H-imidazo[1,5-a][1,2,4]triazolo[1,5-d][1,4]benzodiazepine hydrochlorid (1:1)

a) 2-Fluoro-5-trifluoromethoxy-benzaldehyde

A solution of 1-fluoro-4-trifluoromethoxy-benzene (21.0 g, 117 mmol) in THF (233 mL) was cooled to <−70° C. and tert.-butyllithium (86 mL, 1.5 M in pentane, 129 mmol) was added at such a rate that temperature was kept <−70° C. Stirring in the dry ice bath was continued for 15 min, then DMF (11.6 mL, 150 mmol) was added dropwise keeping temperature <−70° C. After 30 min the reaction mixture was allowed to reach rt, quenched with saturated NH$_4$Cl solution and extracted with diethylether. The organic phase was washed with brine, concentrated and chromatographed (SiO$_2$, heptanes:ethyl acetate=100:0 to 80:2) to afford the title compound (11.0 g, 53%) as a light yellow oil. $^1$H-NMR (300 MHz, DMSO): δ=7.60 (t, J=9.2 Hz, 1H), 7.75-7.85 (m, 2H), 10.20 (s, 1H).

b) E-2-Fluoro-5-trifluoromethoxy-benzaldehyde oxime

A solution of 2-fluoro-5-trifluoromethoxy-benzaldehyde (9.78 g, 47 mmol) in ethanol (50 mL) was treated with hydroxylamine HCl (3.59 g, 52 mmol) and sodium acetate (4.27 g, 52 mmol). The resulting mixture was heated under reflux for 2 h. The solvent was then evaporated and the residue stirred with water (50 mL). The precipitate was filtered off, dried and chromatographed (SiO$_2$, heptanes:ethyl acetate=100:0 to 80:2) to afford the title compound (9.21 g, 88%) as a white solid. MS: m/e=223.0 [M]$^+$.

c) 2-Fluoro-5-trifluoromethoxy-benzonitrile

To a solution of E-2-fluoro-5-trifluoromethoxy-benzaldehyde oxime (47.5 g, 213 mmol) in THF (400 mL) was added triethylamine (65.0 mL, 466 mmol). The mixture was cooled in an ice bath and trifluoroacetic anhydride (32.8 mL, 236 mmol) was added at such a rate that the temperature was kept <30° C. After 1 h at rt all volatiles were evaporated (40° C., 200 mbar). The oily residue was partitioned (ether/water), the organic phase was dried over sodium sulfate and concentrated. Distillation (24 mbar, T=80-83° C.) afforded the title compound (36.1 g, 83%) that was sufficiently pure to be used in the next step. MS: m/e=205 [M]$^+$.

d) 2-(4-Methyl-imidazol-1-yl)-5-trifluoromethoxy benzonitrile

As described for example 84a, 2-fluoro-5-trifluoromethoxy-benzonitrile was reacted with 4-methylimidazole and potassium carbonate for 16 h at 90° C. Aqueous workup afforded a 3:1 mixture of the title compound and its regioisomer [2-(5-methyl-imidazol-1-yl)-5-trifluoromethoxy-benzonitrile] as a light brown viscous oil (yield: 100%). $^1$H-NMR (300 MHz, DMSO): δ=2.19 (s, 3H), 7.37 (s, 1H), 7.75-7.90 (m, 2H), 8.02 (s, 1H), 8.27 (d, J=2.7 Hz, 1H).

e) 2-(5-Dimethylaminomethyl-4-methyl-imidazol-1-yl)-5-trifluoromethoxy-benzonitrile As described for example 84b, 2-(4-methyl-imidazol-1-yl)-5-trifluoromethoxy benzonitrile (+regioisomer) was reacted with Eschenmoser's salt in DMF for 24 h at 90° C. Evaporation of the solvent, aqueous workup and chromatography afforded the title compound as a colorless oil that was sufficiently pure to be used in the next step (yield: 38%). $^1$H-NMR (300 MHz, DMSO): δ=1.93 (s, 6H), 2.17 (s, 3H), 3.21 (s, 2H), 7.80-7.95 (m, 3H), 8.22 (s, 1H).

f) [3-(2-Cyano-4-trifluoromethoxy-phenyl)-5-methyl-3H-imidazol-4-ylmethyl]-trimethyl-ammonium; iodide As described for example 84c, 2-(5-dimethylaminomethyl-4-methyl-imidazol-1-yl)-5-trifluoromethoxy-benzonitrile was reacted with methyl iodide for 2 days at 4° C. The title compound was obtained as a white crystalline material (yield: 53%). MS: m/e=339.1 [M]$^+$.

g) 10-Methyl-6-(2-oxo-pyrrolidin-1-ylmethyl)-3-trifluoromethoxy-9H-imidazo[1,5-a][1,2,4]triazolo[1,5-d][1,4]benzodiazepine hydrochlorid (1:1)

As described for example 84d, [3-(2-cyano-4-trifluoromethoxy-phenyl)-5-methyl-3H-imidazol-4-ylmethyl]-trimethyl-ammonium; iodide was reacted with (2-oxo-pyrrolidin-1-yl)-acetic acid hydrazide in DMF for 4 h at 120° C., then for 16 h at 150° C. Evaporation of the solvent and trituration with methanol afforded the free base of the title compound. Treatment with HCl in methanol and crystallization from methanol/diethylether afforded the title compound as a light yellow solid (yield: 37%). MS: m/e=419.2

EXAMPLE 244

6-(Isoxazol-5-ylmethyl)-10-methyl-3-trifluoromethoxy-9H-imidazo[1,5-a][1,2,4]triazolo[1,5-d][1,4]benzodiazepine As described for example 84d, [3-(2-cyano-4-trifluoromethoxy-phenyl)-5-methyl-3H-imidazol-4-ylmethyl]-trimethyl-ammonium; iodide (example 2430 was reacted with isoxazol-5-yl-acetic acid hydrazide (example 138b). After evaporation of the solvent the residue was chromatographed (SiO$_2$, dichloromethane:methanol=100:0 to 96:4) and triturated with diisopropylether to afford the title compound as a white solid (yield: 17%). MS: m/e=403.4 M+H]$^+$.

EXAMPLE 245

10-methyl-6-(3-methyl-isoxazol-5-ylmethyl)-3-trifluoromethoxy-9H-imidazo[1,5-a][1,2,4]triazolo[1,5-d][1,4]benzodiazepine As described for example 84d, [3-(2-cyano-4-trifluoromethoxy-phenyl)-5-methyl-3H-imidazol-4-ylmethyl]-trimethyl-ammonium; iodide (example 243f) was reacted with (3-methyl-isoxazol-5-yl)-acetic acid hydrazide (example 123a). After evaporation of the solvent the residue was chromatographed (SiO$_2$, dichloromethane:methanol=100:0 to 96:4) and triturated with diisopropylether to afford the title compound as a light brown solid (yield: 50%). MS: m/e=417.3 [M+H]$^+$.

EXAMPLE 246

6-Ethoxy-methyl-10-methyl-3-trifluoromethoxy-9H-imidazo[1,5-a][1,2,4]triazolo[1,5-d][1,4]benzodiazepine As described for example 84d, [3-(2-cyano-4-trifluoromethoxy-phenyl)-5-methyl-3H-imidazol-4-ylmethyl]-trimethyl-ammonium; iodide (example 243f) was reacted with ethoxy-acetic acid hydrazide (Brands, Michael et. al. Preparation of azinyl- and azolylsulfones as chemokine IL-8 receptor binding inhibitors. Brit. UK Pat. Appl. (2003), GB 2379218 A1). After evaporation of the solvent the residue was extracted (ethyl acetate/saturated aqueous sodium bicarbonate solution) and triturated with diisopropylether to afford the title compound as a light brown solid (yield: 64%). MS: m/e=380.1 [M+H]$^+$.

EXAMPLE 247

10-Methyl-6-(5-methyl-2H-pyrazol-3-ylmethyl)-3-trifluoromethoxy-9H-imidazo[1,5-a][1,2,4]triazolo[1,5-d][1,4]benzodiazepine As described for example 84d, [3-(2-cyano-4-trifluoromethoxy-phenyl)-5-methyl-3H-imidazol-4-ylmethyl]-trimethyl-ammonium; iodide (example 243f) was reacted with (5-methyl-2H-pyrazol-3-yl)-acetic acid hydrazide (Boettcher, Henning; et. al. Pyrazolylethylpieridinylindoles with central nervous system effects. Ger. Offen. (1997), DE 19602505 A1). After evaporation of the solvent the residue was chromatographed (SiO$_2$, dichloromethane:methanol: aq.ammonia (25%)=100:0:0:0 to 225:10:1). Trituration with diisopropylether afforded the title compound as a light yellow solid (yield: 41%). MS: m/e=416.3 [M+H]$^+$.

EXAMPLE 248

3-Cyclopropyl-10-methyl-6-(2-oxo-pyrrolidin-1-ylmethyl)-9H-imidazo[1,5-a][1,2,4]triazolo[1,5-d][1,4]benzodiazepine A pressure tube was charged with cyclopropyl zinc chloride solution (6.25 mL of a 0.4 M solution in THF, 2.5 mmol) (De Lang, R-J.; Brandsma, L. Synthetic Communications (1998), 28(2), 225-232) and N-methyl-pyrrolidone (2.2 mL) and flushed with argon for 5 min. After addition of bis-(tri-tert.-butylphoshine) palladium(0) (0.01 g, 0.02 mmol) and 3-iodo-10-methyl-6-(2-oxo-pyrrolidin-1-ylmethyl)-9H-imidazo[1,5-a][1,2,4]triazolo[1,5-d][1,4]benzodiazepine (0.46 g, 1 mmol) (example 199) the tube was sealed and heated to 100° C. for 2.5 h. The reaction mixture was poured onto water (18 mL) and cooled in an ice bath. The precipitate was filtered off, dried and chromatographed (SiO$_2$, dichloromethane: methanol:aq.ammonia (25%)=100:0:0:0 to 150:10:1). Crystallization from methanol/diisopropylether afforded the title compound as a white solid (0.11 g, 41%). MS: m/e=375.1 [M+H]$^+$.

EXAMPLE 249

10-Methyl-6-(2-oxo-pyrrolidin-1-ylmethyl)-3-propyl-9H-imidazo[1,5-a][1,2,4]triazolo[1,5-d][1,4]benzodiazepine As described for example 248, 3-iodo-10-methyl-6-(2-oxo-pyrrolidin-1-ylmethyl)-9H-imidazo[1,5-a][1,2,4]triazolo[1,5-d][1,4]benzodiazepine (example 199) was reacted with n-propyl zinc bromide solution and bis-(tri-tert.-butylphoshine) palladium(0). After workup, chromatographic purification (SiO$_2$, dichloromethane:methanol:aq.ammonia (25%)=100:0:0:0 to 150:10:1) and crystallization from methanol/diisopropylether the title compound was obtained as a light yellow solid (yield: 5%). MS: m/e=377.5 [M+H]$^+$.

EXAMPLE 250

3-Ethyl-10-methyl-6-(2-oxo-pyrrolidin-1-ylmethyl)-9H-imidazo[1,5-a][1,2,4]triazolo[1,5-d][1,4]benzodiazepine As described for example 248, 3-iodo-10-methyl-6-(2-oxo-pyrrolidin-1-ylmethyl)-9H-imidazo[1,5-a][1,2,4]triazolo[1,5-d][1,4]benzodiazepine (example 199) was reacted with diethylzinc solution and bis-(tri-tert.-butylphoshine) palladium(0). After workup, chromatographic purification (SiO$_2$, dichloromethane:methanol:aq.ammonia (25%)=100:0:0:0 to 150:10:1) and crystallization from methanol/diisopropylether the title compound was obtained as a white solid (yield: 7%). MS: m/e=363.3 [M+H]$^+$.

EXAMPLE 251

3-Butyl-10-methyl-6-(2-oxo-pyrrolidin-1-ylmethyl)-9H-imidazo[1,5-a][1,2,4]triazolo[1,5-d][1,4]benzodiazepine As described for example 248, 3-iodo-10-methyl-6-(2-oxo-pyrrolidin-1-ylmethyl)-9H-imidazo[1,5-a][1,2,4]triazolo[1,5-d][1,4]benzodiazepine (example 199) was reacted with di-n-butylzinc solution and bis-(tri-tert.-butylphoshine)-palladium(0). After workup, chromatographic purification (SiO$_2$, dichloromethane:methanol:aq.ammonia (25%)=100:0:0:0 to 150:10:1) and crystallization from methanol/diisopropylether the title compound was obtained as an off-white solid (yield: 12%). MS: m/e=391.4 [M+H]$^+$.

EXAMPLE 252

3-Ethynyl-10-methyl-6-(2-oxo-pyrrolidin-1-ylmethyl)-9H-imidazo[1,5-a][1,2,4]triazolo[1,5-d][1,4] benzodiazepine A suspension of 3-iodo-10-methyl-6-(2-oxo-pyrrolidin-1-ylmethyl)-9H-imidazo[1,5-a][1,2,4]triazolo[1,5-d][1,4]benzodiazepine (0.46 g, 1 mmol) (example 199) in THF (5.0 mL) and N-methyl-pyrrolidone (2.2 mL) was flushed with argon for 5 min. After addition of trimethylsilylacetylene (0.21 mL, 1.55 mmol), bis-(triphenylphospine)-palladium(II)-chloride (0.035 g, 0.05 mmol), triphenylphosphine (0.008 g, 0.03 mmol) and triethylamine (0.50 mL, 3.6 mmol) the slurry was stirred for 20 min. Copper(II) bromide was then added and the mixture was stirred at 70° C. for 18 h. After addition of brine and ethyl acetate the organic phase was separated and stirred with 10% aqueous citric acid. The acidic aqueous phase was neutralized with sodium bicarbonate and extracted with ethyl acetate. The organic phase was dried over sodium sulfate, evaporated and chromatographed (SiO$_2$, dichloromethane:methanol=100:0 to 95:5). Crystallization from ethyl acetate/hexane afforded the title compound as a white solid (0.63 g, 18%). MS: m/e=359.0 [M+H]$^+$.

EXAMPLE 253

3-Cyclopropyl-10-methyl-6-(2-oxo-oxazolidin-3-ylmethyl)-9H-imidazo[1,5-a][1,2,4]triazolo[1,5-d][1, 4]benzodiazepine hydrochloride (1:1)

As described for example 248, 3-iodo-10-methyl-6-(2-oxo-oxazolidin-3-ylmethyl)-9H-imidazo[1,5-a][1,2,4]triazolo[1,5-d][1,4]benzodiazepine (example 212) was reacted with cyclopropyl zinc chloride solution (De Lang, R-J.; Brandsma, L. Synthetic Communications (1998), 28(2), 225-232) and bis-(tri-tert.-butylphoshine) palladium(0). After workup, chromatographic purification (SiO$_2$, dichloromethane:methanol:aq.ammonia (25%)=100:0:0:0 to 150:10:1) the free base of the title compound was obtained. Treatment with HCl in methanol and crystallization from methanol/diethylether afforded the title compound as a white solid (yield: 38%). MS: m/e=377.3 [M+H]$^+$.

EXAMPLE 254

6-Ethoxy-methyl-10-methyl-9H-imidazo[1,5-a][1,2, 4]triazolo[1,5-d][1,4]benzodiazepine a) 2-(4-Methyl-imidazol-1-yl)-benzonitrile As described for example 84a, 2-fluoro-benzonitrile was reacted with 4-methylimidazole and potassium carbonate for 16 h at 90° C. After aqueous workup the title compound was obtained as a white solid (yield: 60%). MS: m/e=184.2 [M+H]$^+$.

b) 2-(5-Dimethylaminomethyl-4-methyl-imidazol-1-yl)-benzonitrile

As described for example 84b, 2-(4-methyl-imidazol-1-yl)-benzonitrile was reacted with Eschenmoser's salt in DMF for 5 h at 90° C. Evaporation of the solvent, aqueous workup and chromatography (SiO$_2$, dichloromethane:methanol=100:0 to 96:4) afforded the title compound as a light yellow oil (yield: 57%). MS: m/e=241.4 [M+H]$^+$.

c) [3-(2-Cyano-phenyl)-5-methyl-3H-imidazol-4-ylmethyl]-trimethyl-ammonium; iodide As described for example 84c, 2-(5-dimethylaminomethyl-4-methyl-imidazol-1-yl)-benzonitrile was reacted with methyl iodide for 2 days at 4° C. The title compound was obtained as a white crystalline material (yield: 98%). MS: m/e=196.1 [M–NMe$_3$]$^+$.

d) 6-Ethoxy-methyl-10-methyl-9H-imidazo[1,5-a][1,2,4]triazolo[1,5-d][1,4]benzodiazepine As described for example 84d, [3-(2-cyano-phenyl)-5-methyl-3H-imidazol-4-ylmethyl]-trimethyl-ammonium; iodide was reacted with ethoxy-acetic acid hydrazide (Brands, Michael et. al. Preparation of azinyl- and azolylsulfones as chemokine IL-8 receptor binding inhibitors. Brit. UK Pat. Appl. (2003), GB 2379218 A1) in DMF for 24 h at 150° C. Evaporation of the solvent and chromatography (SiO$_2$, dichloromethane:methanol=100:0 to 97:3) followed by trituration with diisopropylether afforded the title compound as an off-white solid (yield: 27%). MS: m/e=296.5 [M+H]$^+$.

EXAMPLE 255

6-Cyclopropylmethyl-10-methyl-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with cyclopropylacetic acid hydrazide (Oae, Shigeru et al. Journal of the Chemical Society, Perkin Transactions 2: Physical Organic Chemistry (1972-1999) (1974), (15), 1844-8). After evaporation of the solvent the residue was chromatographed ($SiO_2$, dichloromethane:methanol=100:0 to 97:3) followed by trituration with diisopropylether to afford the title compound as the free base. Treatment with HCl in methanol and crystallization from methanol/diethylether afforded the title compound as a light brown solid (yield: 3%). MS: m/e=292.3 $[M+H]^+$.

EXAMPLE 256

10-Methyl-6-(2-oxo-pyrrolidin-1-ylmethyl)-9H-imidazo[1,5-a][1,2,4]triazolo[1,5-d][1,4]benzodiazepine As described for example 84d, [3-(2-cyano-phenyl)-5-methyl-3H-imidazol-4-ylmethyl]-trimethyl-ammonium; iodide (example 254c) was reacted with (2-oxo-pyrrolidin-1-yl)-acetic acid hydrazide. After evaporation of the solvent the residue was chromatographed ($SiO_2$, dichloromethane:methanol=100:0 to 97:3). Trituration with diisopropylether afforded the title compound as an off-white solid (yield: 10%). MS: m/e=335.3 $[M+H]^+$.

EXAMPLE 257

6-(2-Methoxy-ethyl)-10-methyl-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with 3-methoxy-propionic acid hydrazide. After evaporation of the solvent the residue was chromatographed ($SiO_2$, dichloromethane:methanol=100:0 to 97:3) followed by trituration with diisopropylether to afford the title compound as the free base. Treatment with HCl in methanol and crystallization from methanol/diethylether afforded the title compound as a white solid (yield: 14%). MS: m/e=296.4 $[M+H]^+$.

EXAMPLE 258

(rac.)-6-(1-Hydroxy-ethyl)-10-methyl-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with (rac.)-lacthydrazide. After evaporation of the solvent the residue was chromatographed ($SiO_2$, dichloromethane:methanol=100:0 to 97:3) followed by trituration with diisopropyl diethylether to afford the title compound as the free base. Treatment with HCl in methanol and crystallization from methanol/diethylether afforded the title compound as a white solid (yield: 13%). MS: m/e=282.4 $[M+H]^+$.

EXAMPLE 259

10-Methyl-6-(2,2,2-trifluoro-ethyl)-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with 3,3,3-trifluoro-propionic acid hydrazide (example 108a). After evaporation of the solvent the residue was chromatographed ($SiO_2$, dichloromethane:methanol=100:0 to 97:3) and the title compound was obtained as the free base. Treatment with HCl in methanol and crystallization from methanol/diethylether afforded the title compound as a white solid (yield: 15%). MS: m/e=320.0 $[M+H]^+$.

EXAMPLE 260

10-Methyl-6-(3-oxo-morpholin-4-ylmethyl)-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with (3-oxo-morpholin-4-yl)-acetic acid hydrazide (example 119b). After evaporation of the solvent the residue was chromatographed ($SiO_2$, dichloromethane:methanol=100:0 to 97:3) and the title compound was obtained as the free base. Treatment with HCl in methanol and crystallization from methanol/diethylether afforded the title compound as an off-white solid (yield: 43%). MS: m/e=351.3 $[M+H]^+$.

EXAMPLE 261

10-Methyl-6-(pyridine-2-ylmethyl)-9H-imidazo[1,5-a][1,2,4]triazolo[1,5-d][1,4]benzodiazepine As described for example 84d, [3-(2-cyano-phenyl)-5-methyl-3H-imidazol-4-ylmethyl]-trimethyl-ammonium; iodide (example 254c) was reacted with pyridine-2-yl-acetic acid hydrazide (Cemischev, B.; Popov, D.; Pharmazie (1967), 22(8), 432-4). After evaporation of the solvent the residue was chromatographed ($SiO_2$, dichloromethane:methanol=100:0 to 97:3) and the title compound was obtained as the free base. Treatment with HCl in methanol and crystallization from methanol/diethylether afforded the title compound as a light yellow solid (yield: 14%). MS: m/e=329.1 $[M+H]^+$.

EXAMPLE 262

6-(Cyclohexylmethyl)-10-methyl-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with cyclohexyl-acetic acid hydrazide. After evaporation of the solvent the residue was chromatographed ($SiO_2$, dichloromethane:methanol=100:0 to 97:3) and the title compound was obtained as the free base. Treatment with HCl in methanol and crystallization from methanol/diethylether afforded the title compound as a white solid (yield: 22%). MS: m/e=334.4 [M+H]$^+$.

EXAMPLE 263

6-Methanesulfonylmethyl-10-methyl-9H-imidazo[1,5-a][1,2,4]triazolo[1,5-d][1,4]benzodiazepine As described for example 84d, [3-(2-cyano-phenyl)-5-methyl-3H-imidazol-4-ylmethyl]-trimethyl-ammonium; iodide (example 254c) was reacted with methanesulfonyl-acetic acid hydrazide (Bays, David Edmund; Carey, Linda; Hayes, Roger. 3,5-Disubstituted-1,2,4-triazole compounds and pharmaceutical compositions containing them. Eur. Pat. Appl. (1982), EP 50407). After evaporation of the solvent the residue was chromatographed (SiO$_2$, dichloromethane:methanol=100:0 to 97:3). Trituration with diisopropylether afforded the title compound as a white solid (yield: 29%). MS: m/e=330.3 [M+H]$^+$.

EXAMPLE 264

10-Methyl-6-(1-methyl-1H-pyrrol-2-ylmethyl)-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with (1-methyl-1H-pyrrol-2-yl)-acetic acid hydrazide. After evaporation of the solvent the residue was chromatographed (SiO$_2$, dichloromethane:methanol=100:0 to 96:4) and the title compound was obtained as the free base. Treatment with HCl in methanol and crystallization from methanol/diethylether afforded the title compound as a light brown solid (yield: 18%). MS: m/e=331.3 [M+H]$^+$.

EXAMPLE 265

10-Methyl-6-(pyridine-3-ylmethyl)-9H-imidazo[1,5-a][1,2,4]triazolo[1,5-d][1,4]benzodiazepine As described for example 84d, [3-(2-cyano-phenyl)-5-methyl-3H-imidazol-4-ylmethyl]-trimethyl-ammonium; iodide (example 254c) was reacted with pyridine-3-yl-acetic acid hydrazide (Cemischev, B.; Popov, D.; Pharmazie (1967), 22(8), 432-4). After evaporation of the solvent the residue was chromatographed (SiO$_2$, dichloromethane:methanol=100:0 to 97:). Recrystallization from ethyl acetate/diisopropylether afforded the title compound as a light brown solid (yield: 27%). MS: m/e=329.1 [M+H]$^+$.

EXAMPLE 266

10-Methyl-6-(pyrrolidin-1-ylmethyl)-9H-imidazo[1,5-a][1,2,4]triazolo[1,5-d][1,4]benzodiazepine As described for example 84d, [3-(2-cyano-phenyl)-5-methyl-3H-imidazol-4-ylmethyl]-trimethyl-ammonium; iodide (example 254c) was reacted with pyrrolidin-1-yl-acetic acid hydrazide (Lyakhova, E. A. et al. Pharmaceutical Chemistry Journal (Translation of Khimiko-Farmatsevticheskii Zhurnal) (2003), 37(4), 78-183). After evaporation of the solvent the residue was chromatographed (SiO$_2$, dichloromethane:methanol=100:0 to 95:5). Recrystallization from ethyl acetate afforded the title compound as a light yellow solid (yield: 59%). MS: m/e=321.4[M+H]$^+$.

EXAMPLE 267

10-Methyl-6-(pyridine-4-ylmethyl)-9H-imidazo[1,5-a][1,2,4]triazolo[1,5-d][1,4]benzodiazepine As described for example 84d, [3-(2-cyano-phenyl)-5-methyl-3H-imidazol-4-ylmethyl]-trimethyl-ammonium; iodide (example 254c) was reacted with pyridin-4-yl-acetic acid hydrazide (Iwao, Masatomo; Kuraishi, Tsukasa. Journal of Heterocyclic Chemistry (1978), 15(8), 1425-30). After evaporation of the solvent the residue was chromatographed (SiO$_2$, dichloromethane:methanol=100:0 to 95:5) and triturated with diisopropylether to afford the title compound as a light yellow solid (yield: 14%). MS: m/e=329.1 [M+H]$^+$.

EXAMPLE 268

6-(2,5-Dimethyl-thiazol-4-ylmethyl)-10-methyl-9H-imidazo[1,5-a][1,2,4]triazolo[1,5-d][1,4]benzodiazepine As described for example 84d, [3-(2-cyano-phenyl)-5-methyl-3H-imidazol-4-ylmethyl]-trimethyl-ammonium; iodide (example 254c) was reacted with (2,5-dimethyl-thiazol-4-yl)-acetic acid hydrazide (example 125a). After evaporation of the solvent the residue was triturated with methanol to afford the title compound as a white solid (yield: 9%). MS: m/e=363.1 [M+H]$^+$.

EXAMPLE 269

10-Methyl-6-(3-methyl-isoxazol-5-ylmethyl)-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with (3-methyl-isoxazol-5-yl)-acetic acid hydrazide (example 123a). After evaporation of the solvent the residue was chromatographed (SiO$_2$, dichloromethane:methanol=100:0 to 96:4) and the title compound was obtained as the free base. Treatment with HCl in methanol and crystallization from methanol/diethylether afforded the title compound as a white solid (yield: 20%). MS: m/e=333.3 [M+H]$^+$.

EXAMPLE 270

10-Methyl-6-(6-methyl-pyridin-3-ylmethyl)-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with (6-methyl-pyridin-3-yl)-acetic acid hydrazide (example 124a). After evaporation of the solvent the residue was chromatographed (SiO$_2$, dichloromethane:methanol=100:0 to 96:4) and the title compound was obtained as the free base. Treatment with HCl in methanol and crystallization from methanol/diethylether afforded the title compound as a white solid (yield: 40%). MS: m/e=343.1 [M+H]$^+$.

EXAMPLE 271

(rac.)-10-Methyl-6-(tetrahydro-furan-2-ylmethyl)-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with (rac.)-(tetrahydro-furan-2-yl)-acetic acid hydrazide (example 112a). After evaporation of the solvent the residue was chromatographed (SiO$_2$, dichloromethane:methanol=100:0 to 96:4) and the title compound was obtained as the free base. Treatment with HCl in methanol and crystallization from methanol/diethylether afforded the title compound as a white solid (yield: 34%). MS: m/e=322.1 [M+H]$^+$.

EXAMPLE 272

10-Methyl-6-(1-methyl-1H-pyrazol-3-yl)-9H-imidazo[1,5-a][1,2,4]triazolo[1,5-d][1,4]benzodiazepine As described for example 84d, [3-(2-cyano-phenyl)-5-methyl-3H-imidazol-4-ylmethyl]-trimethyl-ammonium; iodide (example 254c) was reacted with 1-methyl-1H-pyrazole-3-carboxylic acid hydrazide. After evaporation of the solvent the residue was chromatographed (SiO$_2$, dichloromethane:methanol:aq.ammonia (25%)=100:0:0:0 to 180:10:1) and the title compound was obtained as the free base. Treatment with HCl in methanol and crystallization from methanol/diethylether afforded the title compound as a light brown solid (yield: 20%). MS: m/e=318.0 [M+H]$^+$.

EXAMPLE 273

10-Methyl-6-(5-methyl-pyrazol-3-yl)-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with 3-methylpyrazole-5-carboxylic acid hydrazide. After evaporation of the solvent the residue was chromatographed (SiO$_2$, dichloromethane:methanol:aq.ammonia (25%)=100:0:0:0 to 180:10:1) and the title compound was obtained as the free base. Treatment with HCl in methanol and crystallization from methanol/diethylether afforded the title compound as a yellow solid (yield: 27%). MS: m/e=318.0 [M+H]$^+$.

EXAMPLE 274

10-Methyl-6-(2-methyl-imidazol-1-ylmethyl)-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with (2-methyl-imidazol-1-yl)-acetic acid hydrazide (Toth, Jozsef et al. Substituted imidazole derivatives. Hung. (1968), HU 154810). After evaporation of the solvent the residue was chromatographed (SiO$_2$, dichloromethane:methanol:aq.ammonia (25%)=100:0:0 to 180:10:1) and the title compound was obtained as the free base. Treatment with HCl in methanol and crystallization from methanol/diethylether afforded the title compound as an off-white solid (yield: 24%). MS: m/e=332.0 [M+H]$^+$.

EXAMPLE 275

6-(Imidazol-1-ylmethyl)-10-methyl-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with imidazol-1-yl-acetic acid hydrazide (Loccufier, Johan; Lingier, Stefaan; Meeus, Pascal. Photographic material containing a novel hydrazide type. Eur. Pat. Appl. (2001), EP 1085371 A1). After evaporation of the solvent the residue was chromatographed (SiO$_2$, dichloromethane:methanol:aq.ammonia (25%)=100:0:0 to 180:10:1) and the title compound was obtained as the free base. Treatment with HCl in methanol and crystallization from methanol/diethylether afforded the title compound as a white solid (yield: 33%). MS: m/e=318.1 [M+H]$^+$.

EXAMPLE 276

6-(2-Ethyl-imidazol-1-ylmethyl)-10-methyl-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with (2-ethyl-imidazol-1-yl)-acetic acid hydrazide (example 129b). After evaporation of the solvent the residue was chromatographed (SiO$_2$, dichloromethane:methanol:aq.ammonia (25%)=100:0:0 to 180:10:1) and the title compound was obtained as the free base. Treatment with HCl in methanol and crystallization from methanol/diethylether afforded the title compound as a white solid (yield: 20%). MS: m/e=346.3[M+H]$^+$.

EXAMPLE 277

10-Methyl-6-(morpholin-4-ylmethyl)-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with morpholin-4-yl-acetic acid hydrazide (example 130a). After evaporation of the solvent the residue was chromatographed (SiO$_2$, dichloromethane:methanol=100:0 to 95:5) and the title compound was obtained as the free base. Treatment with HCl in methanol and crystallization from methanol/diethylether afforded the title compound as a white solid (yield: 48%). MS: m/e=337.3 [M+H]$^+$.

EXAMPLE 278

4-Fluoro-10-methyl-6-(2-methyl-propyl)-9H-imidazo[1,5-a][1,2,4]triazolo[1,5-d][1,4]benzodiazepine a) 2-Fluoro-6-(4-methyl-imidazol-1-yl)-benzonitrile As described for example 84a, 2,6-difluoro-benzonitrile was reacted with 4-methylimidazole and potassium carbonate for 16 h at 90° C. After aqueous workup and chromatography (SiO$_2$, dichloromethane:methanol=100:0 to 98:2) the title compound was obtained as an off-white solid (yield: 29%). $^1$H-NMR (300 MHz, DMSO): δ=2.19 (d, J=0.8 Hz, 3H), 7.39 (s with fine splitting, 1H), 7.56-7.64 (m, 2H), 7.92 (mc, 1H), 8.04 (d, J=1.2 Hz, 1H).

b) 2-(5-Dimethylaminomethyl-4-methyl-imidazol-1-yl)-6-fluoro-benzonitrile

As described for example 84b, 2-fluoro-6-(4-methyl-imidazol-1-yl)-benzonitrile was reacted with Eschenmoser's salt in DMF for 7 h at 90° C. Evaporation of the solvent, aqueous workup and chromatography (SiO$_2$, dichloromethane:methanol=100:0 to 97:3) afforded the title compound as a light yellow solid (yield: 46%). $^1$H-NMR (400 MHz, DMSO): δ=1.94 (s, 6H), 2.17 (s, 3H), 3.23 (s, 2H), 7.61-7.67 (m, 2H), 7.86 (s, 1H), 7.86-7.96 (m, 1H).

c) [3-(2-Cyano-3-fluoro-phenyl)-5-methyl-3H-imidazol-4-ylmethyl]-trimethyl-ammonium; iodide As described for example 84c, 2-(5-dimethylaminomethyl-4-methyl-imidazol-1-yl)-6-fluoro-benzonitrile was reacted with methyl iodide for 2 days at 4° C. The title compound was obtained as a white crystalline material (yield: 98%). MS: m/e=214.3 [M−NMe$_3$]$^+$.

d) 4-Fluoro-10-methyl-6-(2-methyl-propyl)-9H-imidazo[1,5-a][1,2,4]triazolo[1,5-d][1,4]benzodiazepine As described for example 84d, [3-(2-cyano-3-fluoro-phenyl)-5-methyl-3H-imidazol-4-ylmethyl]-trimethyl-ammonium; iodide was reacted with 3-methyl-butyric acid hydrazide in DMF for 16 h at 150° C. After evaporation of the solvent the residue was chromatographed (SiO$_2$, dichloromethane:methanol=1000:0 to 975:25). Trituration with diisopropylether afforded the title compound as an off-white solid (yield: 24%). MS: m/e=312.3 [M+H]$^+$.

EXAMPLE 279

4-Fluoro-10-methyl-6-(5-methyl-pyrazol-3-yl)-9H-imidazo[1,5-a][1,2,4]triazolo[1,5-d][1,4]benzodiazepine As described for example 84d, [3-(2-cyano-3-fluoro-phenyl)-5-methyl-3H-imidazol-4-ylmethyl]-trimethyl-ammonium; iodide (example 278c) was reacted with 3-methylpyrazole-5-carboxylic acid hydrazide in DMF for 16 h at 150° C. After evaporation of the solvent the residue was stirred with methanol and filtered. The mother liquor was concentrated and chromatographed (SiO$_2$, dichloromethane:methanol=100:0 to 97:3). Trituration with diisopropylether afforded the title compound as a white solid (yield: 4%). MS: m/e=336.4 [M+H]$^+$.

EXAMPLE 280

4-Fluoro-10-methyl-6-(3-methyl-butyl)-9H-imidazo[1,5-a][1,2,4]triazolo[1,5-d][1,4]benzodiazepine hydrochloride (1:1)

As described for example 84d, [3-(2-cyano-3-fluoro-phenyl)-5-methyl-3H-imidazol-4-ylmethyl]-trimethyl-ammonium; iodide (example 278c) was reacted with 4-methyl-pentanoic acid hydrazide (Reitz, David B. Preparation of (triazolylmethyl)biphenyl as cardiovascular agents. PCT Int. Appl. (1991), WO 9117148 A1) in DMF for 16 h at 150° C. After evaporation of the solvent the residue was chromatographed (SiO$_2$, dichloromethane:methanol=1000:0 to 975:25) and the title compound was obtained as the free base. Treatment with HCl in methanol and crystallization from methanol/diethylether afforded the title compound as an off-white solid (yield: 26%). MS: m/e=326.4[M+H]$^+$.

EXAMPLE 281

4-Fluoro-6-ethyl-10-methyl-9H-imidazo[1,5-a][1,2,4]triazolo[1,5-d][1,4]benzodiazepine As described for example 84d, [3-(2-cyano-3-fluoro-phenyl)-5-methyl-3H-imidazol-4-ylmethyl]-trimethyl-ammonium; iodide (example 278c) was reacted with propionic acid hydrazide in DMF for 16 h at 150° C. After evaporation of the solvent the residue was stirred with methanol and filtered. The mother liquor was concentrated and chromatographed (SiO$_2$, dichloromethane:methanol=100:0 to 97:3). Trituration with diisopropylether afforded the title compound as a light orange solid (yield: 28%). MS: m/e=284.1 [M+H]$^+$.

EXAMPLE 282

6-Cyclopropylmethyl-4-fluoro-10-methyl-9H-imidazo[1,5-a][1,2,4]triazolo[1,5-d][1,4]benzodiazepine hydrochloride (1:1)

As described for example 84d, [3-(2-cyano-3-fluoro-phenyl)-5-methyl-3H-imidazol-4-ylmethyl]-trimethyl-ammonium; iodide (example 278c) was reacted with cyclopropylacetic acid hydrazide (Oae, Shigeru et al. Journal of the Chemical Society, Perkin Transactions 2: Physical Organic Chemistry (1972-1999) (1974), (15), 1844-8) for 16 h at 150° C. After evaporation of the solvent the residue was chromatographed (SiO$_2$, dichloromethane:methanol=100:0 to 98:2) and the title compound was obtained as the free base. Treatment with HCl in methanol and crystallization from methanol/diethylether afforded the title compound as a light brown solid (yield: 5%). MS: m/e=310.4[M+H]$^+$.

EXAMPLE 283

4-Chloro-10-methyl-6-(2-oxo-pyrrolidin-1-ylmethyl)-9H-imidazo[1,5-a][1,2,4]triazolo[1,5-d][1,4]benzodiazepine hydrochloride (1:1)

a) 2-Chloro-6-(4-methyl-imidazol-1-yl)-benzonitrile

As described for example 84a, 2-chloro-6-fluoro-benzonitrile was reacted with 4-methylimidazole and potassium carbonate for 16 h at 90° C. After aqueous workup and crystallization from ethyl acetate/diisopropylether the title compound was obtained as an off-white solid (yield: 73%). MS: m/e=218.2 [M+H]$^+$.

b) 2-Chloro-6-(5-dimethylaminomethyl-4-methyl-imidazol-1-yl)-benzonitrile

As described for example 84b, 2-chloro-6-(4-methyl-imidazol-1-yl)-benzonitrile was reacted with Eschenmoser's salt in DMF for 5 h at 90° C. Evaporation of the solvent, aqueous workup and chromatography (SiO$_2$, dichloromethane:methanol=100:0 to 98:2) afforded the title compound as a white solid (yield: 29%). MS: m/e=275.1 [M+H]$^+$.

c) [3-(3-Chloro-2-cyano-phenyl)-5-methyl-3H-imidazol-4-ylmethyl]-trimethyl-ammonium; iodide As described for example 84c, 2-chloro-6-(5-dimethylaminomethyl-4-methyl-imidazol-1-yl)-benzonitrile was reacted with methyl iodide for 2 days at 4° C. The title compound was obtained as a white crystalline material (yield: 88%). MS: m/e=230.3 [M−NMe$_3$]$^+$.

d) 4-Chloro-10-methyl-6-(2-oxo-pyrrolidin-1-ylmethyl)-9H-imidazo[1,5-a][1,2,4]triazolo[1,5-d][1,4]benzodiazepine hydrochloride (1:1)

As described for example 84d, [3-(3-chloro-2-cyano-phenyl)-5-methyl-3H-imidazol-4-ylmethyl]-trimethyl-ammonium; iodide was reacted with (2-oxo-pyrrolidin-1-yl)-acetic acid hydrazide for 24 h at 150° C. After evaporation of the solvent the residue was chromatographed ($SiO_2$, dichloromethane:methanol=100:0 to 97:3) and triturated with diisopropylether to afford the free base of the title compound. Treatment with HCl in methanol and crystallization from methanol/diethylether afforded the title compound as a white solid (yield: 56%). MS: m/e=369.0[M+H]$^+$.

EXAMPLE 284

4-Chloro-6-cyclopropylmethyl-10-methyl-9H-imidazo[1,5-a][1,2,4]triazolo[1,5-d][1,4]benzodiazepine hydrochloride (1:1)

As described for example 84d, [3-(3-chloro-2-cyano-phenyl)-5-methyl-3H-imidazol-4-ylmethyl]-trimethyl-ammonium; iodide (example 283c) was reacted with cyclopropylacetic acid hydrazide (Oae, Shigeru et al. Journal of the Chemical Society, Perkin Transactions 2: Physical Organic Chemistry (1972-1999) (1974), (15), 1844-8) for 24 h at 150° C. After evaporation of the solvent the residue was chromatographed ($SiO_2$, dichloromethane:methanol=100:0 to 97:3) and triturated with diisopropylether to afford the free base of the title compound. Treatment with HCl in methanol and crystallization from methanol/diethylether afforded the title compound as an off-white solid (yield: 10%). MS: m/e=326.3 [M+H]$^+$.

EXAMPLE 285

(rac.)-4-Chloro-6-(1-hydroxy-ethyl)-10-methyl-9H-imidazo[1,5-a][1,2,4]triazolo[1,5-d][1,4]benzodiazepine hydrochloride (1:1)

As described for example 84d, [3-(3-chloro-2-cyano-phenyl)-5-methyl-3H-imidazol-4-ylmethyl]-trimethyl-ammonium; iodide (example 283c) was reacted with (rac.)-lacthydrazide for 24 h at 150° C. After evaporation of the solvent the residue was chromatographed ($SiO_2$, dichloromethane:methanol=100:0 to 97:3) and stirred with diisopropylether. Filtration and concentration of the mother liquor afforded the free base of the title compound. Treatment with HCl in methanol and crystallization from methanol/diethylether afforded the title compound as a white solid (yield: 31%). MS: m/e=316.1 [M+H]$^+$.

EXAMPLE 286

4-Chloro-6-ethoxy-methyl-10-methyl-9H-imidazo[1,5-a][1,2,4]triazolo[1,5-d][1,4]benzodiazepine hydrochloride (1:1)

As described for example 84d, [3-(3-chloro-2-cyano-phenyl)-5-methyl-3H-imidazol-4-ylmethyl]-trimethyl-ammonium; iodide (example 283c) was reacted with ethoxy-acetic acid hydrazide (Brands, Michael et. al. Preparation of azinyl- and azolylsulfones as chemokine IL-8 receptor binding inhibitors. Brit. UK Pat. Appl. (2003), GB 2379218 A1) for 24 h at 150° C. After evaporation of the solvent the residue was chromatographed ($SiO_2$, dichloromethane:methanol=100:0 to 97:3) and triturated with diisopropyl diethylether to afford the free base of the title compound. Treatment with HCl in methanol and crystallization from methanol/diethylether afforded the title compound as a white solid (yield: 31%). MS: m/e=330.1 [M+H]$^+$.

EXAMPLE 287

4-Chloro-6-(2-methoxy-ethyl)-10-methyl-9H-imidazo[1,5-a][1,2,4]triazolo[1,5-d][1,4]benzodiazepine As described for example 84d, [3-(3-chloro-2-cyano-phenyl)-5-methyl-3H-imidazol-4-ylmethyl]-trimethyl-ammonium; iodide (example 283c) was reacted with 3-methoxy-propionic acid hydrazide for 24 h at 150° C. After evaporation of the solvent the residue was chromatographed ($SiO_2$, dichloromethane:methanol=100:0 to 97:3). Trituration with diisopropylether afforded the title compound as a white solid (yield: 32%). MS: m/e=330.3 [M+H]$^+$.

EXAMPLE 288

4-Chloro-10-methyl-6-(2,2,2-trifluoro-ethyl)-9H-imidazo[1,5-a][1,2,4]triazolo[1,5-d][1,4]benzodiazepine hydrochloride (1:1)

As described for example 84d, [3-(3-chloro-2-cyano-phenyl)-5-methyl-3H-imidazol-4-ylmethyl]-trimethyl-ammonium; iodide (example 283c) was reacted with 3,3,3-trifluoro-propionic acid hydrazide (example 108a) for 16 h at 150° C. After evaporation of the solvent the residue was chromatographed ($SiO_2$, dichloromethane:methanol=100:0 to 97:3) and the title compound was obtained as the free base. Treatment with HCl in methanol and crystallization from methanol/diethylether afforded the title compound as a white solid (yield: 55%). MS: m/e=354.0[M+H]$^+$.

EXAMPLE 289

3-Bromo-10-chloro-6-(4,4-dimethyl-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using 4,4-dimethyl-oxazolidin-2-one instead of 2-pyrrolidone was converted to the title compound (80 mg, 74%) which was obtained as a white foam. MS: m/e=463.0/465.0 [M+H]$^+$.

EXAMPLE 290 rac 3-Bromo-10-chloro-6-(4-methyl-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using rac 4-methyl-oxazolidin-2-one instead of 2-pyrrolidone was converted to the title compound (18 mg, 17%) which was obtained as a white foam. MS: m/e=449.2/451.2 [M+H]$^+$.

EXAMPLE 291

3-Bromo-10-chloro-6-((4S,5R)-4-methyl-2-oxo-5-phenyl-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (4S,5R)-4-methyl-5-phenyl-oxazolidin-2-one instead of 2-pyrrolidone was converted to the title compound (83 mg, 68%) which was obtained as a white foam. MS: m/e=526.1/528.0 [M+H]$^+$.

EXAMPLE 292

3-Bromo-10-chloro-6-((4R,5S)-4-methyl-2-oxo-5-phenyl-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (4R,5S)-4-methyl-5-phenyl-oxazolidin-2-one instead of 2-pyrrolidone was converted to the title compound (92 mg, 75%) which was obtained as a white foam. MS: m/e=526.1/528.0 [M+H]$^+$.

EXAMPLE 293

3-Bromo-10-chloro-6-(3,3-diethyl-ureido)-9H-imidazo[1,5-a][1,2,4]triazolo[1,5-d][1,4]benzodiazepine To a suspension of 3-bromo-6-carboxy-10-chloro-9H-imidazo[1,5-a][1,2,4]triazolo[1,5-d][1,4]benzodiazepine (300 mg, 0.79 mmol) in tetrahydrofuran (6 mL) were added triethylamine (0.11 mL, 0.79 mmol), diphenylphosphorylazide (0.17 mL, 0.79 mmol) and tert-butanol (0.15 mL, 1.58 mmol) and the resulting mixture was heated at reflux for 36 h. Filtration and purification by chromatography (SiO$_2$, ethyl acetate:methanol=60:1) afforded the title compound (16 mg, 5%) which was obtained as white solid. MS: m/e=450.9/452.3 [M+H]$^+$.

EXAMPLE 294

3-Bromo-10-chloro-6-((4R)-4-tert-butyl-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (4R)-4-tert-butyl-oxazolidin-2-one instead of 2-pyrrolidone was converted to the title compound (93 mg, 81%) which was obtained as a white foam. MS: m/e=475.0/477.1 [M–CH$_3$]$^+$.

EXAMPLE 295

3-Bromo-10-chloro-6-((4R)-4-tert-butyl-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (4S)-4-tert-butyl-oxazolidin-2-one instead of 2-pyrrolidone was converted to the title compound (78 mg, 68%) which was obtained as a white foam. MS: m/e=475.0/477.1 [M–CH$_3$]$^+$.

EXAMPLE 296 rac 3-Bromo-10-chloro-6-(4-cyano-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using rac-2-oxo-oxazolidine-4-carbonitrile instead of 2-pyrrolidone was converted to the title compound (21 mg, 20%) which was obtained as a white foam. MS: m/e=460.1/461.9 [M+H]$^+$.

EXAMPLE 297

3-Bromo-10-chloro-6-((2R)-2-methoxymethyl-pyrrolidin-1-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (R)-2-methoxymethyl-pyrrolidine instead of 2-pyrrolidone was converted to the title compound (72 mg, 67%) which was obtained as a white foam. MS: m/e=465.0/467.1 [M+H]$^+$.

EXAMPLE 298

3-Bromo-10-chloro-6-((2S)-2-methoxymethyl-pyrrolidin-1-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (S)-2-methoxymethyl-pyrrolidine instead of 2-pyrrolidone was converted to the title compound (99 mg, 92%) which was obtained as a white foam. MS: m/e=465.0/467.1 [M+H]$^+$.

EXAMPLE 299

3-Bromo-10-chloro-6-((2S,5S)-2,5-bis-methoxymethyl-pyrrolidin-1-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (2S,5S)-2,5-bis-methoxymethyl-pyrrolidine instead of 2-pyrrolidone was converted to the title compound (99 mg, 92%) which was obtained as a white foam. MS: m/e=509.2/511.2 [M+H]$^+$.

EXAMPLE 300

3-Bromo-10-chloro-6-(3-methyl-2-oxo-imidazolidin-1-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using 1-methyl-2-imidazolidinone instead of 2-pyrrolidone was converted to the title compound (31 mg, 30%) which was obtained as a white solid. MS: m/e=448.0/450.0 [M+H]$^+$.

EXAMPLE 301

3-Bromo-10-chloro-6-(2-oxo-imidazolidin-1-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using 2-imidazolidinone instead of 2-pyrrolidone was converted to the title compound (28 mg, 18%) which was obtained as a white solid. MS: m/e=433.2/435.2 [M+H]$^+$.

EXAMPLE 302

1,3-Bis-(3-bromo-10-chloro-9H-imidazo[1,5-a][1,2,4]triazolo[1,5-d][1,4]benzodiazepin-6-ylmethyl)-imidazolidin-2-one As described for example 49, 3-bromo-6-bromomethyl-10-chloro-9H-imidazo[1,5-a][1,2,4]triazolo[1,5-d][1,4]benzodiazepine (100 mg, 0.23 mmol) using 2-imidazolidinone instead of 2-pyrrolidone was converted to the title compound (35 mg, 13%) which was obtained as a white solid. MS: m/e=783.0/787.0 [M+H]$^+$.

EXAMPLE 303

3-Bromo-10-chloro-6-((4R)-4-methyl-2-oxo-oxazolidin-3-ylmethyl)-9H-imidazo[1,5-a][1,2,4]triazolo[1,5-d][1,4]benzodiazepine As described for example 49) 3-bromo-6-bromomethyl-10-chloro-9H-imidazo[1,5-a][1,2,4]triazolo[1,5-d][1,4]benzodiazepine (100 mg, 0.23 mmol) using (4R)-4-methyl-oxazolidin-2-one instead of 2-pyrrolidone was converted to the title compound (80 mg, 76%) which was obtained as a white solid. MS: m/e=448.9/451.0 [M+H]$^+$.

EXAMPLE 304

3-Bromo-10-chloro-6-((4S)-4-methyl-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (4S)-4-methyl-oxazolidin-2-one instead of 2-pyrrolidone was converted to the title compound (86 mg, 81%) which was obtained as a white solid. MS: m/e=448.9/451.0 [M+H]$^+$.

EXAMPLE 305

3-Bromo-10-chloro-6-((4R)-4-ethyl-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (4R)-4-ethyl-oxazolidin-2-one instead of 2-pyrrolidone was converted to the title compound (27 mg, 25%) which was obtained as a white solid. MS: m/e=462.9/465.0 [M+H]$^+$.

EXAMPLE 306

3-Bromo-10-chloro-6-((4S)-4-ethyl-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (4S)-4-ethyl-oxazolidin-2-one instead of 2-pyrrolidone was converted to the title compound (38 mg, 35%) which was obtained as a white solid. MS: m/e=462.9/465.0 [M+H]$^+$.

EXAMPLE 307 rac 3-Bromo-10-chloro-6-(5-cyano-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using rac-2-oxo-oxazolidine-5-carbonitrile instead of 2-pyrrolidone was converted to the title compound (57 mg, 53%) which was obtained as a white solid. MS: m/e=460.1/461.9 [M+H]$^+$.

EXAMPLE 308

1,2-Bis-(3-bromo-10-chloro-9H-imidazo[1,5-a][1,2,4]triazolo[1,5-d][1,4]benzodiazepin-6-ylmethyl)-4-methyl-[1,2,4]triazolidine-3,5-dione As described for example 49, 3-bromo-6-bromomethyl-10-chloro-9H-imidazo[1,5-a][1,2,4]triazolo[1,5-d][1,4]benzodiazepine (100 mg, 0.23 mmol) using 4-methyl-urazole instead of 2-pyrrolidone was converted to the title compound (50 mg, 26%) which was obtained as a white solid. MS: m/e=811.1/814.3 [M+H]$^+$.

EXAMPLE 309

3-Bromo-10-chloro-6-(2,4-dioxo-thiazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using 2,4-thiazolidindione instead of 2-pyrrolidone was converted to the title compound (83 mg, 77%) which was obtained as a white solid. MS: m/e=467.0/469.1 [M+H]$^+$.

EXAMPLE 310

3-Bromo-10-chloro-6-(2,5-dioxo-pyrrolidin-1-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using succinimide instead of 2-pyrrolidone was converted to the title compound (76 mg, 73%) which was obtained as a white solid. MS: m/e=448.0/450.0 [M+H]$^+$.

EXAMPLE 311

3-Bromo-10-chloro-6-(4-methyl-3,5-dioxo-[1,2,4] triazolidin-1-ylmethyl)-9H-imidazo[1,5-a][1,2,4] triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using 4-methyl-urazole instead of 2-pyrrolidone was converted to the title compound (62 mg, 57%) which was obtained as a white solid. MS: m/e=464.0/465.2 [M+H]$^+$.

EXAMPLE 312

3-Bromo-10-chloro-6-(2-oxo-thiazolidin-3-ylmethyl)-9H-imidazo[1,5-a][1,2,4]triazolo[1,5-d][1,4] benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using thiazolidin-2-one instead of 2-pyrrolidone was converted to the title compound (77 mg, 73%) which was obtained as a white solid. MS: m/e=450.9/452.9 [M+H]$^+$.

EXAMPLE 313

3-Bromo-10-chloro-6-(3-oxo-pyrazolidin-1-ylmethyl)-9H-imidazo[1,5-a][1,2,4]triazolo[1,5-d][1,4] benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using 3-pyrazolidinone instead of 2-pyrrolidone was converted to the title compound (45 mg, 30%) which was obtained as a white solid. MS: m/e=434.1/436.1 [M+H]$^+$.

EXAMPLE 314

3-Bromo-10-chloro-6-((5S)-5-methyl-2-oxo-oxazolidin-3-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (5S)-5-methyl-oxazolidin-2-one instead of 2-pyrrolidone was converted to the title compound (70 mg, 67%) which was obtained as a white solid. MS: m/e=448.9/451.0 [M+H]$^+$.

EXAMPLE 315

3-Bromo-10-chloro-6-((5R)-5-methyl-2-oxo-oxazolidin-3-ylmethyl)-9H-imidazo[1,5-a][1,2,4]triazolo [1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using (5R)-5-methyl-oxazolidin-2-one instead of 2-pyrrolidone was converted to the title compound (88 mg, 84%) which was obtained as a white solid. MS: m/e=448.9/450.9 [M+H]$^+$.

EXAMPLE 316

3,10-Dichloro-6-(2-oxo-oxazolidin-3-ylmethyl)-9H-imidazo[1,5-a][1,2,4]triazolo[1,5-d][1,4]benzodiazepine As described for example 49, 6-bromomethyl-3,10-dichloro-9H-imidazo[1,5-a][1,2,4]triazolo[1,5-d][1,4]benzodiazepine (200 mg, 0.52 mmol) instead of 3-bromo-6-bromomethyl-10-chloro-9H-imidazo[1,5-a][1,2,4]triazolo[1,5-d][1,4]benzodiazepine using oxazolidin-2-one instead of 2-pyrrolidone was converted to the title compound (65 mg, 36%) which was obtained as a white solid. MS: m/e=391.0/392.8 [M+H]$^+$.

EXAMPLE 317

3-Bromo-10-chloro-6-(pyrazol-1-ylmethyl)-9H-imidazo[1,5-a][1,2,4]triazolo[1,5-d][1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using pyrazole instead of 2-pyrrolidone was converted to the title compound (65 mg, 84%) which was obtained as a white solid. MS: m/e=416.0/417.8 [M+H]$^+$.

EXAMPLE 318 rac 3-Bromo-10-chloro-6-(1-methyl-2-oxo-cyclopentylmethyl)-9H-imidazo[1,5-a][1,2,4]triazolo[1,5-d] [1,4]benzodiazepine As described for example 49, 3-bromo-6-bromomethyl-10-chloro-9H-imidazo[1,5-a][1,2,4]triazolo[1,5-d][1,4]benzodiazepine (100 mg, 0.23 mmol) using 2-methylcyclopentanone instead of 2-pyrrolidone was converted to the title compound (45 mg, 43%) which was obtained as a white solid. MS: m/e=446.0/447.9 [M+H]$^+$.

EXAMPLE 319

3-Bromo-10-methyl-6-(6-methyl-2-oxo-2H-pyridin-1-ylmethyl)-9H-imidazo[1,5-a][1,2,4]triazolo[1,5-d] [1,4]benzodiazepine a) (6-Methyl-2-oxo-2H-pyridin-1-yl)-acetic acid hydrazide As described for example 112a, (6-methyl-2-oxo-2H-pyridin-1-yl)-acetic acid ethyl ester (Petride, Horia; Raileanu, Dan. Revue Roumaine de Chimie (1988), 33(7), 729-39.) in ethanol was reacted with hydrazine hydrate (1.8 equivalents) at rt for 96 h. The mixture was concentrated and crystallized from ethanol/diisopropylether and the compound was obtained as a white solid (yield: 88%). MS: m/e=204.2 [M+Na]$^+$.

b) 3-Bromo-10-methyl-6-(6-methyl-2-oxo-2H-pyridin-1-ylmethyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (6-methyl-2-oxo-2H-pyridin-1-yl)-acetic acid hydrazide. After evaporation of the solvent the residue was triturated with methanol and crystallized from ethyl acetate to afford the title compound as an off-white solid (yield: 46%). MS: m/e=437.2/439.2 [M+H]$^+$.

EXAMPLE 320

3-Bromo-10-methyl-6-(3-methyl-2-oxo-2H-pyridin-1-ylmethyl)-9H-imidazo[1,5-a][1,2,4]triazolo[1,5-d][1,4]benzodiazepine hydrochloride (1:1)

a) (3-Methyl-2-oxo-2H-pyridin-1-yl)-acetic acid ethyl ester

A mixture of 2-hydroxy-3-methyl-pyridine (4.1 g, 37 mmol), ethyl bromoacetate (5.9 g, 35 mmol) and potassium carbonate (4.9 g, 35 mmol) in DMF (60 ml) was stirred at rt for 16 h. After evaporation of the solvent and extractive workup (ethyl acetate/water) the organic phase was concentrated and chromatographed ($SiO_2$, heptane:ethyl acetate=100:0 to 40:60). The title compound elutes as the second product and was isolated as a colorless liquid (6.1g, 84%). MS: m/e=196.0[M+H]$^+$.

b) (3-Methyl-2-oxo-2H-pyridin-1-yl)-acetic acid hydrazide

As described for example 112a, (3-methyl-2-oxo-2H-pyridin-1-yl)-acetic acid ethyl ester in ethanol was reacted with hydrazine hydrate (1.2 equivalents) at rt for 72 h. The mixture was concentrated and crystallized from ethanol/diisopropylether and the compound was obtained as a white solid (yield: 96%). MS: m/e=204.4 [M+Na]$^+$.

c) 3-Bromo-10-methyl-6-(3-methyl-2-oxo-2H-pyridin-1 ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (3-methyl-2-oxo-2H-pyridin-1-yl)-acetic acid hydrazide. After evaporation of the solvent the residue was triturated with methanol to afford the title compound as the free base. Treatment with HCl in methanol and crystallization from methanol/diethylether afforded the title compound as an off-white solid (yield: 59%). MS: m/e=437.1/439.2 [M+H]$^+$.

EXAMPLE 321

3-Bromo-10-methyl-6-(4-methyl-2-oxo-2H-pyridin-1-ylmethyl)-9H-imidazo[1,5-a][1,2,4]triazolo[1,5-d][1,4]benzodiazepine hydrochloride (1:1)

a) (4-Methyl-2-oxo-2H-pyridin-1-yl)-acetic acid ethyl ester

As described for example 320a, 2-hydroxy-4-methyl-pyridine was reacted with ethyl bromoacetate and potassium carbonate. Extractive workup followed by chromatography ($SiO_2$, heptane:ethyl acetate=100:0 to 40:60) afforded the title compound as a colorless liquid (yield: 77%). MS: m/e=196.1 [M+H]$^+$.

b) (4-Methyl-2-oxo-2H-pyridin-1-yl)-acetic acid hydrazide

As described for example 112a, (4-methyl-2-oxo-2H-pyridin-1-yl)-acetic acid ethyl ester in ethanol was reacted with hydrazine hydrate (1.2 equivalents) at rt for 72 h. The mixture was concentrated and crystallized from ethanol/diisopropylether and the compound was obtained as a white solid (yield: 94%). MS: m/e=204.3 [M+Na]$^+$.

c) 3-Bromo-10-methyl-6-(4-methyl-2-oxo-2H-pyridin-1-yl-methyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (4-methyl-2-oxo-2H-pyridin-1-yl)-acetic acid hydrazide. After evaporation of the solvent the residue was triturated with methanol to afford the title compound as the free base. Treatment with HCl in methanol and crystallization from methanol/diethylether afforded the title compound as an off-white solid (yield: 17%). MS: m/e=437.1/439.2 [M+H]$^+$.

EXAMPLE 322

3-Bromo-10-methyl-6-(3-trifluoromethyl-pyridin-2-yloxymethyl)-9H-imidazo[1,5-a][1,2,4]triazolo[1,5-d][1,4]benzodiazepine hydrochloride (1:1)

a) (3-Trifluoromethyl-pyridin-2-yloxy)-acetic acid ethyl ester

As described for example 320a, 2-hydroxy-3-(trifluoromethyl)-pyridine was reacted with ethyl bromoacetate and potassium carbonate. Extractive workup followed by chromatography ($SiO_2$, heptane:ethyl acetate=100:0 to 40:60) afforded 2 compounds. The title compound was eluted first and was obtained as a colorless liquid (yield: 2%). MS: m/e=250.1 [M+H]$^+$.

b) (3-Trifluoromethyl-pyridin-2-yloxy)-acetic hydrazide

As described for example 112a, (3-trifluoromethyl-pyridin-2-yloxy)-acetic acid ethyl ester in ethanol was reacted with hydrazine hydrate (1.2 equivalents) at rt for 72 h. The mixture was concentrated and crystallized from ethanol/diisopropylether and the compound was obtained as a white solid (yield: 77%). MS: m/e=236.2 [M+H]$^+$.

c) 3-Bromo-10-methyl-6-(3-trifluoromethyl-pyridin-2-yloxymethyl)-9H-imidazo[1,5-a][1,2,4]triazolo[1,5-d][1,4] benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (3-trifluoromethyl-pyridin-2-yloxy)-acetic hydrazide. After evaporation of the solvent the residue was triturated with methanol to afford the title compound as the free base. Treatment with HCl in methanol and crystallization from methanol/diethylether afforded the title compound as a white solid (yield: 26%). MS: m/e=491.2/493.2 [M+H]$^+$.

EXAMPLE 323

3-Bromo-10-methyl-6-(2-oxo-3-trifluoromethyl-2H-pyridin-1-ylmethyl)-9H-imidazo[1,5-a][1,2,4]triazolo[1,5-d][1,4]benzodiazepine hydrochloride (1:1)

a) (2-Oxo-3-trifluoromethyl-2H-pyridin-1-yl)-acetic acid ethyl ester

As described in example 322a, reaction of 2-hydroxy-3-(trifluoromethyl)-pyridine with ethyl bromoacetate and potassium carbonate gave 2 products. The title compound was eluted second and was obtained as a colorless liquid (yield: 84%). MS: m/e=250.1[M+H]$^+$.

b) (2-Oxo-3-trifluoromethyl-2H-pyridin-1-yl)-acetic acid hydrazide

As described for example 112a, (2-oxo-3-trifluoromethyl-2H-pyridin-1-yl)-acetic acid ethyl ester in ethanol was reacted with hydrazine hydrate (1.2 equivalents) at rt for 72 h. The mixture was concentrated and crystallized from ethanol/diisopropylether and the compound was obtained as a white solid (yield: 95%). MS: m/e=236.3 [M+H]$^+$.

c) 3-Bromo-10-methyl-6-(2-oxo-3-trifluoromethyl-2H-pyridin-1-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (2-oxo-3-trifluoromethyl-2H-pyridin-1-yl)-acetic acid hydrazide. After evaporation of the solvent the residue was triturated with methanol to afford the title compound as the free base. Treatment with HCl in methanol and crystallization from methanol/diethylether afforded the title compound as a white solid (yield: 53%). MS: m/e=491.2/493.2 [M+H]$^+$.

EXAMPLE 324

3-Bromo-10-methyl-6-(3-methoxy-2-oxo-2H-pyridin-1-ylmethyl)-9H-imidazo[1,5-a][1,2,4]triazolo[1,5-d][1,4]benzodiazepine hydrochloride (1:1)

a) (3-Methoxy-2-oxo-2H-pyridin-1-yl)-acetic acid ethyl ester

As described for example 320a, 2-hydroxy-3-methoxy-pyridine was reacted with ethyl bromoacetate and potassium carbonate. Extractive workup followed by chromatography (SiO$_2$, heptane:ethyl acetate=100:0 to 0: 100) afforded the title compound as a white solid (yield: 92%). MS: m/e=212.3 [M+H]$^+$.

b) (3-Methoxy-2-oxo-2H-pyridin-1-yl)-acetic acid hydrazide

As described for example 112a, (3-methoxy-2-oxo-2H-pyridin-1-yl)-acetic acid ethyl ester in ethanol was reacted with hydrazine hydrate (1.2 equivalents) at rt for 16 h. The mixture was concentrated and crystallized from ethanol/diisopropylether and the compound was obtained as a white solid (yield: 83%). MS: m/e=220.1 [M+Na]$^+$.

c) 3-Bromo-10-methyl-6-(3-methoxy-2-oxo-2H-pyridin-1-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (3-methoxy-2-oxo-2H-pyridin-1-yl)-acetic acid hydrazide. After evaporation of the solvent the residue was triturated with methanol to afford the title compound as the free base. Treatment with HCl in methanol and crystallization from methanol/diethylether afforded the title compound as a light yellow solid (yield: 53%). MS: m/e=453.2/455.2 [M+H]$^+$.

EXAMPLE 325

3-Bromo-10-methyl-6-(5-methyl-2-oxo-2H-pyridin-1-ylmethyl)-9H-imidazo[1,5-a][1,2,4]triazolo[1,5-d][1,4]benzodiazepine hydrochloride (1:1)

a) (5-Methyl-2-oxo-2H-pyridin-1-yl)-acetic acid ethyl ester

As described for example 320a, 2-hydroxy-4-methyl-pyridine was reacted with ethyl bromoacetate and potassium carbonate. Extractive workup followed by chromatography (SiO$_2$, heptane:ethyl acetate=100:0 to 0:100) afforded the title compound as a colorless liquid (yield: 76%). MS: m/e=196.1 [M+H]$^+$.

b) (5-Methyl-2-oxo-2H-pyridin-1-yl)-acetic acid hydrazide

As described for example 112a, (5-methyl-2-oxo-2H-pyridin-1-yl)-acetic acid ethyl ester in ethanol was reacted with hydrazine hydrate (1.2 equivalents) at rt for 16 h. The mixture was concentrated and crystallized from ethanol/diisopropylether and the compound was obtained as a white solid (yield: 92%). MS: m/e=204.1 [M+Na]$^+$.

c) 3-Bromo-10-methyl-6-(5-methyl-2-oxo-2H-pyridin-1-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (5-methyl-2-oxo-2H-pyridin-1-yl)-acetic acid hydrazide. After evaporation of the solvent the residue was triturated with methanol to afford the title compound as the free base. Treatment with HCl in methanol and crystallization from methanol/diethylether afforded the title compound as an off-white solid (yield: 55%). MS: m/e=437.1/439.2 [M+H]$^+$.

EXAMPLE 326

(R)-3-Bromo-10-methyl-6-(5-oxo-pyrrolidin-2-yl)-9H-imidazo[1,5-a][1,2,4]triazolo[1,5-d][1,4]benzodiazepine a) (R)-5-Oxo-pyrrolidine-2-carboxylic acid hydrazide This compound was obtained starting from D-pyroglutamic acid ethyl ester following the procedure from Angier, R. B. et al. (Journal of the American Chemical Society (1950), 72, 74-7). The compound was obtained as a white solid (yield: 82%). [α]$^{20}_D$+11.8 (c=2,water).

b) (R)-3-Bromo-10-methyl-6-(5-oxo-pyrrolidin-2-yl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (R)-5-oxo-pyrrolidine-2-carboxylic acid hydrazide. After evaporation of the solvent the residue was triturated with methanol to afford the title compound as a white solid (yield: 27%). MS: m/e=401.2/399.1 [M+H]$^+$.

EXAMPLE 327

3-Bromo-10-methyl-6-(5-methyl-[1,2,4]oxadiazol-3-ylmethyl)-9H-imidazo[1,5-a][1,2,4]triazolo[1,5-d][1,4]benzodiazepine hydrochloride (1:1)

a) 3-Bromo-6-(N-hydroxycarbamimidoylmethyl)-10-methyl-9H-imidazo[1,5-a][1,2,4]triazolo[1,5-d][1,4]benzodiazepine A mixture of 3-bromo-6-cyanomethyl-10-methyl-9H-imidazo[1,5-a][1,2,4]triazolo[1,5-d][1,4]benzodiazepine (example 136) (0.36 g, 1.0 mmol), hydroxylamine HCl salt (0.14 g, 2.0 mmol) and sodium carbonate (0.11 g, 1.0 mmol) in ethanol (4 mL) and water (2 mL) was reacted under microwave conditions (10 min at 110° C., 15 min at 120° C. and then 30 min at 130° C.). After evaporation of all volatile components the residue was stirred with ethyl acetate and water. The precipitate was filtered and dried to afford the title compound as a white solid (0.26 g, 66%). MS: m/e=390.2/388.2 [M+H]$^+$.

b) 3-Bromo-10-methyl-6-(5-methyl-[1,2,4]oxadiazol-3-ylmethyl)-9H-imidazo[1,5-a][1,2,4]triazolo[1,5-d][1,4]benzodiazepine hydrochloride (1:1)

A stirred mixture of 3-bromo-6-(N-hydroxycarbamimidoylmethyl)-10-methyl-9H-imidazo[1,5-a][1,2,4]triazolo

[1,5-d][1,4]benzodiazepine (0.10 g, 0.26 mmol) and triethylamine (0.050 mL, 0.31 mmol) in THF (5 mL) was cooled in an ice bath. A solution of acetyl chloride (0.020 mL, 0.31 mmol) in THF (1 mL) was added dropwise. Then the mixture was stirred at 70° C. for 2 h followed by reaction under microwave conditions (10 min at 100° C., 15 min at 120° C. and then 30 min at 155° C). After extractive workup (ethyl acetate/water) the organic phase was concentrated and chromatographed (SiO$_2$, dichloromethane:methanol=100:0 to 95:5) and the title compound was obtained as the free base. Treatment with HCl in methanol and crystallization from methanol/diethylether afforded the title compound as a white solid (yield: 16%). MS: m/e=414.2/412.1 [M+H]$^+$.

EXAMPLE 328

3-Bromo-6-(2,5-dimethoxy-benzyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (2,5-dimethoxy-phenyl)-acetic acid hydrazide (Prata, Jose V.; Clemente, Dina-Telma S.; Prabhakar, Sundaresan; Lobo, Ana M.; Mourato, Isabel; Branco, Paula S. Journal of the Chemical Society, Perkin Transactions 1 (2002), (4), 513-528). After evaporation of the solvent the residue was triturated with methanol to afford the title compound as the free base. Treatment with HCl in methanol and crystallization from methanol/diethylether afforded the title compound as a white solid (yield: 40%). MS: m/e=466.1/468.0 [M+H]$^+$.

EXAMPLE 329

3-Bromo-6-(2-chloro-benzyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (2-chloro-phenyl)-acetic acid hydrazide (Rosen, Gerald M.; Popp, Frank D.; Gemmill, Frederick Q., Journal of Heterocyclic Chemistry (1971), 8(4), 659-62). After evaporation of the solvent the residue was triturated with methanol to afford the title compound as the free base. Treatment with HCl in methanol and crystallization from methanol/diethylether afforded the title compound as a white solid (yield: 57%). MS: m/e=442.2/440.1 [M+H]$^+$.

EXAMPLE 330

3-Bromo-10-methyl-6-(6-oxo-6H-pyridazin-1-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (6-oxo-6H-pyridazin-1-yl)-acetic acid hydrazide (McMillan, Freeman H.; Kun, Kenneth A.; McMillan, Carol B.; Schwartz, Benjamin S.; King, John A. Journal of the American Chemical Society (1956), 78, 407-10). After evaporation of the solvent the residue was triturated with methanol to afford the title compound as the free base. Treatment with HCl in methanol and crystallization from methanol/diethylether afforded the title compound as an off-white solid (yield: 59%). MS: m/e=425.9/424.0 [M+H]$^+$.

EXAMPLE 331

3-Bromo-10-methyl-6-(4-oxo-4H-pyridin-1-ylmethyl)-9H-imidazo[1,5-a][1,2,4]triazolo[1,5-d][1,4]benzodiazepine a) (4-Oxo-4H-pyridin-1-yl)-acetic acid hydrazide As described for example 112a, (4-oxo-4H-pyridin-1-yl)-acetic acid ethyl ester (Bambury, Ronald E.; Edwards, Michael Louis; Miller, Laird Foulis. 4-Oxo-1-pyridinylpenicllin and -cephalosporin derivatives. Ger. Offen. (1975)) in ethanol was reacted with hydrazine hydrate (1.2 equivalents) at rt for 72 h. The mixture was concentrated and crystallized from ethanol/diisopropylether and the title compound was obtained as a yellow solid (yield: 98%). MS: m/e=168.3 [M+H]$^+$.

b) 3-Bromo-10-methyl-6-(4-oxo-4H-pyridin-1-ylmethyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (4-oxo-4H-pyridin-1-yl)-acetic acid hydrazide. After evaporation of the solvent the residue was concentrated and chromatographed (SiO$_2$, dichloromethane:methanol=100:0 to 92:8). Trituration with methanol/diisopropylether afforded the title compound as an off-white solid (yield: 33%). MS: m/e=425.0/423.0 [M+H]$^+$.

EXAMPLE 332

3-Bromo-6-(formyl-methyl-aminomethyl)-10-methyl-9H-imidazo[1,5-a][1,2,4]triazolo[1,5-d][1,4]benzodiazepine a) N-Hydrazinocarbonylmethyl-N-methyl-formamide As described for example 112a, (formyl-methyl-amino)-acetic acid ethyl ester (Hay, Michael P.; Wilson, William R.; Denny, William A. Tetrahedron (2000), 56(4), 645-657) in ethanol was reacted with hydrazine hydrate (1.2 equivalents) at rt for 96 h. The mixture was concentrated and chromatographed (SiO$_2$, dichloromethane:methanol:aq.ammonia (25%)=100:0:0 to 50:10:1) to afford the title compound as a colorless oil (yield: 84%). MS: m/e=100.1 [M+H−N$_2$H$_4$]$^+$.

b) 3-Bromo-6-(formyl-methyl-aminomethyl)-10-methyl-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with N-hydrazinocarbonylmethyl-N-methyl-formamide. After evaporation of the solvent the residue was concentrated and chromatographed (SiO$_2$, dichloromethane:methanol=100:0 to 96:4). Trituration with methanol/diisopropylether afforded the title compound as a light brown solid (yield: 52%). MS: m/e=389.1/387.1 [M+H]$^+$.

EXAMPLE 333

3-Bromo-10-methyl-6-(5-trifluoromethyl-[1,2,4] oxadiazol-3-ylmethyl)-9H-imidazo[1,5-a][1,2,4] triazolo[1,5-d][1,4]benzodiazepine hydrochloride (1:1)

As described for example 327b, 3-bromo-6-(N-hydroxycarbamimidoylmethyl)-10-methyl-9H-imidazo[1,5-a][1,2,4]triazolo[1,5-d][1,4]benzodiazepine (example 327a) was treated with triethylamine followed by reaction with trifluoroacetic anhydride. Then the mixture was heated under microwave conditions (15 min at 150° C., and then 15 min at 155° C.). After extractive workup (Ethyl acetate/water) the organic phase was concentrated and chromatographed (SiO$_2$, dichloromethane:methanol=1000:0 to 975:25) and the title compound was obtained as the free base. Treatment with HCl in methanol and crystallization from methanol/diethylether afforded the title compound as a white solid (yield: 39%). MS: m/e=466.1/468.2 [M+H]$^+$.

EXAMPLE 334

3-Bromo-6-(5-methoxy-methyl-[1,2,4]oxadiazol-3-ylmethyl)-10-methyl-9H-imidazo[1,5-a][1,2,4]triazolo[1,5-d][1,4]benzodiazepine hydrochloride (1:1)

As described for example 327b, 3-bromo-6-(N-hydroxycarbamimidoylmethyl)-10-methyl-9H-imidazo[1,5-a][1,2,4]triazolo[1,5-d][1,4]benzodiazepine (example 327a) was treated with triethylamine followed by reaction with methoxyacetyl chloride. Then the mixture was heated under microwave conditions (15 min at 150° C., and then 15 min at 155° C.). After extractive workup (Ethyl acetate/water) the organic phase was concentrated and chromatographed (SiO$_2$, dichloromethane:methanol=1000:0 to 975:25) and the title compound was obtained as the free base. Treatment with HCl in methanol and crystallization from methanol/diethylether afforded the title compound as a light yellow solid (yield: 15%). MS: m/e=442.2/444.2[M+H]$^+$.

EXAMPLE 335

3-Bromo-6-(5-cyclopropyl-[1,2,4]oxadiazol-3-ylmethyl)-10-methyl-9H-imidazo[1,5-a][1,2,4]triazolo[1,5-d][1,4]benzodiazepine hydrochloride (1:1)

As described for example 327b, 3-bromo-6-(N-hydroxycarbamimidoylmethyl)-10-methyl-9H-imidazo[1,5-a][1,2,4]triazolo[1,5-d][1,4]benzodiazepine (example 327a) was treated with triethylamine followed by reaction with cyclopropanecarbonyl chloride. Then the mixture was heated under microwave conditions (15 min at 150° C.). After extractive workup (Ethyl acetate/water) the organic phase was concentrated and chromatographed (SiO$_2$, dichloromethane:methanol=1000:0 to 975:25) and the title compound was obtained as the free base. Treatment with HCl in methanol and crystallization from methanol/diethylether afforded the title compound as a yellow solid (yield: 8%). MS: m/e=440.2/438.3[M+H]$^+$.

EXAMPLE 336

3-Bromo-6-(4,6-dimethyl-2-oxo-2H-pyridin-1-ylmethyl)-10-methyl-9H-imidazo[1,5-a][1,2,4]triazolo[1,5-d][1,4]benzodiazepine hydrochloride (1:1)

a) (4,6-Dimethyl-2-oxo-2H-pyridin-1-yl)-acetic acid hydrazide

As described for example 112a, (4,6-dimethyl-2-oxo-2H-pyridin-1-yl)-acetic acid ethyl ester (Shusherina, N. P.; Slavyanova, O. V.; Petrova, L. K.; Levina, R. Ya. Zhurnal Organicheskoi Khimii (1972), 8(2), 387-9) in ethanol was reacted with hydrazine hydrate (1.2 equivalents) at rt for 120 h. The mixture was concentrated and crystallized from ethanol/diisopropylether and the title compound was obtained as a white solid (yield. 90%). MS: m/e=218.2 [M+Na]$^+$.

b) 3-Bromo-6-(4,6-dimethyl-2-oxo-2H-pyridin-1-ylmethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (4,6-dimethyl-2-oxo-2H-pyridin-1-yl)-acetic acid hydrazide. After evaporation of the solvent the residue was triturated with methanol to afford the title compound as the free base. Treatment with HCl in methanol and crystallization from methanol/diethylether afforded the title compound as an off-white solid (yield: 33%). MS: m/e=453.2/451.1 [M+H]$^+$.

EXAMPLE 337

3-Bromo-6-(2-chloro-6-fluoro-benzyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (2-chloro-6-fluoro-phenyl)-acetic acid hydrazide (Coppo, Frank T.; Evans, Karen A.; Graybill, Todd L.; Burton, George. Tetrahedron Letters (2004), 45(16), 3257-3260). After evaporation of the solvent the residue was triturated with methanol to afford the title compound as the free base. Treatment with HCl in methanol and crystallization from methanol/diethylether afforded the title compound as an off-white solid (yield: 38%). MS: m/e=460.2/458.2 [M+H]$^+$.

EXAMPLE 338

3-Bromo-6-(1-hydroxy-cyclopropyl)-10-methyl-9H-imidazo[1,5-a][1,2,4]triazolo[1,5-d][1,4]benzodiazepine hydrochloride (1:1)

a) 1-Hydroxy-cyclopropanecarboxylic acid hydrazide

As described for example 112a, 1-hydroxy-cyclopropanecarboxylic acid methyl ester in butanol was reacted with hydrazine hydrate (1.2 equivalents) at 80° C. for 16 h. The mixture was concentrated and crystallized from ethanol/diisopropylether and the title compound was obtained as a white solid (yield: 81%). MS: m/e=117.2 [M+Na]$^+$.

b) 3-Bromo-6-(1-hydroxy-cyclopropyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with 1-hydroxycyclopropanecarboxylic acid hydrazide. After evaporation of the solvent the residue was chromatographed (SiO$_2$, dichloromethane:methanol=1000:0 to 955:45) and the title compound was obtained as the free base. Treatment with HCl in methanol and crystallization from methanol/diethylether afforded the title compound as an off-white solid (yield: 20%). MS: m/e=374.1/372.1[M+H]$^+$.

EXAMPLE 339

3-Bromo-10-methyl-6-([1,2,4]triazol-4-ylmethyl)-9H-imidazo[1,5-a][1,2,4]triazolo[1,5-d][1,4]benzodiazepine hydrochloride (1:1)

a) [1,2,4]Triazol-4-yl-acetic acid hydrazide

A solution of [1,2,4]triazol-4-yl-acetic acid (1.0 g, 7.9 mmol) in DMF (10 mL) was treated with 1,1'-carbonyldiimidazole (1.66 g, 10.2 mmol) and stirred at rt for 4 h. Butanol (3.6 mL, 39.3 mmol) was added and stirring was continued for 4 h. After addition of water (30 mL) the aqueous phase was extracted first with ether and then with ethyl acetate. The combined organic phases were dried (Na$_2$SO$_4$) and concentrated to afford the butyl ester as a colorless oil (2.30 g, >100%). Without further purification the butyl ester was dissolved in butanol (10 ml), hydrazine hydrate (0.45 mL, 9.3 mmol) was added and the resulting mixture was stirred at rt for 16 h. Then the mixture was concentrated and crystallized from ethanol/diisopropylether and the title compound was obtained as a white solid (0.73 g, 66%). MS: m/e=141.1 [M]$^+$.

b) 3-Bromo-10-methyl-6-([1,2,4]triazol-4-ylmethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with [1,2,4]triazol-4-yl-acetic acid hydrazide. After evaporation of the solvent the residue was triturated with methanol to afford the title compound as the free base. Treatment with HCl in methanol and crystallization from methanol/diethylether afforded the title compound as an off-white solid (yield: 46%). MS: m/e=399.1/397.1 [M+H]$^+$.

EXAMPLE 340

(rac.)-3-Bromo-10-methyl-6-(2,2,2-trifluoro-1-hydroxy-ethyl)-9H-imidazo[1,5-a][1,2,4]triazolo[1,5-d][1,4]benzodiazepine hydrochloride (1:1)

a) (rac.)-3,3,3-Trifluoro-2-hydroxy-propionic acid hydrazide

As described for example 112a, methyl-3,3,3-trifluoro-DL-lactate in butanol was reacted with hydrazine hydrate (1.2 equivalents) at rt for 16 h. The mixture was concentrated and the title compound was obtained as a light yellow oil (yield: 81%). MS: m/e=158.0 [M]$^+$.

b) (rac.)-3-Bromo-10-methyl-6-(2,2,2-trifluoro-1-hydroxy-ethyl)-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (rac.)-3,3,3-trifluoro-2-hydroxy-propionic acid hydrazide. After evaporation of the solvent the residue was triturated with methanol to afford the title compound as the free base. Treatment with HCl in methanol and crystallization from methanol/diethylether afforded the title compound as an off-white solid (yield: 44%). MS: m/e=416.2/414.2 [M+H]$^+$.

EXAMPLE 341

3-Bromo-10-methyl-6-(methyl-aminomethyl)-9H-imidazo[1,5-a][1,2,4]triazolo[1,5-d][1,4]benzodiazepine hydrochloride (1:1)

A solution of 3-bromo-6-(formyl-methyl-aminomethyl)-10-methyl-9H-imidazo[1,5-a][1,2,4]triazolo[1,5-d][1,4]benzodiazepine (example 332a) (0.39 g, 1 mmol) in 3M HCl in methanol (5 ml) was stirred at 50° C. for 2 h. On cooling the title compound crystallizes as an off-white solid (0.36 g, 91%). MS: m/e=361.1/359.1 [M+H]$^+$.

EXAMPLE 342

3-Bromo-6-[(cyclopropanecarbonyl-methyl-amino)-methyl]-10-methyl-9H-imidazo[1,5-a][1,2,4]triazolo[1,5-d][1,4]benzodiazepine hydrochloride (1:1)

A slurry of 3-bromo-10-methyl-6-(methyl-aminomethyl)-9H-imidazo[1,5-a][1,2,4]triazolo[1,5-d][1,4]benzodiazepine hydrochloride (1:1) (example 341) (0.37 g, 0.94 mmol) and triethylamine (0.29 ml, 2.1 mmol) in THF (5 mL) was cooled to 0° C. and a solution of cyclopropanecarbonyl chloride (0.10 ml, 1.1 mmol) in THF (1 mL) was added dropwise. After stirring for 90 min at rt the mixture was filtered, adsorbed on silica gel and chromatographed (SiO$_2$, dichloromethane:methanol:aq.ammonia (25%)=100:0:0 to 180:10:1) and the title compound was obtained as the free base. Treatment with HCl in methanol and crystallization from methanol/diethylether afforded the title compound as a white solid (yield: 44%). MS: m/e=429.3/427.2 [M+H]$^+$.

EXAMPLE 343

3-Bromo-6-[(isobutyryl-methyl-amino)-methyl]-10-methyl-9H-imidazo[1,5-a][1,2,4]triazolo[1,5-d][1,4]benzodiazepine hydrochloride (1:1)

As described for example 342, 3-bromo-10-methyl-6-(methyl-aminomethyl)-9H-imidazo[1,5-a][1,2,4]triazolo[1,5-d][1,4]benzodiazepine hydrochloride (1:1) (example 341) was reacted with isobutyryl chloride and triethylamine. After filtration and chromatography the free base was treated with HCl in methanol. Crystallization from methanol/diethylether afforded the title compound as a white solid (yield: 19%). MS: m/e=429.3/431.3 [M+H]$^+$.

EXAMPLE 344

3-Bromo-6-{[(2,2-dimethyl-propionyl)-methyl-amino]-methyl}-10-methyl-9H-imidazo[1,5-a][1,2,4]triazolo[1,5-d][1,4]benzodiazepine hydrochloride (1:1)

As described for example 342, 3-bromo-10-methyl-6-(methyl-aminomethyl)-9H-imidazo[1,5-a][1,2,4]triazolo[1,5-d][1,4]benzodiazepine hydrochloride (1:1) (example 341) was reacted with 2,2-dimethyl-propionyl chloride and triethylamine. After filtration and chromatography the free base was treated with HCl in methanol. Crystallization from methanol/diethylether afforded the title compound as a white solid (yield: 29%). MS: m/e=445.2/443.3 [M+H]$^+$.

EXAMPLE 345

3-Bromo-6-[(cyclobutanecarbonyl-methyl-amino)-methyl]-10-methyl-9H-imidazo[1,5-a][1,2,4]triazolo[1,5-d][1,4]benzodiazepine hydrochloride (1:1)

As described for example 342, 3-bromo-10-methyl-6-(methyl-aminomethyl)-9H-imidazo[1,5-a][1,2,4]triazolo[1,5-d][1,4]benzodiazepine hydrochloride (1:1) (example 341) was reacted with cyclobutanecarbonyl chloride and triethylamine. After filtration and chromatography the free base was treated with HCl in methanol. Crystallization from methanol/diethylether afforded the title compound as a white solid (yield: 20%). MS: m/e=441.3/443.3 [M+H]$^+$.

EXAMPLE 346

3-Bromo-6-[(methanesulfonyl-methyl-amino)-methyl]-10-methyl-9H-imidazo[1,5-a][1,2,4]triazolo[1,5-d][1,4]benzodiazepine A slurry of 3-bromo-10-methyl-6-(methyl-aminomethyl)-9H-imidazo[1,5-a][1,2,4]triazolo[1,5-d][1,4]benzodiazepine hydrochloride (1:1) (example 341) (0.37 g, 0.94 mmol) and 4-dimethylaminopyridine (0.018 g, 0.15 mmol) in pyridine (5 mL) was treated with methanesulfonyl chloride (0.18 mL, 2.3 mmol). After stirring for 3 h at rt the mixture was evaporated, adsorbed on silica gel and chromatographed (SiO$_2$, dichloromethane:methanol:aq.ammonia (25%)=100:0:0 to 180:10:1). Trituration with methanol afforded the title compound as a white solid (0.28 g, 51%). MS: m/e=439.2/437.1 [M+H]$^+$.

EXAMPLE 347

3-Bromo-6-[(2-acetoxy-acetylamino)-methyl]-10-methyl-9H-imidazo[1,5-a][1,2,4]triazolo[1,5-d][1,4]benzodiazepine As described for example 142b, 6-aminomethyl-3-bromo-10-methyl-9H-imidazo[1,5-a][1,2,4]triazolo[1,5-d][1,4]benzodiazepine (example 142a) was reacted with acetoxy acetyl chloride and triethylamine. After filtration and evaporation the residue was triturated with dichloromethane to afford the title compound as an off-white solid (yield: 95%). MS: m/e=445.2/447.1 [M+H]$^+$.

EXAMPLE 348

(rac.)-3-Bromo-10-methyl-6-(1-[1,2,4]triazol-1-yl-ethyl)-9H-imidazo[1,5-a][1,2,4]triazolo[1,5-d][1,4]benzodiazepine a) (rac.)-2-[1,2,4]Triazol-1-yl-propionic acid hydrazide As described for example 112a, (rac.)-2-[1,2,4]triazol-1-yl-propionic acid methyl ester in butanol was reacted with hydrazine hydrate (1.2 equivalents) at rt for 16 h. The mixture was concentrated and triturated with toluene to afford the title compound as a white solid (yield: 91%). MS: m/e=155.0 [M]$^+$.

b) (rac.)-3-Bromo-10-methyl-6-(1-[1,2,4]triazol-1-ylethyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (rac.)-2-[1,2,4]triazol-1-yl-propionic acid hydrazide. After evaporation of the solvent the residue was triturated with methanol/diisopropyl ether to afford the title compound as an off-white solid (yield: 45%). MS: m/e=411.0/413.1 [M+H]$^+$.

EXAMPLE 349

3-Bromo-10-methyl-6-(3-methyl-[1,2,4]oxadiazol-5-ylmethyl)-9H-imidazo[1,5-a][1,2,4]triazolo[1,5-d][1,4]benzodiazepine a) 3-Bromo-6-(carboxymethyl)-10-methyl-9H-imidazo[1,5-a][1,2,4]triazolo[1,5-d][1,4]benzodiazepine A mixture of 3-bromo-6-cyanomethyl-10-methyl-9H-imidazo[1,5-a][1,2,4]triazolo[1,5-d][1,4]benzodiazepine (example 136) (0.53 g, 1.5 mmol), aqueous sodium hydroxide (2 M, 10 mL) and dioxane (10 mL) was stirred at reflux for 2 h. After neutralization with aqueous HCl (28%) and evaporation of all volatile components the residue was extracted with hot methanol. Filtration and evaporation provided the title compound as a white amorphous solid (0.56 g, 100%). MS: m/e=374.1/376.2 [M+H]$^+$.

b) 3-Bromo-10-methyl-6-(3-methyl-[1,2,4]oxadiazol-5-yl-methyl)-9H-imidazo[1,5-a][1,2,4]triazolo[1,5-d][1,4]benzodiazepine A stirred mixture of 3-bromo-6-(carboxymethyl)-10-methyl-9H-imidazo[1,5-a][1,2,4]triazolo[1,5-d][1,4]benzodiazepine (0.52 g, 1.4 mmol) and carbonyl diimidazole (0.27 g, 1.7 mmol) in DMF (15 ml) was heated to 50° C. for 1 h. After cooling to rt acetamide oxime (0.11 g, 1.5 mmol) was added and the resulting mixture was stirred at 110° C. for 2 h. Then the solvent was evaporated and partitioned (ethyl acetate/water). The organic phase was concentrated, chromatographed (SiO$_2$, dichloromethane:methanol=1000:0 to 975:25) and triturated with diisopropyllether to afford the title compound as a white solid (yield: 0.04 g, 7%). MS: m/e=412.0/414.1 [M+H]$^+$.

EXAMPLE 350

3-Bromo-6-(3-bromo-2-oxo-2H-pyridin-1-ylmethyl)-10-methyl-9H-imidazo[1,5-a][1,2,4]triazolo[1,5-d][1,4]benzodiazepine hydrochloride (1:1)

a) (3-Bromo-2-oxo-2H-pyridin-1-yl)-acetic acid ethyl ester

As described for example 320a, 3-bromo-2-hydroxy-pyridine was reacted with ethyl bromoacetate and potassium carbonate. Extractive workup followed by chromatography (SiO$_2$, heptane:ethyl acetate=100:0 to 50:50) afforded the title compound as a light yellow oil (yield: 55%), which was directly used in the next step.

b) (3-Bromo-2-oxo-2H-pyridin-1-yl)-acetic acid hydrazide

As described for example 112a, (3-bromo-2-oxo-2H-pyridin-1-yl)-acetic acid ethyl ester in butanol was reacted with hydrazine hydrate (1.2 equivalents) at reflux for 16 h. The precipitate was filtered and triturated with hot methanol to afford the title compound as an off-white solid (yield: 62%). MS: m/e=244.2/246.2 [M–H]$^-$.

c) 3-Bromo-6-(3-bromo-2-oxo-2H-pyridin-1-ylmethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (3-bromo-2- oxo-2H-pyridin-1-yl)-acetic acid hydrazide. After evaporation of the solvent the residue was triturated with methanol to afford the title compound as the free base. Treatment with HCl in methanol and crystallization from methanol/diethylether afforded the title compound as a white solid (yield: 50%). MS: m/e=502.9/504.9 [M+H]$^+$.

EXAMPLE 351

3-Bromo-10-methyl-6-(4-methyl-3-oxo-2,3-dihydro-pyrazol-1-ylmethyl)-9H-imidazo[1,5-a][1,2,4]triazolo[1,5-d][1,4]benzodiazepine a) (4-Methyl-3-oxo-2,3-dihydro-pyrazol-1-yl)-acetic acid ethyl ester As described for example 320a, 4-methyl-2-pyrazolin-5-one was reacted with ethyl bromoacetate and potassium carbonate. Extractive workup followed by chromatography (SiO$_2$, heptane:ethyl acetate=100:0 to 50:50) afforded the title compound as a white solid (yield: 16%). MS: m/e=185.0 [M+H]$^+$.

b) (4-Methyl-3-oxo-2.3-dihydro-pyrazol-1-yl)-acetic acid hydrazide

As described for example 112a, (3-bromo-2-oxo-2H-pyridin-1-yl)-acetic acid ethyl ester in butanol was reacted with hydrazine hydrate (1.2 equivalents) at reflux for 5 h. All volatiles were evaporated and the residue was triturated with toluene to afford the title compound as a white solid (yield: 88%). MS: m/e=170.1 [M]$^+$.

c) 3-Bromo-10-methyl-6-(4-methyl-3-oxo-2,3-dihydro-pyrazol-1-ylmethyl)-9H-imidazo[1,5-a][1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (4-methyl-3-oxo-2,3-dihydro-pyrazol-1-yl)-acetic acid hydrazide. After evaporation of the solvent the residue was chromatographed (SiO$_2$, dichloromethane:methanol=100:0 to 95:5) and triturated with ethyl acetate to afford the title compound as a white solid (yield: 18%). MS: m/e=428.0/425.9 [M+H]$^+$.

EXAMPLE 352

3-Bromo-6-(4-chloro-pyrazol-1-ylmethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (4-chloro-pyrazol-1-yl)-acetic acid hydrazide. After evaporation of the solvent the residue was triturated with methanol to afford the title compound as the free base. Treatment with HCl in methanol and crystallization from methanol/diethylether afforded the title compound as a white solid (yield: 51%). MS: m/e=432.0/430.0 [M+H]$^+$.

EXAMPLE 353

3-Bromo-6-[(2-hydroxy-acetylamino)-methyl]-10-methyl-9H-imidazo[1,5-a][1,2,4]triazolo[1,5-d][1,4]benzodiazepine A mixture of 3-bromo-6-[(2-acetoxy-acetylamino)-methyl]-10-methyl-9H-imidazo[1,5-a][1,2,4]triazolo[1,5-d][1,4]benzodiazepine (example 347) (0.10 g, 0.22 mmol) and aqueous sodium hydroxide (1 N, 0.5 mL) in dioxane (2 mL) was stirred at rt for 2 h. The resulting slurry was filtered, aqueous HCl (1 N, 0.5 mL) was added and stirring was continued for 2 h. The precipitate was filtered and dried to afford the title compound as a white solid (0.050 g, 55%). MS: m/e=403.3/405.2 [M+H]$^+$.

EXAMPLE 354

(S)-3-Bromo-6-(1-hydroxy-ethyl)-10-methyl-9H-imidazo[1,5-a][1,2,4]triazolo[1,5-d][1,4]benzodiazepine hydrochloride (1:1)

a) (S)-2-Hydroxy-propionic acid hydrazide

As described for example 112a, ethyl-L-lactate in ethanol was reacted with hydrazine hydrate (1.0 equivalent) at rt for 72 h. All volatiles were evaporated and the residue was chromatographed (SiO$_2$, dichloromethane:methanol=100:0 to 92:8) to afford the title compound as a colorless oil (yield: 72%). $[\alpha]^{20}_D$–23.1 (c=1, methanol).

b) (S)-3-Bromo-6-(1-hydroxy-ethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (S)-2-hydroxy-propionic acid hydrazide. After evaporation of the solvent the residue was chromatographed (SiO$_2$, dichloromethane:methanol=100:0 to 92:8) to afford the title compound as the free base. Treatment with HCl in methanol and crystallization from methanol/diethylether afforded the title compound as a light yellow solid (yield: 13%). MS: m/e=360.0/362.1 [M+H]$^+$.

EXAMPLE 355

(R)-3-Bromo-6-(1-hydroxy-ethyl)-10-methyl-9H-imidazo[1,5-a][1,2,4]triazolo[1,5-d][1,4]benzodiazepine a) (R)-2-Hydroxy-propionic acid hydrazide As described for example 112a, ethyl-D-lactate in ethanol was reacted with hydrazine hydrate (1.0 equivalent) at rt for 72 h. All volatiles were evaporated and the residue was chromatographed (SiO$_2$, dichloromethane:methanol=100:0 to 92:8) to afford the title compound as a colorless oil (yield: 79%). $[\alpha]^{20}_D$+24.9 (c=1, methanol).

b) (R)-3-Bromo-6-(1-hydroxy-ethyl)-10-methyl-9H-imidazo[1,5-a[]1,2,4]triazolo[1,5-d][1,4]benzodiazepine As described for example 84d, [3-(4-bromo-2-cyano-phenyl)-5-methyl-3H-imidazol-4-ylmethyl]-trimethyl-ammonium; iodide (example 84c) was reacted with (R)-2-hydroxy-propionic acid hydrazide. On cooling the title compound precipitates from the reaction mixture as a light yellow solid (yield: 23%). MS: m/e=362.1/360.0 [M+H]$^+$.

EXAMPLE 356

(S)-3-Bromo-6-(2-hydroxy-propyl)-10-methyl-9H-imidazo[1,5-a][1,2,4]triazolo[1,5-d][1,4]benzodiazepine hydrochloride (1:1)

a) (S)-3-Hydroxy-butyric acid hydrazide

A solution of (S)-3-hydroxy-butyric acid (1.0 g, 9.6 mmol) in methanol/water=10:1 (25 ml) was treated with an ethereal diazomethane solution (approx. 0.5 M) until a yellow colour persisted for 1 min. All volatiles were removed under reduced pressure and the residue was coevaporated with toluene. As described for example 112a, the obtained methyl ester was dissolved in ethanol and reacted with hydrazine hydrate (2.1 equivalents) at 60° C. for 6 h. All volatiles were evaporated to afford the title compound as white solid (yield: 45%). $^1$H-NMR (300 MHz, DMSO): δ=1.04 (d, J=6.2 Hz, 3H), 2.03 (dd, J=6.1 Hz, J=13.7 Hz, 1H), 2.14 (dd, J=7.1 Hz, J=13.7 Hz, 1H), 3.95 (mc, 1H), 4.16 (s, broad, 2H), 4.62 (d, J=4.4 Hz, 1H), 8.92 (s, broad, 1H).

b) (S)-3-Bromo-6-(2-hydroxy-propyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (S)-3-hydroxy-butyric acid hydrazide. After evaporation of the solvent the residue was chromatographed (SiO$_2$, dichloromethane:methanol=100:0 to 95:5) to afford the title compound as the free base. Treatment with HCl in methanol and crystallization from methanol/diethylether afforded the title compound as a white solid (yield: 24%). MS: m/e=374.1/376.2 [M+H]$^+$.

EXAMPLE 357

(R)-3-Bromo-6-(2-hydroxy-propyl)-10-methyl-9H-imidazo[1,5-a][1,2,4]triazolo[1,5-d][1,4]benzodiazepine hydrochloride (1:1)

a) (R)-3-Hydroxy-butyric acid hydrazide

This compound was synthesized starting from (R)-3-hydroxy-butyric acid like the enantiomer described in example 356a.

b) (R)-3-Bromo-6-(2-hydroxy-propyl)-10-methyl-9H-imidazo[1,5-a][1,2,4]triazolo[1,5-d][1,4]benzodiazepine hydrochloride (1:1)

This compound was synthesized starting from (R)-3-hydroxy-butyric acid hydrazide like the enantiomer described in example 356b (yield: 26%). MS: m/e=376.2/374.1 [M+H]$^+$.

EXAMPLE 358

(rac.)-3-Bromo-6-(cyclopropyl-hydroxy-methyl)-10-methyl-9H-imidazo[1,5-a][1,2,4]triazolo[1,5-d][1,4]benzodiazepine hydrochloride (1:1)

a) (rac.)-2-Cyclopropyl-2-hydroxy-acetic acid hydrazide

As described for example 112a, (rac.)-2-cyclopropyl-2-hydroxy-acetic acid methyl ester (Newall, Christopher Earle; Foxton, Michael Walter; Hartley, Charles David; Looker, Brian Edgar. Cephalosporin antibiotics. Eur. Pat. Appl. (1985), 57 pp) in methanol was reacted with hydrazine hydrate (1.0 equivalent) at rt for 76 h. All volatiles were evaporated and the residue was triturated with hexane to afford the title compound as a white solid (yield: 69%). MS: m/e=112.2 [M–H$_2$O]$^+$.

b) (rac.)-3-Bromo-6-(cyclopropyl-hydroxy-methyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with (rac.)-2-cyclopropyl-2-hydroxy-acetic acid hydrazide. After evaporation of the solvent the residue was chromatographed (SiO$_2$, dichloromethane:methanol=100:0 to 95:5) to afford the title compound as the free base. Treatment with HCl in methanol and crystallization from methanol/diethylether afforded the title compound as a white solid (yield: 28%). MS: m/e=386.1/388.2 [M+H]$^+$.

EXAMPLE 359

3-Bromo-6-(2-hydroxy-ethyl)-10-methyl-9H-imidazo[1,5-a][1,2,4]triazolo[1,5-d][1,4]benzodiazepine hydrochloride (1:1)

As described for example 84d, [3-(4-bromo-2-cyano-phenyl)-5-methyl-3H-imidazol-4-ylmethyl]-trimethyl-ammonium; iodide (example 84c) was reacted with 3-hydroxy-propionic acid hydrazide (Allen, Charles F. H.; Magder, Edna W. Journal of Heterocyclic Chemistry (1969), 6(3), 349-60). After evaporation of the solvent the residue was triturated with methanol to afford the title compound as the free base. Treatment with HCl in methanol and crystallization from methanol/diethylether afforded the title compound as an off-white solid (yield: 16%). MS: m/e=362.2/360.1 [M+H]$^+$.

EXAMPLE 360

3-Chloro-10-methyl-6-[1,2,3]triazol-2-ylmethyl-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with [1,2,3]triazol-2-yl-acetic acid hydrazide (example 166a). Upon cooling to rt the title compound crystallized from the reaction mixture as the free base. Treatment with HCl in methanol and crystallization from methanol/diethylether afforded the title compound as a white solid (yield: 50%). MS: m/e=353.2[M+H]$^+$.

EXAMPLE 361

3-Chloro-10-methyl-6-(2-oxo-2H-pyridin-1-ylmethyl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with (2-oxo-2H-pyridin-1-yl)-acetic acid hydrazide (example 151a). Upon cooling to rt the title compound crystallized from the reaction mixture as the free base. Treatment with HCl in methanol and crystallization from methanol/diethylether afforded the title compound as a white solid (yield: 41%). MS: m/e=379.2[M+H]$^+$.

EXAMPLE 362

3-Chloro-10-methyl-6-(2-oxo-oxazolidin-3-ylmethyl)-9H-imidazo[1,5-a][1,2,4]triazolo[1,5-d][1,4]benzodiazepine a) (2-Oxo-oxazolidin-3-yl)-acetic acid hydrazide As described for example 112a, (2-oxo-oxazolidin-3-yl)-acetic acid ethyl ester (Potts, Kevin T.; Bhattacharjee, Debkumar; Kanemasa, Shuji. Journal of Organic Chemistry (1980), 45(24), 4985-8) in ethanol was reacted with hydrazine hydrate (1.0 equivalent) at rt for 72 h. All volatiles were evaporated, the residue was chromatographed (SiO$_2$, dichloromethane:methanol:aq.ammonia (25%)=90:10:1) and the title compound was obtained as a white solid (yield: 77%). MS: m/e=160.4 [M+H]$^+$.

b) 3-Chloro-10-methyl-6-(2-oxo-oxazolidin-3-ylmethyl)-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with (2-oxo-oxazolidin-3-yl)-acetic acid hydrazide. After evaporation of the solvent the residue was chromatographed (SiO$_2$, dichloromethane:methanol=100:0 to 96:4) and triturated with diisopropylether to afford the title compound as a white solid (yield: 27%). MS: m/e=371.0 [M+H]$^+$.

EXAMPLE 363

3-Chloro-10-methyl-6-(3-methyl-pyrazol-1-ylmethyl)-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with (3-methyl-pyrazol-1-yl)-acetic acid hydrazide (example 152b). After evaporation of the solvent the residue was chromatographed (SiO$_2$, dichloromethane:methanol=100:0 to 96:4) and triturated with diisopropylether to afford the title compound as a white solid (yield: 19%). MS: m/e=366.0 [M+H]$^+$.

EXAMPLE 364

3-Chloro-10-methyl-6-[1,2,3]triazol-1-ylmethyl-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with [1,2,3]triazol-1-yl-acetic acid hydrazide (example 162a). After evaporation of the solvent the residue was triturated with methanol to afford the free base of the title compound. Treatment with HCl in methanol and crystallization from methanol/diethylether afforded the title compound as an off-white solid (yield: 23%). MS: m/e=353.2 [M+H]$^+$.

EXAMPLE 365

3-Chloro-10-methyl-6-(5-methyl-pyrazol-1-ylmethyl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with (5-methyl-pyrazol-1-yl)-acetic acid hydrazide (example 155b). Upon cooling to rt the title compound crystallized from the reaction mixture as the free base. Treatment with HCl in methanol and crystallization from methanol/diethylether afforded the title compound as a light yellow solid (yield: 19%). MS: m/e=366.1[M+H]$^+$.

EXAMPLE 366

(R)-3-Chloro-10-methyl-6-(5-oxo-pyrrolidin-2-yl)-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with (R)-5-oxo-pyrrolidine-2-carboxylic acid hydrazide (example 326a). After evaporation of the solvent the residue was chromatographed (SiO$_2$, dichloromethane:methanol=100:0 to 96:4) and triturated with ethyl acetate to afford the title compound as a white solid (yield: 23%). MS: m/e=355.1 [M+H]$^+$.

EXAMPLE 367

(S)-3-Chloro-10-methyl-6-(5-oxo-pyrrolidin-2-yl)-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with (S)-5-oxo-pyrrolidine-2-carboxylic acid hydrazide (Angier, R. B. et al. Journal of the American Chemical Society (1950), 72, 74-7). Upon cooling to rt the title compound crystallized from the reaction mixture as the free base. It was chromatographed (SiO$_2$, dichloromethane:methanol=100:0 to 96:4) and triturated with diisopropylether to afford the title compound as a light yellow solid (yield: 11%). MS: m/e=355.1 [M+H]$^+$.

EXAMPLE 368

3-Chloro-10-methyl-6-(2H-pyrazol-3-ylmethyl)-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with (2H-pyrazol-3-yl)-acetic acid hydrazide (Barker, John M.; Huddleston, Patrick R.; Wood, Michael L. Journal of Chemical Research, Synopses (1992), (9), 291). After evaporation of the solvent the residue was chromatographed (SiO$_2$, dichloromethane:methanol=100:0 to 96:4) and triturated with ethyl acetate to afford the title compound as a white solid (yield: 12%). MS: m/e=352.2 [M+H]$^+$.

EXAMPLE 369

(rac.)-3-Chloro-10-methyl-6-[1-(4-methyl-pyrazol-1-yl)-ethyl]-9H-imidazo[1,5-a][1,2,4]triazolo[1,5-d][1,4]benzodiazepine As described for example 84d, [3-(4-chloro-2-cyano-phenyl)-5-methyl-3H-imidazol-4-ylmethyl]-trimethyl-ammonium; iodide (example 170c) was reacted with (rac.)-2-(4-methyl-pyrazol-1-yl)-propionic acid hydrazide. After evaporation of the solvent the residue was chromatographed ($SiO_2$, dichloromethane:methanol=100:0 to 96:4) and triturated with ethyl acetate to afford the title compound as a light yellow solid (yield: 32%). MS: m/e=380.2 [M+H]$^+$.

EXAMPLE 370

3-Chloro-10-methyl-6-[1,2,4]triazol-1-ylmethyl-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with [1,2,4]triazol-1-yl-acetic acid hydrazide (Leonardi, A.; Nardi, D.; Veronese, M. Bollettino Chimico Farmaceutico (1975), 114(2), 70-2). After evaporation of the solvent the residue was chromatographed ($SiO_2$, dichloromethane:methanol=1000:0 to 955:45) to afford the title compound as the free base. Treatment with HCl in methanol and crystallization from methanol/diethylether afforded the title compound as a yellow solid (yield: 28%). MS: m/e=353.0 [M+H]$^+$.

EXAMPLE 371

3-Chloro-6-(3-hydroxy-isoxazol-5-ylmethyl)-10-methyl-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with (3-hydroxy-isoxazol-5-yl)-acetic acid hydrazide (Nakamura, Norio. Chemical & Pharmaceutical Bulletin (1971), 19(1), 46-51). After evaporation of the solvent the residue was chromatographed ($SiO_2$, dichloromethane:methanol=100:0 to 96:4) to afford the title compound as the free base. Treatment with HCl in methanol and crystallization from methanol/diethylether afforded the title compound as a light yellow solid (yield: 8%). MS: m/e=369.0 [M+H]$^+$.

EXAMPLE 372

3-Chloro-10-methyl-6-(3-methoxy-2-oxo-2H-pyridin-1-ylmethyl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with (3-methoxy-2-oxo-2H-pyridin-1-yl)-acetic acid hydrazide (example 324b). After evaporation of the solvent the residue was triturated with methanol to afford the title compound as the free base. Treatment with HCl in methanol and crystallization from methanol/diethylether afforded the title compound as an off-white solid (yield: 34%). MS: m/e=409.2[M+H]$^+$.

EXAMPLE 373

3-Chloro-10-methyl-6-(pyrazol-1-ylmethyl)-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with pyrazol-1-yl-acetic acid hydrazide. After evaporation of the solvent the residue was triturated with methanol to afford the title compound as the free base. Treatment with HCl in methanol and crystallization from methanol/diethylether afforded the title compound as a light yellow solid (yield: 48%). MS: m/e=352.2[M+H]$^+$.

EXAMPLE 374

(rac.)-3-Chloro-6-(cyclopropyl-hydroxy-methyl)-10-methyl-9H-imidazo[1,5-a][1,2,4]triazolo[1,5-d][1,4]benzodiazepine hydrochloride (1:1)

As described for example 84d, [3-(4-chloro-2-cyano-phenyl)-5-methyl-3H-imidazol-4-ylmethyl]-trimethyl-ammonium; iodide (example 170c) was reacted with (rac.)-2-cyclopropyl-2-hydroxy-acetic acid hydrazide (example 358a). After evaporation of the solvent the residue was chromatographed ($SiO_2$, dichloromethane:methanol=100:0 to 95:5) to afford the title compound as the free base. Treatment with HCl in methanol and crystallization from methanol/diethylether afforded the title compound as a light orange solid (yield: 40%). MS: m/e=342.1 [M+H]$^+$.

EXAMPLE 375

6-Hydroxymethyl-10-methyl-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with hydroxy-acetic acid hydrazide (Crast, Leonard Bruce, Jr. Bactericidal 7-(D-α-amino-α-phenylacetamido)-3-[S-[5-(hydroxymethyl)-1,3,4-oxadiazol-2-yl]thiomethyl]-3-cephem-4-carboxylic acid. Ger. Offen. (1972), 28 pp.). After evaporation of the solvent the residue was chromatographed ($SiO_2$, dichloromethane:methanol=100:0 to 95:5) to afford the title compound as the free base. Treatment with HCl in methanol and crystallization from methanol/diethylether afforded the title compound as a light yellow solid (yield: 24%). MS: m/e=268.1 [M+H]$^+$.

EXAMPLE 376

(R)-10-Methyl-6-(5-oxo-pyrrolidin-2-yl)-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with (R)-5-oxo-pyrrolidine-2-carboxylic acid hydrazide (example 326a). After evaporation of the solvent the residue was chromatographed ($SiO_2$, dichloromethane:methanol=100:0 to 95:5)) to afford the title compound as the free base. Treatment with HCl in methanol and crystallization from methanol/diethylether afforded the title compound as a light yellow solid (yield: 19%). MS: m/e=321.1 [M+H]$^+$.

EXAMPLE 377

(R)-6-(1-Hydroxy-ethyl)-10-methyl-9H-imidazo[1,5-a][1,2,4]triazolo[1,5-d][1,4]benzodiazepine As described for example 84d, [3-(2-cyano-phenyl)-5-methyl-3H-imidazol-4-ylmethyl]-trimethyl-ammonium; iodide (example 254c) was reacted with (R)-2-hydroxy-propionic acid hydrazide (example 355a). After evaporation of the solvent the residue was chromatographed (SiO$_2$, dichloromethane:methanol=100:0 to 95:5)) to afford the title compound as the free base. Treatment with HCl in methanol and crystallization from methanol/diethylether afforded the title compound as a light yellow solid (yield: 22%). MS: m/e=282.3 [M+H]$^+$.

EXAMPLE 378

10-Methyl-6-(2-oxo-2H-pyridin-1-ylmethyl)-9H-imidazo[1,5-a][1,2,4]triazolo[1,5-d][1,4]benzodiazepine As described for example 84d, [3-(2-cyano-phenyl)-5-methyl-3H-imidazol-4-ylmethyl]-trimethyl-ammonium; iodide (example 254c) was reacted with (2-oxo-2H-pyridin-1-yl)-acetic acid hydrazide (example 151a). After evaporation of the solvent the residue was chromatographed (SiO$_2$, dichloromethane:methanol=100:0 to 95:5)) to afford the title compound as a white foam (yield: 26%). MS: m/e=345.2 [M+H]$^+$.

EXAMPLE 379

10-Methyl-6-(2-oxo-oxazolidin-3-ylmethyl)-9H-imidazo[1,5-a][1,2,4]triazolo[1,5-d][1,4]benzodiazepine As described for example 84d, [3-(2-cyano-phenyl)-5-methyl-3H-imidazol-4-ylmethyl]-trimethyl-ammonium; iodide (example 254c) was reacted with (2-oxo-oxazolidin-3-yl)-acetic acid hydrazide (example 362a). After evaporation of the solvent the residue was chromatographed (SiO$_2$, dichloromethane:methanol=100:0 to 95:5)) to afford the title compound as a white foam (yield: 7%). MS: m/e=337.4 [M+H]$^+$.

EXAMPLE 380

10-Methyl-6-(2H-pyrazol-3-ylmethyl)-9H-imidazo[1,5-a][1,2,4]triazolo[1,5-d][1,4]benzodiazepine hydrochloride (1:1)

As described for example 84d, [3-(2-cyano-phenyl)-5-methyl-3H-imidazol-4-ylmethyl]-trimethyl-ammonium; iodide (example 254c) was reacted with (2H-pyrazol-3-yl)-acetic acid hydrazide (Barker, John M.; Huddleston, Patrick R.; Wood, Michael L. Journal of Chemical Research, Synopses (1992), (9), 291). After evaporation of the solvent the residue was chromatographed twice (first: SiO$_2$, dichloromethane:methanol=100:0 to 96:4 and then SiO$_2$, dichloromethane:methanol:aq.ammonia (25%)=100:0:0 to 180:10:1) to afford the title compound as the free base. Treatment with HCl in methanol and crystallization from methanol/diethylether afforded the title compound as a white solid (yield: 5%). MS: m/e=318.1 [M+H]$^+$.

EXAMPLE 381

3-Difluoromethyl-10-methyl-6-(2-oxo-pyrrolidin-1-ylmethyl)-9H-imidazo[1,5-a][1,2,4]triazolo[1,5-d][1,4]benzodiazepine hydrochloride (1:1)

a) 5-Difluoromethyl-2-fluoro-benzonitrile

A solution of 2-fluoro-5-formyl-benzonitrile (10.6 g, 71.1 mmol) in dichloromethane (300 ml) was treated with diethylaminosulfur trifluoride (12.0 ml, 91.6 mmol) and stirred at rt for 4 days. The mixture was cooled in an ice bath and saturated aqueous sodium bicarbonate solution (300 ml) was added slowly. The organic phase was separated, dried (Na$_2$SO$_4$) and evaporated. After chromatography (SiO$_2$, heptane:ethyl acetate=100:0 to 50:50) the title compound was obtained as a light brown liquid (10.8 g, 89%). MS: m/e=171.1 [M]$^+$.

b) 5-Difluoromethyl-2-(4-methyl-imidazol-1-yl)-benzonitrile

As described for example 84a, 5-difluoromethyl-2-fluoro-benzonitrile was reacted with 4-methylimidazole and potassium carbonate for 16 h at 90° C. After aqueous workup the title compound was obtained as a light brown solid (yield: 69%). MS: m/e=234.3 [M+H]$^+$.

c) 5-Difluoromethyl-2-(5-dimethylaminomethyl-4-methyl-imidazol-1-yl)-benzonitrile As described for example 84b, 5-difluoromethyl-2-(4-methyl-imidazol-1-yl)-benzonitrile was reacted with Eschenmoser's salt in DMF for 16 h at 90° C. Evaporation of the solvent, aqueous workup and chromatography (SiO$_2$, dichloromethane:methanol:aq.ammonia (25%)=100:0:0 to 300:10:1) afforded the title compound as alight brown oil (yield: 47%). MS: m/e=291.1 [M+H]$^+$.

d) [3-(2-Cyano-4-difluoromethyl-phenyl)-5-methyl-3H-imidazol-4-ylmethyl]-trimethyl-ammonium; iodide As described for example 84c, 5-difluoromethyl-2-(5-dimethylaminomethyl-4-methyl-imidazol-1-yl)-benzonitrile was reacted with methyl iodide for 3 days at 4° C. The title compound was obtained as a white crystalline material (yield: 77%). MS: m/e=246.1 [M−NMe$_3$]$^+$.

e) 3-Difluoromethyl-10-methyl-6-(2-oxo-pyrrolidin-1-ylmethyl)-9H-imidazo[1,5-a][1,2,4]triazolo[1,5-d][1,4]benzodiazepine hydrochloride (1:1)

As described for example 84d, [3-(2-cyano-4-difluoromethyl-phenyl)-5-methyl-3H-imidazol-4-ylmethyl]-trimethyl-ammonium; iodide was reacted with (2-oxo-pyrrolidin-1-yl)-acetic acid hydrazide. After evaporation of the solvent the residue was triturated with methanol to afford the title compound as the free base. Treatment with HCl in methanol and crystallization from methanol/diethylether afforded the title compound as an off-white solid (yield: 62%). MS: m/e=385.1 [M+H]$^+$.

EXAMPLE 382

3-Difluoromethyl-10-Methyl-6-(2-oxo-2H-pyridin-1-ylmethyl)-9H-imidazo[1,5-a][1,2,4]triazolo[1,5-d][1,4]benzodiazepine hydrochloride (1:1)

As described for example 84d, [3-(2-cyano-4-difluoromethyl-phenyl)-5-methyl-3H-imidazol-4-ylmethyl]-trimethyl-ammonium; iodide (example 381d) was reacted with (2-oxo-2H-pyridin-1-yl)-acetic acid hydrazide (example 151a). After evaporation of the solvent the residue was triturated with methanol to afford the title compound as the free base. Treatment with HCl in methanol and crystallization from methanol/diethylether afforded the title compound as alight yellow solid (yield: 20%). MS: m/e=395.1 [M+H]$^+$.

EXAMPLE 383

3-Difluoromethyl-10-methyl-6-(pyrazol-1-ylmethyl)-9H-imidazo[1,5-a][1,2,4]triazolo[1,5-d][1,4] benzodiazepine hydrochloride (1:1)

As described for example 84d, [3-(2-cyano-4-difluoromethyl-phenyl)-5-methyl-3H-imidazol-4-ylmethyl]-trimethyl-ammonium; iodide (example 381d) was reacted with pyrazol-1-yl-acetic acid hydrazide. After evaporation of the solvent the residue was triturated with methanol to afford the title compound as the free base. Treatment with HCl in methanol and crystallization from methanol/diethylether afforded the title compound as a light yellow solid (yield: 7%). MS: m/e=368.1[M+H]$^+$.

EXAMPLE 384

(R)-3-Difluoromethyl-10-methyl-6-(5-oxo-pyrrolidin-2-yl)-9H-imidazo[1,5-a][1,2,4]triazolo[1,5-d][1,4]benzodiazepine As described for example 84d, [3-(2-cyano-4-difluoromethyl-phenyl)-5-methyl-3H-imidazol-4-ylmethyl]-trimethyl-ammonium; iodide (example 381d) was reacted with (R)-5-oxo-pyrrolidine-2-carboxylic acid hydrazide (example 326a). After evaporation of the solvent the residue was chromatographed (SiO$_2$, dichloromethane:methanol=100:0 to 96:4) and triturated with diisopropylether to afford the tide compound as a white solid (yield: 28%). MS: m/e=371.1 [M+H]$^+$.

EXAMPLE 385

3-Difluoromethyl-10-methyl-6-(2-oxo-oxazolidin-3-ylmethyl)-9H-imidazo[1,5-a][1,2,4]triazolo[1,5-d][1,4]benzodiazepine As described for example 84d, [3-(2-cyano-4-difluoromethyl-phenyl)-5-methyl-3H-imidazol-4-ylmethyl]-trimethyl-ammonium; iodide (example 381d) was reacted with (2-oxo-oxazolidin-3-yl)-acetic acid hydrazide (example 362a). After evaporation of the solvent the residue was chromatographed (SiO$_2$, dichloromethane:methanol=100:0 to 96:4) and triturated with diisopropylether to afford the title compound as a light yellow solid (yield: 35%). MS: m/e=387.1 [M+H]$^+$.

EXAMPLE 386

3-Ethynyl-10-methyl-6-(2-oxo-2H-pyridin-1-ylmethyl)-9H-imidazo[1,5-a][1,2,4]triazolo[1,5-d][1,4]benzodiazepine a) 10-Methyl-6-(2-oxo-2H-pyridin-1-ylmethyl)-3-trimethylsilanylethynyl-9H-imidazo[1,5-a][1,2,4]triazolo[1,5-d][1,4]benzodiazepine As described for example 252, 3-iodo-10-methyl-6-(2-oxo-2H-pyridin-1-ylmethyl)-9H-imidazo[1,5-a][1,2,4]triazolo[1,5-d][1,4]benzodiazepine (example 213) was with trimethylsilylacetylene, bis-(triphenylphospine)-palladium (II)-chloride, triphenylphosphine, triethylamine and copper (II) bromide. After extractive workup and evaporation of the solvent the residue was chromatographed (SiO$_2$, dichloromethane:methanol=100:0 to 95:5) and triturated with methanol to afford the title compound as a white solid (yield: 19%). MS: m/e=441.3[M+H]$^+$.

b) 3-Ethynyl-10-methyl-6-(2-oxo-2H-pyridin-1-ylmethyl)-9H-imidazo[1,5-a][1,2,4]triazolo[1,5-d][1,4]benzodiazepine A mixture of 10-methyl-6-(2-oxo-2H-pyridin-1-ylmethyl)-3-trimethylsilanylethynyl-9H-imidazo[1,5-a][1,2,4]triazolo[1,5-d][1,4]benzodiazepine and aqueous citric acid (10%, 10 mL) was heated under microwave conditions (30 min at 120° C., then 1 h at 140° C.). After extractive workup (ethyl acetate) and evaporation of the solvent the residue was crystallized from dichloromethane/diisopropylether to afford the title compound as an off-white solid (yield: 30%). MS: m/e=369.1[M+H]$^+$.

EXAMPLE 387

3-Cyclopropyl-10-methyl-6-(2-oxo-2H-pyridin-1-ylmethyl)-9H-imidazo[1,5-a][1,2,4]triazolo[1,5-d][1,4]benzodiazepine As described for example 248, 3-iodo-10-methyl-6-(2-oxo-2H-pyridin-1-ylmethyl)-9H-imidazo[1,5-a][1,2,4]triazolo[1,5-d][1,4]benzodiazepine (example 213) was reacted with cyclopropyl zinc chloride solution and bis-(tri-tert.-butylphoshine) palladium(0). After workup, chromatographic purification (SiO$_2$, dichloromethane:methanol:aq.ammonia (25%)=100:0:0:0 to 180:10:1) and trituration with methanol the title compound was obtained as a white solid (yield: 70%). MS: m/e=385.1 [M+H]$^+$.

EXAMPLE 388

3-Hydroxy-10-methyl-6-(3-methyl-isoxazol-5-ylmethyl)-9H-imidazo[1,5-a][1,2,4]triazolo[1,5-d][1,4]benzodiazepine A solution of 3-methoxy-10-methyl-6-(3-methyl-isoxazol-5-ylmethyl)-9H-imidazo[1,5-a][1,2,4]triazolo[1,5-d][1,4]benzodiazepine (example 241) in aqueous hydrobromic acid (48%, 2.7 mL) was stirred at 130° C. for 6 h. The mixture was cooled to rt and aqueous sodium hydroxide (2N, 6.5 mL) was added. Then saturated aqueous sodium bicarbonate solution was added until the solution was slightly basic (pH 8). The precipitate was filtered, dried and triturated with dichloromethane to afford the title compound as a light grey solid (yield: 80%). MS: m/e=349.4 [M+H]$^+$.

What is claimed is:
1. A compound of formula I

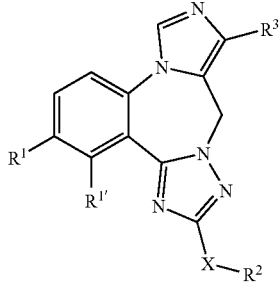

wherein
R¹ and R¹' are each independently hydrogen, hydroxy, lower alkyl, lower alkynyl, halogen, lower alkoxy, cycloalkyl, or lower alkyl or alkoxy each of which is substituted by halogen;
X is —CH₂—, —CH(CH₃)—, —CH₂—O—, —CRR'— or —C(O)—;
R² is —(CH₂)$_n$-O-lower alkyl,
halogen,
—NHCH₃,
—N(CH₃)C(O)-cycloalkyl,
—N(CH₃)C(O)-lower alkyl,
—N(CH₃)S(O₂)CH₃,
—NHC(O)CH₂OC(O)CH₃,
—CF₃,
cycloalkyl,
hydroxy,
—CH₂OH,
cyano,
S(O)₂CH₃,
—CH(OH)-lower alkyl,
aryl unsubstituted or substituted by lower alkoxy,
an aromatic or non aromatic heterocyclic ring, containing from 1 to 3 heteroatoms selected from the group consisting of N, O and S, and wherein the heterocyclic ring is unsubstituted or substituted by 1-4 substituents selected from the group consisting of lower alkyl, lower alkoxy, cycloalkyl, =O, CF₃, CN, C(O)O-lower alkyl, benzyl, phenyl, —CH₂O-lower alkyl, CHO and 3-bromo-10-chloro-9H-imidazo[1,5-a][1,2,4]triazolo[1,5-d][1,4]benzodiazepin-6-ylmethyl,
—C(O)—O-lower alkyl,
—C(O)NH—(CH₂)$_n$-cycloalkyl,
—C(O)NH—(CH₂)$_n$-aromatic or non aromatic heterocyclic ring, wherein the heterocyclic ring contains from 1 to 3 heteroatoms selected from the group consisting of N, O and S,
—C(O)NH—(CH₂)$_n$OH,
—C(O)-aromatic or non aromatic heterocyclic ring, wherein the heterocyclic ring contains from 1 to 3 heteroatoms selected from the group consisting of N, O and S, unsubstituted or substituted by lower alkyl,
—NH—C(O)H,
—N(CH₃)—C(O)H,
—NH—C(O)-lower alkyl,
—NH—C(O)-cycloalkyl,
—NH—C(O)—O-lower alkyl,
—NH—C(O)—N-di-lower alkyl,
—NH—C(O)—CH₂—O-lower alkyl,
—NH—C(O)—CH₂—OH,
—NH—(CH₂)$_n$-cycloalkyl,
—NH—(CH₂)$_n$S(O)₂CH₃,
—NH—(CH₂)$_n$-aromatic or non aromatic heterocyclic ring, wherein the heterocyclic ring contains from 1 to 3 heteroatoms selected from the group consisting of N, O and S, or
—NH—(CH₂)$_n$OH; or
X—R² is lower alkyl with the exception of methyl or is cycloalkyl, which is unsubstituted or substituted by lower alkyl or hydroxy,
an aromatic or non aromatic heterocyclic ring, which contains from 1 to 3 heteroatoms selected from the group consisting of N, O and S, or
—CHRR';
R is hydroxy;
R' is cycloalkyl, lower alkyl, lower alkyl substituted by halogen, phenyl or pyridinyl;
R³ is hydrogen, halogen, C(O)O-lower alkyl, CH₂OH, CHO, lower alkyl, or lower alkyl substituted by halogen; and
n is 0, 1 or 2;
or a pharmaceutically acceptable acid addition salt thereof.

2. The compound of claim 1, wherein X is —CH₂—.

3. The compound of claim 1, in which R² is —(CH₂)$_n$O-lower alkyl.

4. The compound of claim 3, selected from the group consisting of
ethyl 3-chloro-6-methoxymethyl-9H-imidazo[1,5-a][1,2,4]triazolo[1,5-d][1,4]benzodiazepine-10-carboxylate and
ethyl 3-bromo-6-methoxymethyl-9H-imidazo[1,5-a][1,2,4]triazolo[1,5-d][1,4]benzodiazepine-10-carboxylate.

5. The compound of claim 2, in which R² is an aromatic heterocyclic ring, containing from 1 to 3 heteroatoms selected from the group consisting of N, O and S, and wherein the heterocyclic ring is unsubstituted or substituted by 1-4 substituents selected from the group consisting of lower alkyl, =O, CF₃, C(O)O-lower alkyl, benzyl, phenyl, CH₂O-lower alkyl and CHO.

6. The compound of claim 5, selected from the group consisting of
3,10-dichloro-6-[1,2,3]triazol-2-ylmethyl-9H-imidazo[1,5-a][1,2,4]triazolo[1,5-d][1,4]benzodiazepine,
3,10-dichloro-6-[1,2,3]triazol-1-ylmethyl-9H-imidazo[1,5-a][1,2,4]triazolo[1,5-d][1,4]benzodiazepine,
3,10-dichloro-6-[1,2,4]triazol-1-ylmethyl-9H-imidazo[1,5-a][1,2,4]triazolo[1,5-d][1,4]benzodiazepine,
3,10-dichloro-6-pyrazol-1-ylmethyl-9H-imidazo[1,5-a][1,2,4]triazolo[1,5-d][1,4]benzodiazepine,
6-benzotriazol-2-ylmethyl-3,10-dichloro-9H-imidazo[1,5-a][1,2,4]triazolo[1,5-d][1,4]benzodiazepine,
6-benzotriazol-1-ylmethyl-3,10-dichloro-9H-imidazo[1,5-a][1,2,4]triazolo[1,5-d][1,4]benzodiazepine,
3,10-dichloro-6-indazol-2-ylmethyl-9H-imidazo[1,5-a][1,2,4]triazolo[1,5-d][1,4]benzodiazepine, and
3-bromo-10-chloro-6-(5-methyl-[1,2,4]oxadiazol-3-ylmethyl)-9H-imidazo[1,5-a][1,2,4]triazolo[1,5-d][1,4]benzodiazepine.

7. The compound of claim 5, selected from the group consisting of
3-bromo-10-methyl-6-(pyridine-4-ylmethyl)-9H-imidazo[1,5-a][1,2,4]triazolo[1,5-d][1,4]benzodiazepine,
3-bromo-10-methyl-6-(3-methyl-isoxazol-5-ylmethyl)-9H-imidazo[1,5-a][1,2,4]triazolo[1,5-d][1,4]benzodiazepine, 3-bromo-10-methyl-6-(6-methyl-pyridin-3-ylmethyl)-9H-imidazo[1,5-a][1,2,4]triazolo[1,5-d][1,4]benzodiazepine, 3-bromo-10-methyl-6-[1,2,3]triazol-1-ylmethyl-9H-imidazo[1,5-a][1,2,4]triazolo[1,5-d][1,4]benzodiazepine, 3-chloro-10-methyl-6-(3-methyl-isoxazol-5-ylmethyl)-9H-imidazo[1,5-a][1,2,4]triazolo[1,5-d][1,4]benzodiazepine, 3-chloro-10-methyl-6-(6-methyl-pyridin-3-ylmethyl)-9H-imidazo[1,5-a][1,2,4]triazolo[1,5-d][1,4]benzodiazepine, 3-chloro-10-methyl-6-(2-methyl-pyridin-4-ylmethyl)-9H-imidazo[1,5-a][1,2,4]triazolo[1,5-d][1,4]benzodiazepine, and 3,10-dimethyl-6-(3-methyl-isoxazol-5-ylmethyl)-9H-imidazo[1,5-a][1,2,4]triazolo[1,5-d][1,4]benzodiazepine.

8. The compound of claim 5, selected from the group consisting of 10-methyl-6-(pyridine-2-ylmethyl)-9H-imidazo[1,5-a][1,2,4]triazolo[1,5-d][1,4]benzodiazepine, 10-methyl-6-(pyridine-3-ylmethyl)-9H-imidazo[1,5-a][1,2,4]triazolo[1,5-d][1,4]benzodiazepine, 6-(imidazol-1-ylmethyl)-10-methyl-9H-imidazo[1,5-a][1,2,4]triazolo[1,5-d][1,4]benzodiazepine, 3-bromo-10-methyl-6-(6-oxo-6H-pyridazin-1-ylmethyl)-9H-imidazo[1,5-a][1,2,4]triazolo[1,5-d][1,4]benzodiazepine, 3-bromo-10-methyl-6-(3-methyl-[1,2,4]oxadiazol-5-ylmethyl)-9H-imidazo[1,5-a][1,2,4]triazolo[1,5-d][1,4]benzodiazepine, 3-chloro-10-methyl-6-[1,2,3]triazol-1-ylmethyl-9H-imidazo[1,5-a][1,2,4]triazolo[1,5-d][1,4]benzodiazepine, 10-methyl-6-(2-oxo-2H-pyridin-1-ylmethyl)-9H-imidazo[1,5-a][1,2,4]triazolo[1,5-d][1,4]benzodiazepine and 10-methyl-6-(2H-pyrazol-3-ylmethyl)-9H-imidazo[1,5-a][1,2,4]triazolo[1,5-d][1,4]benzodiazepine.

9. The compound of claim 2, in which $R^2$ is a non aromatic heterocyclic ring, containing from 1 to 3 heteroatoms selected from the group consisting of N, O and S, and wherein the heterocyclic ring is unsubstituted or substituted by 1-4 substituents selected from the group consisting of lower alkyl, =O, $CF_3$, C(O)O-lower alkyl, benzyl, phenyl, $CH_2O$-lower alkyl and CHO.

10. The compound of claim 9, selected from the group consisting of 3-bromo-10-chloro-6-(2-oxo-pyrrolidin-1-ylmethyl)-9H-imidazo[1,5-a][1,2,4]triazolo[1,5-d][1,4]benzodiazepine, 3-bromo-10-chloro-6-(2-oxo-oxazolidin-3-ylmethyl)-9H-imidazo[1,5-a][1,2,4]triazolo[1,5-d][1,4]benzodiazepine, 3-bromo-10-chloro-6-(5-methoxymethyl-2-oxo-oxazolidin-3-ylmethyl)-9H-imidazo[1,5-a][1,2,4]triazolo[1,5-d][1,4]benzodiazepine, 3-bromo-10-chloro-6-(3-methyl-2-oxo-imidazolidin-1-ylmethyl)-9H-imidazo[1,5-a][1,2,4]triazolo[1,5-d][1,4]benzodiazepine, 3-bromo-10-chloro-6-(2-oxo-imidazolidin-1-ylmethyl)-9H-imidazo[1,5-a][1,2,4]triazolo[1,5-d][1,4]benzodiazepine, 3-bromo-10-chloro-6-(2,4-dioxo-thiazolidin-3-ylmethyl)-9H-imidazo[1,5-a][1,2,4]triazolo[1,5-d][1,4]benzodiazepine, 3-bromo-10-chloro-6-(2,5-dioxo-pyrrolidin-1-ylmethyl)-9H-imidazo[1,5-a][1,2,4]triazolo[1,5-d][1,4]benzodiazepine, 3-bromo-10-chloro-6-(2-oxo-thiazolidin-3-ylmethyl)-9H-imidazo[1,5-a][1,2,4]triazolo[1,5-d][1,4]benzodiazepine, 3-bromo-10-chloro-6-((5S)-5-methyl-2-oxo-oxazolidin-3-ylmethyl)-9H-imidazo[1,5-a][1,2,4]triazolo[1,5-d][1,4]benzodiazepine and 3,10-dichloro-6-(2-oxo-oxazolidin-3-ylmethyl)-9H-imidazo[1,5-a][1,2,4]triazolo[1,5-d][1,4]benzodiazepine.

11. The compound of claim 2, in which $R^2$ is —C(O)NH—$(CH_2)_n$-cycloalkyl or —C(O)NH—$(CH_2)_n$-aromatic or non aromatic heterocyclic ring, wherein the heterocyclic ring contains from 1 to 3 heteroatoms selected from the group consisting of N, O and S.

12. The compound of claim 11, selected from the group consisting of 3-bromo-10-chloro-6-cyclopentylcarbamoylmethyl-9H-imidazo[1,5-a][1,2,4]triazolo[1,5-d][1,4]benzodiazepine, 3-bromo-10-chloro-6-[(tetrahydro-pyran-4-ylcarbamoyl)-methyl]-9H-imidazo[1,5-a][1,2,4]triazolo[1,5-d][1,4]benzodiazepine, 3-bromo-10-chloro-6-{[(pyridin-3-ylmethyl)-carbamoyl]-methyl}-9H-imidazo[1,5-a][1,2,4]triazolo[1,5-d][1,4]benzodiazepine 3-bromo-10-chloro-6-[(cyclopropylmethyl-carbamoyl)-methyl]-9H-imidazo[1,5-a][1,2,4]triazolo[1,5-d][1,4]benzodiazepine.

13. The compound of claim 2, in which $R^2$ is —C(O)NH—$(CH_2)_n$OH.

14. The compound of claim 13, which compound is 3-bromo-10-chloro-6-[(2-hydroxy-ethylcarbamoyl)-methyl]-9H-imidazo[1,5-a][1,2,4]triazolo[1,5-d][1,4]benzodiazepine.

15. The compound of claim 2, wherein $R^2$ is aryl, which is unsubstituted or substituted by lower alkoxy.

16. The compound of claim 15, which compound is

3-Bromo-6-(2-methoxy-benzyl)-10-methyl-9H-imidazo[1,5-a][1,2,4]triazolo[1,5-d][1,4]benzodiazepine.

17. The compound of claim 1, wherein X is —$CH(CH_3)$.

18. The compound of claim 1, wherein X is $CH_2O$.

19. The compound of claim 1, wherein X is CRR'.

20. The compound of claim 1, wherein X is C(O).

21. The compound of claim 1 wherein X—$R^2$ is lower alkyl, except for methyl.

22. The compound of claim 1, wherein X—$R^2$ is cycloalkyl, which is unsubstituted or substituted by lower alkyl or hydroxyl.

23. The compound of claim 1, wherein X—$R^2$ is an aromatic or non aromatic heterocyclic ring, which contains from 1 to 3 heteroatoms selected from the group consisting of N, O and S.

24. The compound of claim 1, wherein X—$R^2$ is —CHRR' wherein R is hydroxy and R' is cycloalkyl, lower alkyl, phenyl or pyridinyl.

25. The compound of claim 24, selected from the group consisting of 3-bromo-10-chloro-6-(hydroxy-phenyl-ethyl)-9H-imidazo[1,5-a][1,2,4]triazolo[1,5-d][1,4]benzodiazepine and 3-bromo-10-chloro-6-(hydroxy-pyridin-3-yl-methyl)-9H-imidazo[1,5-a][1,2,4]triazolo[1,5-d][1,4]benzodiazepine.

26. The compound of claim 1, wherein $R^3$ is hydrogen, halogen, lower alkyl, or lower alkyl substituted by halogen.

27. The compound of claim 1, wherein $R^3$ is C(O)O-lower alkyl or CHO.

28. The compound of claim 1, wherein $R^3$ is $CH_2OH$.

29. A pharmaceutical composition comprising a compound of formula I

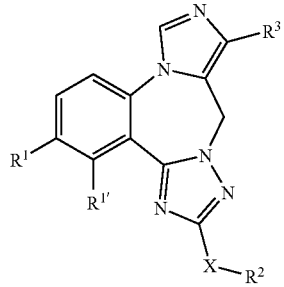

wherein
R' and R$^{1'}$ are each independently hydrogen, hydroxy, lower alkyl, lower alkynyl, halogen, lower alkoxy, cycloalkyl, or lower alkyl or alkoxy each of which is substituted by halogen;
X is —CH$_2$—, —CH(CH$_3$)—, —CH$_2$—O—, —CRR'— or —C(O)—;
R$^2$ is —(CH$_2$)$_n$—O-lower alkyl,
halogen,
—NHCH$_3$,
—N(CH$_3$)C(O)-cycloalkyl,
—N(CH$_3$)C(O)-lower alkyl,
—N(CH$_3$)S(O$_2$)CH$_3$,
—NHC(O)CH$_2$OC(O)CH$_3$,
—CF$_3$,
cycloalkyl,
hydroxy,
—CH$_2$OH,
cyano,
S(O)$_2$CH$_3$,
—CH(OH)-lower alkyl,
aryl unsubstituted or substituted by lower alkoxy,
an aromatic or non aromatic heterocyclic ring, containing from 1 to 3 heteroatoms selected from the group consisting of N, O and S, and wherein the heterocyclic ring is unsubstituted or substituted by 1-4 substituents selected from the group consisting of lower alkyl, lower alkoxy, cycloalkyl, =O, CF$_3$, CN, C(O)O-lower alkyl, benzyl, phenyl, —CH$_2$O-lower alkyl, CHO and 3-bromo-10-chloro-9H-imidazo[1,5-a][1,2,4]triazolo[1,5-d][1,4]benzodiazepin-6-ylmethyl,
—C(O)—O-lower alkyl,
—C(O)NH—(CH$_2$)$_n$-cycloalkyl,
—C(O)NH—(CH$_2$)$_n$-aromatic or non aromatic heterocyclic ring, wherein the heterocyclic ring contains from 1 to 3 heteroatoms selected from the group consisting of N, O and S,
—C(O)NH—(CH$_2$)$_n$OH,
—C(O)-aromatic or non aromatic heterocyclic ring, wherein the heterocyclic ring contains from 1 to 3 heteroatoms selected from the group consisting of N, O and S, unsubstituted or substituted by lower alkyl,
—NH—C(O)H,
—N(CH$_3$)—C(O)H,
—NH—C(O)-lower alkyl,
—NH—C(O)-cycloalkyl,
—NH—C(O)—O-lower alkyl,
—NH—C(O)—N-di-lower alkyl,
—NH—C(O)—CH$_2$—O-lower alkyl,
—NH—C(O)—CH$_2$—OH,
—NH—(CH$_2$)$_n$-cycloalkyl,
—NH—(CH$_2$)$_n$S(O)$_2$CH$_3$,
—NH—(CH$_2$)$_n$-aromatic or non aromatic heterocyclic ring, wherein the heterocyclic ring contains from 1 to 3 heteroatoms selected from the group consisting of N, O and S, or
—NH—(CH$_2$)$_n$OH; or
X—R$^2$ is lower alkyl with the exception of methyl or is cycloalkyl, which is unsubstituted or substituted by lower alkyl or hydroxy,
an aromatic or non aromatic heterocyclic ring, which contains from 1 to 3 heteroatoms selected from the group consisting of N, O and S, or
—CHRR';
R is hydroxy;
R' is cycloalkyl, lower alkyl, lower alkyl substituted by halogen, phenyl or pyridinyl;
R$^3$ is hydrogen, halogen, C(O)O-lower alkyl, CH$_2$OH, CHO, lower alkyl, or lower alkyl substituted by halogen; and
n is 0, 1 or 2;
or a pharmaceutically acceptable acid addition salt thereof and a pharmaceutically acceptable carrier.

* * * * *